US009657043B2

United States Patent
Hamada et al.

(10) Patent No.: US 9,657,043 B2
(45) Date of Patent: May 23, 2017

(54) AMINE COMPOUND AND USE THEREOF FOR MEDICAL PURPOSES

(71) Applicant: MITSUBISHI TANABE PHARMA CORPORATION, Osaka-shi, Osaka (JP)

(72) Inventors: Maiko Hamada, Osaka (JP); Kaoru Tashiro, Osaka (JP); Hiroshi Sakashita, Osaka (JP); Masatoshi Kiuchi, Machida (JP); Shuzo Takeda, Osaka (JP); Kunitomo Adachi, Osaka (JP)

(73) Assignee: MITSUBISHI TANABE PHARMA CORPORATION, Osaka-shi (JP)

( * ) Notice: Subject to any disclaimer, the term of this patent is extended or adjusted under 35 U.S.C. 154(b) by 0 days.

(21) Appl. No.: 14/396,330

(22) PCT Filed: Apr. 23, 2013

(86) PCT No.: PCT/JP2013/061922
§ 371 (c)(1),
(2) Date: Oct. 22, 2014

(87) PCT Pub. No.: WO2013/161816
PCT Pub. Date: Oct. 31, 2013

(65) Prior Publication Data
US 2015/0087620 A1    Mar. 26, 2015

(30) Foreign Application Priority Data

Apr. 23, 2012 (JP) ................ 2012-097741

(51) Int. Cl.
| | |
|---|---|
| A61K 31/67 | (2006.01) |
| A61K 31/665 | (2006.01) |
| A61K 31/382 | (2006.01) |
| A61K 31/352 | (2006.01) |
| C07C 50/18 | (2006.01) |
| C07C 217/48 | (2006.01) |
| C07D 311/82 | (2006.01) |
| C07D 335/12 | (2006.01) |
| C07F 9/6553 | (2006.01) |
| C07D 311/86 | (2006.01) |
| C07F 9/655 | (2006.01) |
| C07F 9/6558 | (2006.01) |
| C07D 335/16 | (2006.01) |
| C07D 409/12 | (2006.01) |
| C07C 225/18 | (2006.01) |
| C07F 7/22 | (2006.01) |

(52) U.S. Cl.
CPC ...... *C07F 9/655372* (2013.01); *C07C 225/18* (2013.01); *C07D 311/82* (2013.01); *C07D 311/86* (2013.01); *C07D 335/12* (2013.01); *C07D 335/16* (2013.01); *C07D 409/12* (2013.01); *C07F 7/2212* (2013.01); *C07F 9/65522* (2013.01); *C07F 9/65586* (2013.01); *C07C 2103/18* (2013.01)

(58) Field of Classification Search
USPC ........ 514/96, 100, 437, 454, 455; 549/5, 26, 549/27, 220, 388, 392; 552/208, 261, 552/265, 271, 290; 564/360
See application file for complete search history.

(56) References Cited

U.S. PATENT DOCUMENTS

| | | |
|---|---|---|
| 5,604,229 A | 2/1997 | Fujita et al. |
| 5,719,176 A | 2/1998 | Fujita et al. |
| 5,948,820 A | 9/1999 | Fujita et al. |
| 5,952,316 A | 9/1999 | Fujita et al. |
| 6,187,821 B1 | 2/2001 | Fujita et al. |

(Continued)

FOREIGN PATENT DOCUMENTS

| | | |
|---|---|---|
| EP | 0 627 406 A1 | 12/1994 |
| EP | 0 778 263 A1 | 6/1997 |

(Continued)

OTHER PUBLICATIONS

Jastrzebska-Wiesek et al., "The Anticonvulsant, Local Anesthetic and Hemodynamic Properties of Some Chiral Aminobutanol Derivatives of Xanthone", Acta Poloniae Pharmaceutica-Drug Research, vol. 65, No. 5, 2008, pp. 591-600.

(Continued)

*Primary Examiner* — Barbara P Badio
(74) *Attorney, Agent, or Firm* — Birch, Stewart, Kolasch & Birch, LLP

(57) ABSTRACT

The present invention provides a compound represented by the following formula (I):

wherein each symbol is as described in the DESCRIPTION, which has a superior peripheral blood lymphocyte decreasing action, and is useful for the treatment or prophylaxis of autoimmune diseases; prophylaxis or suppression of resistance or acute rejection or chronic rejection of transplantation of organ or tissue; treatment or prophylaxis of graft-versus-host (GvH) disease due to bone marrow transplantation; or treatment or prophylaxis of allergic diseases.

13 Claims, No Drawings

(56) References Cited

U.S. PATENT DOCUMENTS

| | | |
|---|---|---|
| 6,214,873 B1 | 4/2001 | Adachi et al. |
| 6,372,800 B1 | 4/2002 | Fujita et al. |
| 6,960,692 B2 | 11/2005 | Kohno et al. |
| 6,963,012 B2 | 11/2005 | Kohno et al. |
| 7,241,812 B2 | 7/2007 | Saha et al. |
| 7,456,157 B2 | 11/2008 | Kohno et al. |
| 7,759,326 B2 | 7/2010 | Kohno et al. |
| 7,825,260 B2 | 11/2010 | Albert et al. |
| 8,114,902 B2 | 2/2012 | Kiuchi et al. |
| 8,809,304 B2 | 8/2014 | Kiuchi et al. |
| 2004/0242654 A1 | 12/2004 | Kohno et al. |
| 2004/0254222 A1 | 12/2004 | Kohno et al. |
| 2006/0135786 A1 | 6/2006 | Saha et al. |
| 2006/0160771 A1 | 7/2006 | Kohno et al. |
| 2006/0211656 A1 | 9/2006 | Albert et al. |
| 2006/0223866 A1 | 10/2006 | Evindar et al. |
| 2008/0064662 A1 | 3/2008 | Saha et al. |
| 2008/0275008 A1 | 11/2008 | Kohno et al. |
| 2009/0082311 A1 | 3/2009 | Kiuchi et al. |
| 2009/0137530 A1 | 5/2009 | Kiuchi et al. |
| 2010/0168140 A1 | 7/2010 | Kigoshi et al. |
| 2014/0296183 A1 | 10/2014 | Kiuchi et al. |

FOREIGN PATENT DOCUMENTS

| | | |
|---|---|---|
| EP | 1 002 792 A1 | 5/2000 |
| EP | 1 431 275 A1 | 6/2004 |
| EP | 1 431 284 A1 | 6/2004 |
| EP | 1 602 660 A1 | 12/2005 |
| EP | 1 961 734 A1 | 8/2008 |
| EP | 2 017 257 A1 | 1/2009 |
| JP | 2004-307442 A | 11/2004 |
| WO | WO 2004/096757 A1 | 11/2004 |
| WO | WO 2007/092190 A2 | 8/2007 |

OTHER PUBLICATIONS

Mandala et al., "Alteration of Lymphocyte Trafficking by Sphingosine-1-Phosphate Receptor Agonists", Science, vol. 296, Apr. 12, 2002, pp. 346-349.

Matloubian et al., "Lymphocyte egress from thymus and peripheral lymphoid organs is dependent on S1P receptor 1", Nature, vol. 427, Jan. 22, 2004. pp. 355-360.

AMINE COMPOUND AND USE THEREOF FOR MEDICAL PURPOSES

TECHNICAL FIELD

The present invention relates to an amine compound and use thereof as a medicament.

BACKGROUND ART

In recent years, calcineurin inhibitors such as cyclosporine and FK506 are used to suppress rejection of patients who underwent organ transplantation. However, a certain kind of calcineurin inhibitor such as cyclosporine sometimes causes adverse side effects such as renal toxicity, liver toxicity, neurotoxicity and the like. Therefore, the development of a safer and highly effective medicament is ongoing to suppress rejection of transplant patients.

Patent references 1-4 disclose that amino alcohol compounds are useful as suppressants of (acute or chronic) rejection in organ or bone marrow transplantation, as well as therapeutic drugs for various autoimmune diseases such as psoriasis, Behcet's disease and the like and rheumatism diseases.

Among them, 2-amino-2-[2-(4-octylphenyl)ethyl]propane-1,3-diol hydrochloride (hereinafter sometimes to be also referred to as FTY720) is a compound commercially available as a therapeutic drug for multiple sclerosis. FTY720 is rapidly converted to phosphorylated FTY720 [hereinafter sometimes to be also referred to as FTY720-P, for example, 2-amino-2-phosphonooxymethyl-4-(4-octylphenyl)butanol] in vivo by sphingosine kinase. FTY720-P acts as an agonist of 4 kinds of S1P receptors (other than S1P2) out of 5 kinds of sphingosine-1-phosphate (hereinafter to be sometimes referred to as S1P) receptors (hereinafter to be sometimes referred to as S1P1-5, respectively) (non-patent document 1).

Recently, it has been suggested that S1P1 in S1P receptors is essential for the emigration of mature lymphocytes from thymus and secondary lymphoid tissues. FTY720-P acts as an S1P1 agonist to down-regulate S1P1 on lymphocytes. As a result, the emigration of mature lymphocytes from thymus and secondary lymphoid tissues is inhibited and circulating mature lymphocytes in blood are sequestered in the secondary lymphoid tissues, whereby the immunosuppressive action is exhibited (non-patent document 2).

On the other hand, conventional amino alcohol compounds are feared to show expression of a transient decrease in the heart rate as side effects, and to solve this problem, a number of novel compounds obtained by modifying the chemical structures of amino alcohol compounds have been reported. Among them, patent document 4 discloses an aminopropanol compound wherein the benzene ring contained in FTY720 is a bicyclic structure. In addition, patent document 5 discloses a biphenylether compound, and patent document 6 discloses a biphenylsulfide compound. However, none of the patent documents 4-6 disclose a derivative having a tricyclic structure, nor do they describe that the decrease in the heart rate was alleviated. While patent document 7 discloses that a compound wherein the substituent on the benzene ring contained in FTY720 is a trihaloalkyl group or a cyano group shows a weak heart rate-decreasing action, it does not disclose a derivative having a tricyclic structure.

DOCUMENT LIST

Patent Documents patent document 1: WO 94/08943
patent document 2: WO 96/06068
patent document 3: WO 98/45249
patent document 4: WO 2004/096757
patent document 5: WO 03/029184
patent document 6: WO 03/029205
patent document 7: WO 2007/069712

Non-Patent Documents non-patent document 1: Science, 2002, No. 296, pages 346-349
non-patent document 2: Nature, 2004, No. 427, pages 355-360

SUMMARY OF THE INVENTION

Problems to be Solved by the Invention

An object of the present invention is to provide a novel amine compound superior in the immunosuppressive action, rejection suppressive action and the like, which shows reduced side effects such as a decrease in the heart rate and the like.

Means of Solving the Problems

The present inventors have conducted further studies in view of the above-mentioned situation and found that an amine compound having the below-mentioned particular structural formula can achieve the object, which resulted in the completion of the present invention. Accordingly, the gist of the present invention is as follows.

(1) An amine compound represented by the following formula (I)

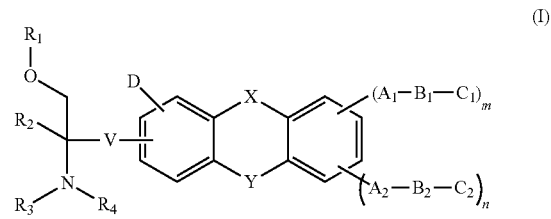

wherein
$R_1$ is a hydrogen atom or $P(=O)(OH)_2$,
V is alkylene having 1-4 carbon atoms or alkenylene having 2-4 carbon atoms,
$R_2$ is a hydrogen atom, or alkyl having 1-4 carbon atoms and optionally substituted by a hydroxy group or a halogen atom,
$R_3$ and $R_4$ are the same or different and each is a hydrogen atom or alkyl having 1-4 carbon atoms,
X and Y are the same or different and each is a single bond, an oxygen atom, a sulfur atom, methylene, —CO—, —SO—, —SO$_2$— or —NR$_5$— (wherein R$_5$ is a hydrogen atom or alkyl having 1-4 carbon atoms and optionally having substituent(s)),
$A_1$ and $A_2$ are the same or different and each is a single bond, an oxygen atom, a sulfur atom, —CO—, —SO—, —SO$_2$— or —NR$_6$— (wherein R$_6$ is a hydrogen atom, alkyl having 1-6 carbon atoms and optionally having substituent(s), acyl having 1-7 carbon atoms and optionally having substituent(s) or alkoxycarbonyl having 2-7 carbon atoms), B$_1$ and B$_2$ are the same or different and each is a single bond, alkylene having 1-10 carbon atoms and optionally having substituent(s), alkenylene having 2-10 carbon atoms and optionally having substituent(s) or alkynylene having 2-10 carbon atoms and optionally having substituent(s), C$_1$ and C$_2$ are the same or different and each is a hydrogen atom, a halogen atom, aryl having 6-10 carbon atoms and optionally having substituent(s), heteroaryl optionally having substituent(s) and having 5 to 10 ring-constituting atoms, which contains 1 or 2 nitrogen atoms, 1 or 2 oxygen atoms or 1 or 2 sulfur atoms as the ring-constituting atom(s), cycloalkyl having 3-7 carbon atoms and optionally having substituent(s), which is optionally fused with benzene optionally having substituent(s), or heterocycloalkyl optionally having substituent(s) and having 5 to 7 ring-constituting atoms, which contains 1 or 2 nitrogen atoms or 1 or 2 oxygen atoms as the ring-constituting atoms, and is optionally fused with benzene optionally having substituent(s), D is a hydrogen atom, a halogen atom or alkyl having 1-4 carbon atoms and optionally having substituent(s), m is 0 or 1, and n is 0 or 1, or a pharmaceutically acceptable acid addition salt thereof.

(2) The compound of the above-mentioned (1), wherein R$_3$ and R$_4$ are both hydrogen atoms, or a pharmaceutically acceptable acid addition salt thereof.

(3) The compound of the above-mentioned (1) or (2), wherein n is 0, or a pharmaceutically acceptable acid addition salt thereof.

(4) The compound of any one of the above-mentioned (1)-(3), wherein V is CH$_2$CH$_2$, or a pharmaceutically acceptable acid addition salt thereof.

(5) The compound of any one of the above-mentioned (1)-(4), wherein C$_1$ is a hydrogen atom, aryl having 6-10 carbon atoms and optionally having substituent(s) or heteroaryl optionally having substituent(s) and having 5 to 10 ring-constituting atoms, which contains 1 or 2 nitrogen atoms, 1 or 2 oxygen atoms or 1 or 2 sulfur atoms as the ring-constituting atom(s), or a pharmaceutically acceptable acid addition salt thereof.

(6) The compound of any one of the above-mentioned (1)-(5), wherein Y is C=O, or a pharmaceutically acceptable acid addition salt thereof.

(7) The compound of any one of the above-mentioned (1)-(6), wherein A$_1$ is a single bond, an oxygen atom, a sulfur atom or —CO—, or a pharmaceutically acceptable acid addition salt thereof.

(8) The compound of any one of the above-mentioned (1)-(7), wherein R$_2$ is hydroxymethyl, or a pharmaceutically acceptable acid addition salt thereof.

(9) The compound of any one of the above-mentioned (1)-(8), wherein R$_1$ is a hydrogen atom, or a pharmaceutically acceptable acid addition salt thereof.

(10) The compound of the above-mentioned (1), wherein

R$_1$ is a hydrogen atom,

V is —CH$_2$CH$_2$— or —CH$_2$CH$_2$CH$_2$—,

R$_2$ is a hydrogen atom, methyl, ethyl, hydroxymethyl, hydroxyethyl, fluoromethyl, fluoroethyl, 2,2-difluoroethyl or 2,2,2-trifluoroethyl, R$_3$ and R$_4$ are the same or different and each is a hydrogen atom, methyl or ethyl, X is a single bond, an oxygen atom, a sulfur atom, methylene or —CO—, Y is an oxygen atom, a sulfur atom, methylene or —CO—, A$_1$ is a single bond, an oxygen atom, a sulfur atom or —CO—, A$_2$ is a single bond or an oxygen atom, B$_1$ is a single bond, methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, 2-methylpropane-1,3-diyl, 2-ethoxyethylene, difluoromethylene, 5,5-difluoropentane-1,5-diyl, 4,4,5,5-tetrafluoropentane-1,5-diyl, 5,5,6,6-tetrafluorohexane-1,6-diyl, 6,6-difluorohexane-1,6-diyl, ethene-1,2-diyl, propene-1,3-diyl, butene-1,4-diyl, pentene-1,5-diyl, hexene-1,6-diyl, heptene-1,7-diyl, 4,4,5,5-tetrafluoropentene-1,5-diyl or 5,5-difluorohexene-1,6-diyl, B$_2$ is a single bond or alkylene having 1-10 carbon atoms and optionally having substituent(s), C$_1$ is a hydrogen atom, a fluorine atom, phenyl, methylphenyl, ethylphenyl, (trifluoromethyl)phenyl, di(trifluoromethyl)phenyl, methoxyphenyl, isopropoxyphenyl, (trifluoromethoxy)phenyl, fluorophenyl, fluoro(methoxy)phenyl, fluoro(trifluoromethyl)phenyl, chlorophenyl, dichlorophenyl, chloro(methyl)phenyl, chloro(fluoro)phenyl, chloro(methoxy)phenyl, chloro(trifluoromethyl)phenyl, dimethylaminomethylphenyl, acetylphenyl, (methylthio)phenyl, cyanophenyl, cyano(fluoro)phenyl, methylthienyl, chlorothienyl or cyclopropyl, C$_2$ is a hydrogen atom, phenyl, methylphenyl or (trifluoromethyl)phenyl, D is a hydrogen atom, a halogen atom or methyl optionally substituted by a halogen atom, m is 1, and n is 0, or a pharmaceutically acceptable acid addition salt thereof.

(11) The compound of the above-mentioned (1), wherein

R$_1$ is a hydrogen atom,

V is —CH$_2$CH$_2$—,

R$_2$ is a hydrogen atom, methyl or hydroxymethyl,

R$_3$ and R$_4$ are both hydrogen atoms,

X is an oxygen atom or a sulfur atom,

Y is methylene or —CO—,

A$_1$ is a single bond, an oxygen atom or a sulfur atom,

A$_2$ is an oxygen atom,

B$_1$ is a single bond, methylene, ethylene, propane-1,3-diyl, butane-1,4-diyl, pentane-1,5-diyl, hexane-1,6-diyl, octane-1,8-diyl, 4,4,5,5-tetrafluoropentane-1,5-diyl, ethene-1,2-diyl or (E)-propene-1,3-diyl wherein A$_1$ and C$_1$ in the formula (I) are bonded to form A$_1$-CH=CH—CH$_2$—C$_1$ or (E)-hexene-1,6-diyl wherein A$_1$ and C$_1$ are bonded to form A$_1$-CH=CH—(CH$_2$)$_4$—C$_1$, B$_2$ is a single bond, C$_1$ is a hydrogen atom, a fluorine atom, (trifluoromethyl)phenyl, methoxyphenyl, (trifluoromethoxy)phenyl, chlorophenyl or chloro(fluoro)phenyl, C$_2$ is a hydrogen atom or methylphenyl, D is a hydrogen atom, m is 1, and n is 0, or a pharmaceutically acceptable acid addition salt thereof.

(12) The compound of the above-mentioned (1), wherein R$_1$ is a hydrogen atom,

V is —CH$_2$CH$_2$—,

R$_2$ is hydroxymethyl,

R$_3$ and R$_4$ are both hydrogen atoms,

X is an oxygen atom or a sulfur atom,

Y is —CO—,

A₁ is a single bond, an oxygen atom or a sulfur atom,
A₂ is an oxygen atom,
B₁ is a single bond, pentane-1,5-diyl, hexane-1,6-diyl or (E)-propene-1,3-diyl wherein A₁ and C₁ in the formula (I) are bonded to form A₁-CH=CH—CH₂—C₁,
B₂ is a single bond,
C₁ is a hydrogen atom, a fluorine atom, (trifluoromethyl) phenyl, methoxyphenyl, (trifluoromethoxy)phenyl, chlorophenyl or chloro(fluoro)phenyl,
C₂ is methylphenyl,
D is a hydrogen atom,
m is 1, and
n is 0,
or a pharmaceutically acceptable acid addition salt thereof.
(13) The compound of any one of the above-mentioned (1)-(8), wherein the compound of the formula (I) is any of the following a to hh, or a pharmaceutically acceptable acid addition salt thereof:
a. 2-[3-amino-4-hydroxy-3-(hydroxymethyl)butyl]-6-[3-(trifluoromethyl)phenoxy]-9H-thioxanthen-9-one,
b. 2-[3-amino-4-hydroxy-3-(hydroxymethyl)butyl]-6-(4-chlorophenoxy)-9H-thioxanthen-9-one,
c. 2-[3-amino-4-hydroxy-3-(hydroxymethyl)butyl]-7-[3-(trifluoromethyl)phenoxy]-9H-thioxanthen-9-one,
d. 2-[3-amino-4-hydroxy-3-(hydroxymethyl)butyl]-7-(3-chlorophenoxy)-9H-thioxanthen-9-one,
e. 2-[3-amino-4-hydroxy-3-(hydroxymethyl)butyl]-6-(4-fluorophenoxy)-9H-xanthen-9-one,
f. 2-[3-amino-4-hydroxy-3-(hydroxymethyl)butyl]-6-(4-methoxyphenoxy)-9H-xanthen-9-one,
g. 6-[3-amino-4-hydroxy-3-(hydroxymethyl)butyl]-2-[3-(trifluoromethyl)phenoxy]-9H-xanthen-9-one,
h. 3-[3-amino-4-hydroxy-3-(hydroxymethyl)butyl]-6-hexyloxy-9H-thioxanthen-9-one,
i. 6-[3-amino-4-hydroxy-3-(hydroxymethyl)butyl]-2-[(1E)-hex-1-en-1-yl]-9H-xanthen-9-one,
j. 3-[3-amino-4-hydroxy-3-(hydroxymethyl)butyl]-6-(4-methoxyphenoxy)-9H-xanthen-9-one,
k. 2-[3-amino-4-hydroxy-3-(hydroxymethyl)butyl]-7-pentyloxy-9H-xanthen-9-one,
l. 2-[3-amino-4-hydroxy-3-(hydroxymethyl)butyl]-7-hexyloxy-9H-xanthen-9-one,
m. 2-[3-amino-4-hydroxy-3-(hydroxymethyl)butyl]-6-(3-chloro-4-fluorophenoxy)-9H-xanthen-9-one,
n. 2-[3-amino-4-hydroxy-3-(hydroxymethyl)butyl]-6-[3-(trifluoromethyl)phenyl]-9H-xanthen-9-one,
o. 3-[3-amino-4-hydroxy-3-(hydroxymethyl)butyl]-6-pentyloxy-9H-xanthen-9-one,
p. 2-[3-amino-4-hydroxy-3-(hydroxymethyl)butyl]-6-[3-(trifluoromethoxy)phenyl]-9H-xanthen-9-one,
q. 6-[3-amino-4-hydroxy-3-(hydroxymethyl)butyl]-2-(3-chloro-4-fluorophenoxy)-9H-xanthen-9-one,
r. mono(2-amino-2-hydroxymethyl-4-{9-oxo-6-[3-(trifluoromethyl)phenoxy]-9H-thioxanthen-2-yl}butyl)phosphate,
s. mono{2-amino-4-[6-(4-chlorophenoxy)-9-oxo-9H-thioxanthen-2-yl]-2-hydroxymethylbutyl}phosphate,
t. mono(2-amino-2-hydroxymethyl-4-{9-oxo-7-[3-(trifluoromethyl)phenoxy]-9H-thioxanthen-2-yl}butyl)phosphate,
u. mono{2-amino-4-[7-(3-chlorophenoxy)-9-oxo-9H-thioxanthen-2-yl]-2-hydroxymethylbutyl}phosphate,
v. mono{2-amino-4-[6-(4-fluorophenoxy)-9-oxo-9H-xanthen-2-yl]-2-hydroxymethylbutyl}phosphate,
w. mono{2-amino-2-hydroxymethyl-4-[6-(4-methoxyphenoxy)-9-oxo-9H-xanthen-2-yl]butyl}phosphate,
x. mono(2-amino-2-hydroxymethyl-4-{9-oxo-7-[3-(trifluoromethyl)phenoxy]-9H-xanthen-3-yl}butyl)phosphate,
y. mono[2-amino-4-(6-hexyloxy-9-oxo-9H-thioxanthen-3-yl)-2-(hydroxymethyl)butyl]phosphate,
z. mono(2-amino-4-{7-[(1E)-hex-1-en-1-yl]-9-oxo-9H-xanthen-3-yl}-2-(hydroxymethyl)butyl)phosphate,
aa. mono{2-amino-2-hydroxymethyl-4-[6-(4-methoxyphenoxy)-9-oxo-9H-xanthen-3-yl]butyl}phosphate,
bb. mono[2-amino-2-hydroxymethyl-4-(9-oxo-7-pentyloxy-9H-xanthen-2-yl)butyl]phosphate,
cc. mono[2-amino-4-(7-hexyloxy-9-oxo-9H-xanthen-2-yl)-2-hydroxymethylbutyl]phosphate,
dd. mono{2-amino-4-[6-(3-chloro-4-fluorophenoxy)-9-oxo-9H-xanthen-2-yl]-2-hydroxymethylbutyl}phosphate,
ee. mono{2-amino-2-hydroxymethyl-4-[9-oxo-6-[3-(trifluoromethyl)phenyl]-9H-xanthen-2-yl]butyl}phosphate,
ff. mono[2-amino-2-hydroxymethyl-4-(9-oxo-6-pentyloxy-9H-xanthen-3-yl)butyl]phosphate,
gg. mono(2-amino-2-hydroxymethyl-4-{9-oxo-6-[3-(trifluoromethoxy)phenyl]-9H-xanthen-2-yl}butyl)phosphate and
hh. mono{2-amino-4-[7-(3-chloro-4-fluorophenoxy)-9-oxo-9H-xanthen-3-yl]-2-(hydroxymethyl)butyl}phosphate.
(14) A pharmaceutical composition comprising the compound of any one of the above-mentioned (1) to (13) and a pharmaceutically acceptable carrier.
(15) The pharmaceutical composition of the above-mentioned (14), which is used for the treatment or prophylaxis of an autoimmune disease; prophylaxis or suppression of resistance or acute rejection or chronic rejection of transplantation of organ or tissue; treatment or prophylaxis of a graft-versus-host (GvH) disease due to bone marrow transplantation; or prophylaxis or treatment of an allergic disease.
(16) The pharmaceutical composition of the above-mentioned (15), wherein the autoimmune disease is rheumatoid arthritis, multiple sclerosis, encephalomyelitis, systemic lupus erythematosus, lupus nephritis, nephrotic syndrome, psoriasis or Type I diabetes mellitus.
(17) The pharmaceutical composition of the above-mentioned (15), wherein the allergic disease is atopic dermatitis, allergic rhinitis or asthma.

Effect of the Invention

According to the present invention, a novel compound showing a superior peripheral blood lymphocyte decreasing action, and reduced side effects such as a decrease in the heart rate and the like can be provided.

DESCRIPTION OF EMBODIMENTS

The present invention is explained in detail in the following.

The compound of the present invention is an amine compound represented by the following formula (I)

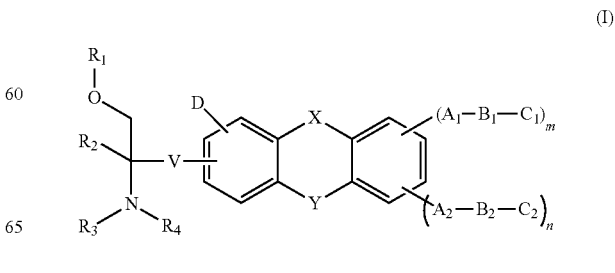

wherein $R_1$ is a hydrogen atom or $P(=O)(OH)_2$,

V is alkylene having 1-4 carbon atoms or alkenylene having 2-4 carbon atoms, $R_2$ is a hydrogen atom, or alkyl having 1-4 carbon atoms and optionally substituted by a hydroxy group or a halogen atom, $R_3$ and $R_4$ are the same or different and each is a hydrogen atom or alkyl having 1-4 carbon atoms, X and Y are the same or different and each is a single bond, an oxygen atom, a sulfur atom, methylene, —CO—, —SO—, —SO$_2$— or —NR$_5$— (wherein $R_5$ is a hydrogen atom or alkyl having 1-4 carbon atoms and optionally having substituent(s)), $A_1$ and $A_2$ are the same or different and each is a single bond, an oxygen atom, a sulfur atom, —CO—, —SO—, —SO$_2$— or —NR$_6$— (wherein $R_6$ is a hydrogen atom, alkyl having 1-6 carbon atoms and optionally having substituent(s), acyl having 1-7 carbon atoms and optionally having substituent(s) or alkoxycarbonyl having 2-7 carbon atoms), $B_1$ and $B_2$ are the same or different and each is a single bond, alkylene having 1-10 carbon atoms and optionally having substituent(s), alkenylene having 2-10 carbon atoms and optionally having substituent(s) or alkynylene having 2-10 carbon atoms and optionally having substituent(s), $C_1$ and $C_2$ are the same or different and each is a hydrogen atom, a halogen atom, aryl having 6-10 carbon atoms and optionally having substituent(s), heteroaryl optionally having substituent(s) and having 5 to 10 ring-constituting atoms, which contains 1 or 2 nitrogen atoms, 1 or 2 oxygen atoms or 1 or 2 sulfur atoms as the ring-constituting atom(s), cycloalkyl having 3-7 carbon atoms and optionally having substituent(s), which is optionally fused with benzene optionally having substituent(s), or heterocycloalkyl optionally having substituent(s) and having 5 to 7 ring-constituting atoms, which contains 1 or 2 nitrogen atoms or 1 or 2 oxygen atoms as the ring-constituting atoms, and is optionally fused with benzene optionally having substituent(s), D is a hydrogen atom, a halogen atom or alkyl having 1-4 carbon atoms and optionally having substituent(s), m is 0 or 1, and n is 0 or 1, (sometimes to be abbreviated as "compound (I)" in the present specification) or a pharmaceutically acceptable acid addition salt thereof.

In the present specification, "alkylene having 1-4 carbon atoms" means straight chain or branched chain alkylene having 1-4 carbon atoms. Examples thereof include methylene, ethylene, propane-1,3-diyl, butane-1,4-diyl, methylethylene and the like, and straight chain alkylene is preferable.

In the present specification, "alkylene having 2-4 carbon atoms" means straight chain or branched chain alkylene having 2-4 carbon atoms. Examples thereof include ethene-1,2-diyl, propene-1,3-diyl, butene-1,4-diyl and the like.

In the present specification, the "halogen atom" is a fluorine atom, a chlorine atom, a bromine atom, or an iodine atom, and preferable examples include a fluorine atom, a chlorine atom and a bromine atom.

In the present specification, alkyl having 1-4 carbon atoms means straight chain or branched chain alkyl having 1-4 carbon atoms. Examples thereof include methyl, ethyl, n-propyl, isopropyl, n-butyl, isobutyl, secondary butyl, tertiary butyl (hereinafter "tertiary" is sometimes indicated as t- or tert-) and the like.

In the present specification, "alkyl having 1-4 carbon atoms" which is substituted by a halogen atom means the aforementioned alkyl having 1-4 carbon atoms, which is substituted by 1-5 halogen atoms. Examples thereof include fluoromethyl, difluoromethyl, trifluoromethyl, fluoroethyl, difluoroethyl, trifluoroethyl, pentafluoroethyl, fluoro n-propyl, trifluoro n-propyl, pentafluoro n-propyl, fluoroisopropyl, difluoroisopropyl, fluoro n-butyl, trifluoro n-butyl, pentafluoro n-butyl and the like, as well as one wherein the fluorine atom as a substituent recited here is partly or entirely substituted by other halogen atom, and the like.

In the present specification, "alkyl having 1-4 carbon atoms" which is substituted by a hydroxy group means the aforementioned alkyl having 1-4 carbon atoms, which is substituted by a hydroxy group. Examples thereof include hydroxymethyl, 1-hydroxyethyl, 2-hydroxyethyl, dihydroxyethyl, 1-hydroxy n-propyl, 2-hydroxy n-propyl, 3-hydroxy n-propyl, hydroxylisopropyl, dihydroxyisopropyl, hydroxybutyl, dihydroxybutyl and the like.

In the present specification, "alkyl having 1-6 carbon atoms" means straight chain or branched chain alkyl having 1-6 carbon atoms. Examples thereof include methyl, ethyl, n-propyl, isopropyl, n-butyl, isobutyl, secondary butyl, tertiary butyl, n-pentyl, isopentyl, neopentyl, n-hexyl, isohexyl, neohexyl and the like.

In the present specification, "acyl having 1-7 carbon atoms" means alkanoyl or aroyl having 1-7 carbon atoms and alkanoyl is straight chain or branched chain alkanoyl having 1-7 carbon atoms. Examples thereof include formyl, acetyl, propionyl, butyryl, isobutyryl, pentanoyl, hexanoyl, heptanoyl and the like. Examples of aroyl include benzoyl and the like.

In the present specification, "alkoxycarbonyl having 2-7 carbon atoms" is straight chain or branched chain alkoxy having 1-6 carbon atoms to which carbonyl is bonded. Examples thereof include methoxycarbonyl, ethoxycarbonyl, propoxycarbonyl, isopropoxycarbonyl, n-butoxycarbonyl, isobutoxycarbonyl, t-butoxycarbonyl, n-pentyloxycarbonyl, isopentyloxycarbonyl, tertiary pentyloxycarbonyl, hexyloxycarbonyl and the like.

In the present specification, "alkylene having 1-10 carbon atoms" means straight chain or branched chain alkylene having 1-10 carbon atoms, or cyclic alkylene having 3-10 carbon atoms. Examples of the straight chain or branched chain alkylene having 1-10 carbon atoms include methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, and methylethylene, and examples of the cyclic alkylene having 3-10 carbon atoms include cyclopropane-1,2-diyl and the like.

In the present specification, "alkenylene having 2-10 carbon atoms" means straight chain or branched chain alkenylene having 2-10 carbon atoms. Examples thereof include ethene-1,2-diyl, propene-diyl such as propene-1,3-diyl and the like, butene-diyl such as butene-1,4-diyl and the like, pentene-diyl such as pentene-1,5-diyl and the like, hexene-diyl such as hexene-1,6-diyl and the like, hexene-diyl such as heptene-1,7-diyl and the like, octene-diyl such as octene-1,8-diyl and the like, nonene-diyl such as nonene-1,9-diyl and the like, and decene-diyl such as decene-1,10-diyl and the like.

In the present specification, "alkynylene having 2-10 carbon atoms" means straight chain or branched chain alkynylene having 2-10 carbon atoms. Examples thereof include ethyne-1,2-diyl, propyne-1,3-diyl, butyne-diyl such as butyne-1,4-diyl and the like, pentyne-diyl such as pentyne-1,5-diyl and the like, hexyne-1,6-diyl, heptyne-diyl such as heptyne-1,7-diyl and the like, octyne-diyl such as octyne-1,8-diyl and the like, nonyne-diyl such as nonyne-1,9-diyl and the like, and decyne-diyl such as decyne-1,10-diyl and the like.

In the present specification, examples of "aryl having 6-10 carbon atoms" include phenyl, 1-naphthyl, 2-naphthyl and the like.

In the present specification, examples of "heteroaryl having 5 to 10 ring-constituting atoms, which contains 1 or 2 nitrogen atoms, 1 or 2 oxygen atoms or 1 or 2 sulfur atoms as the ring-constituting atom(s)" include pyrrolyl, imidazolyl, pyrazolyl, pyridyl, pyridazinyl, pyrimidinyl, pyrazinyl, furyl, thienyl, oxazolyl, isoxazolyl, thiazolyl, isothiazolyl, indolyl, isoindolyl, indolizinyl, indazolyl, benzofuryl, benzothienyl, quinolyl, isoquinolyl and the like.

In the present specification, examples of "cycloalkyl having 3-7 carbon atoms" include cyclopropyl, cyclobutyl, cyclopentyl, cyclohexyl and the like.

In the present specification, examples of "cycloalkyl having 3-7 carbon atoms and optionally fused with benzene" include 1,2,3,4-tetrahydronaphthyl, indanyl, 6,7,8,9-tetrahydro-5H-benzocycloheptyl and the like.

In the present specification, examples of "heterocycloalkyl having 5 to 7 ring-constituting atoms, which contains 1 or 2 nitrogen atoms or 1 or 2 oxygen atoms as the ring-constituting atoms" include piperidyl, piperazinyl, morpholinyl, tetrahydrofuryl, tetrahydropyranyl and the like.

In the present specification, examples of "heterocycloalkyl having 5 to 7 ring-constituting atoms, which contains 1 or 2 nitrogen atoms or 1 or 2 oxygen atoms as the ring-constituting atoms, and is optionally fused with benzene" include piperidyl, piperazinyl, morpholinyl, tetrahydrofuryl, tetrahydropyranyl, indolyl, chromanyl, 1,2,3,4-tetrahydroquinolyl and the like.

In the present specification, the "substituent" in "optionally having substituent(s)" may be present at any substitutable position(s) in any substitutable number, wherein the number is preferably 1-5, more preferably 1-3.

Specific examples of the "substituent" include alkyl having 1-10 carbon atoms and optionally substituted by a halogen atom, alkenyl having 2-10 carbon atoms, alkynyl having 2-10 carbon atoms, alkylidene having 1-10 carbon atoms, a cyclic group, oxo, a hydroxy group, alkyloxy having 1-10 carbon atoms and optionally substituted by a halogen atom, alkenyloxy having 2-10 carbon atoms, alkynyloxy having 2-10 carbon atoms, alkylthio having 1-10 carbon atoms and optionally substituted by a halogen atom, alkenylthio having 2-10 carbon atoms, alkynylthio having 2-10 carbon atoms, alkylsulfinyl having 1-10 carbon atoms, alkenylsulfinyl having 2-10 carbon atoms, alkynylsulfinyl having 2-10 carbon atoms, alkylsulfonyl having 1-10 carbon atoms, alkenylsulfonyl having 2-20 carbon atoms, alkynylsulfonyl having 2-10 carbon atoms, carboxy, alkyloxycarbonyl having 1-10 carbon atoms, acyl having 1-11 carbon atoms, alkyleneoxy having 1-10 carbon atoms, alkylenedioxy having 1-10 carbon atoms, cyano, nitro, amino, a halogen atom and the like.

In the present specification, "alkyl having 1-10 carbon atoms" means straight chain or branched chain alkyl having 1-10 carbon atoms. Examples thereof include methyl, ethyl, n-propyl, n-butyl, n-pentyl, n-hexyl, heptyl, octyl, nonyl, decyl and the like.

In the present specification, "alkenyl having 2-10 carbon atoms" means straight chain or branched chain alkenyl having 2-10 carbon atoms. Examples thereof include ethenyl, propenyl, butenyl, pentenyl, hexenyl, heptenyl, octenyl, nonenyl, decenyl and the like.

In the present specification, "alkynyl having 2-10 carbon atoms" means straight chain or branched chain alkynyl having 2-10 carbon atoms. Examples thereof include ethynyl, propynyl, butynyl, pentynyl, hexynyl, heptynyl, octynyl, nonynyl, decynyl and the like.

In the present specification, "alkylidene having 1-10 carbon atoms" means straight chain or branched chain alkylidene having 1-10 carbon atoms. Examples thereof include methylidene, ethylidene, n-propylidene, n-butylidene, n-pentylidene, isopentylidene, neopentylidene, n-hexylidene, heptylidene, octylidene, nonylidene, decylidene and the like.

In the present specification, "cyclic group" means "carbocyclic group" or "heterocyclic group". Examples thereof include aryl having 6-10 carbon atoms mentioned above, cycloalkyl having 3-7 carbon atoms mentioned above, heteroaryl having 5 to 10 ring-constituting atoms, which contains 1 or 2 nitrogen atoms, 1 or 2 oxygen atoms or 1 or 2 sulfur atoms as the ring-constituting atom(s), mentioned above, and heterocycloalkyl having 5 to 7 ring-constituting atoms, which contains 1 or 2 nitrogen atoms or 1 or 2 oxygen atoms as the ring-constituting atoms, mentioned above.

In the present specification, "alkyloxy having 1-10 carbon atoms" means straight chain or branched chain alkoxy having 1-10 carbon atoms. Examples thereof include methoxy, ethoxy, n-propoxy, isopropoxy, n-butoxy, pentyloxy, hexyloxy, heptyloxy, octyloxy, nonyloxy, decyloxy and the like.

In the present specification, "alkyloxy-carbonyl having 1-10 carbon atoms" means the aforementioned "alkyloxy having 1-10 carbon atoms" which is bonded to carbonyl. Examples thereof include methoxycarbonyl, ethoxycarbonyl, n-propoxycarbonyl, isopropoxycarbonyl, n-butoxycarbonyl, pentyloxycarbonyl, hexyloxycarbonyl, heptyloxycarbonyl, octyloxycarbonyl, nonyloxycarbonyl, decyloxycarbonyl and the like.

In the present specification, "alkenyloxy having 2-10 carbon atoms" means straight chain or branched chain alkenyloxy having 2-10 carbon atoms. Examples thereof include ethenyloxy, n-propenyloxy, n-butenyloxy, pentenyloxy, hexenyloxy, heptenyloxy, octenyloxy, nonenyloxy, decenyloxy and the like.

In the present specification, "alkynyloxy having 2-10 carbon atoms" means straight chain or branched chain alkynyloxy having 2-10 carbon atoms. Examples thereof include ethynyloxy, n-propynyloxy, n-butynyloxy, pentynyloxy, hexynyloxy, heptynyloxy, octynyloxy, nonynyloxy, decynyloxy and the like.

In the present specification, "alkylthio having 1-10 carbon atoms", "alkylsulfinyl having 1-10 carbon atoms", and "alkylsulfonyl having 1-10 carbon atoms" each have an alkyl moiety composed of alkyl having 1-10 carbon atoms mentioned above. Examples thereof include methylthio, ethylthio, propylthio, pentylthio, decylthio, methanesulfinyl, decylsulfinyl, methanesulfonyl, decylsulfonyl and the like.

In the present specification, "alkenylthio having 2-10 carbon atoms", "alkenylsulfinyl having 2-10 carbon atoms", and "alkenylsulfonyl having 2-10 carbon atoms" each have an alkenyl moiety composed of alkenyl having 2-10 carbon atoms mentioned above. Examples thereof include ethenylthio, propenylthio, pentenylthio, decenylthio, ethenylsulfinyl, decenylsulfinyl, ethenylsulfonyl, decenylsulfonyl and the like.

In the present specification, "alkynylthio having 2-10 carbon atoms", "alkynylsulfinyl having 2-10 carbon atoms", and "alkynylsulfonyl having 2-10 carbon atoms" each have an alkynyl moiety composed of alkynyl having 2-10 carbon atoms mentioned above. Examples thereof include ethynylthio, propynylthio, pentynylthio, decynylthio, ethynylsulfinyl, decynylsulfinyl, ethynylsulfonyl, decynylsulfonyl and the like.

In the present specification, "acyl having 1-11 carbon atoms" means straight chain or branched chain alkanoyl having 1-10 carbon atoms and aroyl having 7-11 carbon atoms. Specific examples include formyl, acetyl, propionyl, butyryl, pentanoyl, hexanoyl, heptanoyl, octanoyl, nonanoyl, decanoyl and the like. As aroyl, benzoyl, naphthoyl and the like can be mentioned.

In the present specification, "alkyleneoxy having 1-10 carbon atoms" means straight chain or branched chain alkyleneoxy having 1-10 carbon atoms. Examples thereof include methyleneoxy, ethyleneoxy, trimethyleneoxy ($-(CH_2)_3-O-$), tetramethyleneoxy ($-(CH_2)_4-O-$), pentamethyleneoxy ($-(CH_2)_5-O-$), hexamethyleneoxy ($-(CH_2)_6-O-$), heptamethyleneoxy ($-(CH_2)_7-O-$), octamethyleneoxy ($-(CH_2)_8-O-$), nonamethyleneoxy ($-(CH_2)_9-O-$), and decamethyleneoxy ($-(CH_2)_{10}-O-$).

In the present specification, "alkylenedioxy having 1-10 carbon atoms" means straight chain or branched chain alkylene having 1-10 carbon atoms. Examples thereof include methylenedioxy, ethylenedioxy, trimethylenedioxy ($-O-(CH_2)_3-O-$), tetramethylenedioxy ($-O-(CH_2)_4-O-$), pentamethylenedioxy ($-O-(CH_2)_5-O-$), hexamethylenedioxy ($-O-(CH_2)_6-O-$), heptamethylenedioxy ($-O-(CH_2)_7-O-$), octamethylenedioxy ($-O-(CH_2)_8-O-$), nonamethylenedioxy ($-O-(CH_2)_9-O-$), and decamethylenedioxy ($-O-(CH_2)_{10}-O-$).

Preferable example of $R_1$ in the above-mentioned formula (I) is a hydrogen atom.

Preferable examples of V in the above-mentioned formula (I) include $-CH_2CH_2-$ and $-CH_2CH_2CH_2-$, and a more preferable example thereof is $-CH_2CH_2-$.

Preferable examples of $R_2$ in the above-mentioned formula (I) include a hydrogen atom, methyl, ethyl, hydroxymethyl, hydroxyethyl, fluoromethyl, fluoroethyl, 2,2-difluoroethyl and 2,2,2-trifluoroethyl, and more preferable examples include a hydrogen atom, methyl, ethyl and hydroxymethyl. Further preferable examples include a hydrogen atom, methyl and hydroxymethyl, and a still more preferable example is hydroxymethyl.

Preferable examples of $R_3$ and $R_4$ in the above-mentioned formula (I) include a hydrogen atom, methyl and ethyl, which may be the same or different, and a more preferable example is a hydrogen atom.

Preferable examples of X in the above-mentioned formula (I) include a single bond, an oxygen atom, a sulfur atom, methylene, and $-CO-$. More preferable examples include an oxygen atom and a sulfur atom.

Preferable examples of Y in the above-mentioned formula (I) include an oxygen atom, a sulfur atom, methylene, and $-CO-$. More preferable examples include methylene and $-CO-$, and a still more preferable example is $-CO-$.

Preferable examples of $A_1$ in the above-mentioned formula (I) include a single bond, an oxygen atom, a sulfur atom, and $-CO-$, and more preferable examples include a single bond, an oxygen atom, and a sulfur atom.

Preferable examples of $B_1$ in the above-mentioned formula (I) include a single bond, alkylene having 1-10 carbon atoms and optionally having substituent(s), and alkenylene having 2-10 carbon atoms and optionally having substituent(s). More preferable examples include a single bond, alkyloxy having 1-6 carbon atoms or alkylene having 1-9 carbon atoms and optionally substituted by a halogen atom, and alkenylene having 2-9 carbon atoms. Specific preferable examples include a single bond, methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, 2-methylpropane-1,3-diyl (number showing the substitutable position is based on carbon bonded to $A_1$ as 1, hereinafter the same in this paragraph), 2-ethoxyethylene, difluoromethylene, 5,5-difluoropentane-1,5-diyl, 4,4,5,5-tetrafluoropentane-1,5-diyl, 5,5,6,6-tetrafluorohexane-1,6-diyl, 6,6-difluorohexane-1,6-diyl, ethene-1,2-diyl, propene-1,3-diyl, butene-1,4-diyl, pentene-1,5-diyl, hexene-1,6-diyl, heptene-1,7-diyl, 4,4,5,5-tetrafluoropentene-1,5-diyl, 5,5-difluorohexene-1,6-diyl. More preferable examples include a single bond, methylene, ethylene, propane-1,3-diyl, butane-1,4-diyl, pentane-1,5-diyl, hexane-1,6-diyl, octane-1,8-diyl, 4,4,5,5-tetrafluoropentane-1,5-diyl, ethene-1,2-diyl or (E)-propene-1,3-diyl wherein $A_1$ and $C_1$ in the formula (I) are bonded to form $A_1$-CH=CH-$CH_2$-$C_1$, and (E)-hexene-1,6-diyl wherein $A_1$ and $C_1$ in the formula (I) are bonded to form $A_1$-CH=CH-$(CH_2)_4$-$C_1$, and more preferable examples include a single bond, pentane-1,5-diyl, hexane-1,6-diyl, and (E)-hexene-1,6-diyl wherein $A_1$ and $C_1$ in the formula (I) are bonded to form $A_1$-CH=CH-$(CH_2)_4$-$C_1$.

Preferable examples of $C_1$ in the above-mentioned formula (I) include a hydrogen atom, a halogen atom, phenyl optionally having substituent(s), naphthyl optionally having substituent(s), thienyl optionally having substituent(s), benzothienyl optionally having substituent(s), and cyclohexyl optionally fused with benzene optionally having substituent(s). More preferable examples include a hydrogen atom, a halogen atom, phenyl optionally having substituent(s), thienyl optionally having substituent(s), and cycloalkyl having 3-7 carbon atoms, and a more preferable example is phenyl optionally having substituent(s).

When $C_1$ has substituent(s), preferable examples of the substituent include optionally substituted alkyl having 1-10 carbon atoms, optionally substituted cyclic group, optionally substituted alkyloxy having 1-10 carbon atoms, optionally substituted alkylthio having 1-10 carbon atoms, optionally substituted acyl having 1-11 carbon atoms, cyano, nitro, amino optionally mono- or di-substituted by alkyl having 1-10 carbon atoms, and a halogen atom. In addition, optionally substituted alkylene having 1-10 carbon atoms, optionally substituted alkyleneoxy having 1-10 carbon atoms, and optionally substituted alkylenedioxy having 1-10 carbon atoms may form a spiro ring or a fused ring. More preferable examples include alkyl having 1-3 carbon atoms and optionally substituted by a halogen atom, alkyloxy having 1-3 carbon atoms and optionally substituted by a halogen atom, alkylthio having 1-3 carbon atoms, acyl having 1-4 carbon atoms, cyano, amino optionally mono- or di-substituted by alkyl having 1-3 carbon atoms, and a halogen atom. Specific examples include methyl, ethyl, trifluoromethyl, cyclopropyl, phenyl, methoxy, trifluoromethoxy, isopropoxy, benzyloxy, methylthio, methanesulfinyl, methanesulfonyl, acetyl, cyano, nitro, dimethylamino, a fluorine atom, a chlorine atom, a bromine atom, propane-1,3-diyl, $-C(=O)-CH_2-CH_2-$, ethyleneoxy, methylenedioxy, and difluoromethylenedioxy, more preferable examples include methyl, ethyl, trifluoromethyl, methoxy, trifluoromethoxy, isopropoxy, a fluorine atom, and a chlorine atom, and still more preferable examples include trifluoromethyl, methoxy, trifluoromethoxy, a fluorine atom, and a chlorine atom.

More specific preferable examples of $C_1$ include a hydrogen atom, a fluorine atom, phenyl, methylphenyl, ethylphenyl, (trifluoromethyl)phenyl, di(trifluoromethyl)phenyl, methoxyphenyl, isopropoxyphenyl, (trifluoromethoxy)phenyl, fluorophenyl, fluoro(methoxy)phenyl, fluoro(trifluoromethyl)phenyl, chlorophenyl, dichlorophenyl, chloro(methyl)phenyl, chloro(fluoro)phenyl, chloro(methoxy)phenyl, chloro(trifluoromethyl)phenyl, dimethylaminomethylphenyl, acetylphenyl, (methylthio)phenyl, cyanophenyl, cyano(fluoro)phenyl, methylthienyl, chlorothienyl, and cyclopropyl, and more preferable examples include a hydrogen atom, a fluorine atom, (trifluoromethyl)phenyl, methoxyphenyl, (trifluoromethoxy)phenyl, chlorophenyl, and chloro(fluoro)phenyl.

Preferable examples of $A_2$ in the above-mentioned formula (I) include a single bond and an oxygen atom, and a more preferable example is an oxygen atom.

Preferable examples of $B_2$ in the above-mentioned formula (I) include a single bond and alkylene having 1-10 carbon atoms and optionally having substituent(s), and a more preferable example is a single bond.

Preferable examples of $C_2$ in the above-mentioned formula (I) include a hydrogen atom and phenyl optionally having substituent(s). When phenyl has substituent(s), a preferable substituent is alkyl having 1-10 carbon atoms and optionally substituted by a halogen atom, more preferably, alkyl having 1-3 carbon atoms and optionally substituted by a halogen atom. Specific preferable examples of $C_2$ include a hydrogen atom, phenyl, methylphenyl, and (trifluoromethyl)phenyl, and a hydrogen atom and methylphenyl are more preferable, and methylphenyl is still more preferable.

The substituents -$A_1$-$B_1$-$C_1$ and -$A_2$-$B_2$-$C_2$ can be bonded to any carbon atoms at a, b, c and d in the following structural formula

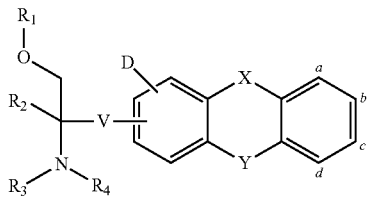

Preferable binding positions of substituent -$A_1$-$B_1$-$C_1$ are b and c, more preferably b or c. Preferable binding position of substituent -$A_2$-$B_2$-$C_2$ is b or c.

V can be bonded to any carbon atoms at e, f, g and h in the following structural formula

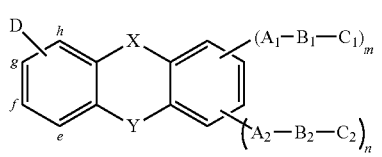

(I)

Preferable binding positions of V is f or g.

Preferable examples of D in the above-mentioned formula (I) include a hydrogen atom, a halogen atom (preferably, a chlorine atom), and methyl optionally substituted by a halogen atom, and a more preferable example is a hydrogen atom.

In the above-mentioned formula (I), m is preferably 1, and n is preferably 0.

A preferable example of compound (I) is the following compound.

[Compound (I-A)]
A compound wherein
$R_1$ is a hydrogen atom,
V is —$CH_2CH_2$— or —$CH_2CH_2CH_2$—,
$R_2$ is a hydrogen atom, methyl, ethyl, hydroxymethyl, hydroxyethyl, fluoromethyl, fluoroethyl, 2,2-difluoroethyl or 2,2,2-trifluoroethyl,
$R_3$ and $R_4$ are the same or different and each is a hydrogen atom, methyl or ethyl,
X is a single bond, an oxygen atom, a sulfur atom, methylene or —CO—,
Y is an oxygen atom, a sulfur atom, methylene or —CO—,
$A_1$ is a single bond, an oxygen atom, a sulfur atom or —CO—,
$A_2$ is a single bond or an oxygen atom,
$B_1$ is a single bond, methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, 2-methylpropane-1,3-diyl, 2-ethoxyethylene, difluoromethylene, 5,5-difluoropentane-1,5-diyl, 4,4,5,5-tetrafluoropentane-1,5-diyl, 5,5,6,6-tetrafluorohexane-1,6-diyl, 6,6-difluorohexane-1,6-diyl, ethene-1,2-diyl, propene-1,3-diyl, butene-1,4-diyl, pentene-1,5-diyl, hexene-1,6-diyl, heptene-1,7-diyl, 4,4,5,5-tetrafluoropentene-1,5-diyl or 5,5-difluorohexene-1,6-diyl,
B2 is a single bond or alkylene having 1-10 carbon atoms and optionally having substituent(s),
$C_1$ is a hydrogen atom, a fluorine atom, phenyl, methylphenyl, ethylphenyl, (trifluoromethyl)phenyl, di(trifluoromethyl)phenyl, methoxyphenyl, isopropoxyphenyl, (trifluoromethoxy)phenyl, fluorophenyl, fluoro(methoxy)phenyl, fluoro(trifluoromethyl)phenyl, chlorophenyl, dichlorophenyl, chloro(methyl)phenyl, chloro(fluoro)phenyl, chloro(methoxy)phenyl, chloro(trifluoromethyl)phenyl, dimethylaminomethylphenyl, acetylphenyl, (methylthio)phenyl, cyanophenyl, cyano(fluoro)phenyl, methylthienyl, chlorothienyl or cyclopropyl,
$C_2$ is a hydrogen atom, phenyl, methylphenyl or (trifluoromethyl)phenyl,
D is a hydrogen atom, a halogen atom (preferably, chlorine atom) or methyl optionally substituted by a halogen atom,
m is 1, and
n is 0.

A more preferable example of compound (I) is the following compound.

[Compound (I-B)]
A compound wherein
$R_1$ is a hydrogen atom,
V is —$CH_2CH_2$—,
$R_2$ is a hydrogen atom, methyl or hydroxymethyl,
$R_3$ and $R_4$ are both hydrogen atoms,
X is an oxygen atom or a sulfur atom,
Y is methylene or —CO—,
$A_1$ is a single bond, an oxygen atom or a sulfur atom,
$A_2$ is an oxygen atom,
$B_1$ is a single bond, methylene, ethylene, propane-1,3-diyl, butane-1,4-diyl, pentane-1,5-diyl, hexane-1,6-diyl, octane-1,8-diyl, 4,4,5,5-tetrafluoropentane-1,5-diyl, ethene-1,2-diyl or (E)-propene-1,3-diyl wherein $A_1$ and $C_1$ in the formula (I) are bonded to form $A_1$-CH=CH—$CH_2$—$C_1$ or (E)-hexene-1,6-diyl wherein $A_1$ and $C_1$ are bonded to form $A_1$-CH=CH—$(CH_2)_4$—$C_1$,
$B_2$ is a single bond,
$C_1$ is a hydrogen atom, a fluorine atom, (trifluoromethyl)phenyl, methoxyphenyl, (trifluoromethoxy)phenyl, chlorophenyl or chloro(fluoro)phenyl,
$C_2$ is a hydrogen atom or methylphenyl, D is a hydrogen atom,
m is 1, and
n is 0.

A further more preferable example of compound (I) is the following compound.

[Compound (I-C)]

A compound wherein
$R_1$ is a hydrogen atom,
V is —$CH_2CH_2$—,
$R_2$ is hydroxymethyl,
$R_3$ and $R_4$ are both hydrogen atoms,
X is an oxygen atom or a sulfur atom,
Y is —CO—,
$A_1$ is a single bond, an oxygen atom or a sulfur atom,
$A_2$ is an oxygen atom,
$B_1$ is a single bond, pentane-1,5-diyl, hexane-1,6-diyl or (E)-propene-1,3-diyl wherein $A_1$ and $C_1$ in the formula (I) are bonded to form $A_1$-CH=CH—$CH_2$—$C_1$,
$B_2$ is a single bond,
$C_1$ is a hydrogen atom, a fluorine atom, (trifluoromethyl)phenyl, methoxyphenyl, (trifluoromethoxy)phenyl, chlorophenyl or chloro(fluoro)phenyl,
$C_2$ is methylphenyl,
D is a hydrogen atom,
m is 1, and
n is 0.

The most preferable compound (I) is a compound selected from the group consisting of
2-[3-amino-4-hydroxy-3-(hydroxymethyl)butyl]-6-[3-(trifluoromethyl)phenoxy]-9H-thioxanthen-9-one (Example 54),
2-[3-amino-4-hydroxy-3-(hydroxymethyl)butyl]-6-(4-chlorophenoxy)-9H-thioxanthen-9-one (Example 55),
2-[3-amino-4-hydroxy-3-(hydroxymethyl)butyl]-7-[3-(trifluoromethyl)phenoxy]-9H-thioxanthen-9-one (Example 44),
2-[3-amino-4-hydroxy-3-(hydroxymethyl)butyl]-7-(3-chlorophenoxy)-9H-thioxanthen-9-one (Example 76),
2-[3-amino-4-hydroxy-3-(hydroxymethyl)butyl]-6-(4-fluorophenoxy)-9H-xanthen-9-one (Example 105),
2-[3-amino-4-hydroxy-3-(hydroxymethyl)butyl]-6-(4-methoxyphenoxy)-9H-xanthen-9-one (Example 108),
6-[3-amino-4-hydroxy-3-(hydroxymethyl)butyl]-2-[3-(trifluoromethyl)phenoxy]-9H-xanthen-9-one (Example 83),
3-[3-amino-4-hydroxy-3-(hydroxymethyl)butyl]-6-hexyloxy-9H-thioxanthen-9-one (Example 20),
6-[3-amino-4-hydroxy-3-(hydroxymethyl)butyl]-2-[(1E)-hex-1-en-1-yl]-9H-xanthen-9-one (Example 180),
3-[3-amino-4-hydroxy-3-(hydroxymethyl)butyl]-6-(4-methoxyphenoxy)-9H-xanthen-9-one (Example 143),
2-[3-amino-4-hydroxy-3-(hydroxymethyl)butyl]-7-pentyloxy-9H-xanthen-9-one (Example 22),
2-[3-amino-4-hydroxy-3-(hydroxymethyl)butyl]-7-hexyloxy-9H-xanthen-9-one (Example 23),
2-[3-amino-4-hydroxy-3-(hydroxymethyl)butyl]-6-(3-chloro-4-fluorophenoxy)-9H-xanthen-9-one (Example 116),
2-[3-amino-4-hydroxy-3-(hydroxymethyl)butyl]-6-[3-(trifluoromethyl)phenyl]-9H-xanthen-9-one (Example 172),
3-[3-amino-4-hydroxy-3-(hydroxymethyl)butyl]-6-pentyloxy-9H-xanthen-9-one (Example 41),
2-[3-amino-4-hydroxy-3-(hydroxymethyl)butyl]-6-[3-(trifluoromethoxy)phenyl]-9H-xanthen-9-one (Example 164),
6-[3-amino-4-hydroxy-3-(hydroxymethyl)butyl]-2-(3-chloro-4-fluorophenoxy)-9H-xanthen-9-one (Example 138),
mono(2-amino-2-hydroxymethyl-4-{9-oxo-6-[3-(trifluoromethyl)phenoxy]-9H-thioxanthen-2-yl}butyl)phosphate (Example 300),
mono{2-amino-4-[6-(4-chlorophenoxy)-9-oxo-9H-thioxanthen-2-yl]-2-hydroxymethylbutyl}phosphate (Example 296),
mono(2-amino-2-hydroxymethyl-4-{9-oxo-7-[3-(trifluoromethyl)phenoxy]-9H-thioxanthen-2-yl}butyl)phosphate (Example 291),
mono{2-amino-4-[7-(3-chlorophenoxy)-9-oxo-9H-thioxanthen-2-yl]-2-hydroxymethylbutyl}phosphate (Example 293),
mono{2-amino-4-[6-(4-fluorophenoxy)-9-oxo-9H-xanthen-2-yl]-2-hydroxymethylbutyl}phosphate (Example 230),
mono{2-amino-2-hydroxymethyl-4-[6-(4-methoxyphenoxy)-9-oxo-9H-xanthen-2-yl]butyl}phosphate (Example 241),
mono(2-amino-2-hydroxymethyl-4-{9-oxo-7-[3-(trifluoromethyl)phenoxy]-9H-xanthen-3-yl}butyl)phosphate (Example 218),
mono[2-amino-4-(6-hexyloxy-9-oxo-9H-thioxanthen-3-yl)-2-(hydroxymethyl)butyl]phosphate (Example 312),
mono(2-amino-4-{7-[(1E)-hex-1-en-1-yl]-9-oxo-9H-xanthen-3-yl}-2-(hydroxymethyl)butyl)phosphate (Example 259),
mono{2-amino-2-hydroxymethyl-4-[6-(4-methoxyphenoxy)-9-oxo-9H-xanthen-3-yl]butyl}phosphate (Example 276),
mono[2-amino-2-hydroxymethyl-4-(9-oxo-7-pentyloxy-9H-xanthen-2-yl)butyl]phosphate (Example 226),
mono[2-amino-4-(7-hexyloxy-9-oxo-9H-xanthen-2-yl)-2-hydroxymethylbutyl]phosphate (Example 227),
mono{2-amino-4-[6-(3-chloro-4-fluorophenoxy)-9-oxo-9H-xanthen-2-yl]-2-hydroxymethylbutyl}phosphate (Example 249),
mono{2-amino-2-hydroxymethyl-4-[9-oxo-6-[3-(trifluoromethyl)phenyl]-9H-xanthen-2-yl]butyl}phosphate (Example 246),
mono[2-amino-2-hydroxymethyl-4-(9-oxo-6-pentyloxy-9H-xanthen-3-yl)butyl]phosphate (Example 287),
mono{2-amino-2-hydroxymethyl-4-(9-oxo-6-[3-(trifluoromethoxy)phenyl]-9H-xanthen-2-yl}butyl)phosphate (Example 247), and
mono{2-amino-4-[7-(3-chloro-4-fluorophenoxy)-9-oxo-9H-xanthen-3-yl]-2-(hydroxymethyl)butyl}phosphate (Example 271)
or a pharmaceutically acceptable acid addition salt thereof.

Examples of the pharmaceutically acceptable acid addition salt of the compound of the present invention include inorganic acid salt, organic acid salt and the like. The compound of the present invention encompasses the above-mentioned compound (I) and a pharmaceutically acceptable acid addition salt thereof, and also a hydrate and a solvate thereof.

The synthetic methods of the compound of the present invention are, for example, as follows.

Each compound in the following reaction schemes also includes a salt form and, as such salt, those similar to the salt of compound (I) are used.

The compound obtained in each step can also be used, as a reaction mixture or as a crude product, for the subsequent reaction. Alternatively, the compound can also be isolated from a reaction mixture according to a conventional method, and can be purified with ease by separation means such as recrystallization, distillation, chromatography and the like.

1) Of the compounds of the present invention, compound (I-1) which is a compound represented by the formula (I)

wherein $R_1$, $R_3$, $R_4$ are hydrogen atoms, $A_1$ is an oxygen atom, a sulfur atom or —$NR_6$— (wherein $R_6$ is a hydrogen atom, alkyl having 1-6 carbon atoms and optionally having substituent(s), acyl having 1-7 carbon atoms and optionally having substituent(s) or alkoxycarbonyl having 2-7 carbon atoms), X is a single bond, a sulfur atom, an oxygen atom or —$NR_5$— (wherein $R_5$ is a hydrogen atom or alkyl having 1-4 carbon atoms and optionally having substituent(s)), Y is C=O, V is —$CH_2CH_2$— or —CH=CH—, m is 1, and n is 0 is synthesized according to the following scheme (I).

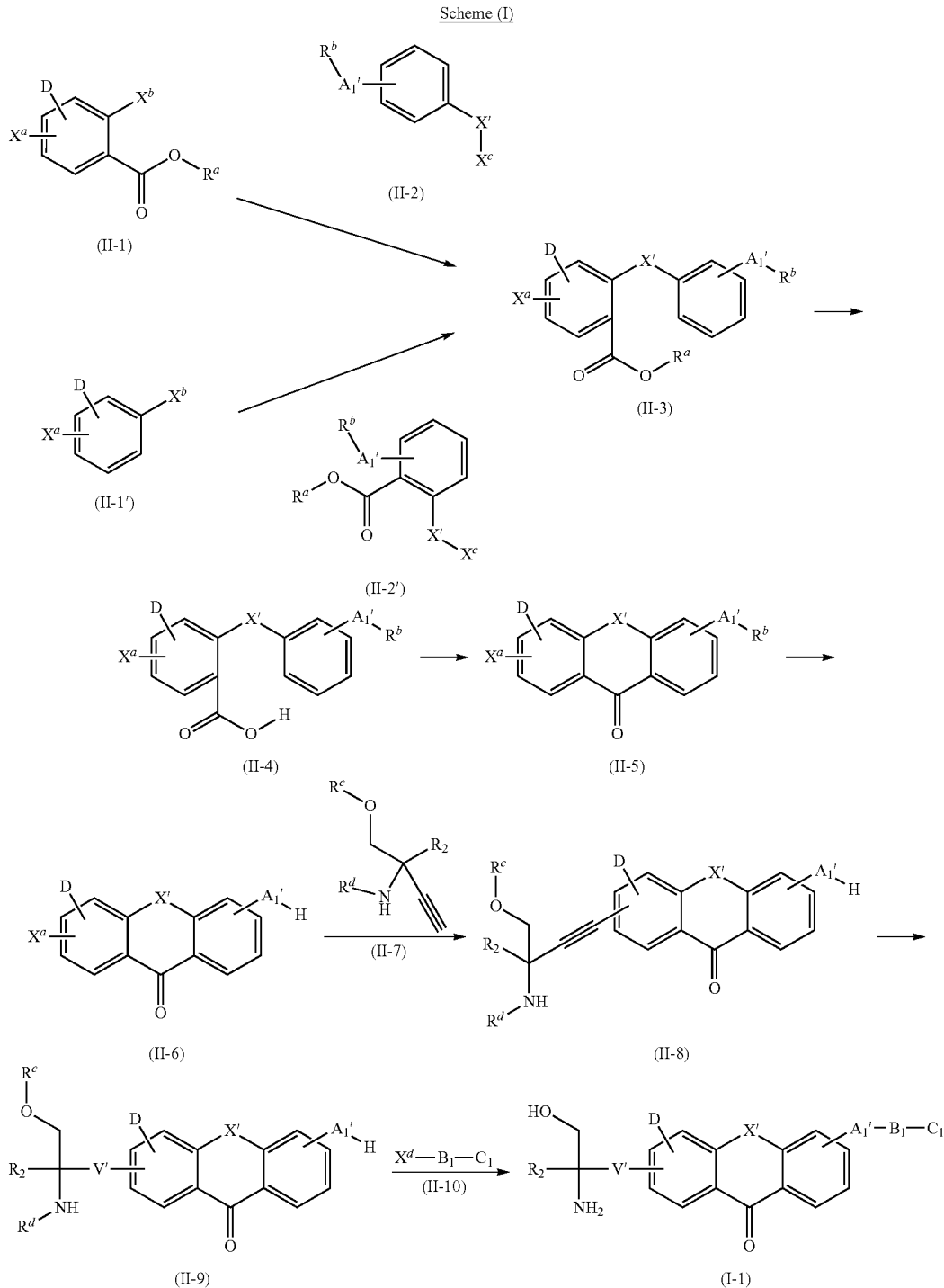

wherein $A_1'$ is an oxygen atom, a sulfur atom or —$NR_6$— (wherein $R_6$ is a hydrogen atom, alkyl having 1-6 carbon atoms and optionally having substituent(s), acyl having 1-7 carbon atoms and optionally having substituent(s) or alkoxycarbonyl having 2-7 carbon atoms), X' is a single bond, an oxygen atom, a sulfur atom or —$NR_5$— (wherein $R_5$ is a hydrogen atom or alkyl having 1-4 carbon atoms and optionally having substituent(s)), V' is —CH$_2$CH$_2$— or —CH=CH—, R$^a$ is a hydrogen atom or a protecting group, R$^b$, R$^c$ and R$^d$ are each a protecting group, X$^a$ and X$^b$ are each a leaving group, X$^c$ is a hydrogen atom or an activating group, X$^d$ is a leaving group, a hydroxy group or an active group. R$_2$, B$_1$, C$_1$ and D are the same as those defined for each symbol in the formula (I).

The protecting group for R$^a$ is not particularly limited as long as it is a conventional carboxyl-protecting group. For example, alkyl (specifically, methyl, ethyl and the like), aralkyl (benzyl and the like) and the like can be mentioned. The protecting group for R$^b$ is not particularly limited as long as it protects A$_1$', and does not cause side reaction in the deprotection. When B$_1$-C$_1$, which is a partial structure of the compound (I-1) of the present invention, is used as R$^b$ (wherein B$_1$ is a single bond, alkylene having 1-10 carbon atoms and optionally having substituent(s), or alkenylene having 2-10 carbon atoms and optionally having substituent(s)), the compound (I-1) of the present invention can be obtained without deprotecting R$^b$. R$^c$ in the formula is not particularly limited as long as it protects a hydroxy group. For example, acyl (preferably one having a carbon number of about 2-4, specifically acetyl and the like), trialkylsilyl (specifically trimethylsilyl and the like), benzyl and a substituent forming acetal compound (specifically methoxymethyl, tetrahydropyranyl and the like) can be mentioned. When R$_2$ has a hydroxy group, the hydroxy group may be protected with a suitable protecting group and, as the hydroxy-protecting group R$^e$, those similar to R$^c$ can be specifically mentioned. When R$^c$ and R$^e$ are bonded, cyclic acetal can also be formed (hereinafter R$^e$ is used in the present specification to mean the same as explained here). The protecting group for R$^d$ in the formula is not particularly limited as long as it protects an amino group. For example, acyl (preferably one having about 2-4 carbon atoms, specifically acetyl and the like), carbamate (specifically t-butyloxycarbonyl, benzyloxycarbonyl and the like) and the like can be mentioned. In addition, R$^c$ and R$^d$ can also be bonded to form a ring. For example, oxazolidinone and the like can be mentioned. The leaving group for X$^a$ is not particularly limited as long as it is activated by a catalyst in the Sonogashira reaction and eliminated. For example, a halogen atom (preferably, iodine atom, bromine atom and the like), trifluoromethanesulfonyloxy and the like can be mentioned. X$^a$ may be a leaving group precursor. In this case, it needs to be converted to a leaving group in a step that does not influence others prior to the Sonogashira reaction. For example, conversion of a methoxy group to a trifluoromethanesulfonyl group and the like can be mentioned. The leaving group for X$^b$ is not particularly limited as long as it is eliminated in a reaction with an X'—X$^c$ group. For example, a halogen atom (specifically, iodine atom, bromine atom and the like), trifluoromethanesulfonyloxy and the like can be mentioned. When X$^c$ is an activating group, boronic acid, boronate and the like can be mentioned as X$^c$. When X$^d$ is a leaving group, the leaving group is not particularly limited as long as it is eliminated in the transformation of A$_1$'H to A$_1$'-B$_1$-C$_1$, and does not inhibit the reaction. For example, a halogen atom (specifically iodine atom, bromine atom, chlorine atom and the like), methanesulfonyloxy and the like can be mentioned. When X$^d$ is an active group, boronic acid, boronate and the like can be mentioned as X$^d$. In the above-mentioned scheme (I), compound (II-3) is also obtained by reacting compound (II-1) with compound (II-2) wherein substituent X$^b$ of compound (II-1) and substituent X'—X$^c$ of compound (II-2) are mutually exchanged. The same applies to compound (II-1') and compound (II-2').

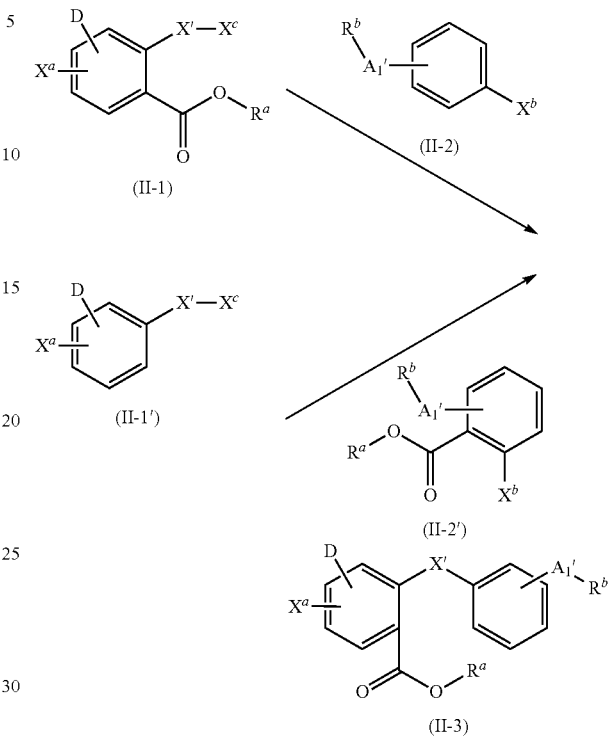

wherein each symbol means the same as explained for each symbol of the aforementioned scheme (I).

In the first step, intermediate (II-3) is obtained by a condensation reaction of compound (II-2) having an X$^b$ group with compound (II-1) having an X'—X$^c$ group. In this reaction, compound (II-2') can be used instead of compound (II-2) and compound (II-1') can be used instead of compound (II-1). The conditions for this step are appropriately selected according to the kind of X'. For example, when X' is a single bond, X$^c$ is an activating group, and general reaction conditions for the Suzuki coupling are used. Specifically, the reaction can be performed in a highly-polar solvent, for example, ether solvents such as 1,2-dimethoxyethane, tetrahydrofuran and the like, hydrocarbon solvents such as toluene and the like, N,N-dimethylformamide and the like, in the presence of a base such as cesium carbonate, tripotassium phosphate and the like and a palladium catalyst. Also, the reaction can be performed in a water-containing solvent or bilayer solvent such as tetrahydrofuran and water, and 1,2-dimethoxyethane and water, in the presence of a base such as sodium hydroxide, sodium carbonate, thallium oxide and the like and a palladium catalyst. In some cases, moreover, a reaction aid such as 2-dicyclohexylphosphino-2',6'-dimethoxybiphenyl and 2-(di t-butylphosphino)biphenyl and the like can be added. The reaction conditions are, for example, room temperature to under reflux for about 30 min-about 24 hr. When X' is an oxygen atom, a sulfur atom or —NR$_5$— (wherein R$_5$ is a hydrogen atom or alkyl having 1-4 carbon atoms and optionally having substituent(s)), then X$^c$ is a hydrogen atom, and the Ullmann condensation using copper, copper compounds such as copper oxide, copper iodide and the like and an inorganic base such as potassium carbonate, potassium hydroxide and the like can be used. As the reaction conditions, for example, a solvent having a high boiling point such as nitrobenzene, dimethyl sulfoxide, water and the like is used at room temperature −250° C. for about 30 min-24 hr. After the reaction, the object product can be obtained by performing purification and the like by a conventional method.

In the second step, protecting group $R^a$ of intermediate (II-3) is deprotected. The conditions are not particularly limited as long as $R^a$ can be removed and no influence is exerted on others. For example, when $R^a$ is a methyl group, a method of using an inorganic base such as sodium hydroxide and the like in a mixed solvent of an alcoholic solvent and water can be used. As the reaction conditions, under ice-cooling to 80° C. for about 10 min-12 hr can be mentioned. After the reaction, the object product can be obtained by performing purification and the like by a conventional method. When $R^a$ is a hydrogen atom, this step can be omitted.

The third step is a ring closing reaction of intermediate (II-4). This step can be performed in the presence of acid. As the acid to be used, sulfuric acid, polyphosphoric acid and the like can be mentioned. The reaction conditions include without solvent or using a solvent such as acetic acid, acetyl chloride and the like, under ice-cooling to about room temperature for about 10 min-10 hr. After the reaction, the object product can be obtained by performing purification and the like by a conventional method.

The fourth step is deprotection of protecting group $R^b$ of $A_1'$ in intermediate (II-5). The conditions of the deprotection of the protecting group $R^b$ are not particularly limited as long as they are used for the removal of conventional protecting groups. For example, when $A_1'$ is an oxygen atom and $R^b$ is methyl, a method of using a Lewis acid such as boron tribromide and the like in methylene chloride can be used. When $R^b$ is acyl such as acetyl and the like, a method of using an inorganic base such as sodium hydroxide and the like in a mixed solvent of an alcoholic solvent and water can be used. When $R^b$ is an ether type protecting group such as methoxymethyl, tetrahydropyranyl, t-butyl and the like, a method of using an acid such as hydrochloric acid, trifluoroacetic acid and the like can be used. The reaction in the fifth step can also be performed before the fourth step. In this case, when $R^b$ is a protecting group which can be removed under hydrogenolysis, catalytic hydrogenation conditions (e.g., benzyl, substituted benzyl, benzyloxymethyl and the like), the removal of $R^b$ can also be performed simultaneously with the reduction of the triple bond in the sixth step. When $B_1$-$C_1$ which is a partial structure of the compound (I-1) of the present invention is used as $R^b$, the removal of $R^b$ is not necessary, and conversion of $A_1'$H to $A_1'$-$B_1$-$C_1$ in the final step can also be omitted.

In the fifth step, intermediate (II-8) having a triple bond is obtained by condensing with intermediate (II-7), which is synthesized from intermediate (II-6) by a known method (e.g., Tetrahedron vol. 57 (2001) 6531-6538), under the Sonogashira reaction condition. Examples of the catalyst used include palladium compound such as tetrakis(triphenylphosphine)palladium(0), tris(dibenzylideneacetone)dipalladium(0), dichlorobis(acetonitrile)palladium(II) and the like. To promote the reaction, an organic base such as triethylamine and the like, an inorganic base such as ammonia and the like, a copper compound such as copper iodide, copper bromide and the like, a phosphine compound such as 2-dicyclohexylphosphino-2',4',6'-triisopropylbiphenyl and the like, and the like can be added. The reaction conditions are, for example, in an ether solvent such as tetrahydrofuran, 1,4-dioxane and the like, a polar solvent such as acetonitrile, dimethylformamide and the like, or a hydrocarbon solvent such as benzene and the like, under ice-cooling to reflux for about 30 min to about 24 hr. After the reaction, the object product can be obtained by performing purification and the like by a conventional method.

In the sixth step, intermediate (II-9) is obtained by reducing the triple bond of intermediate (II-8). The reagent to be used when $R^b$ is $B_1$—$C_1$ which is a partial structure of compound (I-1) of the present invention, $B_1$ is a single bond or alkylene having 1-10 carbon atoms and optionally having substituent(s), and V' is —$CH_2CH_2$— is not limited as long as it is used for general reduction of unsaturated carbon bond. For example, catalytic hydrogenation using a heterogeneous catalyst such as palladium carbon, Raney-nickel, palladium carbon-ethylenediamine complex and the like. The reaction conditions are, for example, in an alcoholic solvent such as ethanol and the like, an ether solvent such as 1,4-dioxane and the like, or a hydrocarbon solvent such as toluene and the like, under 1 to 20 atm of hydrogen pressure, under ice-cooling to reflux for 30 min to 1 weekT. An acid such as acetic acid and the like or a base such as triethylamine and the like can be added to the reaction mixture depending on the reaction speed, stabilities of the compounds used and the like. After the reaction, the object product can be obtained by performing purification and the like by a conventional method. On the other hand, when $B_1$-$C_1$ which is a partial structure of compound (I-1) of the present invention is used as $R^b$, the reaction used when $B_1$ is a single bond, alkylene having 1-10 carbon atoms and optionally having substituent(s) or alkenylene having 2-10 carbon atoms and optionally having substituent(s), and V' is —CH=CH— is, for example, catalytic hydrogenation performed in the presence of a catalyst having a modulated activity such as Lindlar's catalyst, nickel-graphite-ethylenediamine complex, diene compound and phosphine compound, and various complexes of rhodium and ruthenium and the like. After the reaction, the object product can be obtained by performing purification and the like by a conventional method.

In the seventh step, compound (I-1) of the present invention is obtained by converting $A_1'$H group of intermediate (II-9) by using a corresponding reagent or intermediate (II-10) obtained from $B_1$ and $C_1$ by a generally-known synthetic method, and then deprotecting $R^c$, $R^d$ and $R^e$ ($R^e$ is a hydroxy-protecting group when $R_2$ has a hydroxy group; however, $R^e$ is sometimes absent). When $B_1$ of compound (I-1) is a single bond and $C_1$ is a hydrogen atom, a reaction for converting $A_1'$H group to $A_1'$-$B_1$-$C_1$ can be omitted. As the reagent used for transforming $A_1'$H group of intermediate (II-9) into $A_1^1$-$B_1$-$C_1$, an appropriate one is selected according to the combination of $A_1'$, $B_1$, $C_1$ and $X^d$.

(1) When $B_1$ is other than a single bond or when $B_1$ is a single bond and $C_1$ is other than aryl or heteroaryl, the reaction used for transforming $A_1'$H group into $A_1'$-$B_1$-$C_1$ includes a combination of intermediate (II-10) wherein $X^d$ is a leaving group and an inorganic base such as sodium hydroxide, potassium carbonate, sodium hydride and the like. The reaction conditions are, for example, in polar solvents such as N,N-dimethylformamide and the like, ether solvents such as tetrahydrofuran and the like, alcoholic solvents such as ethanol and the like, under ice-cooling to reflux for about 30 min-about 12 hr. When $A_1'$ is an oxygen atom, a Mitsunobu reaction using intermediate (II-10) wherein $X^d$ is a hydroxy group and a phosphine compound such as triphenylphosphine and the like and azodicarboxylic acid derivative such as diisopropyl azodicarboxylate and the like can also be used.

(2) An ether formation reaction using intermediate (II-10) wherein $X^d$ is an active group and copper acetate and an organic base (e.g., Tetrahedron Letters, vol. 39 (1998), pp. 2933-2936) can also be used for a compound not included in (1), wherein $B_1$ is a single bond, and $A_1'$ is an oxygen atom. As the organic base, triethylamine, pyridine and the like can be mentioned. The reaction conditions therefor include the presence of molecular sieves in a nonpolar solvent such as methylene chloride and the like at room temperature—50° C. for about 1 hr-24 hr. In addition, other conditions using intermediate (II-10) wherein $X^d$ is a leaving group and copper (e.g., Angewandte Chemie, vol. 42 (2003), pp. 5400-5449), conditions using palladium (e.g., Journal of the American Chemical Society, vol. 21 (1999), pp. 4369-4378) and the like can also be used. (3) A compound other than (1), wherein $B_1$ is a single bond and $A_1'$ is other than an oxygen atom, can be reacted with intermediate (II-10) wherein $X^c$ is a leaving group in an ether solvent such as 1,4-dioxane, tetrahydrofuran and the like, a hydrocarbon solvent such as toluene and the like or a polar solvent such as 2-propanol and the like, by using, as a catalyst, a base such as potassium carbonate, N,N-diisopropylethylamine and the like, a palladium compound such as tris(dibenzylideneacetone)dipalladium(0) and the like, or a copper compound such as copper iodide and the like and adding, as a reaction aid where necessary, a phosphine compound such as 4,5-bis(diphenylphosphino)-9,9-dimethylxanthene and the like, diol such as salicylaldoxime and the like or diamine such as N,N'-dimethylethylenediamine and the like, and the like. The reaction conditions include 40° C. to under reflux for about 30 min-about 24 hr. After the reaction, the object product can be obtained by performing purification and the like by a conventional method.

This step for converting $A_1'H$ to $A_1'-B_1-C_1$ can also be performed with respect to intermediate (II-6) prior to the fifth step as long as the $B_1-C_1$ group does not inhibit the reaction thereafter and is not influenced. The deprotection of $R^c$, $R^d$ and $R^e$ ($R^e$ is a hydroxy-protecting group when $R_2$ has a hydroxy group; however, $R^e$ is sometimes absent) to be performed sequentially is not particularly limited as long as it is used for general deprotection of protecting groups, and all protecting groups can be deprotected at once or stepwisely. For example, when $R^c$ and $R^e$ are bonded to form a cyclic acetal, and $R^d$ is t-butyloxycarbonyl, they can be simultaneously deprotected by using an acid. Examples of the acid therefor include inorganic acids such as hydrochloric acid and the like, trifluoroacetic acid and the like. The reaction conditions are, for example, in an alcoholic solvent such as ethanol and the like, an ether solvent such as tetrahydrofuran and the like, water or a mixed solvent thereof, under ice-cooling to 80° C. for about 10 min-about 12 hr. When $R^c$ and $R^d$ are bonded to form an oxazolidinone ring, deprotection is easily performed by further protecting the amino group with carbamate (e.g., t-butoxycarbonyl and the like) and then performing hydrolysis. After the reaction, the object product can be obtained by performing purification and the like by a conventional method.

2) Compound (I-1'-8) is also synthesized from compound (I-1'-1), which is compound (I-1) of the present invention shown in scheme (I) wherein $A_1$ is a single bond, an oxygen atom, a sulfur atom, —CO—, —SO—, —SO$_2$— or —NR$_6$— (wherein R$_6$ is a hydrogen atom, alkyl having 1-6 carbon atoms and optionally having substituent(s), acyl having 1-7 carbon atoms and optionally having substituent(s) or alkoxycarbonyl having 2-7 carbon atoms) from the following scheme (II).

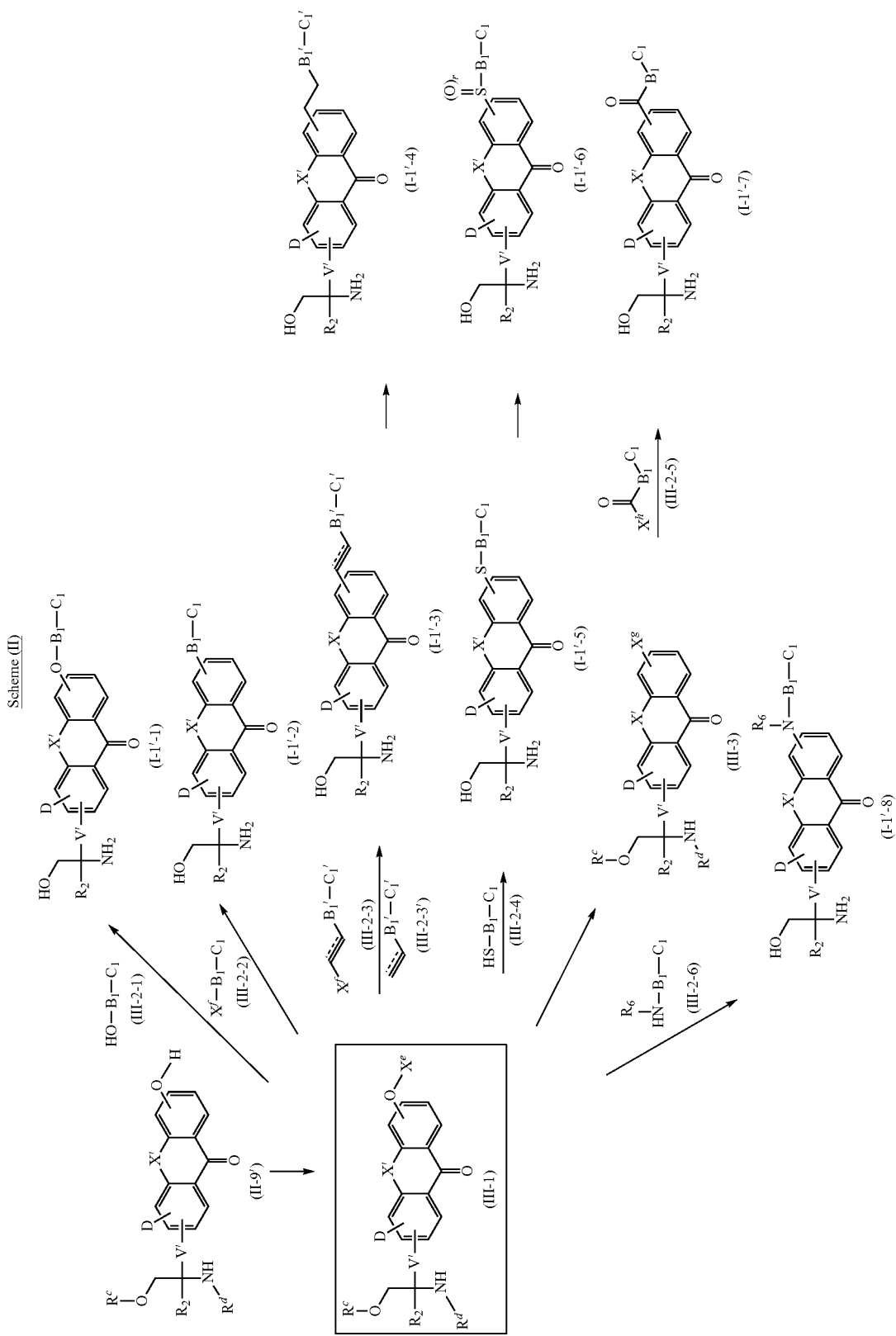

wherein $X^e$, $X^f$ are active groups, $X^g$, $X^h$ are leaving groups, $R^c$, $R^d$ are protecting groups, r is 1 or 2, $B_1'$ is absent or alkylene having 1-8 carbon atoms, alkenylene having 2-8 carbon atoms or alkynylene having 2-8 carbon atoms, $C_1'$ is aryl having 6-10 carbon atoms and optionally having substituent(s), heteroaryl optionally having substituent(s) and having 5 to 10 ring-constituting atoms, which contains 1 or 2 nitrogen atoms, 1 or 2 oxygen atoms or 1 or 2 sulfur atoms as the ring-constituting atom(s), cycloalkyl having 3-7 carbon atoms and optionally having substituent(s), which is optionally fused with benzene optionally having substituent(s), or heterocycloalkyl optionally having substituent(s), which has 5 to 7 ring-constituting atoms containing 1 or 2 nitrogen atoms or 1 or 2 oxygen atoms as the ring-constituting atoms and is optionally fused with benzene optionally having substituent(s). X' and V' are the same as those defined for each symbol in scheme (1). $R_2$, $B_1$, $C_1$ and D are the same as those defined for each symbol in the formula (I).

≡≡≡ shows a double bond or a triple bond.

In the formulas, $R^c$ and $R^d$ are the same as those defined above. The activating group for $X^e$ is not particularly limited as long as it activates a phenolic hydroxy group. For example, a sulfonyl group such as trifluoromethanesulfonyl and the like can be mentioned. As the activating group for $X^f$, boronic acid and boronate can be mentioned. The leaving group for $X^g$ is not particularly limited as long as it is eliminated during the acylation reaction. For example, an organotin compound (trialkylstannyl group etc.), magnesium halide and the like can be mentioned. The leaving group for $X^h$ is not particularly limited as long as it is eliminated during the reaction. For example, a halogen atom (specifically, bromine atom, chlorine atom and the like) can be mentioned.

The first step is a reaction to convert to intermediate (III-1) wherein the phenolic hydroxy group of compound (II-9') has been activated to a leaving group. The reagent is not particularly limited as long as it can convert the phenolic hydroxy group to $X^e$. A reagent used when $X^e$ is trifluoromethanesulfonyl is, for example, trifluoromethanesulfonyl anhydride. The reaction conditions are, for example, in a halogenic solvent such as methylene chloride and the like at 0° C.-50° C. for about 10 min to about 6 hr. After the reaction, the object product can be obtained by performing purification and the like by a conventional method.

The step of converting intermediate (III-1) to the compound (I-1'-1) of the present invention includes a reaction with compound (III-2-1) and deprotection of $R^c$, $R^d$ and $R^e$ ($R^e$ is a hydroxy-protecting group when $R_2$ has a hydroxy group; $R^e$ is sometimes absent) to be performed subsequently. The reaction can be performed in an ether solvent such as 1,4-dioxane, tetrahydrofuran and the like, a hydrocarbon solvent such as toluene and the like or a polar solvent such as 2-propanol and the like, by using, as a catalyst, a base such as cesium carbonate, potassium carbonate, potassium fluoride, N,N-diisopropylethylamine and the like, a palladium compound such as tris(dibenzylideneacetone)dipalladium(0), palladium(II) acetate and the like, and a copper compound such as copper iodide and the like and adding, as a reaction aid where necessary, a phosphine compound such as 2-(di-t-butylphosphino)-1,1'-binaphthyl and the like, and the like. The reaction conditions are, for example, 40° C. to under reflux for about 30 min-about 24 hr. After the reaction, the object product can be obtained by performing purification and the like by a conventional method. For deprotection of $R^c$, $R^d$ and $R^e$ ($R^e$ is a hydroxy-protecting group when $R_2$ has a hydroxy group; $R^e$ is sometimes absent) to be performed subsequently, reaction reagents and reaction conditions similar to those of the deprotection of the protecting group in the seventh step of scheme (I) can be mentioned.

The step of converting intermediate (III-1) to compound (I-1'-2) of the present invention includes a reaction with compound (III-2-2) and deprotection of $R^c$, $R^d$ and $R^e$ ($R^e$ is a hydroxy-protecting group when $R_2$ has a hydroxy group; $R^e$ is sometimes absent) to be performed subsequently. As a reaction with compound (III-2-2) which is arylboronic acid or arylboronate, Suzuki coupling can be mentioned. Specifically, the reaction can be performed in an ether solvents such as 1,2-dimethoxyethane, tetrahydrofuran and the like, a hydrocarbon solvent such as toluene and the like, a highly-polar solvent such as N,N-dimethylformamide and the like, in the presence of a base such as cesium carbonate, tripotassium phosphate and the like and a palladium catalyst. Also, the reaction can be performed in a water-containing solvent or bilayer solvent such as tetrahydrofuran and water, and 1,2-dimethoxyethane and water, in the presence of a base such as sodium hydroxide, sodium carbonate, thallium oxide and the like and a palladium catalyst. In some cases, moreover, a reaction aid such as 2-dicyclohexylphosphino-2',6'-dimethoxybiphenyl and 2-(di t-butylphosphino)biphenyl can be added. The reaction conditions are, for example, room temperature to under reflux for about 30 min-about 24 hr. For deprotection of $R^c$, $R^d$ and $R^e$ ($R^e$ is a hydroxy-protecting group when $R_2$ has a hydroxy group; $R^e$ is sometimes absent) to be performed subsequently, reaction reagents and reaction conditions similar to those of the deprotection of the protecting group in the seventh step of scheme (I) can be mentioned.

The step of converting intermediate (III-1) to the compound (I-1'-3) of the present invention includes a reaction with compound (III-2-3) or compound (III-2-3') and deprotection of $R^c$, $R^d$ and $R^e$ ($R^e$ is a hydroxy-protecting group when $R_2$ has a hydroxy group; $R^e$ is sometimes absent) to be performed subsequently. As a reaction with compound (III-2-3) which is boronic acid or boronate, Suzuki coupling can be mentioned. For this step, reaction reagent and reaction conditions similar to those used for the step for obtaining compound (I-1'-2) can be mentioned. As a reaction with compound (III-2-3') which is alkene or alkyne, Sonogashira reaction, Heck reaction and the like can be mentioned. As the conditions for the Sonogashira reaction, reaction reagent and reaction conditions similar to those used for the step for obtaining compound (II-8) in scheme (I) can be mentioned. The Heck reaction can be performed in an ether solvent such as 1,4-dioxane, tetrahydrofuran and the like, a hydrocarbon solvent such as toluene and the like or a polar solvent such as dimethylformamide and the like, by using, as a catalyst, a base such as sodium carbonate, triethylamine and the like, and a palladium compound such as bis(triphenylphosphine)palladium chloride (II), tris(dibenzylideneacetone)dipalladium(0), palladium(II) acetate and the like, and adding, as a reaction aid where necessary, a phosphine compound such as 1,3-bis(biphenylphosphino)propane, triphenylphosphine and the like, a copper compound such as copper iodide, copper bromide and the like, and the like. The reaction conditions are, for example, 40° C. to under reflux for about 30 min-about 24 hr. After the reaction, the object product can be obtained by performing purification and the like by a conventional method. For deprotection of $R^c$, $R^d$ and $R^e$ ($R^e$ is a hydroxy-protecting group when $R_2$ has a hydroxy group; $R^e$ is sometimes absent) to be performed subsequently, reaction reagents and reaction conditions similar to those of the removal of the protecting group in the seventh step of scheme (I) can be mentioned.

Compound (I-1'-4) of the present invention can be obtained by a reduction reaction of compound (I-1'-3). While the reagent is not limited as long as it is used for general reduction of unsaturated carbon bond, for example, catalytic hydrogenation using a heterogeneous catalyst such as palladium carbon, Raney-nickel, palladium carbon-ethylenediamine complex and the like can be used. The reaction conditions are, for example, in an alcoholic solvent such as ethanol and the like, an ether solvent such as 1,4-dioxane and the like, or a hydrocarbon solvent such as toluene and the like, under 1-20 atm of hydrogen pressure, under ice-cooling to reflux for 30 min to 1 week. An acid such as acetic acid and the like or a base such as triethylamine and the like can be added to the reaction mixture depending on the reaction speed, stabilities of the compounds used and the like. After the reaction, the object product can be obtained by performing purification and the like by a conventional method. This step can also be performed before deprotection of $R^c$, $R^d$ and $R^e$ ($R^e$ is a hydroxy-protecting group when $R_2$ has a hydroxy group; $R^e$ is sometimes absent) to be performed in the synthesis of compound (I-1'-3).

The step of converting intermediate (III-1) to the compound (I-1'-5) of the present invention includes a reaction with compound (III-2-4) and deprotection of $R^c$, $R^d$ and $R^e$ ($R^e$ is a hydroxy-protecting group when $R_2$ has a hydroxy group; $R^e$ is sometimes absent) to be performed subsequently. The reaction with compound (III-2-4) is performed in a solvent, for example, a hydrocarbon solvent such as toluene and the like, an ether solvent such as 1,2-dimethoxyethane, 1,4-dioxane and the like, a polar solvent such as N,N-dimethylacetamide and the like, and the like or a mixed solvent thereof, by using a palladium compound such as tris(dibenzylideneacetone)dipalladium(0), palladium(II) acetate, dichloro(di-t-butylphosphinous acid)palladium (II) and the like as a catalyst, at room temperature to under reflux for about 1-about 48 hr. An inorganic base such as potassium carbonate, sodium carbonate and the like, an organic base such as sodium t-butoxide, potassium t-butoxide, N,N-diisopropylethylamine and the like can be added to this reaction. In addition, a phosphine compound such as 4,5-bis(diphenylphosphino)-9,9-dimethylxanthene, bis[2-(diphenylphosphino)phenyl]ether, 1,1'-bis(di t-butylphosphino)ferrocene and the like, and the like can also be added as a reaction promoter. For deprotection of $R^c$, $R^d$ and $R^e$ ($R^e$ is a hydroxy-protecting group when $R_2$ has a hydroxy group; $R^e$ is sometimes absent) to be performed subsequently, reaction reagents and reaction conditions similar to those of the removal of the protecting group in the seventh step of scheme (I) can be mentioned.

Compound (I-1'-6) of the present invention is obtained by an oxidation reaction of compound (I-1'-5). The reagent to be used for obtaining a compound wherein r is 1, mild oxidants such as sodium periodate, hydrogen peroxide and the like can be mentioned. The reagent to be used in the step for obtaining a compound wherein r is 2 is not particularly limited as long as it is a conventional oxidant. For example, oxidation using permanganate salt, chromic acid, oxygen, hydrogen peroxide, organic peroxide and the like can be mentioned. After the reaction, the object product can be obtained by performing purification and the like by a conventional method. This step can also be performed before deprotection of $R^c$, $R^d$ and $R^e$ ($R^e$ is a hydroxy-protecting group when $R_2$ has a hydroxy group; $R^e$ is sometimes absent) to be performed in the synthesis of compound (I-1'-5).

A step of converting intermediate (III-1) to the compound (I-1'-7) of the present invention includes a reaction of compound (III-3) that can be induced from intermediate (III-1) with compound (III-2-5) and deprotection of $R^c$, $R^d$ and $R^e$ ($R^e$ is a hydroxy-protecting group when $R_2$ has a hydroxy group; $R^e$ is sometimes absent) to be performed subsequently. Intermediate (III-3) can be obtained by reacting intermediate (III-1) with hexaalkyl-distannane. The reaction conditions are, for example, in an ether solvent such as tetrahydrofuran, 1,4-dioxane and the like, using an inorganic salt such as lithium chloride and the like and a palladium compound such as tris(dibenzylideneacetone)dipalladium(0), tetrakis(triphenylphosphine)palladium(0) and the like as catalysts, at room temperature to under reflux for about 1-about 24 hr. In addition, a phosphine compound such as triphenylphosphine and the like, and the like can also be added as a reaction promoter. After the reaction, the object product can be obtained by performing purification and the like by a conventional method. For the subsequent acylation reaction, corresponding acid chloride (III-2-5) and a catalyst such as bis(triphenylphosphine)palladium(II), benzyl chlorobis(triphenylphosphine)palladium(II), tris(dibenzylideneacetone)dipalladium(0) and the like can be used in a hydrocarbon solvent such as benzene, toluene and the like, a halogenated solvent such as chloroform and the like. Where necessary, a phosphine compound such as triphenylphosphine and the like, and the like can be added as a reaction aid. For deprotection of $R^c$, $R^d$ and $R^e$ ($R^e$ is a hydroxy-protecting group when $R_2$ has a hydroxy group; $R^e$ is sometimes absent) to be performed subsequently, reaction reagents and reaction conditions similar to those of the removal of the protecting group in the seventh step of scheme (I) can be mentioned.

The step of converting intermediate (III-1) to compound (I-1'-8) of the present invention includes a reaction with compound (III-2-6) and deprotection of $R^c$, $R^d$ and $R^e$ ($R^e$ is a hydroxy-protecting group when $R_2$ has a hydroxy group; $R^e$ is sometimes absent) to be performed subsequently. As the reaction with compound (III-2-6), a conventional amination reaction using a metal compound such as palladium, copper and the like can be mentioned. The conditions are not particularly limited as long as side reactions do not occur. For example, the reaction can be performed in an ether solvent such as 1,4-dioxane, tetrahydrofuran and the like, a hydrocarbon solvent such as toluene and the like or a polar solvent such as 2-propanol and the like, by using, as a catalyst, a base such as tripotassium phosphate, potassium carbonate, N,N-diisopropylethylamine and the like, palladium such as tris(dibenzylideneacetone)dipalladium(0) and the like and copper such as copper iodide and the like and adding, as a reaction aid where necessary, a phosphine compound such as 4,5-bis(diphenylphosphino)-9,9-dimethylxanthene, di(cyclohexyl)biphenylphosphine and the like, diol such as salicylaldoxime and the like or diamine such as N,N'-dimethylethylenediamine and the like, and the like. The reaction conditions are, for example, 40° C. to under reflux for about 30 min-about 24 hr. For deprotection of $R^c$, $R^d$ and $R^e$ ($R^e$ is a hydroxy-protecting group when $R_2$ has a hydroxy group; $R^e$ is sometimes absent) to be performed subsequently, reaction reagents and reaction conditions similar to those of the removal of the protecting group in the seventh step of scheme (I) can be mentioned.

The conversion step of O—$X^e$ group in scheme (II) is performed for intermediate (IV-1) obtained from compound (II-6') (corresponding to intermediate (II-6) described in scheme (I)) in scheme (III), which is a synthetic precursor of compound (II-9'), and the intermediate can also be led to the compound (I-1') of the present invention (specifically, from compound (I-1'-1) to compound (I-1'-8)).

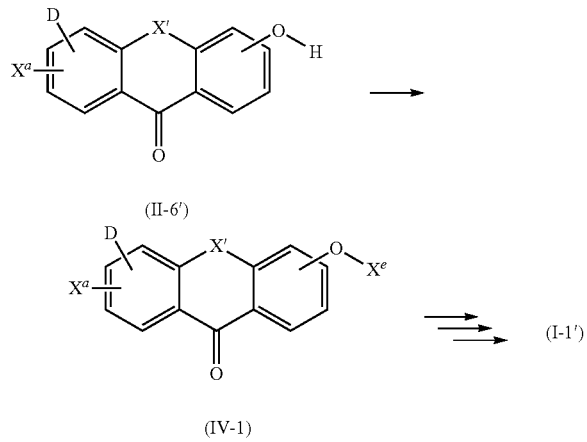

wherein X' and D are the same as those defined for the symbols in scheme (II), $X^a$ is a leaving group, and $X^e$ is an activating group.

$X^a$ and $X^e$ in the formula are the same as those defined above. The conversion step of O—$X^e$ group is similar to that in each step described in scheme (II). Thereafter, compound (I-1'-1) to compound (I-1'-8) in scheme (II) can be respectively obtained by synthesis in the same manner as in the fifth step and the following in scheme (I).

3) Of the compounds of the present invention, compound (I-2) which is a compound represented by the formula (I) wherein $R_1$, $R_3$, $R_4$ are hydrogen atoms, $A_1$ is an oxygen atom, a sulfur atom, —$NR_6$— (wherein $R_6$ is a hydrogen atom, alkyl having 1-6 carbon atoms and optionally having substituent(s), acyl having 1-7 carbon atoms and optionally having substituent(s) or alkoxycarbonyl having 2-7 carbon atoms), X is an oxygen atom, a sulfur atom or —$NR_5$— (wherein $R_5$ is a hydrogen atom or alkyl having 1-4 carbon atoms and optionally having substituent(s)), Y is C=O, V is —$CH_2CH_2$— or —CH=CH—, m is 1, and n is 0 can also be synthesized from the following scheme (IV).

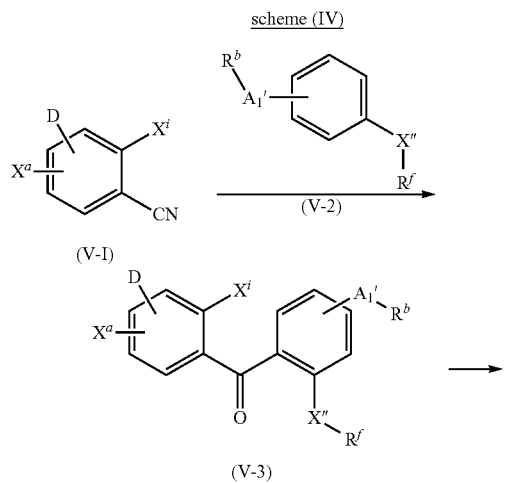

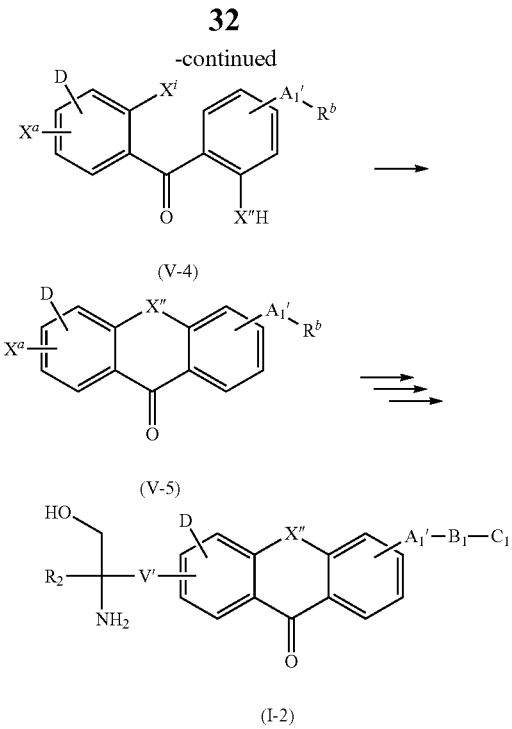

wherein V' is —$CH_2CH_2$— or —CH=CH—, $A_1$' is the same as that defined for the symbol in scheme (I), X" is an oxygen atom, a sulfur atom or —$NR_5$— (wherein $R_5$ is a hydrogen atom or alkyl having 1-4 carbon atoms and optionally having substituent(s)), $R^b$ is a protecting group, $R^f$ is a hydrogen atom or a protecting group, $X^a$, $X^i$ are leaving groups, and $R_2$, $B_1$, $C_1$ and D are the same as those defined for each symbol in the formula (I).

$X^a$ and $R^b$ in the formula are the same as those defined above. When $R^f$ is a protecting group, it is not particularly limited as long as it protects X". When $R^b$ and $R^f$ are different, a combination permitting deprotection of $R^f$ alone can be mentioned and, when $R^b$ and $R^f$ are the same, a protecting group permitting deprotection of $R^f$ position regioselectively, for example, alkyl (specifically, methyl, ethyl and the like), aralkyl (benzyl and the like) and the like can be mentioned. The leaving group for $X^1$ is not particularly limited as long as it is eliminated in a ring closing reaction. For example, a halogen atom (specifically, fluorine atom and the like), toluenesulfonyloxy and the like can be mentioned.

In the first step, intermediate (V-3) is obtained by a condensation reaction of compound (V-1) having a cyano group and compound (V-2). The conditions are not limited as long as benzophenone skeleton can be constructed. A method using palladium(II) acetate and trifluoroacetic acid (e.g., Journal of Organic Chemistry, vol. 71 (2006), pp. 3551-3558), conditions using Lewis acid such as zinc chloride, boron chloride, aluminum chloride and the like and hydrochloric acid, and the like can be mentioned.

The second step is selective deprotection of protecting group $R^f$ of intermediate (V-3). The conditions are not particularly limited as long as $R^f$ can be removed selectively. Even when $R^f$ and $R^b$ are the same group, selective removal is possible depending on the conditions. For example, when $R^f$ and $R^b$ are methyl groups, $R^f$ can be selectively removed by using a Lewis acid such as aluminum chloride and the like. The reaction conditions in this case include, for example, in a nonpolar solvent such as methylene chloride and the like under ice-cooling to about 40° C. for about 10 min-about 10 hr. When $R^f$ is a hydrogen atom, this step can be omitted.

The third step is a ring closing reaction of intermediate (V-4). This step can be performed in a protic polar solvent such as water, methanol and the like, an aprotic polar solvent such as N-methylmorpholine, N,N-dimethylformamide and dimethyl sulfoxide, an ether solvent such as tetrahydrofuran and the like, in the presence of a base. As the base to be used, an inorganic base such as sodium hydride, potassium hydroxide, potassium carbonate and the like or an organic base such as alkoxide (e.g., potassium t-butoxide and the like), 1,8-diazabicyclo[5.4.0]undec-7-en and the like can be used. The reaction conditions are, for example, under ice-cooling to about 100° C. for about 10 min to about 10 hr. After the reaction, compound (V-5) can be obtained by performing purification and the like by a conventional method.

Compound (V-5) can be led to compound (I-2) of the present invention by a method similar to that in scheme (I) or (II). The compound (V-3) described in scheme (IV) can also be synthesized from compound (VI-1) in scheme (V).

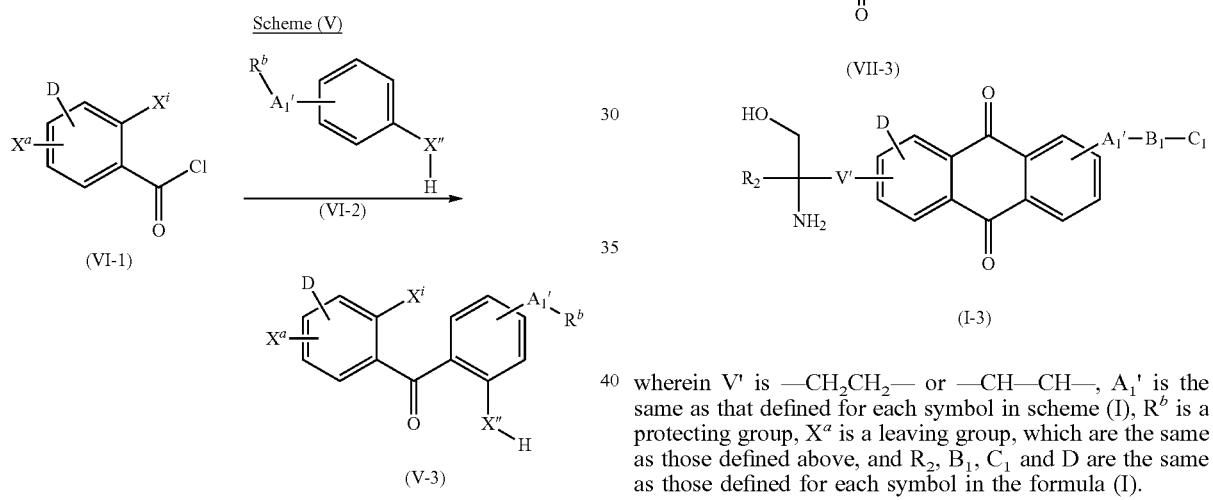

wherein $R^b$ is a protecting group, $X^a$, $X^i$ are leaving groups, and $R^b$, $X^a$, $X^i$, $A_1'$ and $X''$ are the same as those defined for each symbol in scheme (IV).

This step is a reaction to construct a benzophenone skeleton from compound (VI-1) by a Friedel-Crafts acylation reaction. As the reagent to be used for the reaction, Lewis acid reagents such as boron trichloride, boron tribromide, aluminum chloride, zinc chloride and the like can be mentioned. The reaction conditions are, for example, in a nonpolar solvent such as benzene, xylene, methylene chloride and the like, a polar solvent such as nitrobenzene and the like, at room temperature—250° C. for about 30 min-about 24 hr. After the reaction, the object product can be obtained by performing purification and the like by a conventional method.

4) Of the compounds of the present invention, compound (I-3) which is a compound represented by the formula (I) wherein $R_1$, $R_3$, $R_4$ are each a hydrogen atom, X, Y are each C=O, V is —CH$_2$CH$_2$— or —CH=CH—, m is 1, and n is 0 is synthesized by the following scheme (VI).

wherein V' is —CH$_2$CH$_2$— or —CH—CH—, $A_1'$ is the same as that defined for each symbol in scheme (I), $R^b$ is a protecting group, $X^a$ is a leaving group, which are the same as those defined above, and $R_2$, $B_1$, $C_1$ and D are the same as those defined for each symbol in the formula (I).

The first step is a reaction to construct an anthraquinone skeleton from phthalic anhydride (VII-1) and a benzene compound. In this reaction, compound (VII-1') can be used instead of compound (VII-1), and compound (VII-2') can be used instead of compound (VII-2). As the reaction conditions, general conditions for Friedel-Crafts acylation reaction are used. As the reagent to be used for the reaction, Lewis acid reagents such as boron trichloride, boron tribromide, aluminum chloride, zinc chloride and the like can be mentioned.

Compound (VII-3) can be led to compound (I-3) of the present invention by a method similar to that in scheme (I) or (II).

5) Of the compounds of the present invention, compound (I-4) which is a compound represented by the formula (I) wherein $R_1$, $R_3$, $R_4$ are each a hydrogen atom, X, Y may be the same or different and each is a single bond, a sulfur atom, an oxygen atom or —NR$_5$— (wherein $R_5$ is a hydrogen atom or alkyl having 1-4 carbon atoms and optionally having substituent(s)), V is —CH$_2$CH$_2$— or —CH=CH—, m is 1, n is 0, and D is a hydrogen atom or alkyl having 1-4 carbon atoms and optionally having substituent(s) is synthesized by the following scheme (VII).

Scheme (VII)

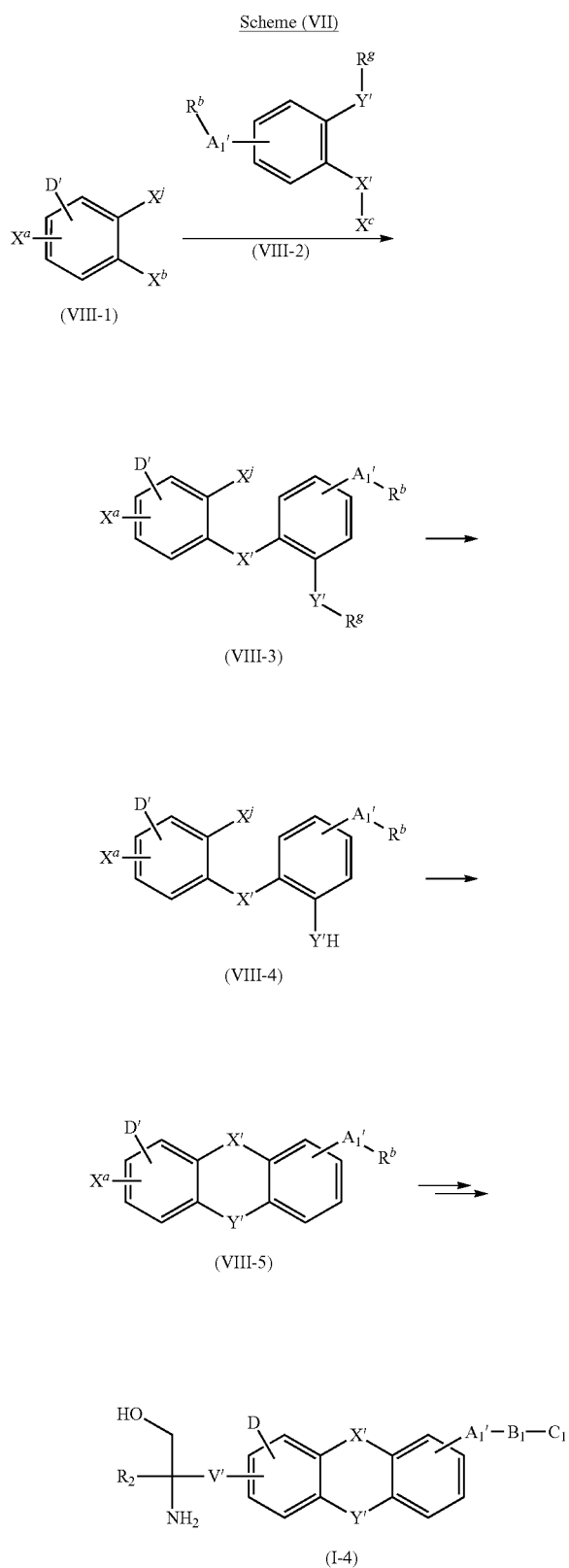

wherein D' is a hydrogen atom or alkyl having 1-4 carbon atoms and optionally having substituent(s), $A_1'$, V' are the same as those defined for each symbol in scheme (I), $R^b$ is a protecting group, $R^g$ is a hydrogen atom or a protecting group, $X^a$, $X^b$, $X^j$ are leaving groups, $X^c$ is a hydrogen atom or an active group, X' and Y' are each a single bond or a sulfur atom or a oxygen atom or —$NR_5$— (wherein $R_5$ is a hydrogen atom or alkyl having 1-4 carbon atoms and optionally having substituent(s)), and $R_2$, $B_1$ and $C_1$ are the same as those defined for each symbol in the formula (I).

In the formula, $X^a$, $X^b$, $X^c$, $R^b$ are the same as those defined above. The leaving group for $X^j$ is not particularly limited as long as it is eliminated during the substitution reaction with Y' group. For example, a halogen atom (specifically, fluorine atom, iodine atom, bromine atom and the like), trifluoromethanesulfonyloxy and the like can be mentioned. The protecting group for $R^g$ is not particularly limited as long as it protects Y' and does not inhibit the reaction. $X^j$ may be exchanged with Y'—$R^g$, and $X^b$ may be exchanged with X'—$X^c$. In addition, a suitable combination enabling stepwise reactions should be selected for $X^a$, $X^b$, $X^j$. For example, a combination of an iodine atom for $X^b$ to be reacted first, a chlorine atom for $X^j$ to be reacted next, and trifluoromethanesulfonyloxy converted from a hydroxy group for $X^a$ to be eliminated finally in the Sonogashira reaction, and the like.

In the first step, intermediate (VIII-3) is obtained by a condensation reaction of compound (VIII-1) having an $X^b$ group and compound (VIII-2) having an X'—$X^c$ group. The conditions for this step are appropriately selected according to the kind of X', and are the same as those for the first step of scheme (I).

The second step is deprotection of protecting group $R^g$ of intermediate (VIII-3). The conditions are not particularly limited as long as $R^g$ can be removed and no influence is exerted on others. For example, when $R^g$ is methyl, a method of using a Lewis acid such as boron tribromide and the like in methylene chloride can be used. When $R^g$ is acyl such as acetyl and the like, a method of using an inorganic base such as sodium hydroxide and the like in a mixed solvent of an alcoholic solvent and water can be used. When $R^g$ is an ether type protecting group such as methoxymethyl, tetrahydropyranyl, t-butyl and the like, a method of using an acid such as hydrochloric acid, trifluoroacetic acid and the like can be used. When $R^g$ is a hydrogen atom, this step can be omitted.

The third step is a ring closing reaction of intermediate (VIII-4). The conditions of this step are appropriately selected according to the kind of Y'. The conditions of this step are those similar to the conditions of the first step.

Compound (VIII-5) can be led to compound (I-4) of the present invention by a method similar to that in scheme (I) or (II).

6) Of the compounds of the present invention, compound (I-5) and compound (I-5') which are compounds represented by the formula (I) wherein X is —SO—, —$SO_2$— are synthesized by the following scheme (VIII).

Scheme (VIII)

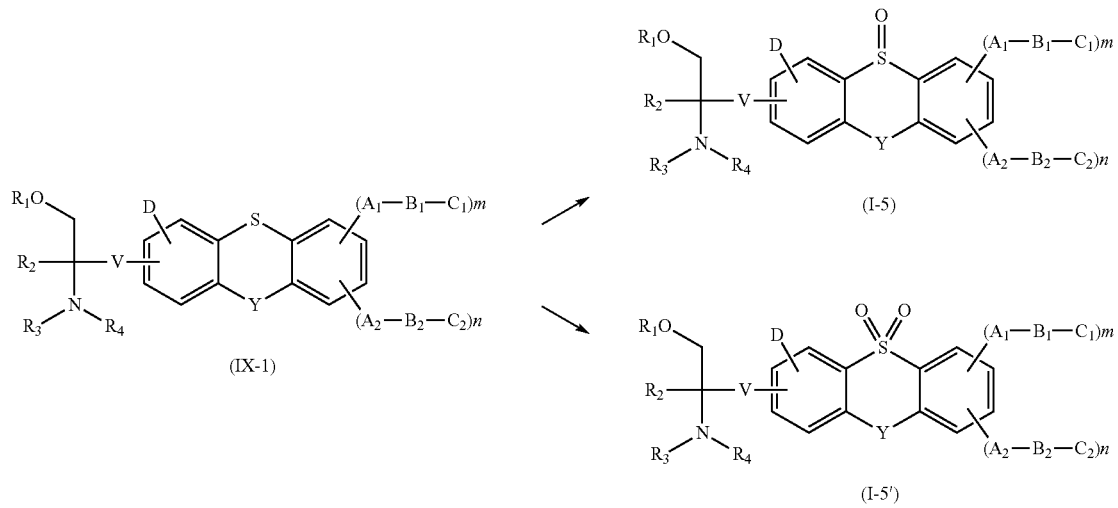

wherein $R_1$, $R_2$, $R_3$, $R_4$, $A_1$, $B_1$, $C_1$, D, $A_2$, $B_2$, $C_2$, m, n, V and Y are the same as those defined for each symbol in the formula (I).

Compound (I-5) and compound (I-5') can be obtained from compound (IX-1) which is a compound of the formula (I) wherein X is a sulfur atom. As the reagent to be used for obtaining compound (I-5), mild oxidants such as sodium periodate, hydrogen peroxide and the like can be mentioned. The reagent to be used in the step for obtaining compound (I-5') is not particularly limited as long as it is a conventional oxidant. For example, oxidation using permanganate salt, chromic acid, oxygen, hydrogen peroxide, organic peroxide and the like can be mentioned. The reaction conditions are, for example, at −78° C.-50° C. for about 30 min-about 24 hr. After the reaction, the object product can be obtained by performing purification and the like by a conventional method. This step can be performed on the intermediate used for synthesizing intermediate (IX-1). For example, it is an intermediate corresponding to intermediate (II-5) in scheme (I) and the like. When $A_1$-$B_1$-$C_1$, $A_2$-$B_2$-$C_2$ group is influenced by an oxidation reaction, this step needs to be performed prior to the introduction of $A_1$-$B_1$-$C_1$, $A_2$-$B_2$-$C_2$ groups into intermediate (IX-1). When Y in intermediate (IX-1) is a sulfur atom, Y in compound (I-5) and compound (I-5') is —SO— or —SO$_2$—, respectively.

7) Of the compounds of the present invention, compound (I-6) which is a compound represented by the formula (I) wherein Y is methylene is synthesized by the following scheme (IX).

Scheme (IX)

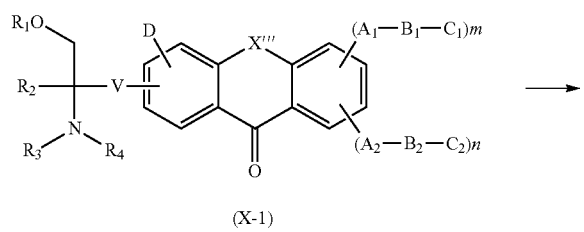

-continued wherein $R_1$, $R_2$, $R_3$, $R_4$, D, $A_1$, $B_1$, $C_1$, $A_2$, $B_2$, $C_2$, m, n and V are the same as those defined for each symbol in the formula (I), X''' is a single bond, an oxygen atom, a sulfur atom, methylene or —NR$_{5'}$— (wherein R$_{5'}$ is a hydrogen atom or alkyl having 1-4 carbon atoms).

Compound (I-6) can be obtained from compound (X-1), which is a compound of the formula (I) wherein Y is C=O. In this step, compound (I-6) is obtained by reducing compound (X-1). A method using a metal hydride complex compound such as lithium borohydride and the like, metal hydride such as diisobutylaluminum hydride and the like, diborane and substituted borane and acid such as hydrochloric acid, Lewis acid and the like can be mentioned. The reaction conditions are, for example, at −78° C.-80° C. for about 30 min-about 24 hr. In addition, catalytic hydrogenation conditions using palladium carbon and the like can also be mentioned. The reaction conditions are, for example, at room temperature −100° C. for about 10 min to about 6 hr. After the reaction, the object product can be obtained by performing purification and the like by a conventional method. This step can be performed on the intermediate used for synthesizing intermediate (X-1). For example, it is an intermediate corresponding to intermediate (II-5) in scheme (I) and the like. When $A_1$-$B_1$-$C_1$, $A_2$-$B_2$-$C_2$ groups are influenced by a reduction reaction, this step needs to be performed prior to the introduction of $A_1$-$B_1$-$C_1$, $A_2$-$B_2$-$C_2$ groups into intermediate (X-1). When X''' in intermediate (X-1) is C=O, X''' in compound (I-6) is methylene.

8) Of the compounds of the present invention, a compound which is a compound represented by the formula (I) wherein m is 1 and n is 1 can be obtained by using a di-substituted compound instead of the corresponding mono-substituted compound in the synthesis of compound (I) of the present invention by any of the methods described in the present specification. For example, when compound (I-7) wherein m and n are 1, and X and Y are —CO— is taken for explanation, compound (XI-2) is used instead of compound (VII-2) of scheme (VI), and compound (XI-2') is used instead of compound (VII-2'), as shown in scheme (X), and the like.

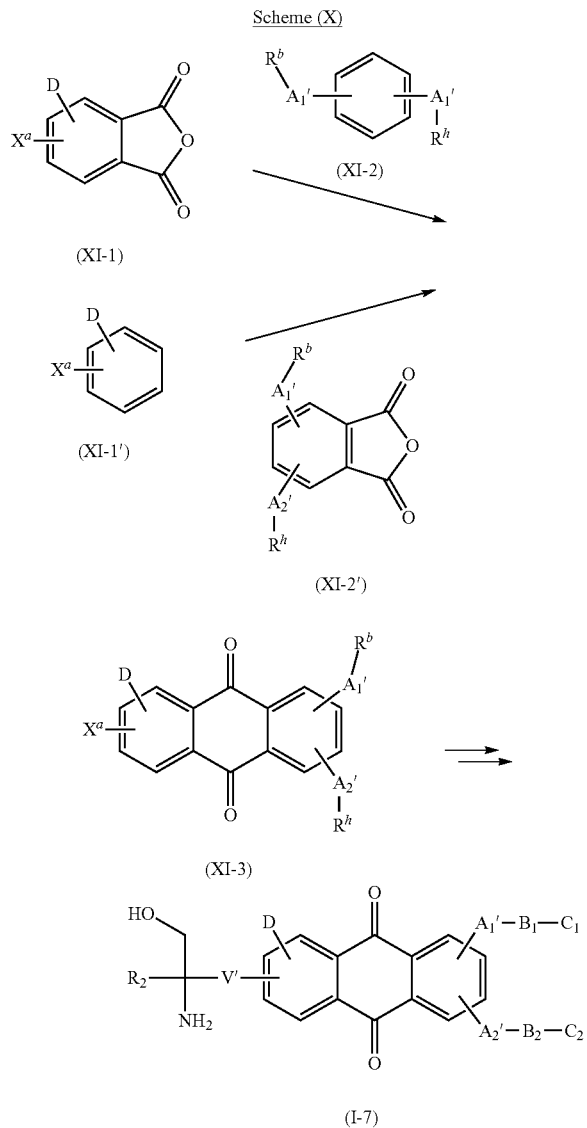

wherein $A_1'$, V' are the same as those defined for each symbol in scheme (VI), $A_2'$ is the same as that defined for $A_1'$, D, $B_1$, $C_1$, $B_2$, $C_2$ are the same as those defined for each symbol in the formula (I), $X^a$ is a leaving group, and $R^b$, $R^h$ are protecting groups.

In the formula, $X^a$, $R^b$ are the same as those defined for each symbol in scheme (I), and the protecting group for $R^h$ is not particularly limited as long as it protects $A_2'$, and does not cause side reactions during deprotection. When conversion of $A_1'$-H, $A_2'$-H to $A_1'$-$B_1$-$C_1$, $A_2'$-$B_2$-$C_2$ is each performed stepwisely, and $R^b$, $R^h$ are used in a combination permitting selective deprotection.

Each step of scheme (X) is the same as in scheme (VI). Similarly, other compound (I) of the present invention can be obtained by using a di-substituted compound instead of the corresponding mono-substituted compound in the synthesis according to any of the methods described in the present specification.

9) A compound (I-8) represented by the formula (I) wherein one or both of $R_3$ and $R_4$ is(are) alkyl having 1-4 carbon atoms is synthesized by the following scheme (XI).

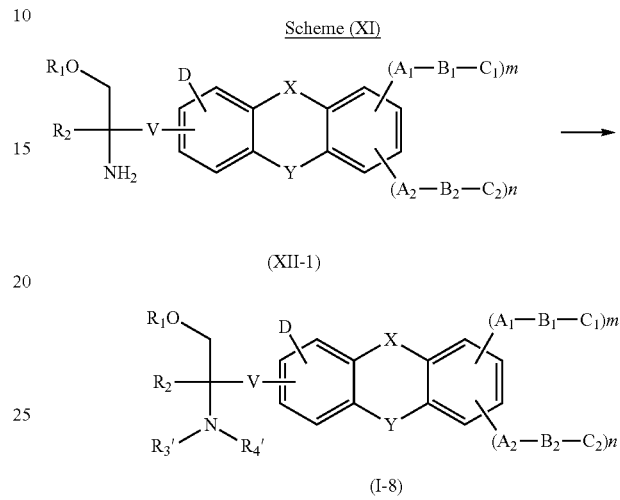

wherein one of or both of $R_3'$ and $R_4'$ is/are alkyl having 1-4 carbon atoms, and X, Y, V, $R_1$, $R_2$, D, $A_1$, $B_1$, $C_1$, $A_2$, $B_2$, $C_2$, m and n are the same as those defined for each symbol in the formula (I).

In this step, compound (I-8) of the present invention is synthesized by alkylation of the amino group of compound (XII-1) of the present invention having a primary amino group. For this synthesis, reductive amination reaction or alkylation reaction of amine using alkyl halide and a base can be used. When the compound does not have a moiety influenced by the reduction reaction, reductive amination reaction can be used, and the object product is obtained by reacting an aldehyde having the same carbon number as that of $R_3$ or $R_4$ with compound (XII-1) in an alcoholic solvent such as ethanol and the like or a halogenic solvent such as dichloroethane and the like using a reducing agent such as sodium borohydride, sodium cyanoborohydride, sodium triacetoxyborohydride and the like. The reduction can also be performed using hydrogen and a catalyst such as Raney-nickel, platinum oxide and the like. For this reaction, generation of Schiff base and reduction reaction may also be sequentially performed. An acid such as acetic acid and the like can be added as a reaction promoter for the reductive amination reaction. The reaction conditions are, for example, under ice-cooling—about 50° C. for about 30 min-10 hr. After the reaction, the object product can be obtained by performing purification and the like by a conventional method. When $R_3$ and $R_4$ are methyl, methylation reaction of Eschweiler-Clarke can also be performed using a reducing agent such as formic acid and formaldehyde, or formaldehyde and sodium cyanoborohydride and the like.

10) Of the compounds of the present invention, compound (I-9) which is compound (I-1) shown in scheme (I), wherein V is alkylene having 1-4 carbon atoms or alkenylene having 2-4 carbon atoms, is synthesized by the following scheme (XII).

Scheme (XII)

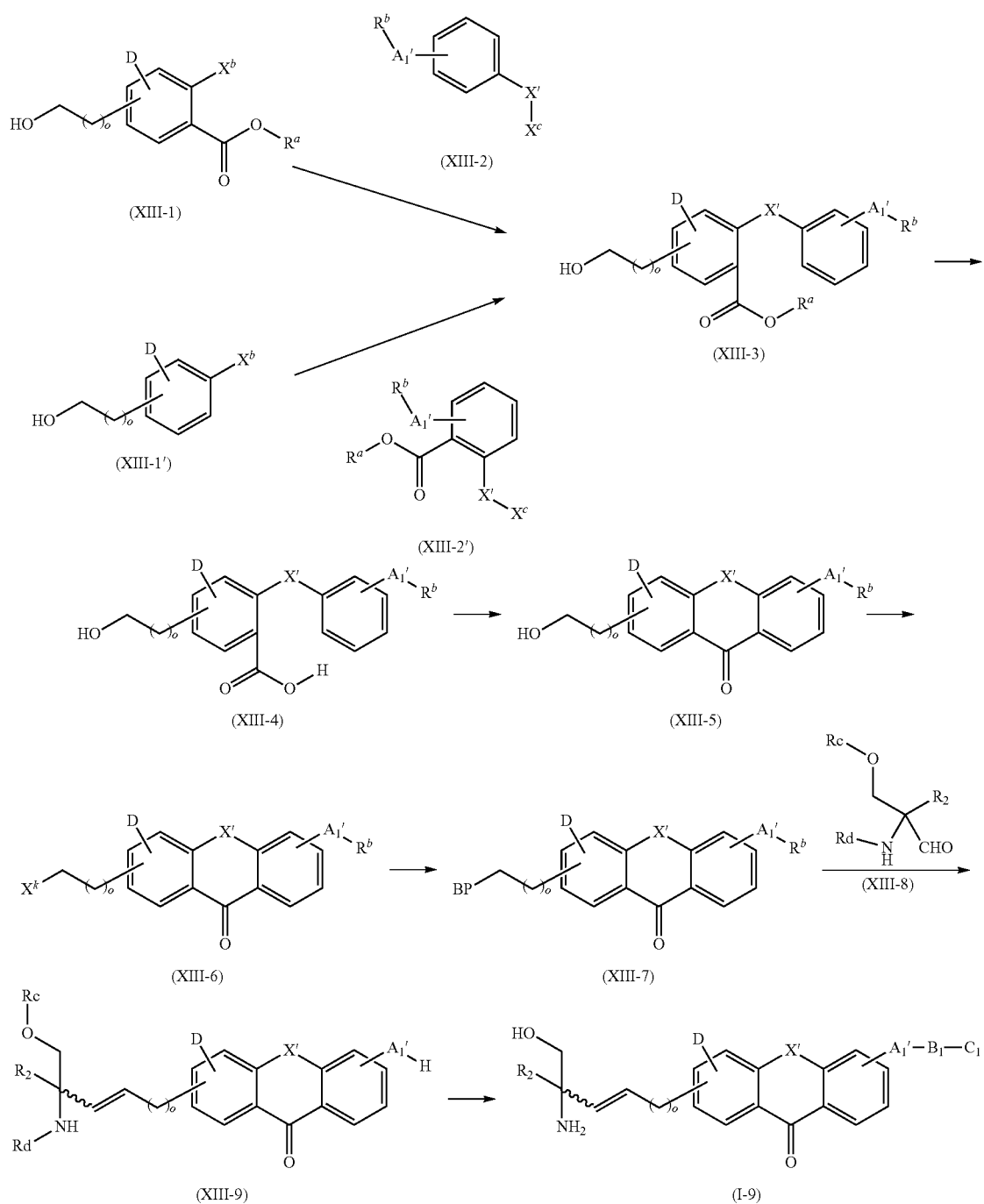

wherein $A_1'$, $X'$ are the same as those defined for each symbol in scheme (I), $R^a$, $R^b$, $R^c$, $R^d$ are protecting groups, $X^b$, $X^k$ are leaving groups, $X^c$ is a hydrogen atom or an activating group, o is 0-2, PB is a leaving group containing phosphorus, and $R_2$, $B_1$, $C_1$ and D are the same as those defined for each symbol in the formula (I).

═══ shows a single bond or a double bond.

In the formula, $R^a$, $R^b$, $R^c$, $R^d$, $X^b$, $X^c$ are the same as those defined for each symbol in scheme (I). The leaving group for $X^k$ is not particularly limited as long as it is eliminated in a reaction of intermediate (XIII-6) with a phosphorus compound and does not inhibit the subsequent reaction with aldehyde (XIII-8). For example, a halogen atom (specifically iodine atom, bromine atom, chlorine atom and the like), methanesulfonyloxy, toluenesulfonyloxy and the like can be mentioned. As the leaving group for PB containing phosphorus, triarylphosphonium (specifically, $P(C_6H_5)_3$) and $P(O)(OR^i)_2$ ($R^i$ is alkyl having 1-4 carbon atoms, hereinafter the same) can be mentioned.

The conditions from the first step to the third step are the same as those for the first step to the third step in scheme (I).

In the forth step, the hydroxy group of intermediate (XIII-5) is converted into leaving group $X^k$. The reagent is not particularly limited as long as it is a reagent capable of converting an alcoholic hydroxy group into $X^k$. Examples of the reagent used when $X^k$ is a halogen atom include N-chlorosuccinimide, N-bromosuccinimide, carbon tetrachloride, a combination of them and a reaction aid such as triphenylphosphine, a base and the like, inorganic acids such as hydrochloric acid, hydrobromic acid, hydroiodic acid, phosphorus tribromide, phosphorus pentabromide, phosphorus trichloride, phosphorus pentachloride, iodine, bromine, chlorine, thionyl halide, α-haloenamine and the like. The reaction conditions are, for example, in an organic solvent such as a halogenic solvent (e.g., methylene chloride and the like), an ether solvent (e.g., tetrahydrofuran and the like) and the like at −30° C. to 130° C. for about 10 min to about 6 hr. When an inorganic acid is used, the reaction can be performed in an aqueous solution or a two-layer system of an organic solvent such as toluene and the like and water. Examples of the reagent used when $X^k$ is sulfonyloxy include a combination of sulfonyl chloride (e.g., methanesulfonyl chloride. toluenesulfonyl chloride and the like) and an organic base (e.g., triethylamine, pyridine and the like). The reaction conditions are, for example, in an organic solvent such as a halogenic solvent (e.g., methylene chloride and the like), an ether solvent (e.g., tetrahydrofuran and the like), and the like at −30° C.-50° C. for about 5 min-about 3 hr. After the reaction, the object product can be obtained by performing purification and the like by a conventional method.

In the fifth step, intermediate (XIII-7) having a leaving group PB containing phosphorus is obtained by reacting intermediate (XIII-6) having a leaving group $X^k$ with a phosphorus compound. When PB is triarylphosphonium, intermediate (XIII-7) can be obtained by reacting intermediate (XIII-6) with triarylphosphine. The reaction conditions are, for example, in an inert solvent such as diethyl ether, benzene, toluene and the like at room temperature—refluxing temperature for about 30 min-about 12 hr. After the reaction, the object product can be obtained by solvent evaporation, cooling and addition of poorly soluble solvent such as diisopropyl ether, hexane and the like, as necessary, after which collection of the precipitated solid by filtration. When PB is $P(O)(OR^i)_2$, intermediate (XIII-7) can be obtained by Arbuzov reaction by reacting intermediate (XIII-6) with phosphite triester. The reaction conditions are, for example, without solvent or in an inert solvent such as xylene and the like at 50° C.-170° C. for about 30 min-about 12 hr. After the reaction, the object product can be obtained by evaporation or distillation of excess phosphite triester. When PB is $P(O)(OR^i)_2$, intermediate (XIII-7) can also be obtained by reacting intermediate (XIII-6) with phosphonic diester in the presence of additives such as tetraalkylammonium, cesium carbonate and the like. The reaction conditions are, for example, in an inert solvent such as tetrahydrofuran, xylene and the like or a polar solvent such as N,N-dimethylformamide and the like, under ice-cooling to 50° C. for about 30 min-about 6 hr. After the reaction, the object product can be obtained by performing purification and the like by a conventional method.

In the sixth step, $A_1'H$ intermediate (XIII-9) is obtained by condensing intermediate (XIII-7) containing phosphoru c and aldehyde (XIII-8) synthesized by a known method (e.g., Tetrahedron, vol. 57 (2001), pp. 6531-6538, and Journal of Organic Chemistry, vol. 69 (2004), pp. 7765-7768), successively reducing the obtained olefin, and deprotecting protecting group $R^b$. When PB is triarylphosphonium, the conventional conditions for Wittig reaction are used. For example, reaction is performed in an ether solvent such as tetrahydrofuran and the like, using a base such as sodium hydride, potassium t-butoxide and the like at −30° C. to refluxing temperature for about 30 min-about 12 hr. A Z form can be preferentially obtained by reaction in an aprotic polar solvent under salt-free conditions, or an E form can also be preferentially obtained by Schlosser's modified method. After the reaction, the object product can be obtained by performing purification and the like by a conventional method. When PB is $P(O)(OR^i)_2$, the conventional conditions of Horner-Wadsworth-Emmons reaction are used. For example, the reaction is performed in a hydrocarbon solvent such as benzene and the like, or an ether solvent such as tetrahydrofuran and the like using a base such as sodium hydride, potassium t-butoxide, lithium hexamethyldisilazane and the like at −20° C.—refluxing temperature for about 30 min-about 12 hr. An E form olefin can be preferentially obtained. After the reaction, the object product can be obtained by performing purification and the like by a conventional method. When V is alkylene having 1-4 carbon atoms, the reagent to be used for the subsequent reduction of double bond is not limited as long as it is used for general reduction of olefin. For example, catalytic hydrogenation using a heterogeneous catalyst such as palladium carbon, Raney-nickel and the like can be mentioned. The reaction conditions are, for example, in an alcoholic solvent such as ethanol and the like, an ether solvent such as 1,4-dioxane and the like, or a hydrocarbon solvent such as toluene and the like at 1-20 atm of hydrogen pressure under ice-cooling to reflux for 30 min-1 week. An acid such as acetic acid and the like or a base such as triethylamine and the like can be added to the reaction mixture depending on the reaction speed, stabilities of the compounds used and the like. After the reaction, the object product can be obtained by performing purification and the like by a conventional method. The conditions of the subsequent deprotection of the protecting group $R^b$ are not particularly limited as long as they are used for the deprotection of conventional protecting groups. For example, when $R^b$ is methyl, a method of using a Lewis acid such as boron tribromide and the like in methylene chloride can be used. When $R^b$ is acyl such as acetyl and the like, a method of using an inorganic base such as sodium hydroxide and the like in a mixed solvent of an alcoholic solvent and water can be used. When $R^b$ is an ether type protecting group such as methoxymethyl, tetrahydropyranyl, t-butyl and the like, a method of using an acid such as hydrochloric acid, trifluoroacetic acid and the like can be used. When $R^b$ is a protecting group (e.g., benzyl, substituted benzyl, benzyloxymethyl and the like) which can also be deprotected by hydrogenolysis or catalytic hydrogenation, the deprotection of $R^b$ can be performed simultaneously with the aforementioned reduction of the double bond. When V is alkenylene having 2-4 carbon atoms, deprotection of protecting group $R^b$ is performed without reduction of the double bond. The conditions for deprotection are not particularly limited as long as alkenylene is not damaged. For example, when $R^i$ is 4-methoxybenzyl, an oxidation reaction with 2,3-dichloro-5,6-dicyano-1,4-benzoquinone (DDQ) and the like can be mentioned, and when $R^b$ is silyl such as trialkylsilyl and the like, deprotection by an inorganic acid such as hydrochloric acid and the like or a fluorine compound such as tetrabutylammonium fluoride and the like can be mentioned. When $B_1-C_1$, which is a partial structure of compound (I-1) of the present invention, is not influenced by the above-mentioned reduction conditions, $B_1-C_1$, which is a partial structure of compound (I-1) of the present invention, can be used for $R^b$.

In this case, the deprotection of $R^b$ is not necessary, and conversion of $A_1'H$ to $A_1'$-$B_1$-$C_1$ in the final step can also be omitted.

Compound (I-9) of the present invention can be synthesized from compound (XIII-9) by a method similar to schemes (I) and (II).

The compound (I) of the present invention described in the other schemes (e.g., compound (I-1'), compound (I-3), compound (I-4) etc.) wherein V is alkylene having 1-4 carbon atoms or alkenylene having 2-4 carbon atoms can be obtained by reacting leaving group PB containing phosphorus with an aldehyde in the same manner as in scheme (XII).

11) Of the compounds of the present invention, compound (I-10) which is a compound represented by the formula (I) wherein V is alkylene having 1-4 carbon atoms, and $R_2$ is a hydroxymethyl group is also synthesized from the following scheme (XIII).

Scheme (XIII)

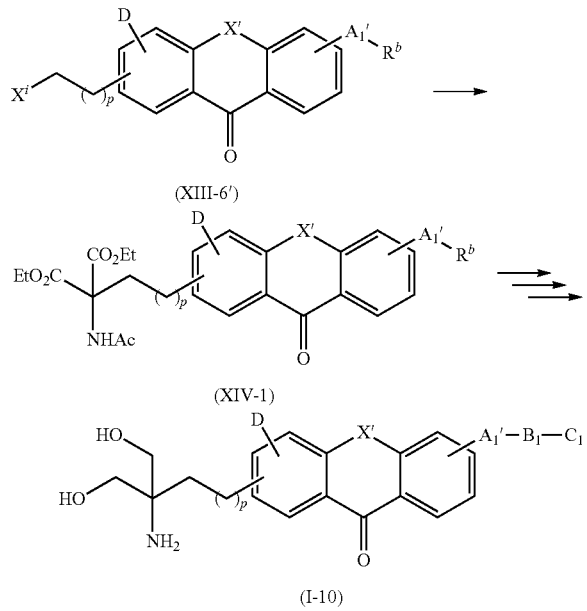

wherein $A_1'$, X' are the same as those defined for each symbol in scheme (I), $R^b$ is a protecting group, $X^1$ is a leaving group, p is 0-3, and $B_1$, $C_1$ and D are the same as those defined for each symbol in the formula (I).

In the formula, $R^b$ is the same as that defined for the symbol in scheme (I). The leaving group for $X^1$ is not particularly limited as long as it is eliminated in the reaction of intermediate (XIII-6') with aminomalonic acid. For example, a halogen atom (specifically, iodine atom, bromine atom, chlorine atom and the like), methanesulfonyloxy, toluenesulfonyloxy and the like can be mentioned.

In the first step, intermediate (XIV-1) is obtained by a condensation reaction of intermediate (XIII-6') obtained by a method similar to the synthesis of compound (XIII-6) and acetamido diethyl malonate. This step can be performed in a polar solvent such as N,N-dimethylformamide, dimethylsulfoxide and the like or an ether solvent such as tetrahydrofuran and the like in the presence of a base. As the base, sodium hydride, potassium hydroxide, potassium t-butoxide and the like can be mentioned. The reaction conditions include, for example, under ice-cooling—about 50° C. for about 10 min-about 5 hr. After the reaction, the object product can be obtained by performing purification and the like by a conventional method.

The obtained intermediate (XIV-1) can be led to compound (I-10) of the present invention by a known method (e.g., Journal of Medicinal Chemistry, vol. 43 (2000), pp. 2946-2961). $A_1'H$ can be converted to $A_1'$-$B_1$-$C_1$ by synthesizing according to a method similar to schemes (I) and (II).

12) Of the compounds of the present invention, compound (I-11) which is a compound represented by the formula (I) wherein $R_1$, $R_3$, $R_4$ are each a hydrogen atom, and $R_2$ is ω-fluoroalkyl is also synthesized by the following scheme (XIV).

Scheme (XIV)

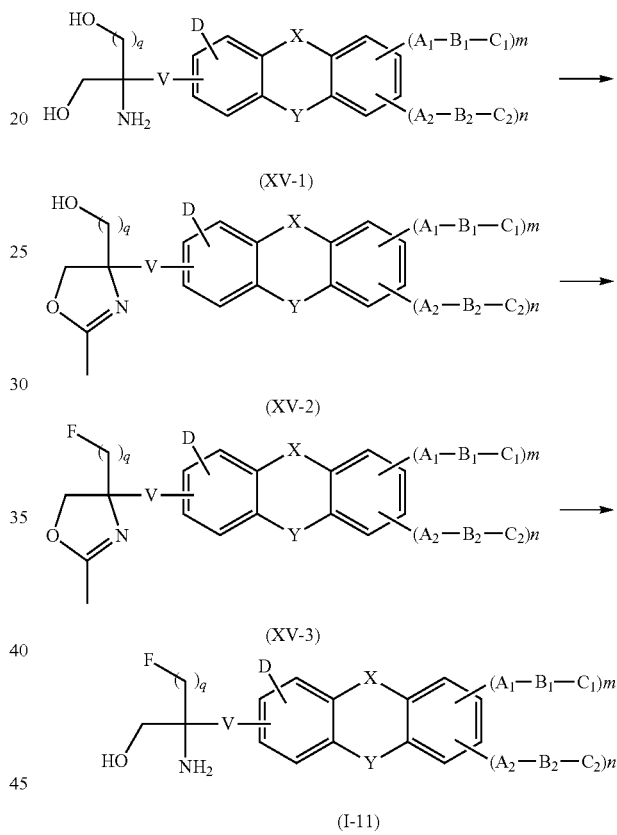

wherein q is an integer of 1-4, and X, Y, V, $A_1$, $B_1$, $C_1$, $A_2$, $B_2$, $C_2$, m, n and D are the same as those defined for each symbol in the formula (I).

In the first step, oxazoline form (XV-2) is synthesized by protecting compound (XV-1) of the formula (I) wherein R is a hydrogen atom, and $R_2$ is ω-hydroxyalkyl. This step can be performed by reacting in a polar solvent such as acetonitrile, N,N-dimethylformamide and the like, a halogenic solvent such as methylene chloride and the like, or a hydrocarbon solvent such as toluene and the like, using orthoacetic acid ester as a reagent. In addition, for promotion of the reaction, a base such as N,N-diisopropylethylamine and the like, or an acid such as p-toluenesulfonic acid and the like can be added. The reaction conditions are, for example, at room temperature—refluxing for about 30 min-about 12 hr. After the reaction, the object product can be obtained by performing purification and the like by a conventional method.

In the second step, fluorinated compound (XV-3) is synthesized by fluorinating the hydroxy group of compound (XV-2). As the fluorination reagent, (diethylamino)sulfur trifluoride (DAST), 2,2-difluoro-1,3-dimethylimidazolidine (DFI) and the like can be mentioned. In this step, the reaction can be performed in a halogenic solvent such as methylene chloride and the like or a hydrocarbon solvent such as hexane and the like. The reaction conditions are, for example, at −78° C.—room temperature for about 30 min-about 12 hr. After the reaction, the object product can be obtained by performing purification and the like by a conventional method. This step can also be performed by a method including converting the hydroxy group of compound (XV-2) to the corresponding sulfonate form, and subsequently reacting same with fluoride ion. For example, when p-toluenesulfonyl fluoride and tetrabutylammonium fluoride (TBAF) are used, the reaction is performed in an ether solvent such as tetrahydrofuran and the like at room temperature—80° C. for about 1 hr-about 24 hr. In this reaction, a dehydrating agent such as molecular sieves and the like can be added. After the reaction, the object product can be obtained by performing purification and the like by a conventional method.

In the third step, compound (I-11) of the present invention is prepared by deprotecting compound (XV-3). This step can be performed by a conventional deprotection reaction. Specifically, it can be performed using an acid such as hydrochloric acid, trifluoroacetic acid and the like. The reaction conditions are, for example, in an alcoholic solvent such as ethanol and the like or a mixed solvent thereof with water at room temperature—100° C. for about 30 min-about 12 hr. The object product can be obtained by purification and the like of the reaction mixture by a conventional method.

13) Of the compounds of the present invention, the compound which is a compound represented by the formula (I) wherein V is alkylene having 2-4 carbon atoms or alkylene having 2-4 carbon atoms can also be synthesized by using compound (XVI-3) or compound (XVI-3') synthesized by the following scheme (XV) instead of compound (II-7) in scheme (I).

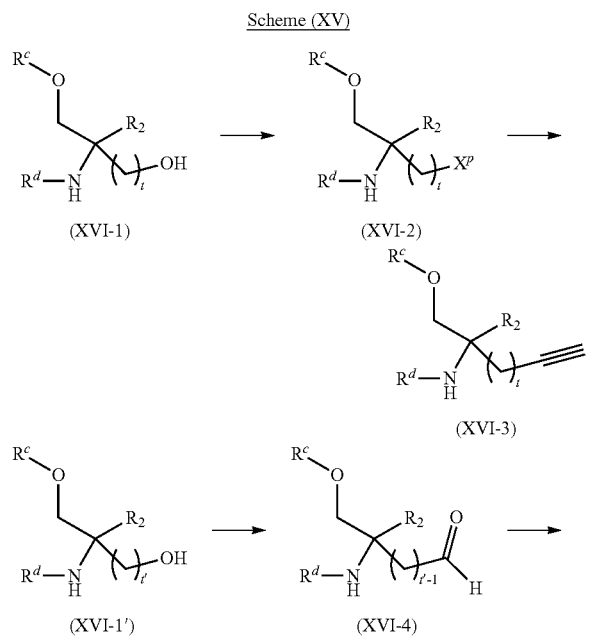

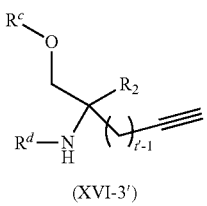

wherein $X^p$ is a leaving group, t is 0-2, t' is 1-3, and $R_2$ is the same as that defined for the symbol in the formula (I).

In the formula, $R^c$, $R^d$ are the same as those defined above. The leaving group $X^p$ is not particularly limited as long as it is eliminated during the introduction of acetylene. For example, a halogen atom (specifically, iodine atom, bromine atom, chlorine atom and the like), methanesulfonyloxy, toluenesulfonyloxy and the like can be mentioned.

The first step for synthesizing compound (XVI-2) is conversion of a hydroxy group to leaving group $X^p$. For this step, reaction conditions similar to those for the step from compound (XIII-5) to compound (XIII-6) in scheme (XII) can be mentioned.

The second step is an introduction reaction of acetylene into a leaving group. While the conditions are not particularly limited as long as acetylene can be introduced, for example, metal acetylide such as lithium acetylide and the like is reacted. The reaction conditions are in a solvent such as dimethyl sulfoxide, tetrahydrofuran and the like at −50° C.-room temperature.

Compound (XVI-3') can be synthesized from compound (XVI-1') via compound (XVI-4). The step for synthesizing compound (XVI-4) is an oxidation reaction, and is not particularly limited as long as hydroxymethyl group can be oxidized to aldehyde. For example, conditions for the Dess-Martin reaction using a Dess-Martin periodinane reagent, the Swern oxidation using oxalyl chloride and DMSO and the like can be mentioned. As the conditions for converting aldehyde (XVI-4) to compound (XVI-3'), the conditions for the Seyferth-Gilbert alkyne synthesis reaction using tosyl azide and phosphonic acid ester, which are described in SYNTHESIS, 2006, pp. 753-755, can be mentioned.

14) Of the compounds of the present invention, compound (I-12) represented by the formula (I) wherein $R_1$ is P(=O)(OH)$_2$, and $R_3$ and $R_4$ are both hydrogen atoms is synthesized by the following scheme (XVI).

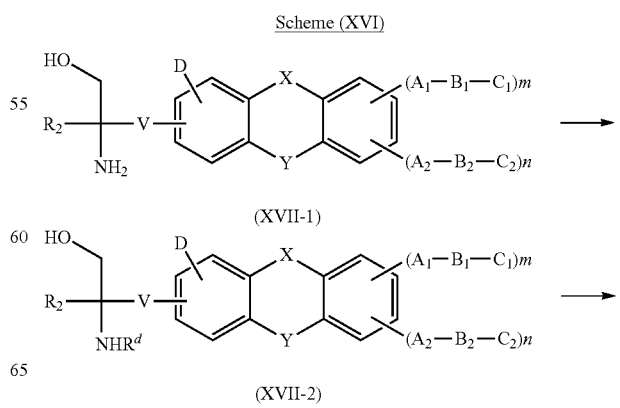

-continued

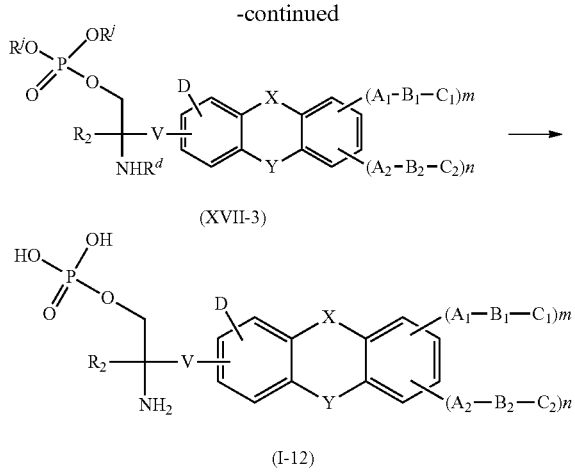

(XVII-3)

(I-12)

wherein $R^d$, $R^j$ are protecting groups, and $R_2$, X, Y, V, $A_1$, $B_1$, $C_1$, $A_2$, $B_2$, $C_2$, m, n and D are the same as those defined for each symbol in the formula (I).

$R^d$ in the formula is the same as that defined above. When $R_2$ of compound (XVII-2) contains a hydroxy group, the hydroxy group may be protected by a protecting group $R^e$ ($R^e$ is the same as that defined above). When $R_2$ is protected hydroxymethyl or protected hydroxyethyl, its protecting group $R^e$ is bonded to $R^d$ or the nitrogen atom to which $R^d$ is bonded to form the following cyclic compound (XVII-2', XVII-2"):

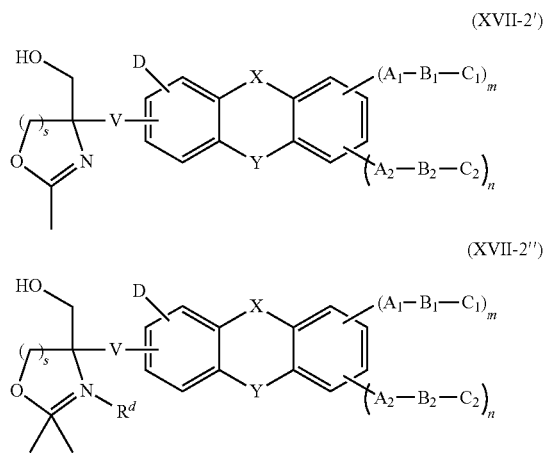

(XVII-2')

(XVII-2")

wherein s is 1 or 2, and other symbols are the same as those defined for scheme (XVI), whereby amino group and hydroxy group can be protected. The protecting group for $R^j$ in the formula is not particularly limited as long as it protects phosphate group. For example, alkyl (preferably having a carbon number of about 1-6, specifically t-butyl and the like), benzyl, phenyl and the like can be mentioned.

In the first step, amino group-protected compound (XVII-2) is synthesized by protecting the amino group of compound (XVII-1) which is a compound of the formula (I) wherein $R_1$ is a hydrogen atom. This step can be performed by a conventional amino group protection reaction. Specifically, when acyl, alkyloxycarbonyl, benzyloxycarbonyl or the like is used as protecting group $R^d$, this step can be performed in alcohol such as methanol and the like, or a two-layer system or mixture of water and an organic solvent such as ethyl acetate, chloroform and the like. Examples of the reagent to be used include acid chloride such as acetyl chloride, benzyloxycarbonyl chloride and the like, acid anhydride such as acetic anhydride, di-t-butyl dicarbonate and the like. An organic base such as triethylamine and the like, or an inorganic base such as sodium bicarbonate and the like can be added as a reaction promoter for this reaction. The reaction conditions are, for example, under ice-cooling—50° C. for about 30 min-about 24 hr. After the reaction, the amino group-protected compound (XVII-2) can be obtained by performing purification and the like by a conventional method. When amino group and hydroxy group contained in $R_2$ are protected simultaneously as an oxazoline of the formula (XVII-2'), this step can be performed by the reaction in a polar solvent such as acetonitrile, N,N-dimethylformamide and the like, a halogenic solvent such as methylene chloride and the like, or a hydrocarbon solvent such as toluene and the like, using orthoacetic acid ester as a reagent. In addition, for promotion of the reaction, a base such as N,N-diisopropylethylamine and the like, or an acid such as p-toluenesulfonic acid and the like can be added. The reaction conditions are, for example, at room temperature—refluxing for about 30 min-about 12 hr. After the reaction, the amino group-protected compound (XVII-2') can be obtained by performing purification and the like by a conventional method.

In the second step, phosphorylation compound (XVII-3) is synthesized by reacting amino group-protected compound (XVII-2) with a phosphorylation reagent (e.g., phosphorous acid triester, phosphoryl chloride, phosphoramidite and oxidant, pyrophosphoric acid tetrabenzylester and the like). When phosphorous acid ester is used as the phosphorylation reagent, this step can be performed under non-aqueous conditions, preferably in a halogenic solvent such as methylene chloride and the like and using an organic base such as pyridine, triethylamine and the like and an additive such as carbon tetrabromide and the like. The reaction conditions include under ice-cooling—80° C. for about 5-about 24 hr. After the reaction, the object product can be obtained by performing purification and the like by a conventional method. For this reaction, a conventional phosphorylating reagent (phosphorus chloride and base, phosphoramidite and oxidant and the like) can also be reacted by a known method and synthesized. For example, when phosphoramidite and an oxidant are used, reaction is performed in a halogenic solvent such as methylene chloride and the like, an ether solvent such as tetrahydrofuran and the like, a polar solvent such as acetonitrile and the like or a mixed solvent thereof, using phosphoramidite such as di-t-butyl diisopropylphosphoramidite and the like under ice-cooling—50° C. for about 10 min-5 hr. 1H-Tetrazole and the like can be added as a reaction promoter for this reaction. For an oxidation reaction of phosphorus successively performed after the phosphorylation, organic peroxide such as m-chloroperbenzoic acid, t-butyl hydroperoxide and the like or an inorganic peroxide such as hydrogen peroxide and the like can be used. The reaction is performed under ice-cooling—50° C. for about 3 min-about 1 hr. After the reaction, phosphorylate (XVII-3) can be obtained by performing purification and the like by a conventional method.

In the third step, compound (I-12) of the present invention is prepared from a phosphorylated form (XVII-3). This step can be performed by a conventional deprotection. Specifically, the step can be performed by hydrogenolysis using an acid such as hydrochloric acid, trifluoroacetic acid and the like, a Lewis acid such as trimethylsilyl bromide and the like. When hydrogenolysis is used for this reaction, this step is performed, for example, in an alcoholic solvent such as methanol and the like using a catalyst such as palladium carbon and the like under a hydrogen atmosphere. The reaction conditions are, for example, at room temperature—60° C. for about 1-about 24 hr. After the reaction, the object product can be obtained by performing purification and the like by a conventional method. The reaction conditions when an acid is used for this reaction are, for example, in an alcoholic solvent such as ethanol and the like or a mixed solvent thereof with water at room temperature—100° C. for about 30 min-12 hr. After the reaction, the object product can be obtained by performing purification and the like by a conventional method. A compound wherein one of $R_3$, $R_4$ is a hydrogen atom, and the other is alkyl having 1-4 carbon atoms can also be synthesized by a similar method.

15) Of the compounds of the present invention, a compound which is a compound represented by the formula (I) wherein R is $P(=O)(OH)_2$, and $R_3$ and $R_4$ are each alkyl having 1-4 carbon atoms can be synthesized by using, as a starting material, a compound represented by the following formula (XVII-1') instead of compound (XVII-1):

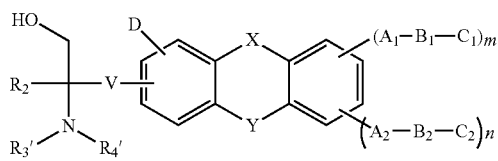

(XVII-1')

wherein $R_3'$ and $R_4'$ are each alkyl having 1-4 carbon atoms, and each of other symbols is the same as that defined for scheme (XVI), omitting the first step of scheme (XVI), and by a similar method.

The compound of the present invention can be converted to an acid addition salt as necessary by treatment with an acid in a suitable solvent (water, alcohol, ether and the like). In addition, the obtained compound of the present invention can be converted to a hydrate or solvate by treatment with water, water-containing solvent or other solvent (e.g., alcohol etc.).

The thus-obtained compound of the present invention can be isolated and purified by a separation means known per se, for example, concentration, concentration under reduced pressure, solvent extraction, crystallization, recrystallization, phase transfer, chromatography and the like. When the compound of the present invention is obtained as a free form, it can be converted to an object salt by a method known per se or a method analogous thereto, and when it is obtained as a salt, it can be converted to a free form or other object salt by a method known per se or a method analogous thereto.

When the compound of the present invention has isomers such as optical isomer, stereoisomer, regioisomer, rotamer and the like, any one of the isomers and mixtures are also encompassed in the compound of the present invention. For example, when the compound of the present invention has an optical isomer, an optical isomer resolved from a racemate is also encompassed in the compound of the present invention. Such isomers can be obtained as single species by synthetic method and separation method known per se (e.g., concentration, solvent extraction, column chromatography, recrystallization).

The compound of the present invention may be a crystal, and such crystal is encompassed in the compound of the present invention whether the crystal form is monomorphous or crystal form mixture. The crystal can be produced by crystallization by applying a crystallization method known per se. In addition, the compound of the present invention may be a pharmaceutically acceptable cocrystal or cocrystal salt. As used herein, the cocrystal or cocrystal salt means a crystalline substance composed of two or more kinds of unique solid at room temperature, each having different physical properties (e.g., structure, melting point, melting heat, hygroscopicity, stability). The cocrystal and cocrystal salt can be produced according to a cocrystallization method known per se.

A compound labeled with an isotope (e.g., $^2H$, $^3H$, $^{13}C$, $^{14}C$, $^{15}N$, $^{35}S$) and the like is also encompassed in the compound of the present invention.

The compound of the present invention is useful for the treatment or prophylaxis of autoimmune diseases (e.g., rheumatoid arthritis, multiple sclerosis, encephalomyelitis, systemic lupus erythematosus, lupus nephritis, nephrosis syndrome, psoriasis, Type I diabetes mellitus etc.); prophylaxis or suppression of resistance or acute rejection or chronic rejection of transplantation of organ or tissue (e.g., including transplantation and heterogenous transplantation of heart, kidney, liver, lung, bone marrow, cornea, pancreas, small intestine, extremity, muscle, nerve, fatty marrow, duodenum, skin, islet cells of the pancreas and the like) in mammals such as human, dog, cat, bovine, horse, swine, monkey, mouse and the like; graft-versus-host (GvH) disease due to bone marrow transplantation; and the treatment or prophylaxis of allergic diseases (e.g., atopic dermatitis, allergic rhinitis, asthma etc.).

The subject of administration of the compound of the present invention includes mammals such as human, dog, cat, bovine, horse, swine, monkey, mouse and the like, and the like.

In the present specification, the "prophylaxis" means the act of administering the compound of the present invention or a pharmaceutical composition containing the compound to an individual who has not developed a disease or symptom. In addition, the "treatment" means the act of administering the compound of the present invention or a pharmaceutical composition containing the compound to an individual who has already developed a disease or disorder or symptom. Accordingly, the act of administration to an individual who has already developed a disease or disorder or symptom for the prevention of aggravation of the symptom and the like, prevention of attacks or prevention of recurrence is one embodiment of the "treatment".

When the compound of the present invention is used as a medicament, the compound of the present invention is mixed with a pharmaceutically acceptable carrier (excipient, binder, disintegrant, corrigent, flavor, emulsifier, diluent, solubilizer and the like) and the obtained pharmaceutical composition or preparation (oral preparation, injection and the like) can be orally or parenterally administered. A pharmaceutical composition can be prepared according to a general method.

In the present specification, parenteral includes subcutaneous injection, intravenous injection, intramuscular injection, intraperitoneal injection, drip method or topical administration (transdermal administration, transocular administration, transpulmonic•bronchial administration, transnasal administration, transrectal administration and the like) and the like.

The content of the compound of the present invention that can be combined with a carrier can be varied depending on the individual to be treated and particular dosage form.

However, the particular dose of particular patients is determined depending on various factors including age, body weight, general health conditions, sex, diet, administration time, administration method, clearance rate and severity of the particular disease under treatment.

The dose of the compound of the present invention is determined in consideration of the age, body weight, general health conditions, sex, diet, administration time, administration method, clearance rate and severity of the disease of patients under treatment, as well as other factors. The compound of the present invention does not affect the heart rate and can be used safely. Its daily dose varies depending on the condition and body weight of patients, the kind of compound, administration route and the like. For example, for parenteral administration, it is administered subcutaneously, intravenously, intramuscularly, transdermally, transocularly, transpulmonically or bronchially, transnasally or rectally at about 0.01-50 mg/patient/day, and for oral administration, it is administered at about 0.01-150 mg/patient/day.

EXAMPLES

The present invention is explained in detail in the following by referring to Examples and Experimental Examples, which are not to be construed as limitative.

Reference Example 1

Synthesis of [2-acetoxymethyl-2-acetylamino-4-(7-hydroxy-9-oxo-9H-thioxanthen-2-yl)butyl]acetate 1) Synthesis of 5-chloro-2-(4-methoxyphenylthio)benzoic acid (Reference Example compound 1-1)

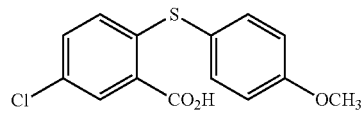 [SMILES: COc1ccc(Sc2ccc(Cl)cc2C(=O)O)cc1]

A mixture of 5-chloro-2-iodobenzoic acid (25.0 g), 4-methoxybenzenethiol (10.9 mL), potassium hydroxide (19.3 g), copper powder (0.60 g) and water (300 ml) was stirred under reflux for 9 hr. The reaction mixture was poured into a mixed solution of ethyl acetate and water, the aqueous layer was acidified with concentrated hydrochloric acid with stirring, and the organic layer was separated. The organic layer was washed with saturated brine, and dried over anhydrous magnesium sulfate. The solvent was evaporated under reduced pressure and the residue was washed with diisopropyl ether and hexane (1:10) to give Reference Example compound 1-1 (25.0 g) as a white powder.

$^1$H-NMR (CDCl$_3$) δ (ppm): 3.87 (3H, s), 6.69 (1H, d, J=8.7 Hz), 6.99 (2H, d, J=8.8 Hz), 7.23 (1H, dd, J=2.6, 9.0 Hz), 7.49 (2H, d, J=8.8 Hz), 8.09 (1H, d, J=2.4 Hz).

2) Synthesis of 2-chloro-7-methoxy-9H-thioxanthen-9-one (Reference Example compound 1-2)

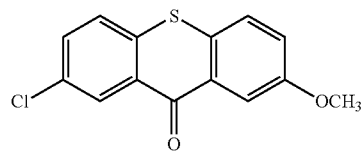 [SMILES: COc1ccc2sc3ccc(Cl)cc3c(=O)c2c1]

To Reference Example compound 1-1 (25.0 g) was added sulfuric acid (120 ml) under ice-cooling, and the mixture was stirred at 5° C. for 25 min while pulverizing powder lumps. The reaction mixture was poured into ice water (1000 ml), and the mixture was stirred at room temperature for 40 min. The precipitated solid was collected by filtration, suspended in 0.5M aqueous sodium hydroxide solution (1000 ml), and the suspension was stirred at room temperature for 10 min. The solid was collected by filtration and dried to give Reference Example compound 1-2 (9.30 g) as a yellow powder.

$^1$H-NMR (DMSO-d$_6$) δ (ppm): 3.91 (3H, s), 7.48 (1H, dd, J=3.0, 8.7 Hz) 7.84 (1H, dd, J=2.8, 8.8 Hz), 7.85 (1H, d, J=8.8 Hz), 7.93 (1H, d, J=3.0 Hz), 7.95 (1H, d, J=8.7 Hz), 8.41 (1H, d, J=2.3 Hz).

3) Synthesis of 2-chloro-7-hydroxy-9H-thioxanthen-9-one (Reference Example compound 1-3)

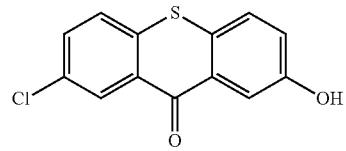 [SMILES: O=c1c2cc(O)ccc2sc2ccc(Cl)cc12]

To a solution of Reference Example compound 1-2 (9.30 g) in 1,2-dichloroethane (120 ml) was added a 1M solution (168 ml) of boron tribromide in methylene chloride, and the mixture was stirred at 60° C. for 10 hr. Under ice-cooling, methanol (250 ml) was gradually added, and the solvent was evaporated under reduced pressure. Water (500 ml) was added to the residue, and the precipitated solid was collected by filtration. The solid was suspended in chloroform (200 ml), and collected by filtration. The obtained solid was suspended in diethyl ether (200 ml) and collected by filtration to give Reference Example compound 1-3 (4.80 g) as a brown powder.

$^1$H-NMR (DMSO-d$_6$) δ (ppm): 7.31 (1H, dd, J=2.5, 8.6 Hz), 7.74 (1H, d, J=8.6 Hz), 7.82 (1H, dd, J=2.4, 8.6 Hz), 7.85 (1H, d, J=2.6 Hz), 7.92 (1H, d, J=8.7 Hz), 8.38 (1H, d, J=2.4 Hz), 10.24 (1H, s).

4) Synthesis of 2-benzyloxy-7-chloro-9H-thioxanthen-9-one (Reference Example compound 1-4)

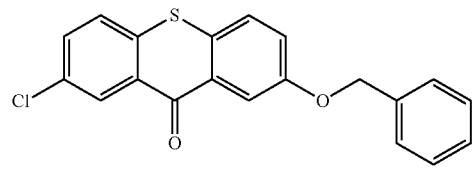 [SMILES: O=c1c2cc(Cl)ccc2sc2ccc(OCc3ccccc3)cc12]

To a solution of Reference Example compound 1-3 (6.15 g) in N,N-dimethylformamide (50 ml) were added potassium carbonate (9.71 g) and benzyl bromide (2.92 ml), and the mixture was stirred at room temperature for 2 hr and further at 50° C. for 2 hr. The reaction mixture was added to water, and the precipitated solid was collected by filtration, and washed with water and diisopropyl ether to give Reference Example compound 1-4 (7.49 g) as a brown powder.

$^1$H-NMR (DMSO-d$_6$) δ (ppm): 5.28 (2H, s), 7.33-7.37 (1H, m) 7.42 (2H, t, J=7.4 Hz), 7.51 (2H, d, J=7.2 Hz), 7.55 (1H, dd, J=2.9, 8.7 Hz), 7.84 (1H, dd, J=2.4, 8.7 Hz), 7.86 (1H, d, J=9.0 Hz), 7.95 (1H, d, J=8.7 Hz), 8.02 (1H, d, J=3.0 Hz), 8.40 (1H, d, J=2.4 Hz).

5) Synthesis of t-butyl {5-[(7-benzyloxy-9-oxo-9H-thioxanthen-2-yl)ethynyl]-2,2-dimethyl-1,3-dioxan-5-yl}carbamate (Reference Example compound 1-5)

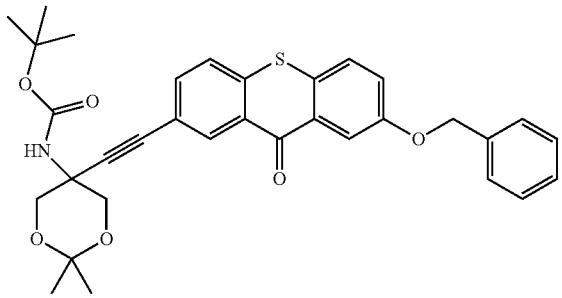 [SMILES: CC(C)(C)OC(=O)NC1(C#Cc2ccc3sc4ccc(OCc5ccccc5)cc4c(=O)c3c2)COC(C)(C)OC1]

A mixture of Reference Example compound 1-4 (8.83 g), t-butyl (5-ethynyl-2,2-dimethyl-1,3-dioxan-5-yl)carbamate (6.71 g), cesium carbonate (22.4 g), 2-dicyclohexylphosphino-2',4',6'-triisopropylbiphenyl (715 mg), dichlorobis(acetonitrile)palladium(II) (130 mg) and acetonitrile (220 ml) was stirred under reflux for 10 hr. The reaction mixture was poured into water (1200 ml), and the mixture was extracted with ethyl acetate. The organic layer was washed with saturated brine, and dried over anhydrous magnesium sulfate. The solvent was evaporated under reduced pressure and the residue was purified by silica gel column chromatography, and the obtained residue was washed with a mixture of diethyl ether and hexane (1:2) to give Reference Example compound 1-5 (9.45 g) as a yellow powder.

$^1$H-NMR (CDCl$_3$) δ (ppm): 1.47 (3H, s), 1.50 (9H, s), 1.53 (3H, s), 4.09 (2H, d, J=11.4 Hz), 4.13 (2H, d, J=11.4 Hz), 5.21 (2H, s), 5.24 (1H, brs),7.34-7.37 (2H, m), 7.42 (2H, t, J=7.4 Hz), 7.48-7.53 (4H, m), 7.63 (1H, dd, J=1.7, 8.5 Hz), 8.18 (1H, d, J=2.7 Hz), 8.68 (1H, d, J=1.6 Hz).

6) Synthesis of [2-acetoxymethyl-2-acetylamino-4-(7-benzyloxy-9-oxo-9H-thioxanthen-2-yl)butyl]acetate (Reference Example compound 1-6)

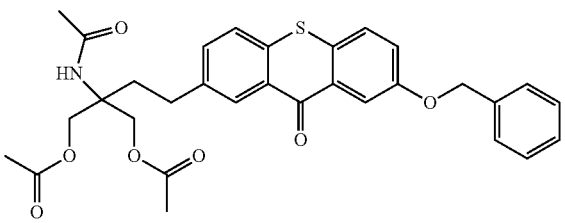 [SMILES: CC(=O)NC(CCc1ccc2sc3ccc(OCc4ccccc4)cc3c(=O)c2c1)(COC(C)=O)COC(C)=O]

To a solution of Reference Example compound 1-5 (9.45 g) in 1,4-dioxane (250 ml) was added 10% palladium carbon (containing about 50% water, 9.5 g), and the mixture was stirred at room temperature for 7 hr under a hydrogen atmosphere. The reaction mixture was filtered through celite, concentrated, and a mixture of the obtained residue, potassium carbonate (6.84 g), benzyl bromide (1.96 ml) and N,N-dimethylformamide (40 ml) was stirred at 50° C. for 1.5 hr. The reaction mixture was added to water, and the mixture was extracted with ethyl acetate. The organic layer was washed with saturated brine, dried over anhydrous magnesium sulfate, and the solvent was evaporated under reduced pressure. To the obtained residue were added 2M hydrogen chloride ethanol solution (150 ml) and concentrated hydrochloric acid (20 ml), and the mixture was stirred at 60° C. for 5 hr. The reaction mixture was concentrated under reduced pressure, ethyl acetate (100 ml) was added, and the precipitated solid was collected by filtration. To the obtained solid were added pyridine (60 ml) and acetic anhydride (50 ml) under ice-cooling, and the mixture was stirred under ice-cooling for 1 hr and further at room temperature for 16 hr. The reaction mixture was added to ice water (500 ml) and ethyl acetate (800 ml), and saturated aqueous sodium hydrogen carbonate (500 ml) was gradually added. The organic layer was separated, washed with 1M hydrochloric acid, saturated aqueous sodium hydrogen carbonate and saturated brine, dried over anhydrous magnesium sulfate, and the solvent was evaporated under reduced pressure. The obtained residue was washed with a mixture of diethyl ether and diisopropyl ether to give Reference Example compound 1-6 (6.80 g) as a yellow powder.

$^1$H-NMR (CDCl$_3$) δ (ppm): 2.00 (3H, s), 2.12 (6H, s), 2.27-2.31 (2H, m), 2.75-2.79 (2H, m), 4.37 (4H, s), 5.22 (2H, s), 5.76 (1H, brs), 7.34 (1H, dd, J=2.8, 8.7 Hz), 7.35-7.37 (1H, m), 7.42 (2H, t, J=7.5 Hz), 7.47-7.55 (5H, m), 8.19 (1H, d, J=2.6 Hz), 8.44 (1H, d, J=1.4 Hz).

7) Synthesis of [2-acetoxymethyl-2-acetylamino-4-(7-hydroxy-9-oxo-9H-thioxanthen-2-yl)butyl]acetate (Reference Example compound 1)

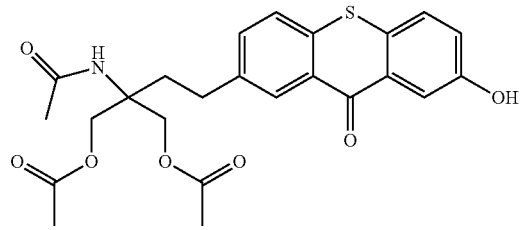 [SMILES: CC(=O)NC(CCc1ccc2sc3ccc(O)cc3c(=O)c2c1)(COC(C)=O)COC(C)=O]

To a suspension of Reference Example compound 1-6 (6.80 g) in methylene chloride (26 ml) was added iodotrimethylsilane (2.3 mL), and the mixture was stirred at room temperature for 3 days. Iodotrimethylsilane (2.3 mL) was further added, and the mixture was stirred at room temperature for 1 day. To the reaction mixture was added methanol under ice-cooling to quench the reaction. Water was added, and the mixture was extracted with methylene chloride. The organic layer was dried over anhydrous sodium sulfate, and the solvent was evaporated under reduced pressure. The obtained residue was purified by silica gel column chromatography to give Reference Example compound 1 (3.09 g) as a yellow powder.

$^1$H-NMR (DMSO-d$_6$) δ (ppm): 1.87 (3H, s), 2.02-2.06 (2H, m), 2.04 (6H, s), 2.69-2.73 (2H, m), 4.22 (2H, d, J=11.1 Hz), 4.31 (2H, d, J=11.1 Hz), 7.27 (1H, dd, J=2.7, 8.9 Hz), 7.58 (1H, dd, J=1.7, 8.3 Hz), 7.69 (1H, d, J=8.7 Hz), 7.73 (1H, brs), 7.75 (1H, d, J=8.3 Hz), 7.86 (1H, d, J=2.9 Hz), 8.30 (1H, d, J=1.7 Hz), 10.13 (1H, s).

Reference Example 2

Synthesis of [2-acetoxymethyl-2-acetylamino-4-(7-hydroxy-9-oxo-9H-thioxanthen-3-yl)butyl]acetate 1) Synthesis of 4-chloro-2-(4-methoxyphenylthio)benzoic acid (Reference Example compound 2-1)

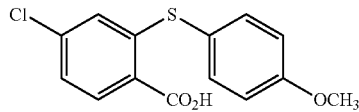 [SMILES: COc1ccc(Sc2cc(Cl)ccc2C(=O)O)cc1]

A mixture of 4-chloro-2-iodobenzoic acid (20.0 g), 4-methoxybenzenethiol (8.71 ml), potassium hydroxide (15.4 g), copper powder (0.48 g) and water (240 ml) was stirred under reflux for 4 hr. The reaction mixture was poured into a mixed solution of ethyl acetate and 1M hydrochloric acid, and the organic layer was separated. The organic layer was washed with saturated brine, and dried over anhydrous magnesium sulfate. The solvent was evaporated under reduced pressure and the residue was washed in diisopropyl ether and hexane (1:8) to give Reference Example compound 2-1 (18.8 g) as a white powder.

$^1$H-NMR (CDCl$_3$) δ (ppm): 3.89 (3H, s), 6.69 (1H, d, J=1.8 Hz), 7.01 (2H, d, J=8.6 Hz), 7.09 (1H, dd, J=2.0, 8.3 Hz), 7.50 (2H, d, J=8.6 Hz), 8.04 (1H, d, J=8.5 Hz).

2) Synthesis of 6-chloro-2-methoxy-9H-thioxanthen-9-one (Reference Example compound 2-2)

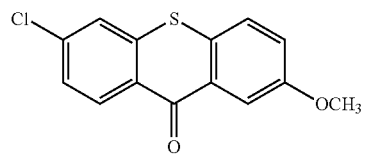 [SMILES: COc1ccc2sc3cc(Cl)ccc3c(=O)c2c1]

To Reference Example compound 2-1 (18.8 g) was added sulfuric acid (110 ml) under ice-cooling, and the mixture was stirred at room temperature for 50 min while pulverizing powder lumps. The reaction mixture was poured into ice water (700 ml), and the mixture was stirred at room temperature for 2 hr. The precipitated solid was collected by filtration, suspended in 1M aqueous sodium hydroxide solution (800 ml), and the suspension was stirred at room temperature for 2 hr. The solid was collected by filtration, washed with water, and dried to give Reference Example compound 2-2 (12.3 g) as a yellow powder.

$^1$H-NMR (CDCl$_3$) δ (ppm): 3.95 (3H, s), 7.29 (1H, dd, J=2.7, 8.7 Hz), 7.43 (1H, dd, J=2.0, 8.9 Hz), 7.50 (1H, d, J=8.7 Hz), 7.60 (1H, d, J=1.9 Hz), 8.07 (1H, d, J=2.8 Hz), 8.57 (1H, d, J=8.7 Hz).

3) Synthesis of 6-chloro-2-hydroxy-9H-thioxanthen-9-one (Reference Example compound 2-3)

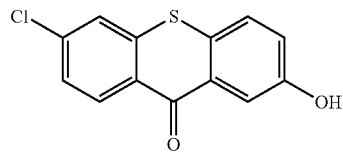 [SMILES: O=c1c2ccc(Cl)cc2sc2ccc(O)cc12]

To a solution of Reference Example compound 2-2 (12.3 g) in 1,2-dichloroethane (200 ml) was added a 1M solution (200 ml) of boron tribromide in methylene chloride, and the mixture was stirred at 60° C. for 7 hr. Under ice-cooling, methanol (250 ml) was gradually added, and the solvent was evaporated under reduced pressure. Water (350 ml) was added to the residue, and the mixture was stirred at room temperature for 2 hr. The precipitated solid was collected by filtration to give Reference Example compound 2-3 (10.7 g) as a yellow powder.

$^1$H-NMR (DMSO-d$_6$) δ (ppm): 7.29 (1H, dd, J=2.8, 8.7 Hz), 7.59 (1H, dd, J=1.7, 8.7 Hz), 7.72 (1H, d, J=8.7 Hz), 7.84 (1H, d, J=2.8 Hz), 8.06 (1H, d, J=1.8 Hz), 8.43 (1H, d, J=8.7 Hz), 10.24 (1H, brs).

4) Synthesis of t-butyl {5-[(7-benzyloxy-9-oxo-9H-thioxanthen-3-yl)ethynyl]-2,2-dimethyl-1,3-dioxan-5-yl}carbamate (Reference Example compound 2-4)

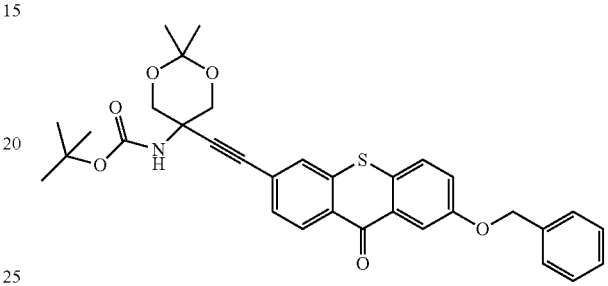

By a method similar to that for synthesizing Reference Example compound 1-5 from Reference Example compound 1-3, Reference Example compound 2-4 was obtained as a yellow powder from Reference Example compound 2-3.

$^1$H-NMR (CDCl$_3$) δ (ppm): 1.47 (3H, s), 1.50 (9H, s), 1.53 (3H, s), 4.08 (2H, d, J=11.4 Hz), 4.13 (2H, d, J=11.4 Hz), 5.21 (2H, s), 5.25 (1H, brs), 7.33-7.37 (2H, m), 7.41 (2H, t, J=7.3 Hz), 7.46-7.52 (4H, m), 7.67 (1H, d, J=1.3 Hz), 8.16 (1H, d, J=2.9 Hz), 8.55 (1H, d, J=8.4 Hz).

5) Synthesis of [2-acetoxymethyl-2-acetylamino-4-(7-benzyloxy-9-oxo-9H-thioxanthen-3-yl)butyl]acetate (Reference Example compound 2-5)

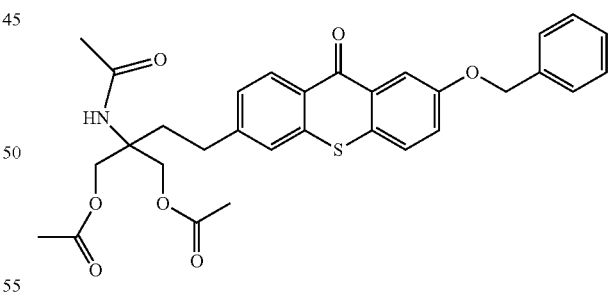

By a method similar to that for synthesizing Reference Example compound 1-6 from Reference Example compound 1-5, Reference Example compound 2-5 was obtained as a yellow powder from Reference Example compound 2-4.

$^1$H-NMR (CDCl$_3$) δ (ppm): 2.01 (3H, s), 2.11 (6H, s), 2.28-2.32 (2H, m), 2.71-2.76 (2H, m), 4.36 (4H, s), 5.21 (2H, s), 5.75 (1H, brs), 7.31 (1H, dd, J=1.3, 8.6 Hz), 7.32-7.37 (2H, m), 7.40-7.43 (3H, m), 7.48-7.52 (3H, m), 8.18 (1H, d, J=2.7 Hz), 8.55 (1H, d, J=8.4 Hz).

6) Synthesis of [2-acetoxymethyl-2-acetylamino-4-(7-hydroxy-9-oxo-9H-thioxanthen-3-yl)butyl]acetate (Reference Example compound 2)

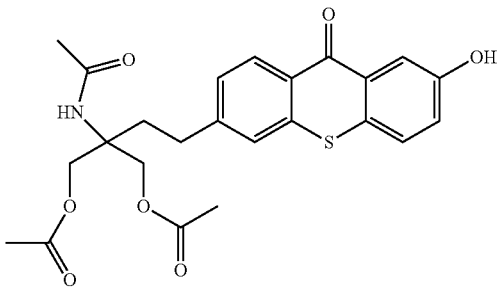 [SMILES: CC(=O)NC(CCc1ccc2c(=O)c3cc(O)ccc3sc2c1)(COC(C)=O)COC(C)=O]

By a method similar to that for synthesizing Reference Example compound 1 from Reference Example compound 1-6, Reference Example compound 2 was obtained as a yellow powder from Reference Example compound 2-5.

$^1$H-NMR (DMSO-$d_6$) δ (ppm): 1.86 (3H, s), 2.03-2.08 (2H, m), 2.04 (6H, s) 2.68-2.72 (2H, m), 4.20 (2H, d, J=11.0 Hz), 4.30 (2H, d, J=11.0 Hz), 7.26 (1H, dd, J=3.0, 8.7 Hz), 7.38 (1H, dd, J=1.2, 8.6 Hz), 7.61 (1H, s), 7.68-7.72 (2H, m), 7.85 (1H, d, J=2.6 Hz), 8.38 (1H, d, J=8.4 Hz), 10.14 (1H, brs).

Reference Example 3

Synthesis of [2-acetoxymethyl-2-acetylamino-4-(7-hydroxy-9H-thioxanthen-3-yl)butyl]acetate 1) Synthesis of 6-chloro-2-methoxy-9H-thioxanthene (Reference Example compound 3-1)

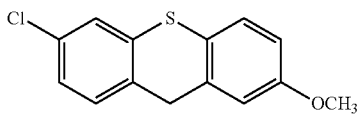

To a solution of Reference Example compound 2-2 (17.9 g) in tetrahydrofuran (350 ml) was added lithium borohydride (2.81 g), and the mixture was stirred at room temperature for 30 min and under reflux for 3 hr. The reaction mixture was ice-cooled, and water (15 ml) and then 1M hydrogen chloride solution (2-propanol/1,4-dioxane=3/1, 300 ml) were added. The mixture was stirred at 50° C. for 5 hr, and the organic solvent was evaporated under reduced pressure. Water (200 ml) was added to the obtained residue, and the precipitated solid was collected by filtration, washed with water, and dried to give Reference Example compound 3-1 (13.0 g) as a gray powder.

$^1$H-NMR (CDCl$_3$) δ (ppm): 3.79 (2H, s), 3.80 (3H, s), 6.77 (1H, dd, J=2.6, 8.5 Hz), 6.89 (1H, d, J=2.6 Hz), 7.16 (1H, dd, J=2.1, 8.1 Hz), 7.21 (1H, d, J=8.1 Hz), 7.32 (1H, d, J=8.5 Hz), 7.42 (1H, d, J=2.1 Hz).

2) Synthesis of t-butyl {5-[(7-benzyloxy-9H-thioxanthen-3-yl)ethynyl]-2,2-dimethyl-1,3-dioxan-5-yl}carbamate (Reference Example compound 3-2)

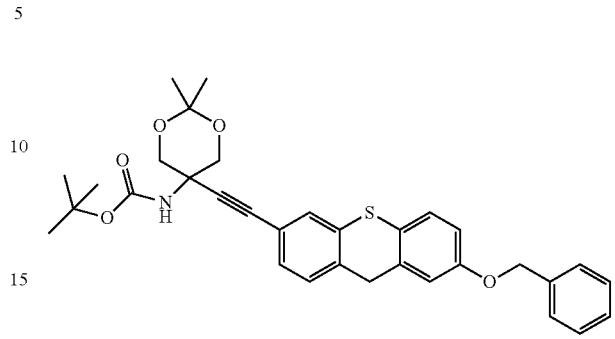

By a method similar to that for synthesizing Reference Example compound 2-4 from Reference Example compound 2-2, Reference Example compound 3-2 was obtained as a yellow powder from Reference Example compound 3-1.

$^1$H-NMR (CDCl$_3$) δ (ppm): 1.44 (3H, s), 1.47 (9H, s), 1.50 (3H, s), 3.80 (2H, s), 4.02 (2H, d, J=11.5 Hz), 4.09 (2H, d, J=11.5 Hz), 5.06 (2H, s), 5.18 (1H, brs), 6.83 (1H, dd, J=2.8, 8.5 Hz), 6.96 (1H, d, J=2.6 Hz), 7.21 (1H, d, J=7.8 Hz), 7.25 (1H, dd, J=1.3, 7.8 Hz), 7.30-7.42 (1H, m), 7.49 (1H, d, J=1.3 Hz).

3) Synthesis of t-butyl {5-[2-(7-benzyloxy-9H-thioxanthen-3-yl)ethyl]-2,2-dimethyl-1,3-dioxan-5-yl}carbamate (Reference Example compound 3-3)

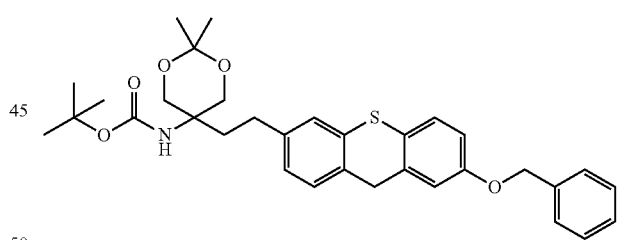

To a solution of Reference Example compound 3-2 (11.5 g) in 1,4-dioxane (200 ml), methanol (100 ml) and N,N-dimethylformamide (60 ml) was added 10% palladium carbon (containing about 50% water, 5.0 g), and the mixture was stirred at room temperature for 20 hr under a hydrogen atmosphere. The reaction mixture was filtered through celite and concentrated. Water was added to the obtained residue, and the mixture was extracted with methylene chloride. The organic layer was washed with brine, dried over magnesium sulfate, and the solvent was evaporated under reduced pressure. The obtained residue was purified by silica gel column chromatography to give Reference Example compound 3-3 (9.11 g) as a yellow powder.

¹H-NMR (CDCl₃) δ (ppm): 1.41 (3H, s), 1.43 (3H, s), 1.47 (9H, s), 1.93-1.97 (2H, m), 2.51-2.55 (2H, m), 3.67 (2H, d, J=11.7 Hz), 3.78 (2H, s), 3.88 (2H, d, J=11.7 Hz), 4.95 (1H, brs), 5.05 (2H, s), 6.81 (1H, dd, J=2.6, 8.5 Hz), 6.96 (1H, d, J=2.6 Hz), 7.01 (1H, dd, J=1.3, 7.7 Hz), 7.19 (1H, d, J=7.7 Hz), 7.25 (1H, d, J=1.3 Hz), 7.30-7.33 (2H, m), 7.36-7.42 (4H, m).

4) Synthesis of [2-acetoxymethyl-2-acetylamino-4-(7-hydroxy-9H-thioxanthen-3-yl)butyl]acetate (Reference Example compound 3)

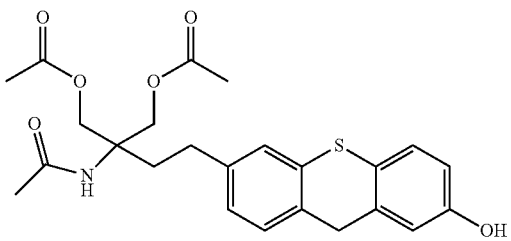 [SMILES: CC(=O)NC(CCc1ccc2c(c1)Sc1ccc(O)cc1C2)(COC(C)=O)COC(C)=O]

To Reference Example compound 3-3 (8.6 g) were added ethanol (175 ml) and concentrated hydrochloric acid (40 ml), the mixture was stirred at 80° C. for 3 hr, and the precipitated solid was collected by filtration. To the obtained solid were added pyridine (50 ml) and acetic anhydride (3.9 mL), and the mixture was stirred at room temperature for one day. Water was added to the reaction mixture, the mixture was extracted with ethyl acetate, washed with water and saturated brine, dried over anhydrous sodium sulfate, and the solvent was evaporated under reduced pressure. The obtained residue was purified by silica gel column chromatography to give [2-acetoxymethyl-2-acetylamino-4-(7-benzyloxy-9H-thioxanthen-3-yl)butyl]acetate (6.13 g) as a yellow powder. To a suspension of the obtained yellow powder (4.83 g) in methylene chloride (8.8 mL) was added iodotrimethylsilane (1.25 ml) at 0° C., and the mixture was stirred at room temperature for 2 hr. Iodotrimethylsilane (2.5 mL) was further added, and the mixture was stirred at room temperature for 1.5 hr. Iodotrimethylsilane (3.75 ml) was added, and the mixture was stirred at room temperature for one day. The reaction mixture was added to a suspension of ethyl acetate and aqueous sodium hydrogen carbonate, the mixture was extracted with ethyl acetate, washed with saturated brine, and dried over anhydrous sodium sulfate. The solvent was evaporated under reduced pressure and the organic layer was dried over anhydrous sodium sulfate. The solvent was evaporated under reduced pressure. The obtained residue was purified by silica gel column chromatography to give Reference Example compound 3 (3.70 g) as a yellow powder.

¹H-NMR (DMSO-d₆) δ (ppm): 1.85 (3H, s), 1.91-1.99 (2H, m), 2.02 (6H, s) 2.50-2.52 (2H, m), 3.72 (2H, s), 4.17 (2H, d, J=11.0 Hz), 4.27 (2H, d, J=11.0 Hz), 6.64 (1H, dd, J=2.7, 8.4 Hz), 6.84 (1H, d, J=2.4 Hz), 7.22 (1H, d, J=8.2 Hz), 7.23 (1H, dd, J=1.2, 7.8 Hz), 7.24 (3H, brs), 7.29 (1H, d, J=7.8 Hz), 7.62 (1H, s).

Reference Example 4

Synthesis of ({4-[2-(6-hydroxy-9-oxo-9H-thioxanthen-3-yl)ethyl]-2-methyl-4,5-dihydro-1,3-oxazol-4-yl}methyl)acetate 1) Synthesis of [2-acetoxymethyl-2-acetylamino-4-(6-benzyloxy-9-oxo-9H-thioxanthen-3-yl)butyl]acetate (Reference Example compound 4-1)

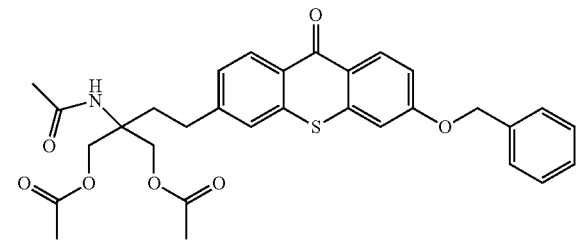 [SMILES: CC(=O)NC(CCc1ccc2c(=O)c3ccc(OCc4ccccc4)cc3sc2c1)(COC(C)=O)COC(C)=O]

Using 3-methoxybenzenethiol instead of 4-methoxybenzenethiol and by a method similar to that for synthesizing Reference Example compound 1-6 from 5-chloro-2-iodobenzoic acid, Reference Example compound 4-1 was obtained as a pale-brown powder from 4-chloro-2-iodobenzoic acid.

¹H-NMR (CDCl₃) δ (ppm): 2.01 (3H, s), 2.11 (6H, s), 2.27-2.31 (2H, m), 2.70-2.74 (2H, m), 4.36 (4H, s), 5.18 (2H, s), 5.76 (1H, brs), 7.06 (1H, d, J=2.3 Hz), 7.10 (1H, dd, J=2.5, 9.2 Hz), 7.29 (1H, dd, J=1.3, 8.1 Hz), 7.35 (1H, s), 7.37-7.47 (5H, m), 8.51 (1H, d, J=8.4 Hz), 8.55 (1H, d, J=8.8 Hz).

2) Synthesis of ({4-[2-(6-hydroxy-9-oxo-9H-thioxanthen-3-yl)ethyl]-2-methyl-4,5-dihydro-1,3-oxazol-4-yl}methyl)acetate (Reference Example compound 4)

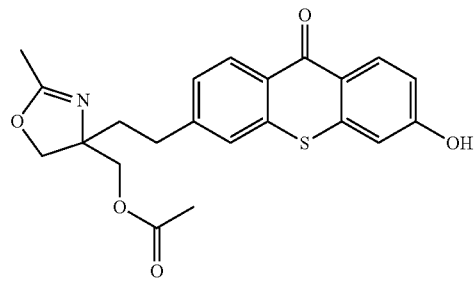 [SMILES: CC(=O)OCC1(CCc2ccc3c(=O)c4ccc(O)cc4sc3c2)COC(C)=N1]

To a suspension of Reference Example compound 4-1 (6.38 g) in methylene chloride (25 ml) was added iodotrimethylsilane (8.0 ml), and the mixture was stirred at room temperature for 3 days. Iodotrimethylsilane (8.0 ml) was further added, and the mixture was stirred at room temperature for 1 day. Methanol was added to the reaction mixture under ice-cooling to quench the reaction, water was added, and the mixture was extracted with methylene chloride. The organic layer was dried over anhydrous sodium sulfate, and the solvent was evaporated under reduced pressure. The obtained residue was purified by silica gel column chromatography to give Reference Example compound 4 (1.3 g) as a pale-yellow powder.

¹H-NMR (DMSO-d₆) δ (ppm): 1.78-1.88 (2H, m), 1.93 (3H, s), 2.04 (3H, s), 2.57-2.65 (1H, m), 2.70-2.78 (1H, m), 4.01 (2H, s), 4.08-4.14 (2H, m), 6.99 (1H, dd, J=2.3, 8.7 Hz), 7.04 (1H, d, J=2.2 Hz), 7.41 (1H, dd, J=1.2, 9.0 Hz), 7.62 (2H, s), 8.32 (1H, d, J=2.3 Hz), 8.34 (1H, d, J=1.3 Hz), 10.85 (1H, brs).

Reference Example 5

Synthesis of [2-acetoxymethyl-2-acetylamino-4-(6-hydroxy-9-oxo-9H-thioxanthen-2-yl)butyl]acetate 1) Synthesis of 2-chloro-6-methoxy-9H-thioxanthen-9-one (Reference Example compound 5-1)

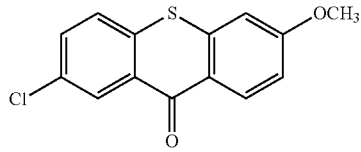 [SMILES: COc1ccc2c(=O)c3cc(Cl)ccc3sc2c1]

By a method similar to that for synthesizing Reference Example compound 1-2 from 5-chloro-2-iodobenzoic acid, and using 3-methoxybenzenethiol instead of 4-methoxybenzenethiol, Reference Example compound 5-1 was obtained as a brown powder.

$^1$H-NMR (DMSO-d$_6$) δ (ppm): 3.93 (3H, s) 7.18 (1H, d, J=8.3 Hz) 7.41 (1H, s), 7.82 (1H, d, J=7.5 Hz), 7.91 (1H, d, J=8.5 Hz), 8.36-8.41 (2H, m).

2) Synthesis of t-butyl {5-[2-(6-benzyloxy-9-oxo-9H-thioxanthen-2-yl)ethyl]-2,2-dimethyl-1,3-dioxan-5-yl}carbamate (Reference Example compound 5-2)

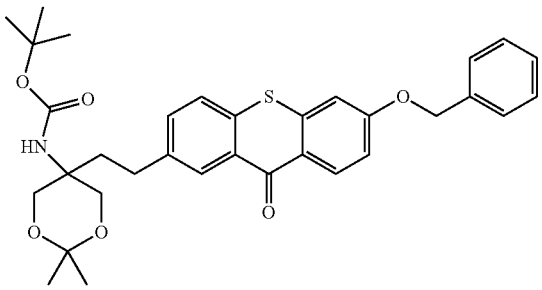 [SMILES: CC(C)(C)OC(=O)NC1(CCc2ccc3sc4cc(OCc5ccccc5)ccc4c(=O)c3c2)COC(C)(C)OC1]

To a solution of Reference Example compound 5-1 (13.9 g) in 1,4-dioxane (200 ml) was added 10% palladium carbon (containing about 50% water, 10.0 g), and the mixture was stirred at room temperature for 6 hr under a hydrogen atmosphere. The reaction mixture was filtered through celite and concentrated. To a solution of the obtained residue in N,N-dimethylformamide (50 ml) were added potassium carbonate (10.1 g) and benzyl bromide (3.17 ml), and the mixture was stirred at room temperature for 16 hr. The reaction mixture was poured into water, and the mixture was extracted with ethyl acetate. The organic layer was washed with brine, dried over magnesium sulfate, and the solvent was evaporated under reduced pressure. The obtained residue was suspended in diisopropyl ether, collected by filtration, and washed with hexane to give Reference Example compound 5-2 (10.0 g) as a gray powder.

$^1$H-NMR (CDCl$_3$) δ (ppm): 1.43 (3H, s), 1.44 (3H, s), 1.48 (9H, s), 2.02-2.06 (2M, m), 2.69-2.73 (2H, m), 3.71 (2H, d, J=11.7 Hz), 3.91 (2M, d, J=11.7 Hz), 5.03 (1H, brs), 5.18 (2H, s), 7.06 (1M, d, J=2.4 Hz), 7.11 (1H, dd, J=2.4, 8.8 Hz), 7.35-7.52 (7H, m), 8.41 (1H, s), 8.57 (1H, d, J=8.8 Hz).

3) Synthesis of [2-acetoxymethyl-2-acetylamino-4-(6-hydroxy-9-oxo-9H-thioxanthen-2-yl)butyl]acetate (Reference Example compound 5)

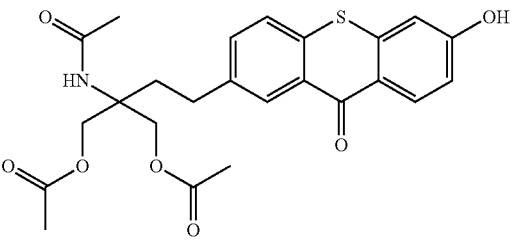 [SMILES: CC(=O)NC(CCc1ccc2sc3cc(O)ccc3c(=O)c2c1)(COC(C)=O)COC(C)=O]

By a method similar to that for synthesizing Reference Example compound 3 from Reference Example compound 3-3, Reference Example compound 5 was obtained as a yellow powder from Reference Example compound 5-2.

$^1$H-NMR (DMSO-d$_6$) δ (ppm): 1.87 (3H, s), 1.99-2.04 (2H, m), 2.04 (6H, s), 2.68-2.72 (2H, m), 4.22 (2H, d, J=11.1 Hz), 4.32 (2H, d, J=11.0 Hz), 7.00 (1H, dd, J=2.2, 8.8 Hz), 7.05 (1H, d, J=2.2 Hz), 7.56 (1H, dd, J=2.0, 8.4 Hz), 7.70 (1H, d, J=8.3 Hz), 7.75 (1H, s), 8.27 (1H, d, J=1.7 Hz), 8.35 (1H, d, J=8.7 Hz), 10.87 (1H, brs).

Reference Example 6

Synthesis of t-butyl {5-[2-(7-hydroxy-9-oxo-9H-thioxanthen-3-yl)ethyl]-2,2-dimethyl-1,3-dioxan-5-yl}carbamate 1) Synthesis of t-butyl {5-[(7-hydroxy-9-oxo-9H-thioxanthen-3-yl)ethynyl]-2,2-dimethyl-1,3-dioxan-5-yl}carbamate (Reference Example compound 6-1)

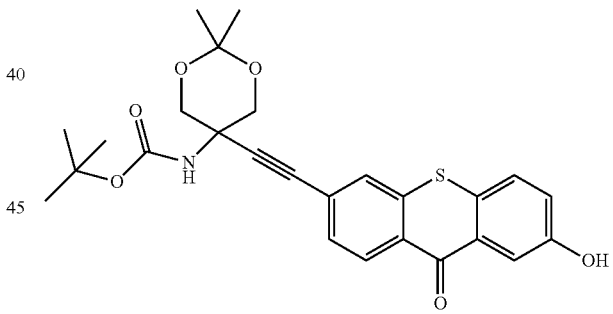

A mixture of Reference Example compound 2-3 (10.7 g), t-butyl (5-ethynyl-2,2-dimethyl-1,3-dioxan-5-yl)carbamate (10.4 g), cesium carbonate (34.5 g), 2-dicyclohexylphosphino-2',4',6'-triisopropylbiphenyl (1.16 g), dichlorobis(acetonitrile)palladium(II) (211 mg) and acetonitrile (250 ml) was stirred under reflux for 7 hr. The reaction mixture was poured into water (1500 ml), and the mixture was extracted with chloroform. The organic layer was washed with saturated brine, and dried over anhydrous magnesium sulfate. The solvent was evaporated under reduced pressure and the residue was suspended in a mixed solution (1:5) of diethyl ether and diisopropyl ether, and collected by filtration to give a mixture (5:1) of Reference Example compound 6-1 and Reference Example compound 2-3 which is a starting material. This mixture and a mixture of t-butyl (5-ethynyl-2,2-dimethyl-1,3-dioxan-5-yl)carbamate (3.47 g), cesium carbonate (34.5 g), 2-dicyclohexylphosphino-2',4',6'- triisopropylbiphenyl (387 mg), dichlorobis(acetonitrile) palladium(II) (70.3 mg) and acetonitrile (200 ml) were stirred under reflux for 6 hr. The reaction mixture was poured into water (1000 ml), and the mixture was extracted with chloroform. The organic layer was washed with saturated brine, and dried over anhydrous magnesium sulfate. The solvent was evaporated under reduced pressure and the residue was suspended in a mixed solution (1:1) of ethyl acetate and diethyl ether, and collected by filtration to give Reference Example compound 6-1 (13.7 g) as a yellow powder.

$^1$H-NMR (DMSO-d$_6$) δ (ppm): 1.36 (3H, s), 1.41 (3H, s), 1.42 (9H, s), 4.02-4.08 (4H, m), 7.28 (1H, dd, J=2.9, 8.7 Hz), 7.29 (1H, brs), 7.50 (1H, dd, J=1.3, 8.5 Hz), 7.71 (1H, d, J=8.8 Hz), 7.84 (1H, d, J=2.9 Hz), 7.88 (1H, d, J=1.0 Hz), 8.42 (1H, d, J=8.5 Hz), 10.24 (1H, brs).

2) Synthesis of t-butyl {5-[2-(7-hydroxy-9-oxo-9H-thioxanthen-3-yl)ethyl]-2,2-dimethyl-1,3-dioxan-5-yl}carbamate (Reference Example compound 6)

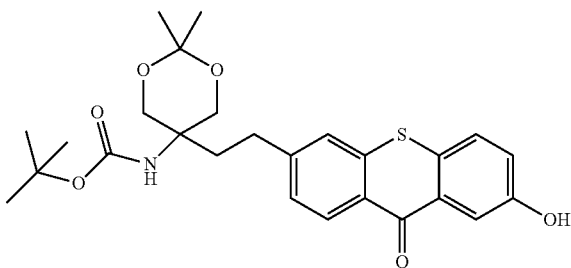 [SMILES: CC(C)(C)OC(=O)NC1(CCc2ccc3c(=O)c4cc(O)ccc4sc3c2)COC(C)(C)OC1]

To a solution of Reference Example compound 6-1 (13.7 g) in 1,4-dioxane (400 ml) was added 10% palladium carbon (containing about 50% water, 13.7 g), and the mixture was stirred at room temperature for 3 hr under a hydrogen atmosphere. The reaction mixture was warmed, and the precipitated solid was dissolved and filtered through celite. The filtrate was concentrated, and the obtained residue was washed with diethyl ether to give Reference Example compound 6 (10.3 g) as a white powder.

$^1$H-NMR (DMSO-d$_6$) δ (ppm): 1.33 (3H, s), 1.34 (3H, s), 1.41 (9H, s), 2.02-2.07 (2H, m), 2.60-2.65 (2H, m), 3.70 (2H, d, J=11.6 Hz), 3.90 (2H, d, J=11.6 Hz), 6.72 (1H, brs), 7.26 (1H, dd, J=2.6, 8.6 Hz), 7.36 (1H, dd, J=1.1, 8.6 Hz), 7.59 (1H, d, J=0.9 Hz), 7.68 (1H, d, J=8.7 Hz), 7.85 (1H, d, J=3.0 Hz), 8.37 (1H, d, J=8.4 Hz), 10.15 (1H, brs).

Reference Example 7

Synthesis of t-butyl {5-[2-(6-hydroxy-9-oxo-9H-thioxanthen-2-yl)ethyl]-2,2-dimethyl-1,3-dioxan-5-yl}carbamate (Reference Example compound 7)

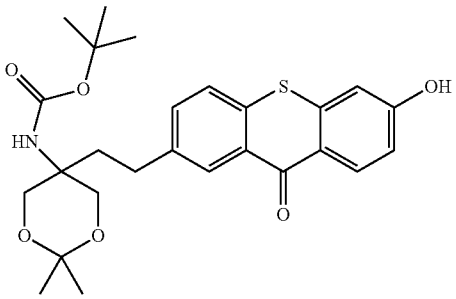 [SMILES: CC(C)(C)OC(=O)NC1(CCc2ccc3sc4cc(O)ccc4c(=O)c3c2)COC(C)(C)OC1]

By a method similar to that for synthesizing Reference Example compound 6 from Reference Example compound 2-2, Reference Example compound 7 was obtained as a yellow powder from Reference Example compound 5-1.

$^1$H-NMR (DMSO-d$_6$) δ (ppm): 1.33 (3H, s), 1.34 (3H, s), 1.42 (9H, s), 1.99-2.04 (2H, m), 2.60-2.64 (2H, m), 3.71 (2H, d, J=11.6 Hz), 3.90 (2H, d, J=11.6 Hz), 6.71 (1H, brs), 6.99 (1H, dd, J=2.3, 8.7 Hz), 7.05 (1H, d, J=2.3 Hz), 7.54 (1H, dd, J=1.6, 8.3 Hz), 7.69 (1H, d, J=8.4 Hz), 8.25 (1H, d, J=1.2 Hz), 8.34 (1H, d, J=8.8 Hz), 10.88 (1H, brs).

Reference Example 8

Synthesis of t-butyl {5-[2-(6-hydroxy-9-oxo-9H-thioxanthen-3-yl)ethyl]-2,2-dimethyl-1,3-dioxan-5-yl}carbamate (Reference Example compound 8)

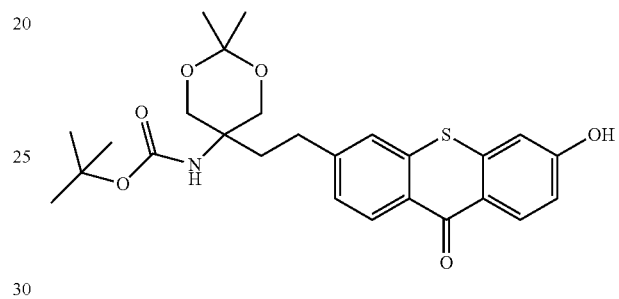

By a method similar to the synthetic method of Reference Example compound 1-1 and Reference Example compound 1-2, 3-chloro-6-methoxy-9H-thioxanthen-9-one was obtained from 4-chloro-2-iodobenzoic acid and 3-methoxybenzenethiol. Thereafter, by a method similar to the method for synthesizing Reference Example compound 7, Reference Example compound 8 was obtained as a yellow powder.

$^1$H-NMR (DMSO-d$_6$) δ (ppm): 1.32 (3H, s), 1.34 (3H, s), 1.40 (9H, s), 2.01-2.09 (2H, m), 2.59-2.67 (2H, m), 3.69 (2H, d, J=11.5 Hz), 3.90 (2H, d, J=11.5 Hz), 6.70 (1H, brs), 6.99 (1H, dd, J=2.2, 9.0 Hz), 7.03 (1H, d, J=2.2 Hz), 7.34 (1H, dd, J=1.2, 8.5 Hz), 7.53 (1H, d, J=0.9 Hz), 8.32 (1H, d, J=8.7 Hz), 8.34 (1H, d, J=8.1 Hz), 10.93 (1H, brs).

Reference Example 9

Synthesis of t-butyl {5-[2-(7-hydroxy-9H-thioxanthen-3-yl)ethyl]-2,2-dimethyl-1,3-dioxan-5-yl}carbamate (Reference Example compound 9)

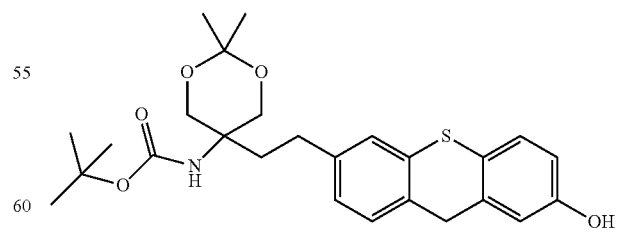

To a solution of Reference Example compound 2-4 (5.83 g) in 1,4-dioxane (250 ml) was added 10% palladium carbon (containing about 50% water, 5.8 g), and the mixture was stirred at room temperature for 12 hr under a hydrogen atmosphere. The reaction mixture was filtered through celite and concentrated. To the obtained residue was added diethyl ether (100 ml), and the precipitated solid was collected by filtration. The obtained powder was purified by silica gel column chromatography to give Reference Example compound 9 (2.66 g) as a yellow amorphous solid.

$^1$H-NMR (CDCl$_3$) δ (ppm): 1.41 (3H, s), 1.43 (3H, s), 1.47 (9H, s), 1.93-1.97 (2H, m), 2.51-2.55 (2H, m), 3.67 (2H, d, J=11.7 Hz), 3.74 (2H, s), 3.88 (2H, d, J=11.7 Hz), 4.99 (1H, brs), 5.20 (2H, s), 6.67 (1H, dd, J=2.6, 8.2 Hz), 6.82 (1H, d, J=2.6 Hz), 7.00 (1H, dd, J=1.2, 7.8 Hz), 7.17 (1H, d, J=7.8 Hz), 7.25-7.26 (2H, m).

Reference Example 10

Synthesis of t-butyl {5-[2-(6-benzyloxy-9H-thioxanthen-3-yl)ethyl]-2,2-dimethyl-1,3-dioxan-5-yl}carbamate (Reference Example compound 10)

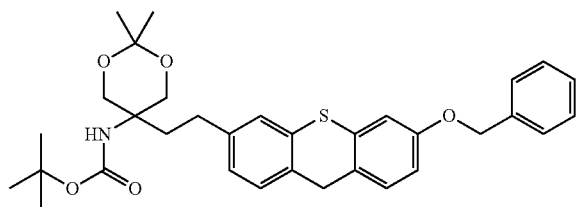 [SMILES: CC(C)(C)OC(=O)NC1(CCc2ccc3c(c2)Sc2cc(OCc4ccccc4)ccc2C3)COC(C)(C)OC1]

Using 3-methoxybenzenethiol instead of 4-methoxybenzenethiol, and by a method similar to the method for synthesizing Reference Example compound 3-3 from 4-chloro-2-iodobenzoic acid, Reference Example compound 10 was obtained as a yellow powder.

$^1$H-NMR (DMSO-d$_6$) δ (ppm): 1.31 (3H, s), 1.32 (3H, s), 1.40 (9H, s), 1.91-1.95 (2H, m), 2.42-2.46 (2H, m), 3.66 (2H, d, J=11.6 Hz), 3.76 (2H, s), 3.86 (2H, d, J=11.7 Hz), 5.11 (2H, s), 6.60 (1H, brs), 6.90 (1H, dd, J=2.4, 8.3 Hz), 7.03 (1H, d, J=7.0 Hz), 7.12 (1H, d, J=2.3 Hz), 7.24 (1H, s), 7.29-7.44 (7H, m).

Reference Example 11

Synthesis of t-butyl {5-[2-(7-hydroxy-9-oxo-9H-xanthen-3-yl)ethyl]-2,2-dimethyl-1,3-dioxan-5-yl}carbamate 1) Synthesis of 4-chloro-2-fluoro-2',5'-dimethoxybenzophenone (Reference Example compound 11-1)

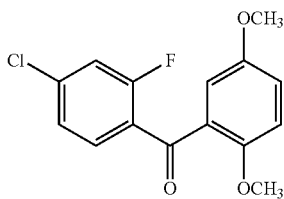 [SMILES: COc1ccc(OC)c(C(=O)c2ccc(Cl)cc2F)c1]

A mixture of 4-chloro-2-fluorobenzonitrile (20.0 g), 1,4-dimethoxybenzene (35.5 g), palladium(II) acetate (2.88 g), dimethyl sulfoxide (12.8 mL) and trifluoroacetic acid (180 ml) was stirred in a sealed vessel at 95° C. for 10 hr. The reaction mixture was poured into water (500 ml), and the mixture was stirred at 70° C. for 2 hr. The mixture was cooled, extracted with ethyl acetate, washed with 1M aqueous sodium hydroxide solution and saturated brine, and dried over anhydrous magnesium sulfate. The solvent was evaporated under reduced pressure and the residue was purified by silica gel column chromatography to give Reference Example compound 11-1 (21.7 g) as a yellow powder.

$^1$H-NMR (CDCl$_3$) δ (ppm): 3.62 (3H, s), 3.81 (3H, s), 6.88 (1H, d, J=8.9 Hz), 7.06 (1H, dd, J=3.2, 9.2 Hz), 7.10 (1H, dd, J=2.1, 10.2 Hz). 7.13 (1H, d, J=3.2 Hz), 7.22 (1H, dd, J=1.7, 8.4 Hz), 7.64 (1H, t, J=8.0 Hz).

2) Synthesis of 4-chloro-2-fluoro-2'-hydroxy-5'-methoxybenzophenone (Reference Example compound 11-2)

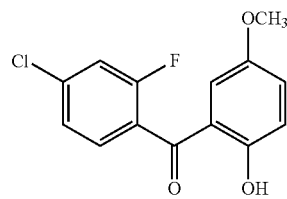 [SMILES: COc1ccc(O)c(C(=O)c2ccc(Cl)cc2F)c1]

To a solution of Reference Example compound 11-1 (23.9 g) in methylene chloride (300 ml) was added anhydrous aluminum chloride (32.4 g) in two portions under ice-cooling, and the mixture was stirred for 1 hr under ice-cooling and further at room temperature for 1 hr. The reaction mixture was poured into ice water (700 ml), and the mixture was extracted with methylene chloride. The methylene chloride layer was washed with saturated brine, and dried over anhydrous magnesium sulfate. The solvent was evaporated under reduced pressure and the residue was crystallized from hexane and diisopropyl ether to give Reference Example compound 11-2 (20.7 g) as a yellow powder.

$^1$H-NMR (CDCl$_3$) δ (ppm): 3.69 (3H, s), 6.81 (1H, t, J=2.9 Hz), 7.02 (1H, d, J=9.0 Hz), 7.17 (1H, dd, J=3.1, 9.2 Hz), 7.25 (1H, dd, J=1.6, 9.2 Hz), 7.30 (1H, dd, J=1.6, 8.2 Hz), 7.44 (1H, t, J=7.7 Hz), 11.47 (1H, s).

3) Synthesis of 6-chloro-2-methoxy-9H-xanthen-9-one (Reference Example compound 11-3)

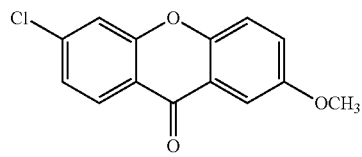 [SMILES: COc1ccc2oc3cc(Cl)ccc3c(=O)c2c1]

To a solution of Reference Example compound 11-2 (22.5 g) in N,N-dimethylformamide (170 ml) was added sodium hydride (60%, 3.53 g) in three portions under ice-cooling, and the mixture was stirred for 20 min under ice-cooling and further at room temperature for 50 min. Water (1000 ml) was poured into the reaction mixture and the mixture was ice-cooled. The precipitated solid was collected by filtration, and washed with water and a small amount of hexane to give Reference Example compound 11-3 (20.7 g) as a pale-yellow powder.

$^1$H-NMR (CDCl$_3$) δ (ppm): 3.93 (3H, s), 7.35 (2H, dd, J=2.5, 8.8 Hz), 7.44 (1H, d, J=9.0 Hz), 7.52 (1H, d, J=2.0 Hz), 7.69 (1H, d, J=3.1 Hz), 8.29 (1H, d, J=8.5 Hz).

4) Synthesis of 6-chloro-2-hydroxy-9H-xanthen-9-one (Reference Example compound 11-4)

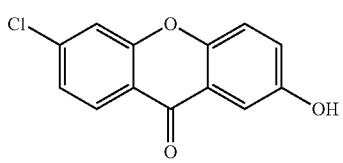 [SMILES: O=c1c2ccc(Cl)cc2oc2ccc(O)cc12]

To a solution of Reference Example compound 11-3 (20.6 g) in 1,2-dichloroethane (200 ml) was added a 1M solution (395 ml) of boron tribromide in methylene chloride, and the mixture was stirred at 60° C. for 10 hr. Under ice-cooling, methanol (500 ml) was gradually added, and the solvent was evaporated under reduced pressure. Water (500 ml) was added to the residue, and the precipitated solid was collected by filtration to give Reference Example compound 11-4 (19.6 g) as a pale-yellow powder.

$^1$H-NMR (DMSO-d$_6$) δ (ppm): 7.34 (1H, dd, J=3.0, 9.2 Hz), 7.46 (1H, d, J=3.0 Hz), 7.50 (1H, dd, J=1.7, 8.5 Hz), 7.55 (1H, d, J=9.2 Hz), 7.83 (1H, d, J=1.6 Hz), 8.17 (1H, d, J=8.6 Hz), 10.06 (1H, brs).

5) Synthesis of t-butyl {5-[(7-hydroxy-9-oxo-9H-xanthen-3-yl)ethynyl]-2,2-dimethyl-1,3-dioxan-5-yl}carbamate (Reference Example compound 11-5)

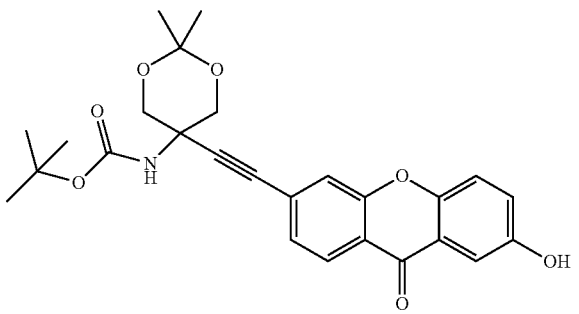 [SMILES: CC(C)(C)OC(=O)NC1(C#Cc2ccc3c(=O)c4cc(O)ccc4oc3c2)COC(C)(C)OC1]

A mixture of Reference Example compound 11-4 (14.4 g), t-butyl (5-ethynyl-2,2-dimethyl-1,3-dioxan-5-yl)carbamate (16.4 g), cesium carbonate (49.5 g), 2-dicyclohexylphosphino-2',4',6'-triisopropylbiphenyl (1.67 g), dichlorobis(acetonitrile)palladium(II) (304 mg) and acetonitrile (300 ml) was stirred under reflux for 9 hr. The reaction mixture was poured into water (1000 ml), and the mixture was extracted with ethyl acetate. The organic layer was washed with water, 0.1M hydrochloric acid, saturated aqueous sodium hydrogen carbonate and saturated brine, dried over anhydrous magnesium sulfate, and the solvent was evaporated under reduced pressure. Diethyl ether and diisopropyl ether (1:8) were added to the residue, and the precipitated solid was collected by filtration to give Reference Example compound 11-5 (25.3 g) as a brown powder.

$^1$H-NMR (CDCl$_3$) δ (ppm): 1.48 (3H, s), 1.53 (3H, s), 1.54 (9H, s), 4.09 (2H, d, J=11.5 Hz), 4.13 (2H, d, J=11.5 Hz), 5.43 (1H, brs), 7.10-7.24 (4H, m), 7.58 (1H, d, J=1.7 Hz), 7.99 (1H, d, J=7.1 Hz).

6) Synthesis of t-butyl {5-[2-(7-hydroxy-9-oxo-9H-xanthen-3-yl)ethyl]-2,2-dimethyl-1,3-dioxan-5-yl}carbamate (Reference Example compound 11)

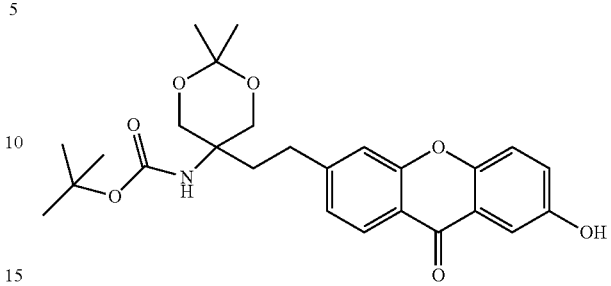

To a solution of Reference Example compound 11-5 (25.3 g) in 1,4-dioxane (350 ml) was added 10% palladium carbon (containing about 50% water, 12.5 g), and the mixture was stirred at room temperature for 4 hr under a hydrogen atmosphere. The reaction mixture was filtered through celite and concentrated. To the obtained residue was added diisopropyl ether to allow for solidification, and the solid was collected by filtration to give Reference Example compound 11 (22.4 g) as a gray white powder.

$^1$H-NMR (CDCl$_3$) δ (ppm): 1.44 (3H, s), 1.45 (3H, s), 1.50 (9H, s), 2.07-2.11 (2H, m), 2.70-2.74 (2H, m), 3.74 (2H, d, J=11.7 Hz), 3.92 (2H, d, J=11.7 Hz), 5.07 (1H, brs), 6.78 (1H, brs), 7.18 (1H, dd, J=1.1, 8.0 Hz), 7.24 (1H, s), 7.31 (1H, dd, J=3.0, 9.2 Hz), 7.38 (1H, d, J=8.9 Hz), 7.89 (1H, d, J=2.9 Hz), 8.18 (1H, d, J=8.2 Hz).

Reference Example 12

Synthesis of t-butyl {5-[2-(7-hydroxy-9-oxo-9H-xanthen-2-yl)ethyl]-2,2-dimethyl-1,3-dioxan-5-yl}carbamate (Reference Example compound 12)

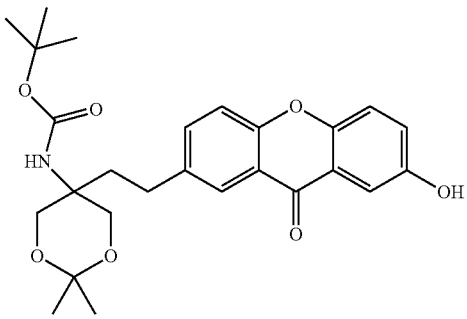 [SMILES: CC(C)(C)OC(=O)NC1(CCc2ccc3oc4ccc(O)cc4c(=O)c3c2)COC(C)(C)OC1]

By a method similar to the method for synthesizing Reference Example compound 11 from 4-chloro-2-fluorobenzonitrile, Reference Example compound 12 was obtained as a pale-yellow powder from 5-chloro-2-fluorobenzonitrile.

$^1$H-NMR (DMSO-d$_6$) δ (ppm): 1.33 (3H, s), 1.34 (3H, s), 1.42 (9H, s), 2.00-2.04 (2H, m), 2.60-2.64 (2H, m), 3.71 (2H, d, J=11.5 Hz), 3.91 (2H, d, J=11.5 Hz), 6.71 (1H, brs), 7.32 (1H, dd, J=3.0, 8.8 Hz), 7.47 (1H, d, J=2.9 Hz), 7.54 (1H, d, J=9.2 Hz), 7.57 (1H, d, J=8.6 Hz), 7.64 (1H, dd, J=2.1, 8.6 Hz), 7.97 (1H, d, J=1.7 Hz), 9.96 (1H, brs).

Reference Example 13

Synthesis of t-butyl {5-[2-(6-hydroxy-9-oxo-9H-xanthen-3-yl)ethyl]-2,2-dimethyl-1,3-dioxan-5-yl}carbamate 1) Synthesis of 4-chloro-2-fluorobenzoyl chloride (Reference Example compound 13-1)

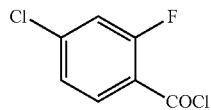 [SMILES: O=C(Cl)c1ccc(Cl)cc1F]

To a solution of 4-chloro-2-fluorobenzoic acid (14.0 g) in 1,2-dichloroethane (140 ml) were added N,N-dimethylformamide (0.31 ml) and thionyl chloride (8.75 ml), and the mixture was stirred at 90° C. for 4 hr. The reaction mixture was concentrated under reduced pressure, benzene (50 ml) was added to the obtained residue and the mixture was concentrated under reduced pressure to give Reference Example compound 13-1 (15.5 g) as a gray oil.

2) Synthesis of 4-chloro-2-fluoro-2'-hydroxy-4'-methoxybenzophenone (Reference Example compound 13-2)

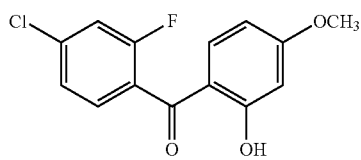 [SMILES: COc1ccc(C(=O)c2ccc(Cl)cc2F)c(O)c1]

To a 1M solution (100 ml) of boron trichloride in p-xylene were added, under ice-cooling, a solution of 3-methoxyphenol (9.64 ml) in benzene (110 ml) and a solution of Reference Example compound 13-1 (15.5 g) in benzene (50 ml). The mixture was stirred under reflux for 11 hr. Under ice-cooling, 1M hydrochloric acid (300 ml) was added to the reaction mixture, and the mixture was extracted with ethyl acetate. The organic layer was washed with 0.1M hydrochloric acid and saturated brine, and dried over anhydrous magnesium sulfate. The solvent was evaporated under reduced pressure and the residue was washed with diisopropyl ether and hexane (1:10) to give Reference Example compound 13-2 (12.2 g) as a pale-brown powder.

$^1$H-NMR (CDCl$_3$) δ (ppm): 3.87 (3H, dd, J=2.5, 9.1 Hz), 6.41 (1H, dd, J=2.5, 9.1 Hz), 6.50 (1H, d, J=2.4 Hz), 7.23 (1H, dd, J=1.7, 9.2 Hz), 7.25-7.29 (2H, m), 7.41 (1H, d, J=7.8 Hz), 12.41 (1H, s).

3) Synthesis of 3-chloro-6-methoxy-9H-xanthen-9-one (Reference Example compound 13-3)

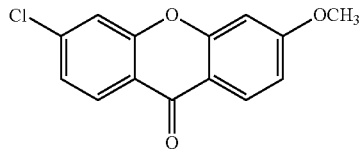 [SMILES: COc1ccc2c(=O)c3ccc(Cl)cc3oc2c1]

To a solution of Reference Example compound 13-2 (12.2 g) in N,N-dimethylformamide (120 ml) was added, under ice-cooling, sodium hydride (60%, 1.91 g) in two portions, and the mixture was stirred for 1.5 hr under ice-cooling. Water (400 ml) was poured into the reaction mixture, and the mixture was ice-cooled. The precipitated solid was collected by filtration, and washed with water and a small amount of hexane to give Reference Example compound 13-3 (11.6 g) as a white powder.

$^1$H-NMR (CDCl$_3$) δ (ppm): 3.95 (3H, s), 6.89 (1H, d, J=2.3 Hz), 6.97 (1H, dd, J=2.3, 8.7 Hz), 7.34 (1H, dd, J=1.8, 8.4 Hz), 7.48 (1H, d, J=1.8 Hz), 8.24 (1H, d, J=8.8 Hz), 8.26 (1H, d, J=8.8 Hz).

4) Synthesis of 3-chloro-6-hydroxy-9H-xanthen-9-one (Reference Example compound 13-4)

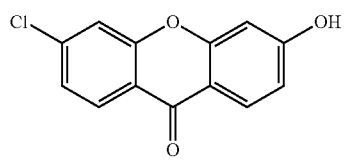 [SMILES: O=c1c2ccc(O)cc2oc2cc(Cl)ccc12]

To a solution of Reference Example compound 13-3 (11.6 g) in 1,2-dichloroethane (150 ml) was added a 1M solution (200 ml) of boron tribromide in methylene chloride, and the mixture was stirred at 60° C. for 17 hr. Under ice-cooling, methanol (200 ml) was gradually added, and the solvent was evaporated under reduced pressure. Water (500 ml) was added to the residue, and the precipitated solid was collected by filtration to give Reference Example compound 13-4 (11.2 g) as a gray powder.

$^1$H-NMR (DMSO-d$_6$) δ (ppm): 6.87 (1H, d, J=2.0 Hz), 6.93 (1H, dd, J=2.2, 8.6 Hz), 7.50 (1H, dd, J=2.2, 8.5 Hz), 7.80 (1H, d, J=1.8 Hz), 8.04 (1H, d, J=8.7 Hz), 8.14 (1H, d, J=8.6 Hz), 11.08 (1H, brs).

5) Synthesis of 3-benzyloxy-6-chloro-9H-xanthen-9-one (Reference Example compound 13-5)

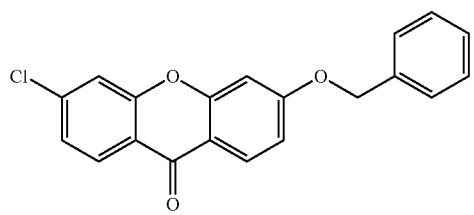 [SMILES: O=c1c2ccc(Cl)cc2oc2cc(OCc3ccccc3)ccc12]

A mixture of Reference Example compound 13-4 (11.1 g), potassium carbonate (18.7 g), benzyl bromide (5.61 ml) and N,N-dimethylformamide (100 ml) was stirred at 40° C. for 1.5 hr. Water was added to the reaction mixture, and the precipitated solid was collected by filtration, and washed with water and a small amount of hexane to give Reference Example compound 13-5 (14.2 g) as a gray white powder.

$^1$H-NMR (DMSO-d$_6$) δ (ppm): 5.32 (2H, s), 7.16 (1H, dd, J=2.3, 8.7 Hz) 7.24 (1H, d, J=2.3 Hz), 7.37 (1H, t, J=7.2 Hz), 7.43 (2H, t, J=7.4 Hz), 7.50-7.53 (3H, m), 7.82 (1H, d, J=1.7 Hz), 8.11 (1H, d, J=9.1 Hz), 8.16 (1H, d, J=8.6 Hz).

6) Synthesis of t-butyl {5-[(6-benzyloxy-9-oxo-9H-xanthen-3-yl)ethynyl]-2,2-dimethyl-1,3-dioxan-5-yl}carbamate (Reference Example compound 13-6)

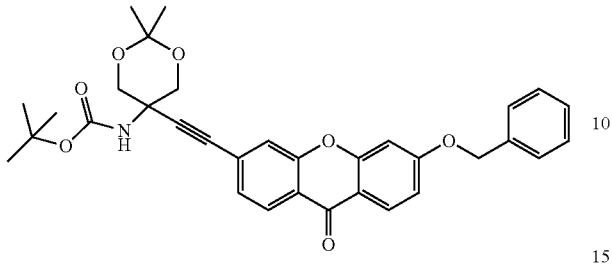

A mixture of Reference Example compound 13-5 (14.1 g), t-butyl (5-ethynyl-2,2-dimethyl-1,3-dioxan-5-yl)carbamate (11.8 g), cesium carbonate (35.5 g), 2-dicyclohexylphosphino-2',4',6'-triisopropylbiphenyl (1.20 g), dichlorobis(acetonitrile)palladium(II) (217 mg) and acetonitrile (300 ml) was stirred under reflux for 9 hr. The reaction mixture was poured into water (1000 ml), and the mixture was extracted with ethyl acetate. The organic layer was washed with saturated brine, and dried over anhydrous magnesium sulfate. The solvent was evaporated under reduced pressure and the residue was purified by silica gel column chromatography. The obtained residue was washed with diisopropyl ether to give Reference Example compound 13-6 (12.9 g) as a pale-yellow powder.

$^1$H-NMR (CDCl$_3$) δ (ppm): 1.47 (3H, s), 1.50 (3H, s), 1.53 (9H, s), 4.08 (2H, d, J=11.4 Hz), 4.13 (2H, d, J=11.4 Hz), 5.20 (2H, s), 5.25 (1H, brs), 6.96 (1H, d, J=2.3 Hz), 7.03 (1H, dd, J=2.3, 9.0 Hz), 7.36-7.48 (6H, m), 7.52 (1H, d, J=1.0 Hz), 8.23 (1H, dd, J=2.3 Hz), 8.25 (1H, d, J=3.2 Hz).

7) Synthesis of t-butyl {5-[2-(6-hydroxy-9-oxo-9H-xanthen-3-yl)ethyl]-2,2-dimethyl-1,3-dioxan-5-yl}carbamate (Reference Example compound 13)

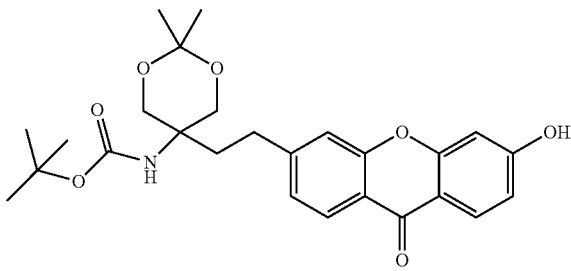 [SMILES: CC(C)(C)OC(=O)NC1(CCc2ccc3c(=O)c4ccc(O)cc4oc3c2)COC(C)(C)OC1]

To a solution of Reference Example compound 13-6 (12.8 g) in 1,4-dioxane (250 ml) was added 10% palladium carbon (containing about 50% water, 2.56 g), and the mixture was stirred under a hydrogen atmosphere at room temperature for 15 hr. The reaction mixture was filtered through celite and concentrated. The obtained residue was washed with diisopropyl ether to give Reference Example compound 13 (10.8 g) as a pale-yellow powder.

$^1$H-NMR (CDCl$_3$) δ (ppm): 1.44 (3H, s), 1.46 (3H, s), 1.50 (9H, s), 2.03-2.07 (2H, m), 2.68-2.72 (2H, m), 3.73 (2H, d, J=11.2 Hz), 3.93 (2H, d, J=11.2 Hz), 5.14 (1H, brs), 6.93 (1H, dd, J=2.1, 8.7 Hz), 6.96 (1H, d, J=2.1 Hz), 7.17 (1H, dd, J=1.1, 7.9 Hz), 7.30 (1H, s), 7.88 (1H, s), 8.19 (1H, d, J=8.0 Hz), 8.21 (1H, d, J=8.0 Hz).

Reference Example 14

Synthesis of t-butyl {5-[2-(6-hydroxy-9-oxo-9H-xanthen-2-yl)ethyl]-2,2-dimethyl-1,3-dioxan-5-yl}carbamate (Reference Example compound 14)

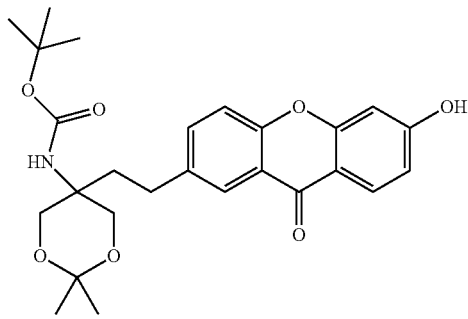 [SMILES: CC(C)(C)OC(=O)NC1(CCc2ccc3oc4cc(O)ccc4c(=O)c3c2)COC(C)(C)OC1]

By a method similar to the method for synthesizing Reference Example compound 13 from Reference Example compound 13-1, Reference Example compound 14 was obtained as a gray white powder from 2-fluoro-5-chlorobenzoyl chloride.

$^1$H-NMR (CDCl$_3$) δ (ppm): 1.44 (3H, s), 1.45 (3H, s), 1.50 (9H, s), 2.02-2.07 (2H, m), 2.66-2.70 (2H, m), 3.74 (2H, d, J=11.7 Hz), 3.91 (2H, d, J=11.7 Hz), 5.15 (1H, brs), 6.81 (1H, d, J=1.3 Hz), 6.87 (1H, dd, J=2.2, 8.7 Hz), 7.28 (1H, d, J=8.9 Hz), 7.47 (1H, dd, J=2.2, 8.9 Hz), 7.66 (1H, brs), 8.03 (1H, d, J=1.3 Hz), 8.16 (1H, d, J=8.7 Hz).

Reference Example 15

Synthesis of t-butyl {5-[2-(8-hydroxy-9-oxo-9H-xanthen-2-yl)ethyl]-2,2-dimethyl-1,3-dioxan-5-yl}carbamate 1) Synthesis of 5-chloro-2-(3-methoxyphenoxy)benzoic acid (Reference Example compound 15-1)

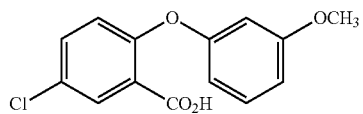

To a solution of potassium t-butoxide (47.3 g) in N-methyl-2-pyrrolidone (250 ml) was added 3-methoxyphenol (31.4 mL) under ice-cooling, and the mixture was stirred for 20 min. A solution of 5-chloro-2-fluorobenzoic acid (25.0 g) in N-methyl-2-pyrrolidone (150 ml) was added, and the mixture was stirred at 200° C. for 10 hr while removing t-butanol. The mixture was cooled, 1M hydrochloric acid (500 ml) was added, and the mixture was extracted with ethyl acetate. The organic layer was washed with saturated brine, dried over anhydrous sodium sulfate and the solvent was evaporated under reduced pressure. The residue was purified by silica gel column chromatography, and the obtained residue was washed with diisopropyl ether and hexane to give Reference Example compound 15-1 (19.0 g) as a white powder.

$^1$H-NMR (CDCl$_3$) δ (ppm): 3.83 (3H, s), 6.64-6.68 (2H, m), 6.81 (1H, dd, J=2.1, 8.6 Hz), 6.86 (1H, d, J=8.8 Hz), 7.33 (1H, t, J=8.2 Hz), 7.43 (1H, dd, J=2.9, 8.8 Hz), 8.17 (1H, d, J=2.5 Hz).

2) Synthesis of 7-chloro-1-methoxy-9H-xanthen-9-one (Reference Example compound 15-2)

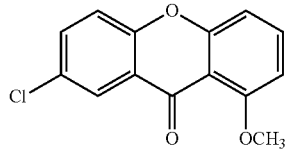 [SMILES: COc1cccc2oc3ccc(Cl)cc3c(=O)c12]

To a solution of Reference Example compound 15-1 (20.1 g) in acetyl chloride (200 ml) was added dropwise sulfuric acid (6.7 mL) under ice-cooling, and the mixture was stirred for 10 min under ice-cooling and further at room temperature for 7 hr. The reaction mixture was poured into ice water (1000 ml), and the mixture was extracted with ethyl acetate. The organic layer was washed with 2M aqueous sodium hydroxide solution and saturated brine, dried over anhydrous sodium sulfate and the solvent was evaporated under reduced pressure. The residue was purified by silica gel column chromatography to give Reference Example compound 15-2 (498 mg) as a pale-brown powder. In the silica gel column chromatography, 2-chloro-6-methoxyxanthen-9-one, which is an isomer, was eluted earlier, and Reference Example compound 15-2 was eluted later.

$^1$H-NMR (CDCl$_3$) δ (ppm): 4.03 (3H, s), 6.82 (1H, d, J=8.3 Hz), 7.06 (1H, d, J=8.2 Hz), 7.38 (1H, d, J=8.9 Hz), 7.61 (1H, dd, J=2.7, 8.9 Hz), 7.62 (1H, d, J=8.4 Hz), 8.25 (1H, d, J=2.5 Hz).

3) Synthesis of 7-chloro-1-hydroxy-9H-xanthen-9-one (Reference Example compound 15-3)

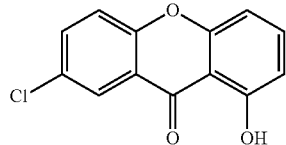 [SMILES: O=c1c2cc(Cl)ccc2oc2cccc(O)c12]

To a solution of Reference Example compound 15-2 (490 mg) in 1,2-dichloroethane (30 ml) was added a 1M solution (9.4 mL) of boron tribromide in methylene chloride, and the mixture was stirred at 60° C. for 9 hr. Under ice-cooling, methanol (70 ml) was gradually added, and the solvent was evaporated under reduced pressure. Water (80 ml) was added to the residue, and the precipitated solid was collected by filtration to give Reference Example compound 15-3 (473 mg) as a brown powder.

$^1$H-NMR (DMSO-d$_6$) δ (ppm): 6.87 (1H, d, J=8.2 Hz), 7.11 (1H, d, J=8.4 Hz) 7.74 (1H, d, J=8.9 Hz), 7.77 (1H, t, J=8.5 Hz), 7.96 (1H, dd, J=2.6, 8.9 Hz), 8.12 (1H, d, J=2.5 Hz), 12.32 (1H, s).

4) Synthesis of 1-benzyloxy-7-chloro-9H-xanthen-9-one (Reference Example compound 15-4)

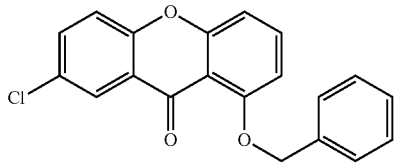 [SMILES: O=c1c2cc(Cl)ccc2oc2cccc(OCc3ccccc3)c12]

A mixture of Reference Example compound 15-3 (472 mg), potassium carbonate (810 mg), benzyl bromide (0.244 ml) and N,N-dimethylformamide (5 mL) was stirred at room temperature for 2 hr, and further at 50° C. for 3 hr. Water was added to the reaction mixture and the mixture was extracted with ethyl acetate. The organic layer was washed with saturated brine, dried over anhydrous sodium sulfate and the solvent was evaporated under reduced pressure. The residue was washed with diisopropyl ether and diethyl ether to give Reference Example compound 15-4 (408 mg) as a brown powder.

$^1$H-NMR (CDCl$_3$) δ (ppm): 5.32 (2H, s), 6.86 (1H, d, J=8.2 Hz), 7.06 (1H, d, J=8.4 Hz), 7.33 (1H, t, J=7.4 Hz), 7.39 (1H, d, J=9.0 Hz), 7.43 (2H, t, J=7.6 Hz), 7.58 (1H, t, J=8.4 Hz), 7.61 (1H, dd, J=2.6, 9.0 Hz), 7.64 (2H, d, J=7.6 Hz), 8.29 (1H, d, J=2.4 Hz).

5) Synthesis of t-butyl {5-[(8-benzyloxy-9-oxo-9H-xanthen-2-yl)ethynyl]-2,2-dimethyl-1,3-dioxan-5-yl}carbamate (Reference Example compound 15-5)

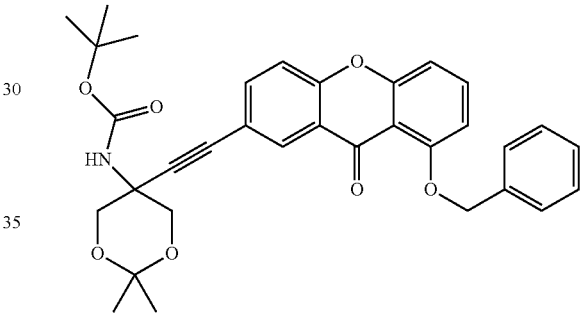

A mixture of Reference Example compound 15-4 (408 mg), t-butyl (5-ethynyl-2,2-dimethyl-1,3-dioxan-5-yl)carbamate (340 mg), cesium carbonate (1.03 g), 2-dicyclohexylphosphino-2',4',6'-triisopropylbiphenyl (34.6 mg), dichlorobis(acetonitrile)palladium(II) (6.3 mg) and acetonitrile (12 ml) was stirred under reflux for 9 hr. The reaction mixture was poured into water (100 ml), and the mixture was extracted with ethyl acetate. The organic layer was washed with saturated brine, and dried over anhydrous magnesium sulfate. The solvent was evaporated under reduced pressure and the residue was purified by silica gel column chromatography to give Reference Example compound 15-5 (512 mg) as a brown oil.

$^1$H-NMR (CDCl$_3$) δ (ppm): 1.46 (3H, s), 1.49 (9H, s), 1.53 (3H, s), 4.06 (2H, d, J=11.2 Hz), 4.12 (2H, d, J=11.2 Hz), 5.24 (1H, brs), 5.32 (2H, s), 6.86 (1H, d, J=8.4 Hz), 7.06 (1H, d, J=8.2 Hz), 7.33 (1H, t, J=7.5 Hz), 7.35 (1H, d, J=8.8 Hz), 7.43 (2H, t, J=7.5 Hz), 7.57 (1H, t, J=8.3 Hz), 7.65 (2H, d, J=7.6 Hz), 7.70 (1H, dd, J=2.1, 8.7 Hz), 8.39 (1H, d, J=2.1 Hz).

6) Synthesis of t-butyl {5-[2-(8-hydroxy-9-oxo-9H-xanthen-2-yl)ethyl]-2,2-dimethyl-1,3-dioxan-5-yl}carbamate (Reference Example compound 15)

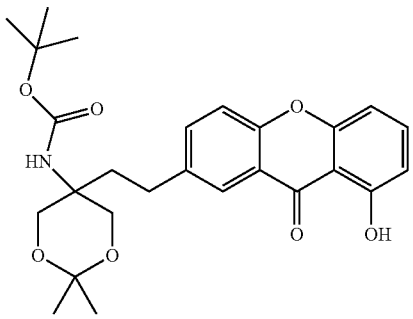 [SMILES: CC(C)(C)OC(=O)NC1(CCc2ccc3oc4cccc(O)c4c(=O)c3c2)COC(C)(C)OC1]

To a solution of Reference Example compound 15-5 (510 mg) in 1,4-dioxane (25 ml) was added 10% palladium carbon (containing about 50% water, 260 mg), and the mixture was stirred at room temperature for 3 hr under a hydrogen atmosphere. The reaction mixture was filtered through celite, concentrated, and hexane was added to the obtained residue. The precipitated solid was collected by filtration to give Reference Example compound 15 (329 mg) as a yellow powder.

$^1$H-NMR (CDCl$_3$) δ (ppm): 1.44 (3H, s), 1.45 (3H, s), 1.49 (9H, s), 2.03-2.07 (2H, m), 2.69-2.73 (2H, m), 3.72 (2H, d, J=11.6 Hz), 3.91 (2H, d, J=11.6 Hz), 5.05 (1H, brs), 6.80 (1H, d, J=8.3 Hz), 6.93 (1H, d, J=8.3 Hz), 7.41 (1H, d, J=8.6 Hz), 7.57-7.62 (2H, m), 8.06 (1H, s), 12.69 (1H, s).

Reference Example 16

Synthesis of [2-acetoxymethyl-2-acetylamino-4-(9-oxo-9H-thioxanthene-7-trifluoromethanesulfonyloxy-2-yl)butyl]acetate (Reference Example compound 16)

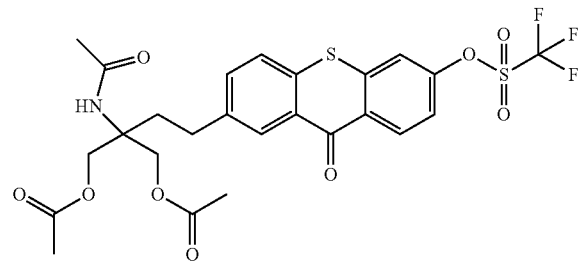 [SMILES: CC(=O)NC(CCc1ccc2sc3cc(OS(=O)(=O)C(F)(F)F)ccc3c(=O)c2c1)(COC(C)=O)COC(C)=O]

To Reference Example compound 1 (1.0 g) were added methylene chloride (15 ml) and pyridine (0.82 ml), and a solution of trifluoromethanesulfonic anhydride (0.43 ml) in methylene chloride (5 mL) was added dropwise under ice-cooling. After stirring at room temperature for 1 hr, saturated aqueous sodium hydrogen carbonate was added to the reaction mixture, and the mixture was extracted with methylene chloride. The organic layer was dried over anhydrous sodium sulfate, and the solvent was evaporated under reduced pressure. The obtained residue was purified by silica gel column chromatography to give Reference Example compound 16 (1.19 g) as a pale-yellow powder.

$^1$H-NMR (DMSO-d$_6$) δ (ppm): 1.87 (3H, s), 2.04 (6H, s), 2.02-2.07 (2H, m), 2.72-2.76 (2H, m), 4.22 (2H, d, J=11.0 Hz), 4.32 (2H, d, J=11.1 Hz), 7.69 (1H, dd, J=1.7, 8.3 Hz), 7.75 (1H, s), 7.86 (1H, d, J=8.2 Hz), 7.98 (1H, dd, J=2.6, 8.8 Hz), 8.13 (1H, d, J=8.8 Hz), 8.32 (1H, d, J=1.7 Hz), 8.41 (1H, d, J=2.6 Hz).

Reference Example 17

Synthesis of [2-acetoxymethyl-2-acetylamino-4-(9-oxo-6-trifluoromethanesulfonyloxy-9H-thioxanthen-2-yl)butyl]acetate (Reference Example compound 17)

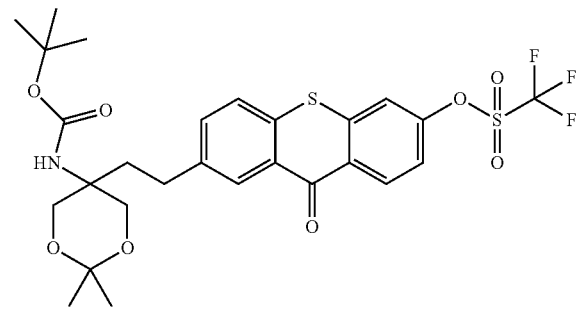

By a method similar to the method for synthesizing Reference Example compound 16 from Reference Example compound 1, Reference Example compound 17 was obtained as a white powder from Reference Example compound 5.

$^1$H-NMR (DMSO-d$_6$) δ (ppm): 1.87 (3H, s), 2.04 (6H, s), 2.02-2.06 (2H, m), 2.71-2.75 (2H, m), 4.22 (2H, d, J=11.0 Hz), 4.32 (2H, d, J=11.0 Hz), 7.64-7.69 (2H, m), 7.74 (1H, s), 7.84 (1H, d, J=8.2 Hz), 8.26 (1H, d, J=2.4 Hz), 8.31 (1H, d, J=1.5 Hz), 8.61 (1H, d, J=9.1 Hz).

Reference Example 18

Synthesis of t-butyl {5-[2-(9-oxo-6-trifluoromethanesulfonyloxy-9H-thioxanthen-2-yl)ethyl]-2,2-dimethyl-1,3-dioxan-5-yl}carbamate (Reference Example compound 18)

By a method similar to the method for synthesizing Reference Example compound 16 from Reference Example compound 1, Reference Example compound 18 was obtained as a white powder from Reference Example compound 7.

$^1$H-NMR (DMSO-d$_6$) δ (ppm): 1.33 (3H, s), 1.35 (3H, s), 1.42 (9H, s), 2.02-2.06 (2H, m), 2.63-2.67 (2H, m), 3.71 (2H, d, J=11.7 Hz), 3.91 (2H, d, J=11.4 Hz), 6.71 (1HH, brs), 7.64 (1H, dd, J=1.7, 8.3 Hz), 7.68 (1HH, dd, J=2.5, 9.1 Hz), 7.83 (1H, d, J=8.3 Hz), 8.25 (1H, d, J=2.5 Hz), 8.29 (1H, d, J=1.5 Hz), 8.61 (1H, d, J=9.0 Hz).

Reference Example 19

Synthesis of t-butyl {5-[2-(9-oxo-7-trifluoromethanesulfonyloxy-9H-xanthen-3-yl)ethyl]-2,2-dimethyl-1,3-dioxan-5-yl}carbamate (Reference Example compound 19)

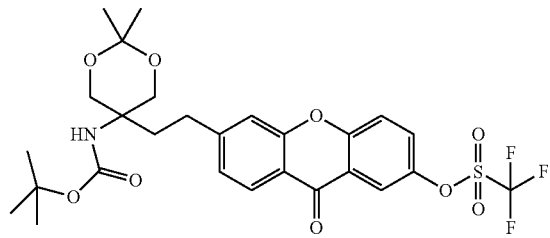 [SMILES: CC(C)(C)OC(=O)NC1(CCc2ccc3c(=O)c4cc(OS(=O)(=O)C(F)(F)F)ccc4oc3c2)COC(C)(C)OC1]

By a method similar to the method for synthesizing Reference Example compound 16 from Reference Example compound 1, Reference Example compound 19 was obtained as a white powder from Reference Example compound 11.

$^1$H-NMR (DMSO-$d_6$) δ (ppm): 1.33 (3H, s), 1.35 (3H, s), 1.41 (9H, s), 2.05-2.09 (2H, m), 2.66-2.70 (2H, m), 3.71 (2H, d, J=11.7 Hz), 3.91 (2H, d, J=11.5 Hz), 6.70 (1HH, brs), 7.34 (1H, dd, J=1.1, 8.2 Hz), 7.49 (1HH, s), 7.88 (1H, d, J=9.2 Hz), 8.03 (1H, dd, J=3.1, 9.2 Hz), 8.12 (1H, d, J=8.2 Hz), 8.15 (1H, d, J=3.1 Hz).

Reference Example 20

Synthesis of t-butyl {5-[2-(9-oxo-6-trifluoromethanesulfonyloxy-9H-xanthen-2-yl)ethyl]-2,2-dimethyl-1,3-dioxan-5-yl}carbamate (Reference Example compound 20)

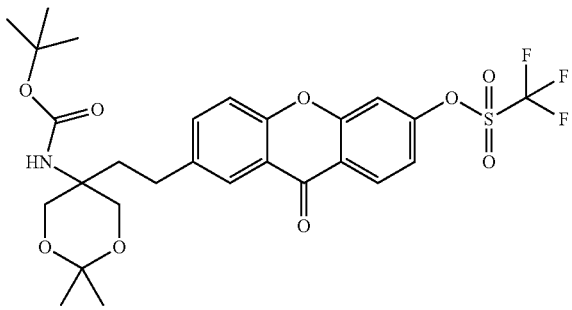 [SMILES: CC(C)(C)OC(=O)NC1(CCc2ccc3oc4cc(OS(=O)(=O)C(F)(F)F)ccc4c(=O)c3c2)COC(C)(C)OC1]

By a method similar to the method for synthesizing Reference Example compound 16 from Reference Example compound 1, Reference Example compound 20 was obtained as a white powder from Reference Example compound 14.

$^1$H-NMR (DMSO-$d_6$) δ (ppm): 1.33 (3H, s), 1.34 (3H, s), 1.42 (9H, s), 2.00-2.05 (2H, m), 2.62-2.66 (2H, m), 3.71 (2H, d, J=11.7 Hz), 3.91 (2H, d, J=11.3 Hz), 6.72 (1HH, brs), 7.60 (1H, dd, J=2.3, 9.0 Hz), 7.64 (1HH, d, J=8.6 Hz), 7.72 (1H, dd, J=2.1, 8.6 Hz), 8.00 (1H, d, J=1.8 Hz), 8.02 (1H, d, J=2.4 Hz), 8.37 (1H, d, J=9.1 Hz).

Reference Example 21

Synthesis of t-butyl {5-[2-(7-bromo-9H-xanthen-2-yl)ethyl]-2,2-dimethyl-1,3-dioxan-5-yl}carbamate 1) Synthesis of 2-bromo-7-(2-iodoethyl)-9H-xanthene (Reference Example compound 21-1)

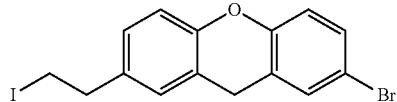 [SMILES: Brc1ccc2c(c1)Cc1cc(CCI)ccc1O2]

4-Hydroxyphenethyl alcohol (17 g) and 5-bromo-2-fluorobenzonitrile (23.5 g) were dissolved in N,N-dimethylformamide (200 ml), potassium carbonate (18 g) was added, and the mixture was stirred at 80° C. for 2.5 hr. Water was added to the reaction mixture, the mixture was extracted with ethyl acetate, washed with water and saturated brine, dried over anhydrous sodium sulfate and the solvent was evaporated under reduced pressure to give an oil (36 g). The obtained oil was dissolved in ethoxyethanol (150 ml) and water (100 ml), potassium hydroxide (15 g) was added, and the mixture was heated under reflux for 14 hr. Water was added to the reaction mixture, the aqueous layer was washed with ethyl acetate, acidified with concentrated hydrochloric acid, extracted with ethyl acetate, washed with water and saturated brine, and dried over anhydrous sodium sulfate. The solvent was evaporated under reduced pressure and the obtained residue was washed with a mixture of diisopropyl ether/hexane and collected by filtration to give 5-bromo-2-[4-(2-hydroxyethyl)phenoxy]benzoic acid (22 g) as a white powder. The obtained 5-bromo-2-[4-(2-hydroxyethyl)phenoxy]benzoic acid (22 g) was dissolved in acetic anhydride (80 ml), and the mixture was heated under reflux for 1 hr. The solvent was evaporated under reduced pressure, and the obtained residue was dissolved in 1,2-dichloroethane (200 ml). Aluminum chloride (13.5 g) was added, and the mixture was heated under reflux for 5 hr. The reaction mixture was added to ice water, the mixture was extracted with chloroform, washed with water and saturated brine, and dried over anhydrous sodium sulfate. The solvent was evaporated under reduced pressure and the obtained residue was washed with a mixture of diisopropyl ether/hexane, and collected by filtration to give [2-(7-bromo-9-oxo-9H-xanthen-2-yl)ethyl]acetate (17.3 g) as a white powder. The obtained [2-(7-bromo-9-oxo-9H-xanthen-2-yl)ethyl]acetate (17.3 g) was dissolved in tetrahydrofuran (200 ml), and lithium borohydride (3.5 g) was added in three portions and the mixture was heated under reflux for 8 hr. The reaction mixture was added to 1M hydrogen chloride isopropyl alcohol solution (200 ml), and the mixture was stirred at room temperature for 1 hr. The solvent was evaporated under reduced pressure, and the residue was extracted with ethyl acetate, washed with water and saturated brine, and dried over anhydrous sodium sulfate. The solvent was evaporated under reduced pressure and the obtained residue was washed with a mixture of ethyl acetate/hexane and collected by filtration to give 2-bromo-7-(2-hydroxyethyl)-9H-xanthene (11.8 g) as a white powder. The obtained 2-bromo-7-(2-hydroxyethyl)-9H-xanthene (11.8 g) and triethylamine (6.5 mL) were dissolved in methylene chloride (200 ml), methanesulfonylchloride (3.3 mL) was added dropwise at 0° C., and the mixture was stirred at the same temperature for 1.5 hr. Water was added to the reaction mixture, and the mixture was extracted with methylene chloride, washed with water and saturated brine, and dried over anhydrous sodium sulfate. The solvent was evaporated under reduced pressure and the obtained residue was dissolved in methyl ethyl ketone (200 ml). Sodium iodide (5.7 g) was added, and the mixture was heated under reflux for 5 hr. The reaction mixture was concentrated under reduced pressure, water was added to the residue, and the mixture was extracted with ethyl acetate, washed with water and saturated brine, and dried over anhydrous sodium sulfate. The solvent was evaporated under reduced pressure and the obtained residue was washed with diisopropyl ether and collected by filtration to give Reference Example compound 21-1 (11.8 g) as a white powder.

$^1$H-NMR (DMSO-$d_6$) δ (ppm): 3.05-3.11 (2H, m), 3.45 (2H, t, J=7.4 Hz), 4.04 (2H, s), 6.98-7.05 (2H, m), 7.10-7.19 (2H, m), 7.38 (1H, d, J=6.2 Hz), 7.49 (1H, s).

2) Synthesis of t-butyl {5-[2-(7-bromo-9H-xanthen-2-yl)ethyl]-2,2-dimethyl-1,3-dioxan-5-yl}carbamate (Reference Example compound 21)

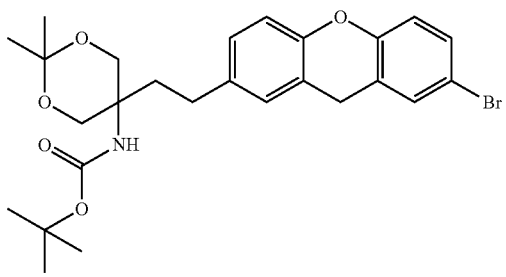 [SMILES: CC(C)(C)OC(=O)NC1(CCc2ccc3c(c2)Cc2cc(Br)ccc2O3)COC(C)(C)OC1]

To a solution of (t-butyloxycarbonyl)aminodiethyl malonate (10.0 g) in tetrahydrofuran (50 ml) was added t-butylsodium (3.8 g) in portions, and the mixture was stirred at the same temperature for 30 min. To this reaction mixture was added a solution of Reference Example compound 21-1 (10 g) in tetrahydrofuran (50 ml), and the mixture was heated under reflux for 1 hr. The reaction mixture was poured into water, extracted with ethyl acetate, washed with water and saturated brine, and dried over anhydrous sodium sulfate. The solvent was evaporated under reduced pressure, and the obtained residue was purified by silica gel column chromatography to give [2-(7-bromo-9H-xanthen-2-yl)ethyl][(t-butyloxycarbonyl)amino]diethyl malonate (15.2 g) as an oil. The obtained [2-(7-bromo-9H-xanthen-2-yl)ethyl][(t-butyloxycarbonyl)amino]diethyl malonate (5.45 g) was dissolved in a mixed solution of ethanol (80 ml), tetrahydrofuran (30 ml) and water (30 ml), calcium chloride (2.2 g) was added at room temperature, and the mixture was stirred for 20 min. To this solution was added sodium borohydride (1.5 g) in portions, and the mixture was stirred for 24 hr. 1M Hydrochloric acid was added to the reaction mixture, and the reaction solvent was evaporated under reduced pressure. The reaction mixture was added to 1M hydrochloric acid, and the mixture was extracted with ethyl acetate, washed with water and saturated brine, and dried over anhydrous sodium sulfate. The solvent was evaporated under reduced pressure, and the obtained residue was washed with ethyl acetate and collected by filtration to give t-butyl [3-(7-bromo-9H-xanthen-2-yl)-1,1-bis(hydroxymethyl)propyl}carbamate (1.5 g) as a white powder. A solution of the obtained t-butyl [3-(7-bromo-9H-xanthen-2-yl)-1,1-bis(hydroxymethyl)propyl}carbamate (580 mg), acetonedimethylacetal (0.45 ml) and a catalytic amount of p-toluenesulfonic acid in acetone (20 ml) was stirred for 6 hr. The reaction mixture was concentrated under reduced pressure, and the residue was extracted with ethyl acetate, washed with water and saturated brine, and dried over anhydrous sodium sulfate. The solvent was evaporated under reduced pressure to give Reference Example compound 21 (620 mg) as a white powder.

$^1$H-NMR (DMSO-$d_6$) δ (ppm): 1.32 (3H, s), 1.33 (3H, s), 1.41 (9H, s), 1.90-1.98 (2H, m), 2.39-2.47 (2H, m), 3.64-3.71 (2H, m), 3.82-3.92 (2H, m), 4.02 (2H, s), 6.62 (1H, brs), 6.95-7.06 (4H, m), 7.35-7.40 (1H, m), 7.47 (1H, s).

Reference Example 22

Synthesis of t-butyl {5-[2-(6-bromo-9H-xanthen-2-yl)ethyl]-2,2-dimethyl-1,3-dioxan-5-yl}carbamate (Reference Example compound 22)

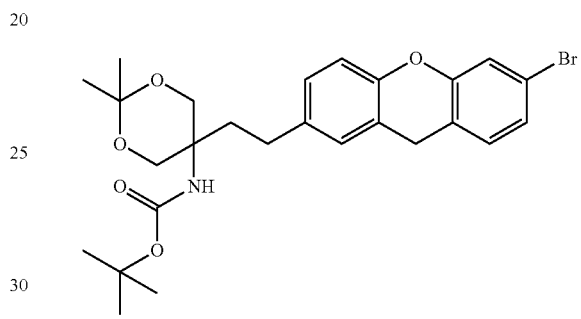

By a method similar to the method described in Reference Example 21, Reference Example compound 22 was obtained as a white powder from 4-bromo-2-fluorobenzonitrile.

$^1$H-NMR (DMSO-$d_6$) δ (ppm): 1.32 (3H, s), 1.33 (3H, s), 1.41 (9H, s), 1.91-1.97 (2H, m), 2.39-2.48 (2H, m), 3.63-3.72 (2H, m), 3.82-3.91 (2H, m), 3.98 (2H, s), 6.62 (1H, brs), 6.95-7.06 (3H, m), 7.20-7.25 (2H, m), 7.27 (1H, s).

Reference Example 23

Synthesis of t-butyl {5-[2-(6-bromo-9H-xanthen-3-yl)ethyl]-2,2-dimethyl-1,3-dioxan-5-yl}carbamate (Reference Example compound 23)

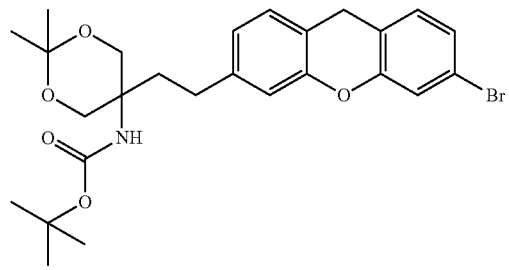 [SMILES: CC(C)(C)OC(=O)NC1(CCc2ccc3c(c2)Oc2cc(Br)ccc2C3)COC(C)(C)OC1]

By a method similar to the method described in Reference Example 21, Reference Example compound 23 was obtained as a white powder from 3-hydroxyphenethylalcohol.

$^1$H-NMR (DMSO-$d_6$) δ (ppm): 1.32 (3H, s), 1.33 (3H, s), 1.41 (9H, s), 1.91-2.00 (2H, m), 2.41-2.48 (2H, m), 3.64-

3.71 (2H, m), 3.82-3.91 (2H, m), 3.96 (2H, s), 6.60 (1H, brs), 6.85-6.94 (2H, m), 7.15 (1H, d, J=8.0 Hz), 7.20-7.30 (3H, m).

Reference Example 24

Synthesis of t-butyl {5-[2-(7-hydroxy-9-oxo-9H-fluoren-3-yl)ethyl]-2,2-dimethyl-1,3-dioxan-5-yl}carbamate 1) Synthesis of 6-chloro-2-methoxyfluoren-9-one (Reference Example compound 24-1)

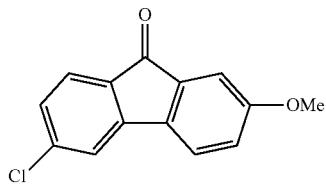 [SMILES: COc1ccc2c(c1)C(=O)c1ccc(Cl)cc1-2]

To methyl 4-chloro-2-iodobenzoate (10.0 g), 4-methoxyphenylboronic acid (6.15 g), palladium(II) acetate (378 mg), 2-dicyclohexylphosphino-2',6'-dimethoxybiphenyl (S-phos) (692 mg) and tripotassium phosphate (17.9 g) was added tetrahydrofuran (112 ml), and the mixture was stirred at room temperature for 18 hr. 4-Methoxyphenylboronic acid (3.07 g), palladium(II) acetate (189 mg) and 2-dicyclohexylphosphino-2',6'-dimethoxybiphenyl (S-phos) (346 mg) were further added, and the mixture was stirred for 3 hr. Water was added to the reaction mixture, and the mixture was extracted with ethyl acetate, washed with water and saturated brine, dried over anhydrous sodium sulfate. The solvent was evaporated under reduced pressure and the obtained residue was purified by silica gel column chromatography to give methyl 4-chloro-2-(4-methoxyphenyl)benzoate as a red solid. To the obtained red solid were added methanol (100 ml) and 1N aqueous sodium hydroxide solution (25 ml), and the mixture was stirred at 80° C. for 2 hr. 1N Sodium hydroxide (15 ml) was further added, and the mixture was stirred at 80° C. Water was added to the reaction mixture, and the mixture was extracted with ethyl acetate. The obtained aqueous layer was adjusted to pH 4 with hydrochloric acid, extracted with ethyl acetate, washed with saturated brine, and dried over anhydrous sodium sulfate. The solvent was evaporated under reduced pressure and the obtained residue was washed with diethyl ether and water to give 4-chloro-2-(4-methoxyphenyl)benzoic acid (7.5 g) as a gray solid. To the obtained gray solid (7.5 g) was added methanesulfonic acid (30 ml), and the mixture was stirred at 110° C. for 2 hr. The precipitated solid was collected by filtration, and washed with n-hexane to give Reference Example compound 24-1 (5.74 g) as an orange solid.

¹H-NMR (DMSO-d₆) δ (ppm): 3.84 (3H, s), 7.16-7.19 (2H, m), 7.33 (1H, dd, J=1.6, 7.8 Hz), 7.55 (1H, d, J=7.8 Hz), 7.78 (1H, d, J=8.6 Hz), 7.87 (1H, d, J=1.6 Hz).

2) Synthesis of 2-(tert-butyldimethylsilyloxy)-6-chlorofluoren-9-one (Reference Example compound 24-2)

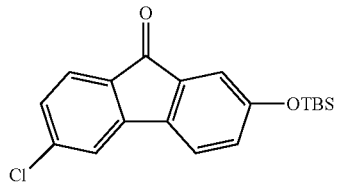 [SMILES: CC(C)(C)[Si](C)(C)Oc1ccc2c(c1)C(=O)c1ccc(Cl)cc1-2]

To Reference Example compound 24-1 (5.74 g) were added acetic acid (120 ml) and 47% hydrobromic acid (60 ml), the mixture was heated under reflux for 8 hr, and the resulting solid was collected by filtration and washed with water and n-hexane. To a solution of the obtained solid in N,N-dimethylformamide (75 ml) were added imidazole (2.0 g) and tert-butyldimethylsilylchloride (4.42 g), and the mixture was stirred at room temperature for 24 hr. Water was added to the reaction mixture, and the precipitated solid was collected by filtration, and washed with water to give Reference Example compound 24-2 (7.41 g) as a yellow powder.

¹H-NMR (DMSO-d₆) δ (ppm): 0.23 (6H, s), 0.97 (9H, s) 7.02 (1H, d, J=2.4 Hz), 7.10 (1H, dd, J=2.4, 7.8 Hz), 7.34 (1H, dd, J=1.6, 7.8 Hz), 7.56 (1H, d, J=7.8 Hz), 7.76 (1H, d, J=8.6 Hz), 7.88 (1H, d, J=1.6 Hz).

3) Synthesis of t-butyl {5-[(7-hydroxy-9-oxo-9H-fluoren-3-yl)ethynyl]-2,2-dimethyl-1,3-dioxan-5-yl}carbamate (Reference Example compound 24-3)

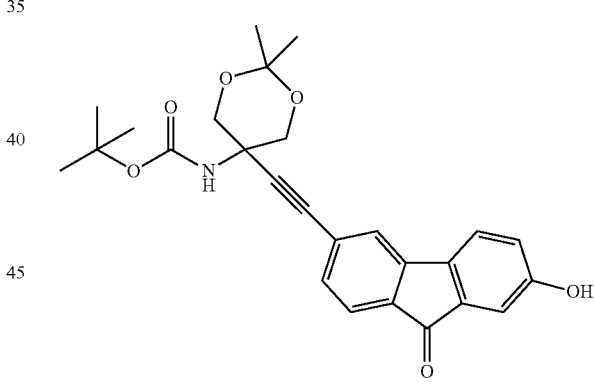

A mixture of Reference Example compound 24-2 (7.41 g), t-butyl (5-ethynyl-2,2-dimethyl-1,3-dioxan-5-yl)carbamate (5.08 g), cesium carbonate (17.7 g), 2-dicyclohexylphosphino-2',4',6'-triisopropylbiphenyl (3.1 g), dichlorobis(acetonitrile)palladium(II) (557 mg) and acetonitrile (72 ml) was stirred under reflux for 6.5 hr. Water was added to the reaction mixture, the mixture was extracted with ethyl acetate, washed with water and saturated brine, and dried over anhydrous sodium sulfate. The solvent was evaporated under reduced pressure, and the obtained residue was purified by silica gel column chromatography to give Reference Example compound 24-3 (4.24 g) as a solid.

¹H-NMR ((DMSO-d₆) δ (ppm): 1.35 (3H, s), 1.40 (3H, s), 1.42 (9H, s). 3.99-4.07 (4H, m), 6.93-6.97 (2H, m), 7.22 (1H, d, J=1.6 Hz), 7.23 (1H, s), 7.51 (1H, d, J=6.2 Hz), 7.65-7.67 (2H, m), 10.14 (1H, s).

4) Synthesis of t-butyl {5-[2-(7-hydroxy-9-oxo-9H-fluoren-3-yl)ethyl]-2,2-dimethyl-1,3-dioxan-5-yl}carbamate (Reference Example compound 24)

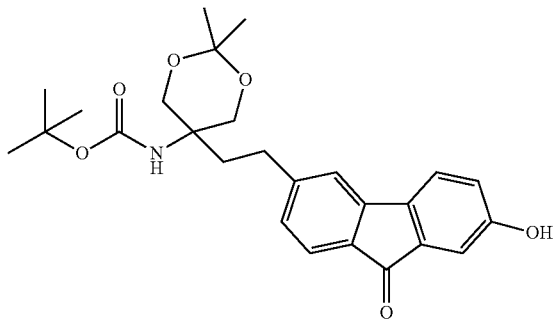 [SMILES: CC(C)(C)OC(=O)NC1(CCc2ccc3c(c2)-c2ccc(O)cc2C3=O)COC(C)(C)OC1]

To a solution of Reference Example compound 24-3 (4.24 g) in 1,4-dioxane (95 ml) was added 10% palladium carbon (containing about 50% water, 950 mg), and the mixture was stirred at room temperature for 3 hr under a hydrogen atmosphere. 10% Palladium carbon (containing about 50% water, 470 mg) was further added, and the mixture was stirred at room temperature for 10 hr under a hydrogen atmosphere. The reaction mixture was filtered through celite and concentrated. The obtained residue was purified by silica gel column chromatography to give Reference Example compound 24 (2.85 g) as a yellow solid.

$^1$H-NMR ((DMSO-d$_6$) δ (ppm): 1.33 (3H, s), 1.34 (3H, s), 1.41 (9H, s), 1.98-2.02 (2H, m), 2.50-2.54 (2H, m), 3.69 (2H, d, J=11.7 Hz), 3.89 (2H, d, J=11.7 Hz), 6.68 (1H, brs), 6.91-6.94 (2H, m), 7.01 (1H, d, J=8.6 Hz), 7.41 (1H, s), 7.43 (1H, d, J=7.8 Hz), 7.52 (1H, d, J=7.8 Hz), 10.05 (1H, brs).

Example 1

Synthesis of 2-[3-amino-4-hydroxy-3-(hydroxymethyl)butyl]-7-propyloxy-9H-thioxanthen-9-one (compound 1)

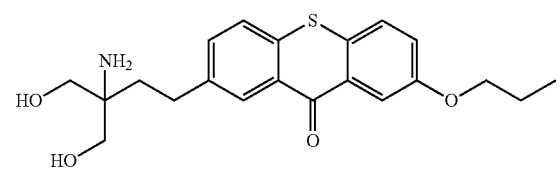 [SMILES: CCCOc1ccc2sc3ccc(CCC(N)(CO)CO)cc3c(=O)c2c1]

To Reference Example compound 1 (150 mg) were added potassium carbonate (130 mg), N,N-dimethylformamide (1 mL) and 1-bromopropane (0.04 ml), and the mixture was stirred at room temperature for one day. Water was added to the reaction mixture, the mixture was extracted with ethyl acetate, washed with water and saturated brine, and dried over anhydrous sodium sulfate. The solvent was evaporated under reduced pressure, and the obtained residue was washed with diethyl ether to give [2-acetoxymethyl-2-acetylamino-4-(9-oxo-7-propyloxy-9H-thioxanthen-2-yl)butyl] acetate (157 mg) as a pale-yellow powder. The obtained pale-yellow powder was dissolved in a mixed solvent of water (1 mL), methanol (1 mL) and tetrahydrofuran (1 mL), lithium hydroxide monohydrate (50 mg) was added, and the mixture was stirred at 80° C. for 2.5 hr. The reaction mixture was concentrated, and the obtained residue was washed with water to give compound 1 (110 mg) as a yellow powder.

MS (ESI) m/z: 388 [M+H];

$^1$H-NMR (DMSO-d$_6$) δ (ppm): 1.02 (3H, t, J=7.2 Hz), 1.34 (2H, brs), 1.55-1.59 (2H, m), 1.75-1.82 (2H, m), 2.74-2.79 (2H, m), 3.23-3.35 (4H, m), 4.08 (2H, t, J=6.4 Hz), 4.52 (2H, brs), 7.43 (1H, dd, J=3.0, 9.1 Hz), 7.63 (1H, dd, J=1.9, 8.4 Hz), 7.75-7.79 (2H, m), 7.92 (1H, d, J=2.9 Hz), 8.31 (1H, d, J=1.4 Hz).

By a method similar to that of Example 1, and using the corresponding starting materials and reagents, the compounds of the following Examples 2-9 were synthesized.

TABLE 1

| Ex. No. | | MS (ESI) m/z [M + 1] |
|---|---|---|
| 2 | ![structure] | 402 |
| 3 | ![structure] | 416 |

TABLE 1-continued

| Ex. No. | | MS (ESI) m/z [M + 1] |
|---|---|---|
| 4 | | 444 |
| 5 | | 430 |
| 6 | | 504 |
| 7 | | 402 |
| 8 | | 402 |
| 9 | | 388 |

Example 10

Synthesis of 2-[3-amino-4-hydroxy-3-(hydroxymethyl)butyl]-6-(pentyloxy)-9H-thioxanthen-9-one hydrochloride (compound 10)

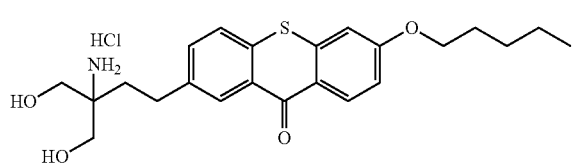 [SMILES: CCCCCOc1ccc2c(=O)c3cc(CCC(N)(CO)CO)ccc3sc2c1 ; Cl]

Reference Example compound 5 (100 mg) and potassium carbonate (85 mg) were dissolved in N,N-dimethylformamide (2 mL), 1-bromopentane (0.025 ml) was added, and the mixture was stirred at room temperature for one day. Water was added to the reaction mixture, the mixture was extracted with ethyl acetate, washed with water and saturated brine, and dried over anhydrous sodium sulfate. The solvent was evaporated under reduced pressure, and the obtained residue was washed with diethyl ether to give t-butyl {5-[2-(9-oxo-6-pentyloxy-9H-thioxanthen-2-yl)ethyl]-2,2-dimethyl-1,3-dioxan-5-yl}carbamate as a yellow oil. To the obtained yellow oil was added 2M hydrogen chloride ethanol solution (5 mL), and the mixture was stirred at 50° C. for 4 hr. The reaction mixture was concentrated, and the obtained residue was washed with diethyl ether to give compound 10 (62 mg) as a pale-yellow powder.

MS (ESI) m/z: 416 [M+H];

$^1$H-NMR (DMSO-$d_6$) δ (ppm): 0.91 (3H, t, J=7.0 Hz), 1.32-1.46 (4H, m), 1.73-1.80 (2H, m), 1.84-1.89 (2H, m), 2.75-2.80 (2H, m), 3.56 (4H, d, J=5.2 Hz), 4.14 (2H, t, J=6.4 Hz), 5.46 (2H, t, J=2.4 Hz), 7.63 (1H, dd, J=2.0, 8.4 Hz), 7.35 (1H, d, J=5.2 Hz), 7.63 (1H, dd, J=1.9, 8.4 Hz), 7.77 (1H, d, J=8.2 Hz), 7.91 (3H, brs), 8.33 (1H, d, J=1.5 Hz), 7.39 (1H, d, J=9.2).

By a method similar to that of Example 10, and using the corresponding starting materials and reagents, the compounds of the following Examples 11-43 were synthesized. When the column of salt in the Table is blank, the compound is a free form (hereinafter the same for Tables showing Example compounds).

TABLE 2

| Ex. No. | structure | salt | MS(ESI) m/z [M + 1] |
|---|---|---|---|
| 11 | 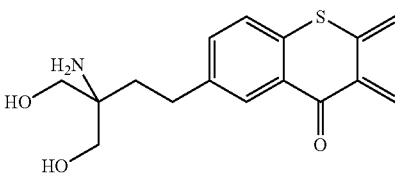 | HCl | 430 |
| 12 | 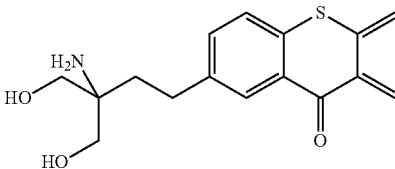 | HCl | 418 |
| 13 | 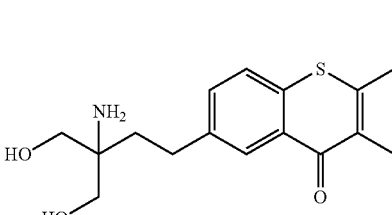 | HCl | 478 |
| 14 | 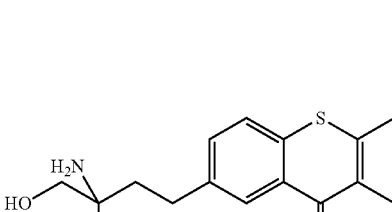 | HCl | 484 |
| 15 | 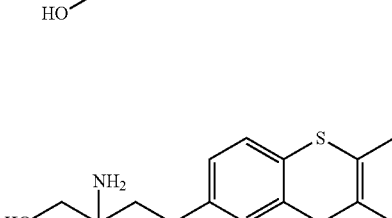 | HCl | 512 |

TABLE 2-continued

| Ex. No. | Structure | salt | MS(ESI) m/z [M + 1] |
|---|---|---|---|
| 16 | (thioxanthone with aminodiol propyl group and O-pentyl) | HCl | 416 |
| 17 | (thioxanthone with aminodiol propyl group and O-hexyl) | HCl | 430 |
| 18 | (thioxanthone with aminodiol propyl group and O-butyl, different regiochemistry) | HCl | 402 |

TABLE 3

| Ex. No. | Structure | salt | MS(ESI) m/z [M + 1] |
|---|---|---|---|
| 19 | (thioxanthone with aminodiol propyl group and O-pentyl) | HCl | 416 |
| 20 | (thioxanthone with aminodiol propyl group and O-hexyl) | HCl | 430 |
| 21 | (xanthone with aminodiol propyl group and O-butyl) | HCl | 386 |

TABLE 3-continued

| Ex. No. | Structure | salt | MS(ESI) m/z [M + 1] |
|---|---|---|---|
| 22 | | HCl | 400 |
| 23 | | HCl | 414 |
| 24 | | HCl | 490 |
| 25 | | HCl | 420 |
| 26 | | HCl | 420 |

TABLE 4

| Ex. No. | Structure | salt | MS(ESI) m/z [M + 1] |
|---|---|---|---|
| 27 | | HCl | 372 |
| 28 | | HCl | 386 |

TABLE 4-continued
| Ex. No. | | salt | MS(ESI) m/z [M + 1] |
|---|---|---|---|
| 29 | 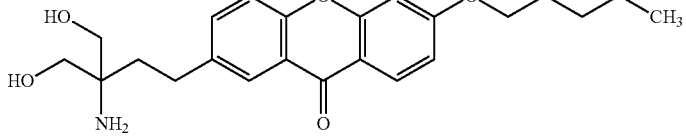 | HCl | 400 |
| 30 | 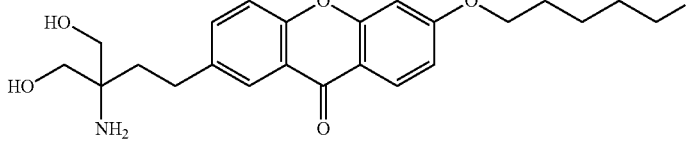 | HCl | 414 |
| 31 | 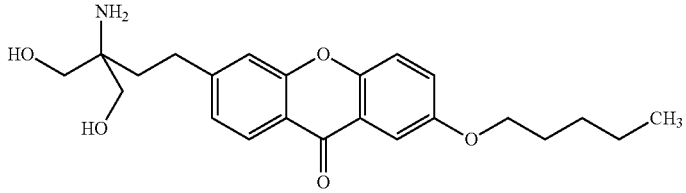 [SMILES: CCCCCOc1ccc2oc3cc(CCC(N)(CO)CO)ccc3c(=O)c2c1] | HCl | 400 |
| 32 | 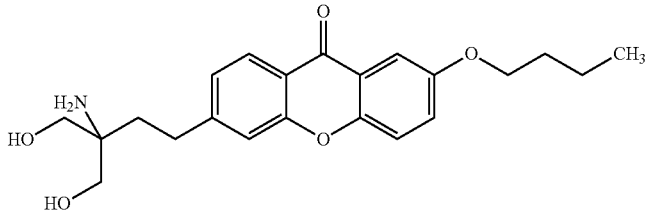 | HCl | 386 |
| 33 | 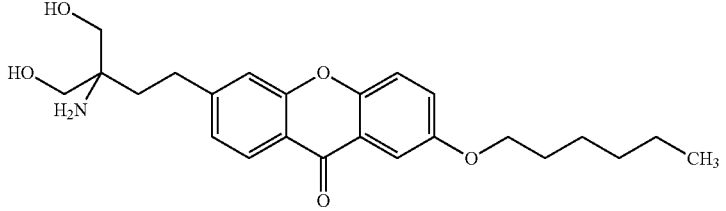 [SMILES: CCCCCCOc1ccc2oc3cc(CCC(N)(CO)CO)ccc3c(=O)c2c1] | HCl | 414 |
| 34 | 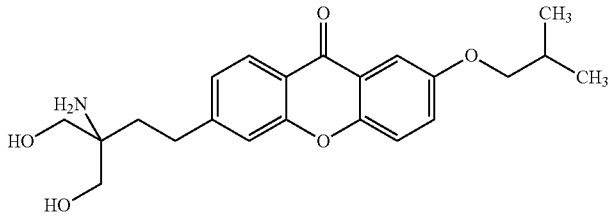 [SMILES: CC(C)COc1ccc2oc3cc(CCC(N)(CO)CO)ccc3c(=O)c2c1] | HCl | 386 |

TABLE 5
| Ex. No. | | salt | MS(ESI) m/z [M + 1] |
|---|---|---|---|
| 35 | 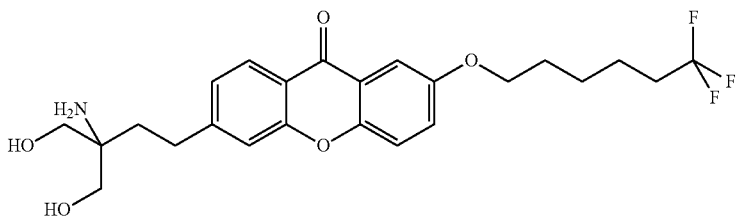 [SMILES: NC(CO)(CO)CCc1ccc2c(=O)c3cc(OCCCCCC(F)(F)F)ccc3oc2c1] | HCl | 468 |
| 36 | 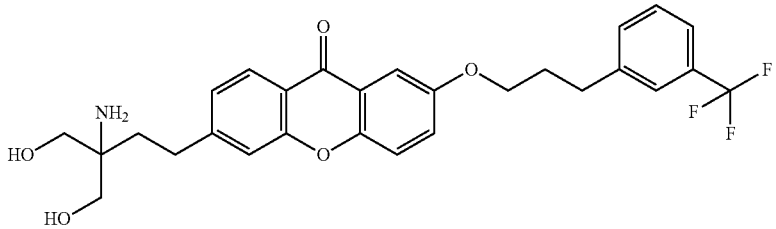 [SMILES: NC(CO)(CO)CCc1ccc2c(=O)c3cc(OCCCc4cccc(C(F)(F)F)c4)ccc3oc2c1] | HCl | 516 |
| 37 | 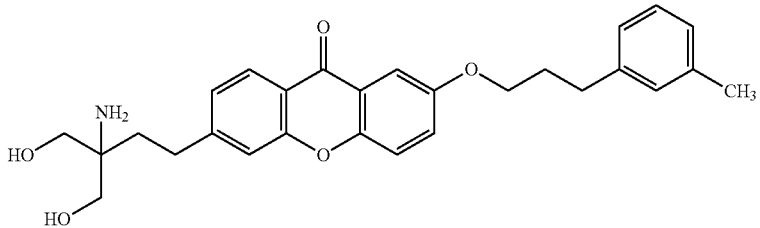 [SMILES: Cc1cccc(CCCOc2ccc3oc4cc(CCC(N)(CO)CO)ccc4c(=O)c3c2)c1] | HCl | 462 |
| 38 | 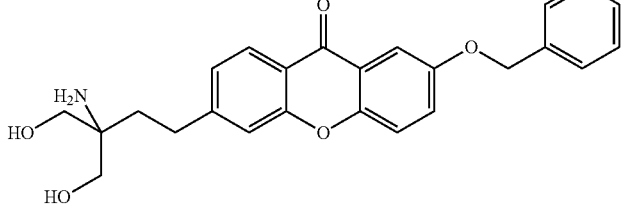 | HCl | 420 |
| 39 | 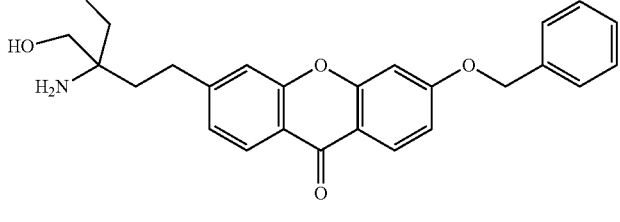 | HCl | 420 |
| 40 | 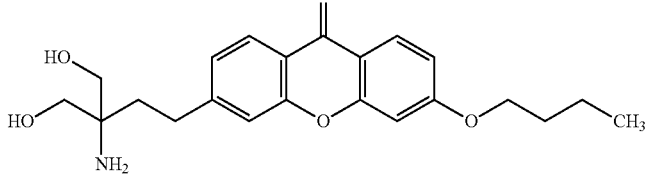 | HCl | 386 |

TABLE 5-continued

| Ex. No. | | salt | MS(ESI) m/z [M + 1] |
|---|---|---|---|
| 41 | | HCl | 400 |
| 42 | | HCl | 414 |

TABLE 6

| Ex. No. | | salt | MS(ESI) m/z [M + 1] |
|---|---|---|---|
| 43 | | | 400 |

Example 44

Synthesis of 2-[3-amino-4-hydroxy-3-(hydroxymethyl)butyl]-7-[3-(trifluoromethyl)phenoxy]-9H-thioxanthen-9-one 1) Synthesis of (2-acetoxymethyl-2-acetylamino-4-{9-oxo-7-[3-(trifluoromethyl)phenoxy]-9H-thioxanthen-2-yl}butyl) acetate (compound 44-1)

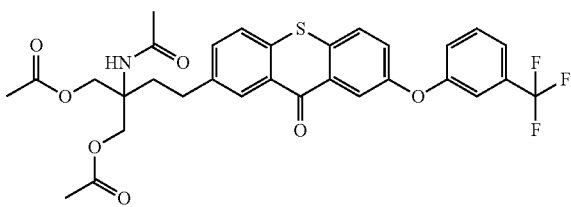 [SMILES: CC(=O)NC(CCc1ccc2sc3ccc(Oc4cccc(C(F)(F)F)c4)cc3c(=O)c2c1)(COC(C)=O)COC(C)=O]

To a suspension of Reference Example compound 1 (300 mg), 4 Å molecular sieves (300 mg), and 3-(trifluoromethyl)phenylboronic acid (485 mg) in methylene chloride (6.5 mL) were added pyridine (0.520 ml) and copper acetate (230 mg), and the mixture was stirred at room temperature for one day. Water was added to the reaction mixture, and the mixture was extracted with methylene chloride, and dried over anhydrous sodium sulfate. The solvent was evaporated under reduced pressure, and the obtained residue was purified by silica gel column chromatography to give compound 44-1 (240 mg) as a yellow powder.

MS (ESI) m/z: 616 [M+H];

$^{1}$H-NMR (DMSO-$d_6$) δ (ppm): 1.86 (3H, s), 1.99 (3H, s), 2.03 (5H, m), 2.70-2.74 (2H, m), 4.21 (2H, d, J=11.1 Hz), 4.31 (2H, d, J=11.1 Hz), 7.44 (1H, d, J=8.2 Hz), 7.50 (1H, s), 7.59-7.74 (5H, m), 7.82 (1H, d, J=8.2 Hz), 7.96-7.98 (2H, m), 8.29 (1H, s).

2) Synthesis of 2-[3-amino-4-hydroxy-3-(hydroxymethyl)butyl]-7-[3-(trifluoromethyl)phenoxy]-9H-thioxanthen-9-one (compound 44)

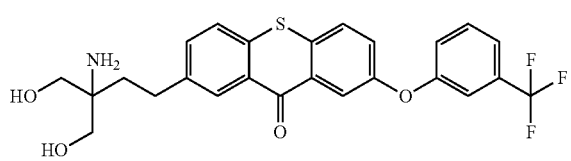 [SMILES: NC(CO)(CO)CCc1ccc2sc3ccc(Oc4cccc(C(F)(F)F)c4)cc3c(=O)c2c1]

Compound 44-1 (240 mg) was dissolved in a mixed solvent of water (1.3 mL), methanol (1.3 mL), and tetrahydrofuran (1.3 mL), lithium hydroxide monohydrate (65 mg) was added, and the mixture was stirred at 80° C. for 2 hr. The reaction mixture was concentrated, and the obtained residue was washed with water and diethyl ether to give compound 44 (140 mg) as a yellow powder.

MS (ESI) 490 m/z: [M+H];

$^1$H-NMR (DMSO-$d_6$) δ (ppm): 1.34 (2H, brs), 1.54-1.58 (2H, m), 2.74-2.78 (2H, m), 3.22-3.30 (4H, m), 4.52 (2H, brs), 7.44 (1H, d, J=8.2 Hz), 7.50 (1H, s), 7.59-7.71 (4H, m), 7.80 (1H, d, J=8.2 Hz), 7.95-7.97 (2H, m), 8.28 (1H, s).

The compounds of the following Examples 45-71 were synthesized by a method similar to that in Example 44 and using the corresponding starting materials and reagents.

TABLE 7

| Ex. No. | Structure | salt | MS(ESI) m/z [M + 1] |
|---|---|---|---|
| 45 | | | 436 |
| 46 | | | 436 |
| 47 | | | 490 |
| 48 | | | 440 |
| 49 | | | 440 |
| 50 | | | 456 |
| 51 | | | 506 |

TABLE 7-continued
| Ex. No. | | salt | MS(ESI) m/z [M + 1] |
|---|---|---|---|
| 52 | 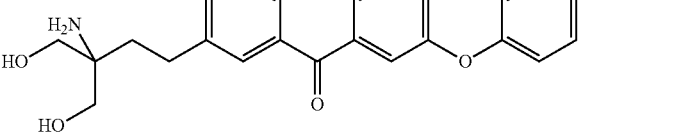 | | 464 |
TABLE 8
| Ex. No. | | salt | MS(ESI) m/z [M + 1] |
|---|---|---|---|
| 53 | 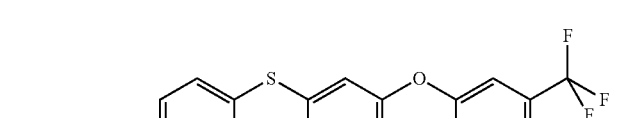 | | 422 |
| 54 | 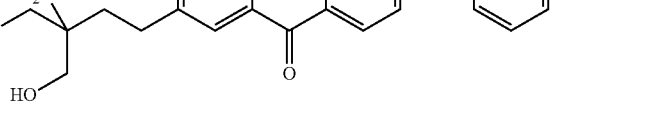 | | 490 |
| 55 | 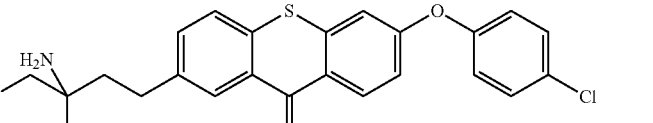 | | 456 |
| 56 | 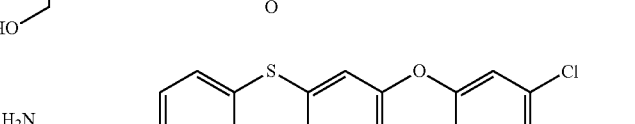 | | 456 |
| 57 | | | 452 |
| 58 | 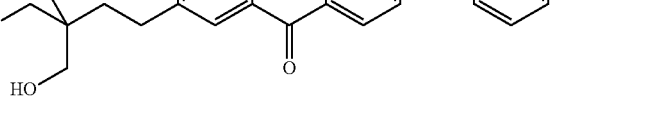 | | 490 |

TABLE 8-continued

| Ex. No. | salt | MS(ESI) m/z [M + 1] |
|---|---|---|
| 59 | | 436 |
| 60 | | 490 |

TABLE 9

| Ex. No. | salt | MS(ESI) m/z [M + 1] |
|---|---|---|
| 61 | | 436 |
| 62 | | 440 |
| 63 | | 456 |
| 64 | | 440 |

TABLE 9-continued
| Ex. No. | | salt | MS(ESI) m/z [M + 1] |
|---|---|---|---|
| 65 | 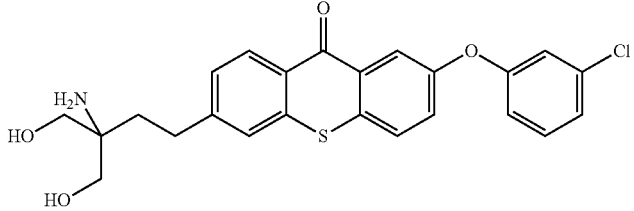 | | 456 |
| 66 | 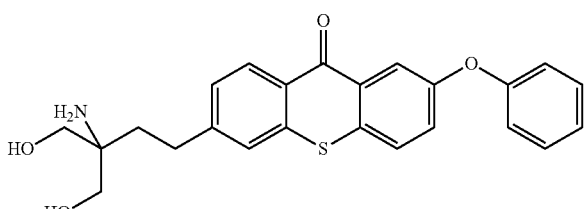 | | 422 |
| 67 | 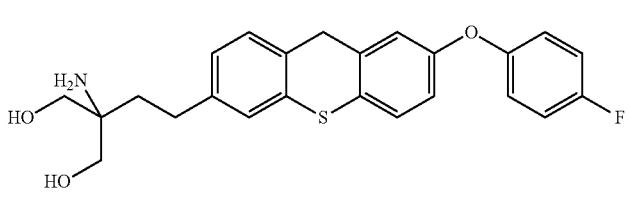 [SMILES: NC(CO)(CO)CCc1ccc2c(c1)Sc1ccc(Oc3ccc(F)cc3)cc1C2] | | 426 |
| 68 | 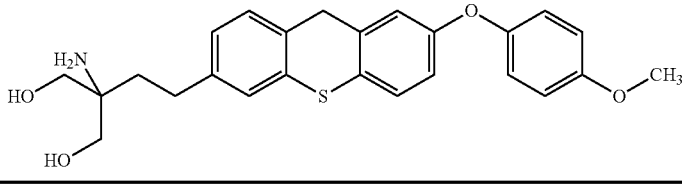 | | 438 |
TABLE 10
| Ex. No. | | salt | MS(ESI) m/z [M + 1] |
|---|---|---|---|
| 69 | 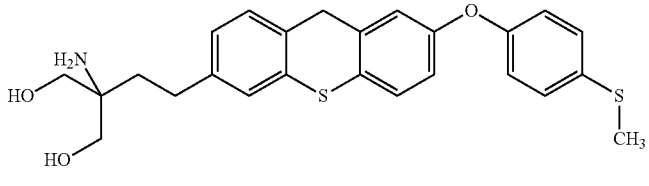 [SMILES: CSc1ccc(Oc2ccc3c(c2)Cc2ccc(CCC(N)(CO)CO)cc2S3)cc1] | | 454 |
| 70 | 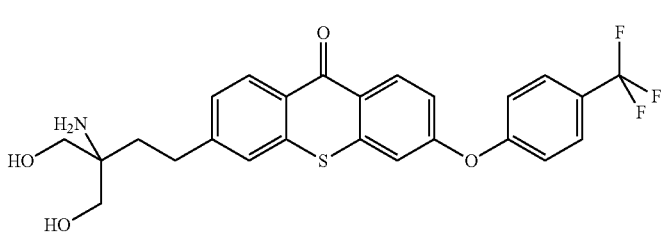 [SMILES: NC(CO)(CO)CCc1ccc2c(=O)c3ccc(Oc4ccc(C(F)(F)F)cc4)cc3sc2c1] | | 490 |

TABLE 10-continued

| Ex. No. | | salt | MS(ESI) m/z [M + 1] |
|---|---|---|---|
| 71 | 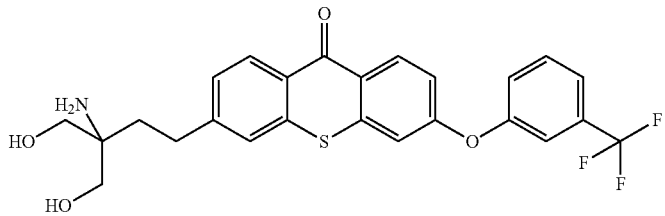 [SMILES: NC(CO)(CO)CCc1ccc2c(=O)c3ccc(Oc4cccc(C(F)(F)F)c4)cc3sc2c1] | | 490 |

Example 72

Synthesis of 3-[3-amino-4-hydroxy-3-(hydroxymethyl)butyl]-6-(4-fluorophenoxy)-9H-thioxanthen-9-one hydrochloride (compound 72)

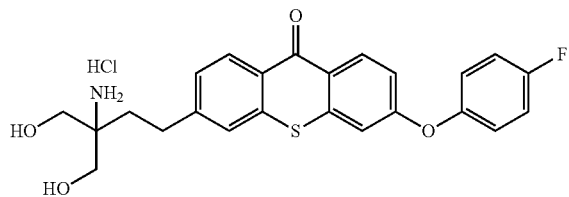 [SMILES: NC(CO)(CO)CCc1ccc2c(=O)c3ccc(Oc4ccc(F)cc4)cc3sc2c1 ; Cl]

To a suspension of Reference Example compound 4 (250 mg), 4 Å molecular sieves (250 mg), 4-fluorophenylboronic acid (340 mg) in methylene chloride (6.0 ml) were added pyridine (0.490 ml) and copper acetate (220 mg), and the mixture was stirred at room temperature for one day. Water was added to the reaction mixture, and the mixture was extracted with ethyl acetate, washed with saturated brine, and dried over anhydrous sodium sulfate. The solvent was evaporated under reduced pressure, and the obtained residue was purified by silica gel column chromatography to give [(4-{2-[6-(4-fluorophenoxy)-9-oxo-9H-thioxanthen-3-yl]ethyl}-2-methyl-4,5-dihydro-1,3-oxazol-4-yl)methyl]acetate as a yellow oil. To the obtained yellow oil were added ethanol (5 mL) and concentrated hydrochloric acid (1 mL), and the mixture was stirred at 50° C. for 4.5 hr. The reaction mixture was concentrated, and the obtained residue was washed with methanol and diethyl ether to give compound 72 (113 mg) as a white powder.

MS (ESI) m/z: 440 [M+H];
$^1$H-NMR (DMSO-$d_6$) δ (ppm): 1.85-1.89 (2H, m), 2.76-2.80 (2H, m), 3.55 (4H, d, J=5.2 Hz), 5.44 (2H, t, J=5.3 Hz), 7.15 (2H, dd, J=2.4, 9.2 Hz), 7.26-7.37 (5H, m), 7.45 (1H, dd, J=1.1, 8.6 Hz), 7.64 (1H, s), 7.93 (3H, brs), 8.40 (1H, d, J=8.2 Hz), 8.46 (1H, d, J=9.1 Hz).

The compounds of the following Examples 73-82 were synthesized by a method similar to that in Example 72 and using the corresponding starting materials and reagents. The compounds of Examples 76, 77 were synthesized from Reference Example compound 1, and the compounds of Examples 78-82 were synthesized from Reference Example compound 5.

TABLE 11

| Ex. No. | | salt | MS(ESI) m/z [M + 1] |
|---|---|---|---|
| 73 | 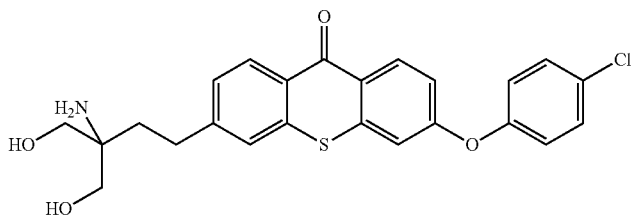 [SMILES: NC(CO)(CO)CCc1ccc2c(=O)c3ccc(Oc4ccc(Cl)cc4)cc3sc2c1] | HCl | 456 |
| 74 | 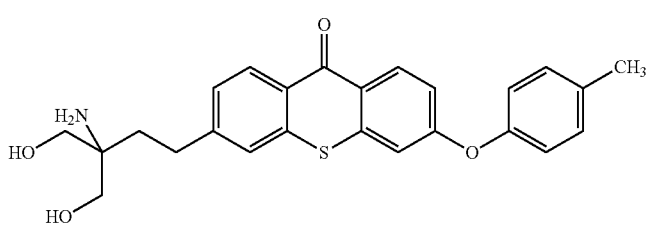 [SMILES: Cc1ccc(Oc2ccc3c(=O)c4ccc(CCC(N)(CO)CO)cc4sc3c2)cc1] | HCl | 436 |

TABLE 11-continued
| Ex. No. | | salt | MS(ESI) m/z [M + 1] |
|---|---|---|---|
| 75 | | HCl | 436 |
| 76 | | HCl | 456 |
| 77 | | HCl | 452 |
| 78 | | HCl | 436 |
| 79 | | HCl | 440 |
| 80 | | HCl | 490 |
| Ex. No. | | salt | MS(ESI) m/z [M + 1] |
|---|---|---|---|
| 81 |  | HCl | 436 |

-continued

| Ex. No. | | salt | MS(ESI) m/z [M + 1] |
|---|---|---|---|
| 82 | (structure) | HCl | 440 |

Example 83

Synthesis of 6-[3-amino-4-hydroxy-3-(hydroxymethyl)butyl]-2-[3-(trifluoromethyl)phenoxy]-9H-xanthen-9-one hydrochloride (compound 83)

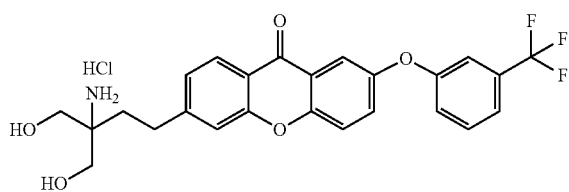 [SMILES: NC(CO)(CO)CCc1ccc2c(=O)c3cc(Oc4cccc(C(F)(F)F)c4)ccc3oc2c1 ; Cl]

To a suspension of Reference Example compound 11 (300 mg), 4 Å molecular sieves (300 mg), and 3-(trifluoromethyl) phenylboronic acid (485 mg) in methylene chloride (6.4 mL) were added pyridine (0.515 ml) and copper acetate (232 mg) and the mixture was stirred at room temperature for 8.5 hr. Water was added to the reaction mixture, and the mixture was extracted with methylene chloride, and dried over anhydrous sodium sulfate. The solvent was evaporated under reduced pressure, and the obtained residue was purified by silica gel column chromatography to give t-butyl [5-(2-{9-oxo-7-[3-(trifluoromethyl)phenoxy]-9H-xanthen-3-yl}ethyl)-2,2-dimethyl-1,3-dioxan-5-yl]carbamate (316 mg) as a white powder. To the obtained white powder was added 2M hydrogen chloride ethanol solution (10 ml), and the mixture was stirred at 50° C. for 1 hr. The reaction mixture was concentrated, the obtained residue was washed with diethyl ether to give compound 83 (215 mg) as a white powder.

MS (ESI) m/z: 474 [M+H];

$^1$H-NMR (DMSO-$d_6$) δ (ppm): 1.88-1.93 (2H, m), 2.82-2.86 (2H, m), 3.57 (4H, d, J=5.0H), 5.46 (2H, t, J=5.0H), 7.37-7.42 (2H, m), 7.45 (1H, s), 7.56-7.58 (2H, m), 7.66-7.72 (3H, m), 7.79 (1H, d, J=9.1 Hz), 7.96 (3H, brs), 8.13 (1H, d, J=8.3 Hz).

The compounds of the following Examples 84-151 were synthesized by a method similar to that in Example 83 and using the corresponding starting materials and reagents.

TABLE 13

| Ex. No. | | salt | MS(ESI) m/z [M + 1] |
|---|---|---|---|
| 84 | (structure) | HCl | 422 |
| 85 | (structure) | HCl | 452 |
| 86 | (structure) | HCl | 506 |

TABLE 13-continued

| Ex. No. | | salt | MS(ESI) m/z [M + 1] |
|---|---|---|---|
| 87 | | HCl | 506 |
| 88 | | HCl | 490 |
| 89 | | HCl | 474 |
| 90 | | HCl | 558 |
| 91 | | HCl | 474 |

TABLE 14

| Ex. No. | | salt | MS(ESI) m/z [M + 1] |
|---|---|---|---|
| 92 | | HCl | 524 |

TABLE 14-continued
| Ex. No. | | salt | MS(ESI) m/z [M + 1] |
|---|---|---|---|
| 93 | 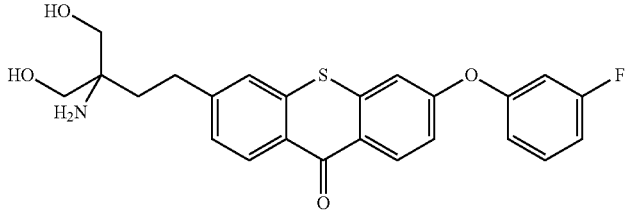 [SMILES: NC(CO)(CO)CCc1ccc2c(=O)c3ccc(Oc4cccc(F)c4)cc3sc2c1] | HCl | 440 |
| 94 | 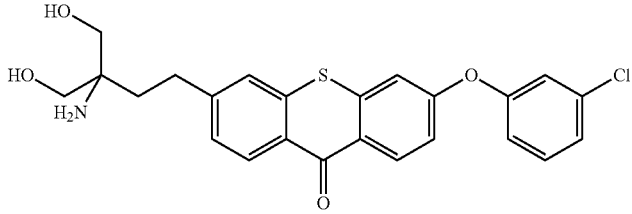 [SMILES: NC(CO)(CO)CCc1ccc2c(=O)c3ccc(Oc4cccc(Cl)c4)cc3sc2c1] | HCl | 456 |
| 95 | 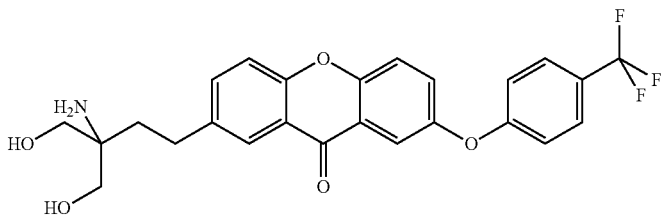 [SMILES: NC(CO)(CO)CCc1ccc2oc3ccc(Oc4ccc(C(F)(F)F)cc4)cc3c(=O)c2c1] | HCl | 474 |
| 96 | 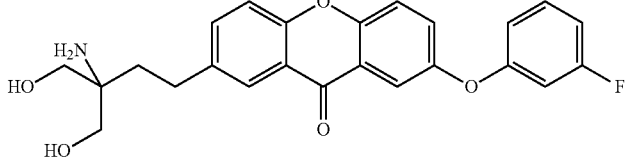 | HCl | 424 |
| 97 | 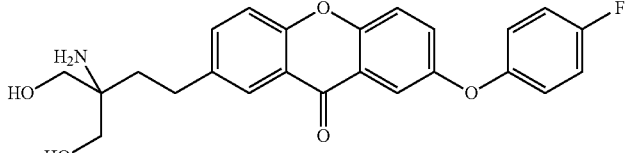 | HCl | 424 |
| 98 | 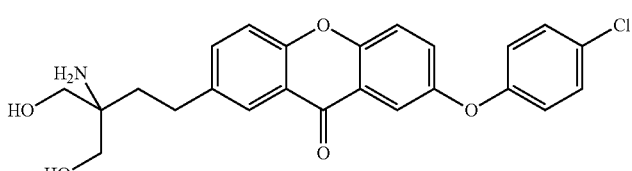 | HCl | 440 |
| 99 | 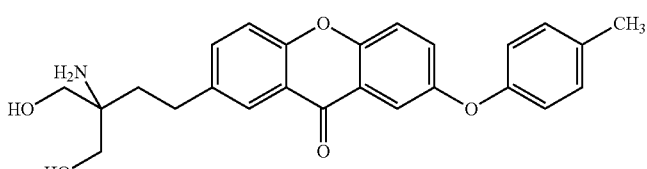 | HCl | 420 |

TABLE 15

| Ex. No. | structure | salt | MS(ESI) m/z [M + 1] |
|---|---|---|---|
| 100 | | HCl | 420 |
| 101 | | HCl | 440 |
| 102 | | HCl | 474 |
| 103 | | HCl | 406 |
| 104 | | HCl | 420 |
| 105 | | HCl | 424 |
| 106 | | HCl | 441 |
| 107 | | HCl | 474 |

TABLE 16
| Ex. No. | | salt | MS(ESI) m/z [M + 1] |
|---|---|---|---|
| 108 | 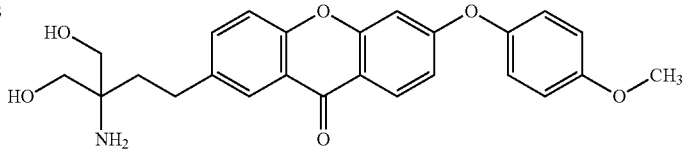 | HCl | 436 |
| 109 | 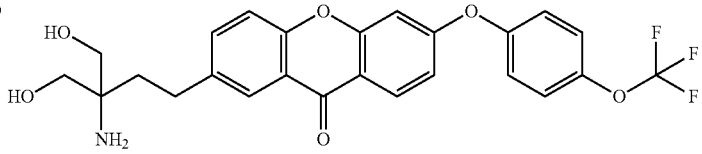 | HCl | 490 |
| 110 | 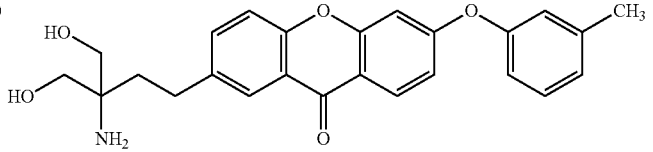 | HCl | 420 |
| 111 | 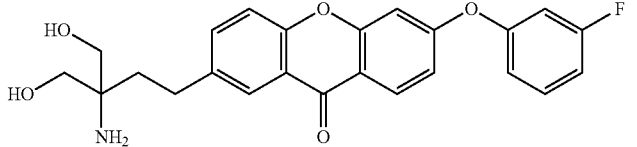 [SMILES: NC(CO)(CO)CCc1ccc2oc3cc(Oc4cccc(F)c4)ccc3c(=O)c2c1] | HCl | 424 |
| 112 | 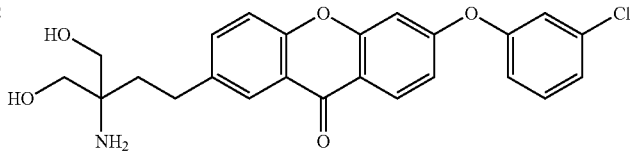 | HCl | 440 |
| 113 | 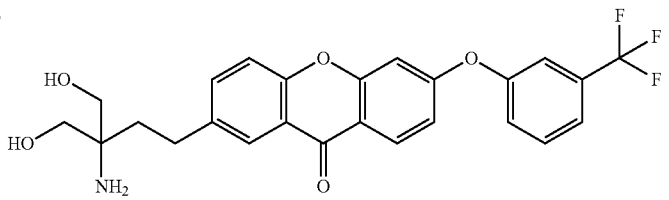 [SMILES: NC(CO)(CO)CCc1ccc2oc3cc(Oc4cccc(C(F)(F)F)c4)ccc3c(=O)c2c1] | HCl | 474 |
| 114 | 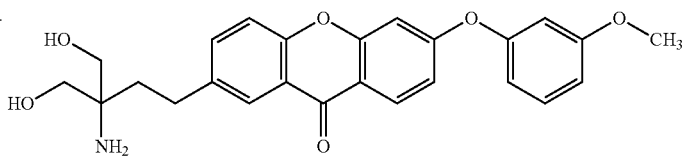 | HCl | 436 |
| 115 | 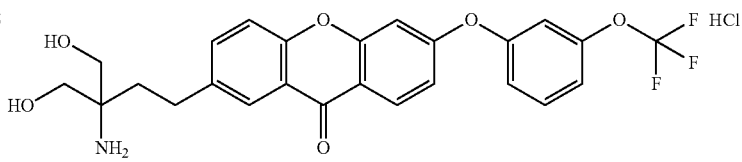 | HCl | 490 |

TABLE 17

| Ex. No. | Structure | salt | MS(ESI) m/z [M + 1] |
|---|---|---|---|
| 116 | (structure) | HCl | 458 |
| 117 | (structure) | HCl | 542 |
| 118 | (structure) | HCl | 470 |
| 119 | (structure) | HCl | 454 |
| 120 | (structure) | HCl | 420 |
| 121 | (structure) | HCl | 474 |
| 122 | (structure) | HCl | 424 |

TABLE 17-continued

| Ex. No. | | salt | MS(ESI) m/z [M + 1] |
|---|---|---|---|
| 123 | (structure) | HCl | 440 |

15

TABLE 18

| Ex. No. | | salt | MS(ESI) m/z [M + 1] |
|---|---|---|---|
| 124 | (structure) | HCl | 436 |
| 125 | (structure) | HCl | 490 |
| 126 | (structure) | HCl | 420 |
| 127 | (structure) | HCl | 424 |
| 128 | (structure) | HCl | 440 |

TABLE 18-continued

| Ex. No. | Structure | salt | MS(ESI) m/z [M + 1] |
|---|---|---|---|
| 129 | | HCl | 490 |
| 130 | | HCl | 406 |
| 131 | | HCl | 474 |

TABLE 19

| Ex. No. | Structure | salt | MS(ESI) m/z [M + 1] |
|---|---|---|---|
| 132 | | HCl | 449 |
| 133 | | HCl | 492 |
| 134 | | HCl | 509 |

TABLE 19-continued
| Ex. No. | | salt | MS(ESI) m/z [M + 1] |
|---|---|---|---|
| 135 | 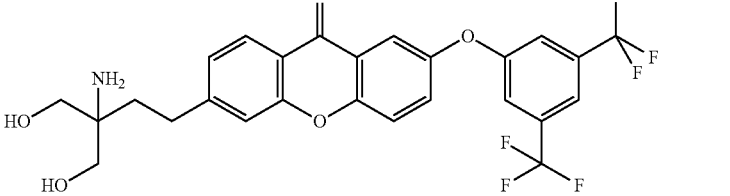 | HCl | 542 |
| 136 | 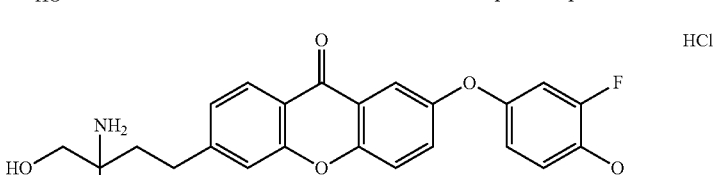 | HCl | 454 |
| 137 | 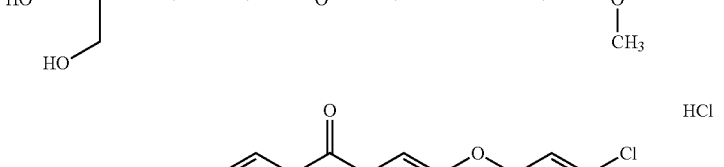 | HCl | 474 |
| 138 | 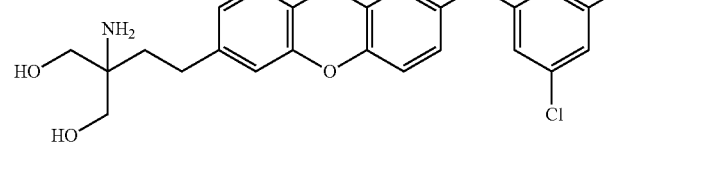 | HCl | 458 |
| 139 | 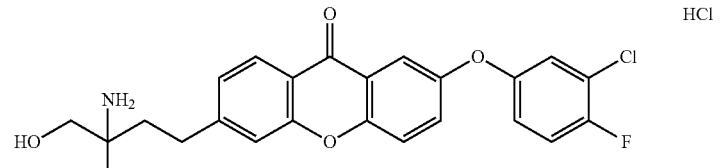 | HCl | 470 |
TABLE 20
| Ex. No. | | salt | MS(ESI) m/z [M + 1] |
|---|---|---|---|
| 140 | | HCl | 420 |

TABLE 20-continued

| Ex. No. | Structure | salt | MS(ESI) m/z [M + 1] |
|---|---|---|---|
| 141 | (structure) | HCl | 440 |
| 142 | (structure) | HCl | 424 |
| 143 | (structure) | HCl | 436 |
| 144 | (structure) | HCl | 490 |
| 145 | (structure) | HCl | 474 |
| 146 | (structure) | HCl | 420 |

TABLE 20-continued

| Ex. No. | | salt | MS(ESI) m/z [M + 1] |
|---|---|---|---|
| 147 | 3-[(3-fluorophenoxy)]-6-[3-amino-4-hydroxy-3-(hydroxymethyl)butyl]xanthen-9-one | HCl | 424 |

TABLE 21

| Ex. No. | | salt | MS(ESI) m/z [M + 1] |
|---|---|---|---|
| 148 | 3-[3-(trifluoromethyl)phenoxy]-6-[3-amino-4-hydroxy-3-(hydroxymethyl)butyl]xanthen-9-one | HCl | 474 |
| 149 | 3-(3-chlorophenoxy)-6-[3-amino-4-hydroxy-3-(hydroxymethyl)butyl]xanthen-9-one | HCl | 440 |
| 150 | 3-[3-(trifluoromethoxy)phenoxy]-6-[3-amino-4-hydroxy-3-(hydroxymethyl)butyl]xanthen-9-one | HCl | 490 |
| 151 | 3-(3-methoxyphenoxy)-6-[3-amino-4-hydroxy-3-(hydroxymethyl)butyl]xanthen-9-one | HCl | 436 |

Example 152

Synthesis of 2-[3-amino-4-hydroxy-3-(hydroxymethyl)butyl]-7-(4-methylphenylthio)-9H-thioxanthen-9-one hydrochloride (compound 152)

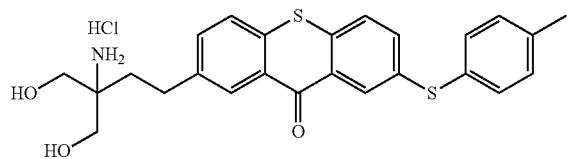 [SMILES: Cc1ccc(Sc2ccc3sc4ccc(CCC(N)(CO)CO)cc4c(=O)c3c2)cc1 ; Cl]

To Reference Example compound 16 (300 mg) were added 1,4-dioxane (1 mL), 4-methylbenzenethiol (0.55 mL), tris(dibenzylideneacetone)dipalladium(0)chloroform adduct (13 mg), 4,5-bis(diphenylphosphino)-9,9-dimethylxanthene (Xantphos) (15 mg) and N,N-diisopropylethylamine (0.175 mL), and the mixture was stirred at 120° C. for 7.5 hr. Water was added to the reaction mixture, and the mixture was extracted with ethyl acetate, washed with water and saturated brine, and dried over anhydrous sodium sulfate. The solvent was evaporated under reduced pressure, and the obtained residue was purified by silica gel column chromatography to give {2-acetoxymethyl-2-acetylamino-4-[7-(4-methylphenylthio)-9-oxo-9H-thioxanthen-2-yl]butyl}acetate (220 mg) as a yellow powder. To the obtained yellow powder were added ethanol (5 mL) and concentrated hydrochloric acid (1 mL) and the mixture was stirred at 80° C. for 2 hr. The reaction mixture was concentrated, and the obtained residue was washed with diethyl ether to give compound 152 (125 mg) as a yellow powder.

MS (ESI) m/z: 452 [M+H];
$^1$H-NMR (DMSO-$d_6$) δ (ppm): 1.84-1.88 (2H, m), 2.35 (3H, s), 2.75-2.80 (2H, m), 3.55 (4H, d, J=5.0H), 5.45 (2H, t, J=5.0H), 7.29 (2H, d, J=8.0 Hz), 7.40 (2H, d, J=8.0 Hz), 7.59 (1H, dd, J=2.2, 8.6 Hz), 7.67 (1H, dd, J=2.0, 8.4 Hz), 7.82-7.85 (2H, m), 7.88 (3H, brs), 8.23 (1H, d, J=2.0 Hz), 8.32 (1H, d, J=1.8 Hz).

The compounds of the following Examples 153-159 were synthesized by a method similar to that in Example 152 and using the corresponding starting materials and reagents.

TABLE 22

| Ex. No. | Structure | salt | MS(ESI) m/z [M + 1] |
|---|---|---|---|
| 153 | (structure) | | 452 |
| 154 | (structure) | | 506 |
| 155 | (structure) | HCl | 506 |
| 156 | (structure) | TFA | 422 |
| 157 | (structure) | | 422 |

TABLE 22-continued

| Ex. No. | | salt | MS(ESI) m/z [M + 1] |
|---|---|---|---|
| 158 | (structure) | | 422 |
| 159 | (structure) | HCl | 422 |

Example 160

Synthesis of 2-[3-amino-4-hydroxy-3-(hydroxymethyl)butyl]-6-(4-methylphenylthio)-9H-thioxanthen-9-one (compound 160)

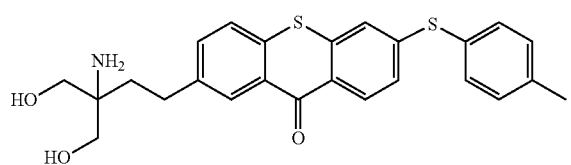 [SMILES: Cc1ccc(Sc2ccc3c(=O)c4cc(CCC(N)(CO)CO)ccc4sc3c2)cc1]

To Reference Example compound 17 (250 mg) were added 1,4-dioxane (1 mL), 4-methylbenzenethiol (0.455 mL), tris(dibenzylideneacetone)dipalladium(0)chloroform adduct (11 mg), 4,5-bis(diphenylphosphino)-9,9-dimethylxanthene (Xantphos) to (12 mg), and N,N-diisopropylethylamine (0.145 mL), and the mixture was stirred at 120° C. for 2 hr. Water was added to the reaction mixture, and the mixture was extracted with ethyl acetate, washed with water and saturated brine, and dried over anhydrous sodium sulfate. The solvent was evaporated under reduced pressure, and the obtained residue was purified by silica gel column chromatography to give {2-acetoxymethyl-2-acetylamino-4-[6-(4-methylphenylthio)-9-oxo-9H-thioxanthen-2-yl]butyl}acetate as an orange solid. The obtained orange solid was dissolved in a mixed solvent of water (1.5 mL), methanol (1.5 mL) and tetrahydrofuran (1.5 mL), lithium hydroxide monohydrate (70 mg) was added, and the mixture was stirred at 80° C. for 1.5 hr. The reaction mixture was concentrated, and the obtained residue was washed with water and diethyl ether to give compound 160 (153 mg) as an orange powder.

MS (ESI) m/z: 452 [M+H];

$^1$H-NMR (DMSO-$d_6$) δ (ppm): 1.53-1.57 (2H, m), 2.39 (3H, s), 2.72-2.77 (2H, m), 3.24-3.29 (4H, m), 5.31 (2H, brs), 7.18 (1H, dd, J=2.0, 8.6 Hz), 7.36 (2H, d, J=8.0 Hz), 7.41 (1H, d, J=1.9 Hz), 7.50-7.52 (2H, m), 7.61 (1H, dd, J=2.0, 8.4 Hz), 7.70 (1H, d, J=8.1 Hz), 8.26 (1H, d, J=1.7 Hz), 8.33 (1H, d, J=8.6 Hz).

The compounds of the following Examples 161-163 were synthesized by a method similar to that in Example 160 and using the corresponding starting materials and reagents.

TABLE 23

| Ex. No. | | salt | MS(ESI) m/z [M + 1] |
|---|---|---|---|
| 161 | (structure) | | 452 |
| 162 | (structure) | | 506 |

TABLE 23-continued

| Ex. No. | | salt | MS(ESI) m/z [M + 1] |
|---|---|---|---|
| 163 | 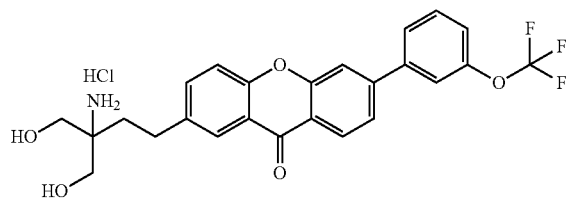 [SMILES: NC(CO)(CO)CCc1ccc2oc3cc(-c4cccc(OC(F)(F)F)c4)ccc3c(=O)c2c1 ; Cl] | HCl | 506 |

Example 164

Synthesis of 2-[3-amino-4-hydroxy-3-(hydroxymethyl)butyl]-6-[3-(trifluoromethoxy)phenyl]-9H-xanthen-9-one hydrochloride (compound 164)

Reference Example compound 20 (250 mg) was dissolved in tetrahydrofuran (0.83 mL), palladium(II) acetate (9.4 mg), 2-dicyclohexylphosphino-2',6'-dimethoxybiphenyl (S-phos) (17 mg), 3-(trifluoromethoxy)phenylboronic acid (120 mg), and tripotassium phosphate (220 mg) were added, and the mixture was stirred at 100° C. for 3 hr. Water was added to the reaction mixture, and the mixture was extracted with ethyl acetate, washed with saturated brine, and dried over anhydrous sodium sulfate. The solvent was evaporated under reduced pressure, and to the obtained residue was added 2M hydrogen chloride ethanol solution (10 ml) and the mixture was stirred at 50° C. for 3.5 hr. The reaction mixture was concentrated, and the obtained residue was washed with diethyl ether to give compound 164 (195 mg) as a white powder.

MS (ESI) m/z: 474 [M+H];
$^1$H-NMR (DMSO-d$_6$) δ (ppm): 1.86-1.90 (2H, m), 2.77-2.81 (2H, m), 3.57 (4H, d, J=5.0H), 5.46 (2H, t, J=5.2H), 7.50 (1H, d, J=8.7 Hz), 7.66-7.71 (2H, m), 7.78 (1H, dd, J=2.1, 8.6 Hz), 7.85-7.95 (6H, m), 8.07 (1H, d, J=1.4 Hz), 8.10 (1H, d, J=2.1 Hz), 8.28 (1H, d, J=2.0 Hz).

The compounds of the following Examples 165-182 were synthesized by a method similar to that in Example 164 and using the corresponding starting materials and reagents.

TABLE 24

| Ex. No. | | salt | MS(ESI) m/z [M + 1] |
|---|---|---|---|
| 165 | | HCl | 474 |
| 166 | | HCl | 490 |

TABLE 24-continued

| Ex. No. | | salt | MS(ESI) m/z [M + 1] |
|---|---|---|---|
| 167 | | HCl | 412 |
| 168 | | HCl | 446 |
| 169 | | HCl | 404 |
| 170 | | HCl | 458 |
| 171 | | HCl | 474 |
| 172 | | HCl | 458 |

TABLE 25
| Ex. No. | | salt | MS(ESI) m/z [M + 1] |
|---|---|---|---|
| 173 | 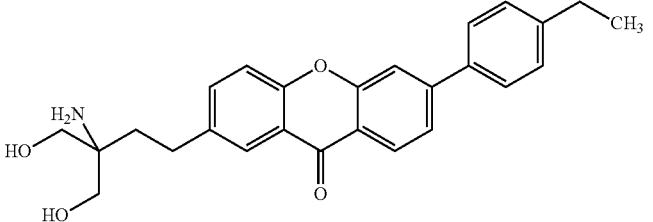 [SMILES: CCc1ccc(-c2ccc3c(=O)c4cc(CCC(N)(CO)CO)ccc4oc3c2)cc1] | HCl | 418 |
| 174 | 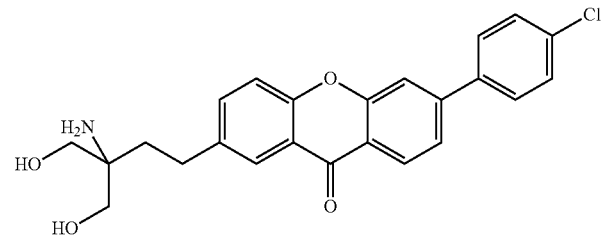 [SMILES: NC(CO)(CO)CCc1ccc2oc3cc(-c4ccc(Cl)cc4)ccc3c(=O)c2c1] | HCl | 424 |
| 175 | 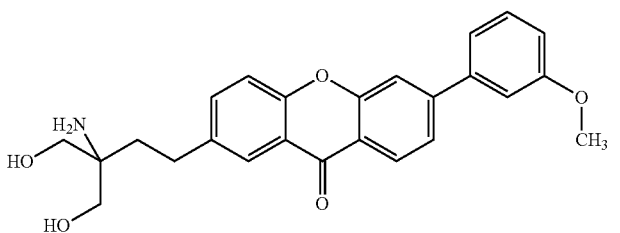 [SMILES: COc1cccc(-c2ccc3c(=O)c4cc(CCC(N)(CO)CO)ccc4oc3c2)c1] | HCl | 420 |
| 176 | 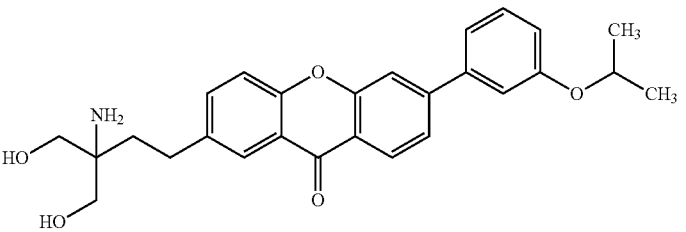 [SMILES: CC(C)Oc1cccc(-c2ccc3c(=O)c4cc(CCC(N)(CO)CO)ccc4oc3c2)c1] | HCl | 448 |
| 177 | 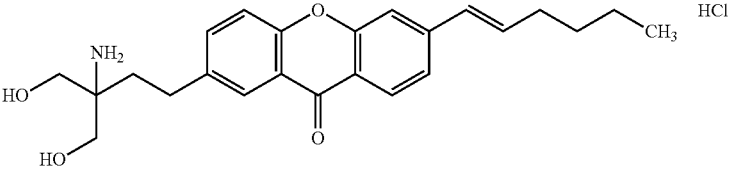 | HCl | 396 |
| 178 | 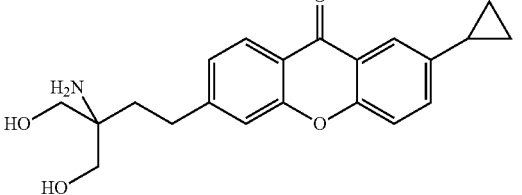 | HCl | 354 |

TABLE 25-continued

| Ex. No. | | salt | MS(ESI) m/z [M + 1] |
|---|---|---|---|
| 179 | ![structure] | HCl | 416 |
| 180 | ![structure] | HCl | 396 |

TABLE 26

| Ex. No. | | salt | MS(ESI) m/z [M + 1] |
|---|---|---|---|
| 181 | ![structure] | HCl | 430 |
| 182 | ![structure] | HCl | 430 |

Example 183

Synthesis of 6-[3-amino-4-hydroxy-3-(hydroxymethyl)butyl]-2-hexyl-9H-xanthen-9-one hydrochloride (compound 183)

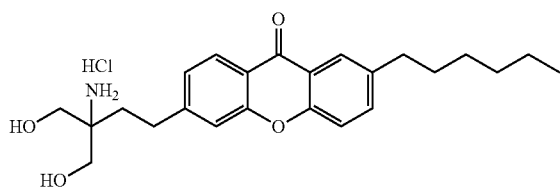 [SMILES: CCCCCCc1ccc2oc3cc(CCC(N)(CO)CO)ccc3c(=O)c2c1 ; Cl]

To a solution of compound 180 (60 mg) in ethanol (3 mL) was added 10% palladium carbon (containing about 50% water, 30 mg), and the mixture was stirred under a hydrogen atmosphere at room temperature for 2 hr. The reaction mixture was filtered through celite and concentrated. To the obtained residue was added 2M hydrogen chloride ethanol solution (2 mL), and the mixture was stirred at room temperature for 5 min. The reaction mixture was concentrated, and the obtained residue was washed with diethyl ether to give compound 183 (40 mg) as a white powder.

MS (ESI) m/z: 398 [M+H];

$^1$H-NMR (DMSO-$d_6$) δ (ppm): 0.86 (3H, t, J=6.8 Hz), 1.27-1.32 (6H, m) 1.59-1.66 (2H, m), 1.86-1.90 (2H, m), 2.73 (2H, t, J=7.6 Hz), 2.78-2.82 (2H, m), 3.55 (4H, d, J=5.0 Hz), 5.44 (2H, t, J=5.2 Hz), 7.35 (1H, dd, J=1.1, 8.5 Hz), 7.52 (1H, s), 7.59 (1H, d, J=8.6 Hz), 7.73 (1H, dd, J=2.2, 8.6 Hz), 7.85 (3H, brs), 7.98 (1H, d, J=1.9 Hz), 8.15 (1H, d, J=8.3).

The compounds of the following Examples 184-187 were synthesized by a method similar to that in Example 183 and using the corresponding starting materials and reagents.

TABLE 27

| Ex. No. | | salt | MS(ESI) m/z [M + 1] |
|---|---|---|---|
| 184 | | HCl | 448 |
| 185 | | HCl | 398 |
| 186 | | HCl | 418 |
| 187 | | HCl | 432 |

Example 188

Synthesis of 2-[3-amino-4-hydroxy-3-(hydroxymethyl)butyl]-7-(4-methylphenylthio)-9H-thioxanthene hydrochloride (compound 188)

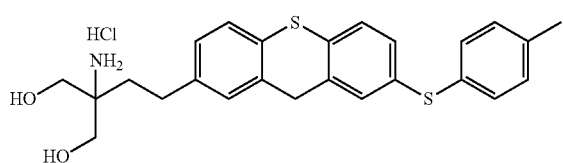 [SMILES: Cc1ccc(Sc2ccc3c(c2)Cc2cc(CCC(N)(CO)CO)ccc2S3)cc1 ; Cl]

To a solution of compound 152 (70 mg) in tetrahydrofuran (1.5 mL) was added lithium borohydride (13 mg), and the mixture was stirred at 80° C. for 1.5 hr. To the reaction mixture was added a mixed solution of isopropyl alcohol (3 mL) and 4M hydrogen chloride 1,4-dioxane solution (1 mL), and the mixture was stirred at 80° C. for 15 min. The reaction mixture was evaporated under reduced pressure, and the obtained residue was washed with diethyl ether and methanol to give compound 188 (51 mg) as a white powder.

MS (ESI) m/z: 438 [M+H];

$^1$H-NMR (DMSO-d$_6$) δ (ppm): 1.75-1.79 (2H, m), 2.30 (3H, s), 2.57-2.62 (2H, m), 3.52 (4H, d, J=5.0H), 3.81 (2H, s), 5.40 (2H, t, J=5.0H), 7.08-7.13 (2H, m), 7.19-7.27 (5H, m), 7.38-7.45 (3H, m), 7.84 (3H, brs).

The compounds of the following Examples 189-200 were synthesized by a method similar to that in Example 188 and using the corresponding starting materials and reagents.

TABLE 28

| Ex. No. | Structure | salt | MS(ESI) m/z [M + 1] |
|---|---|---|---|
| 189 | 2-(2-aminomethyl-4-(7-(heptyloxy)-9H-thioxanthen-2-yl)butane-1,3-diol derivative) | HCl | 430 |
| 190 | 2-(2-aminomethyl-4-(7-((3-(trifluoromethyl)benzyl)oxy)-9H-thioxanthen-2-yl)butane-1,3-diol derivative) | HCl | 490 |
| 191 | 2-(2-aminomethyl-4-(7-(pentyloxy)-9H-thioxanthen-2-yl)butane-1,3-diol derivative) | HCl | 416 |
| 192 | 2-(2-aminomethyl-4-(7-(p-tolyloxy)-9H-thioxanthen-2-yl)butane-1,3-diol derivative) | HCl | 422 |
| 193 | 2-(2-aminomethyl-4-(7-(m-tolyloxy)-9H-thioxanthen-2-yl)butane-1,3-diol derivative) | HCl | 422 |
| 194 | 2-(2-aminomethyl-4-(7-(4-(trifluoromethyl)phenoxy)-9H-thioxanthen-2-yl)butane-1,3-diol derivative) | HCl | 476 |
| 195 | 2-(2-aminomethyl-4-(7-(3-(trifluoromethyl)phenoxy)-9H-thioxanthen-2-yl)butane-1,3-diol derivative) | | 476 |
| 196 | 2-(2-aminomethyl-4-(7-(3-fluorophenoxy)-9H-thioxanthen-2-yl)butane-1,3-diol derivative) | HCl | 426 |

TABLE 29

| Ex. No. | | salt | MS(ESI) m/z [M + 1] |
|---|---|---|---|
| 197 | | HCl | 406 |
| 198 | | HCl | 460 |
| 199 | | HCl | 410 |
| 200 | | HCl | 406 |

Example 201

Synthesis of 6-[3-amino-4-hydroxy-3-(hydroxymethyl)butyl]-2-benzyloxy-9H-thioxanthen-9-one (compound 201)

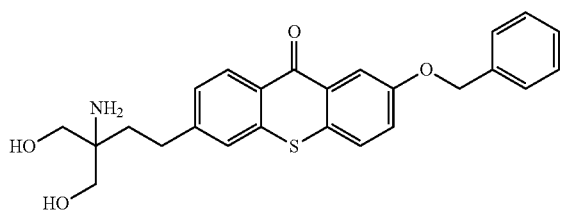 [SMILES: NC(CO)(CO)CCc1ccc2c(=O)c3cc(OCc4ccccc4)ccc3sc2c1]

Reference Example compound 2-5 (100 mg) was dissolved in a mixed solvent of water (0.6 mL), methanol (0.61 ml) and tetrahydrofuran (0.6 mL), lithium hydroxide monohydrate (30 mg) was added, and the mixture was stirred at 80° C. for 1.5 hr. The reaction mixture was concentrated, and the obtained residue was washed with water and diethyl ether to give compound 201 (60 mg) as a pale-yellow powder.

MS (ESI) m/z: 436 [M+H];

$^1$H-NMR (DMSO-$d_6$) δ (ppm): 1.32 (2H, brs), 1.55-1.60 (2H, m), 2.74-2.78 (2H, m), 3.21-3.30 (4H, m), 4.51 (2H, t, J=5.4H), 5.27 (2H, s), 7.33-7.37 (1H, m), 7.40-7.44 (3H, m), 7.49-7.52 (3H, m), 7.64 (1H, s), 7.80 (1H, d, J=8.8 Hz), 8.02 (1H, d, J=2.7 Hz), 8.38 (1H, d, J=8.2 Hz).

The compounds of the following Example 202 was synthesized by a method similar to that in Example 201 and using the corresponding starting material and reagents.

TABLE 30

| Ex. No. | | salt | MS(ESI) m/z [M + 1] |
|---|---|---|---|
| 202 | 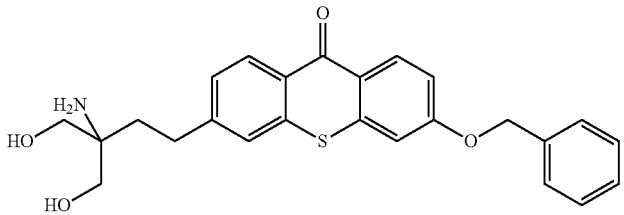 [SMILES: NC(CO)(CO)CCc1ccc2c(=O)c3ccc(OCc4ccccc4)cc3sc2c1] | | 436 |

Example 203

Synthesis of 6-[3-amino-4-hydroxy-3-(hydroxymethyl)butyl]-2-benzyloxy-9H-thioxanthene hydrochloride (compound 203)

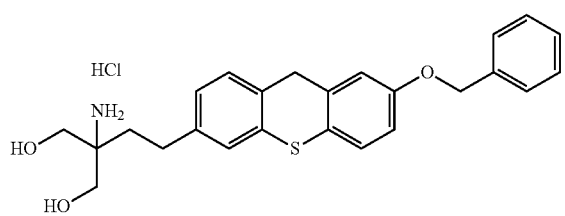 [SMILES: NC(CO)(CO)CCc1ccc2c(c1)Sc1ccc(OCc3ccccc3)cc1C2 ; Cl]

To Reference Example compound 3-3 (500 mg) were added ethanol (10 ml) and concentrated hydrochloric acid (2.5 mL), and the mixture was stirred at 80° C. for 1 hr. The reaction mixture was concentrated, and the obtained residue was washed with diethyl ether to give compound 203 (340 mg) as a pale-yellow powder.

MS (ESI) m/z: 422 [M+H];
$^1$H-NMR (DMSO-$d_6$) δ (ppm): 1.75-1.80 (2H, m), 2.57-2.61 (2H, m) 3.52 (4H, t, J=2.6H), 3.80 (2H, s), 5.11 (2H, s), 5.37 (2H, t, J=5.0H), 6.90 (1H, dd, J=2.7, 8.6 Hz), 7.09 (1H, dd, J=1.1, 8.3 Hz), 7.14 (1H, d, J=2.5 Hz), 7.31-7.45 (8H, m), 7.83 (3H, brs).

The compounds of the following Examples 204-207 were synthesized by a method similar to that in Example 203 and using the corresponding starting materials and reagents.

TABLE 31

| Ex. No. | | salt | MS(ESI) m/z [M + 1] |
|---|---|---|---|
| 204 | 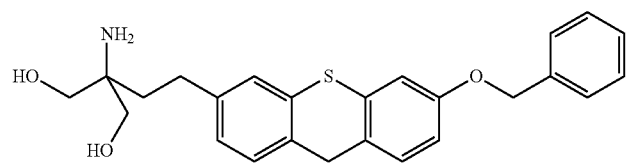 [SMILES: NC(CO)(CO)CCc1ccc2c(c1)Sc1cc(OCc3ccccc3)ccc1C2] | HCl | 422 |
| 205 | 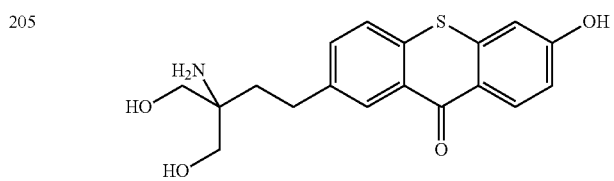 | HCl | 346 |
| 206 | 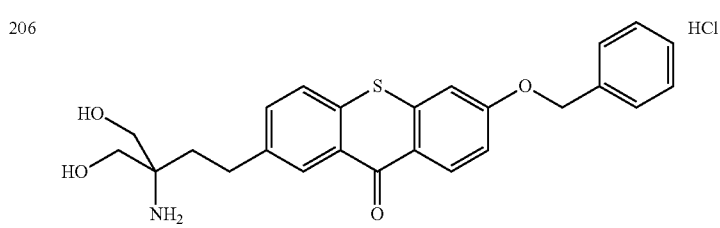 | HCl | 436 |

| Ex. No. | | salt | MS(ESI) m/z [M + 1] |
|---|---|---|---|
| 207 | 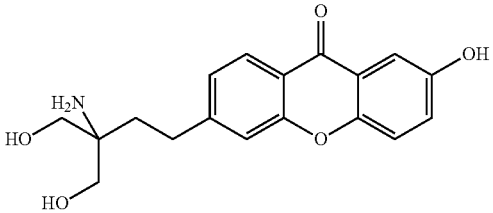 [SMILES: NC(CO)(CO)CCc1ccc2c(=O)c3cc(O)ccc3oc2c1] | HCl | 330 |

Example 208

Synthesis of 2-[3-amino-4-hydroxy-3-(hydroxymethyl)butyl]-7-benzyloxy-9H-thioxanthene (compound 208)

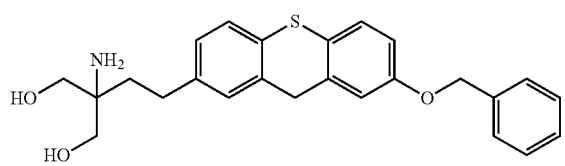 [SMILES: NC(CO)(CO)CCc1ccc2c(c1)Cc1cc(OCc3ccccc3)ccc1S2]

To Reference Example compound 1-6 (520 mg) were added tetrahydrofuran (10 ml) and LiBH$_4$ (70 mg), and the mixture was stirred at 80° C. for 4.5 hr. To the reaction mixture was added a mixed solution of isopropyl alcohol:1N hydrogen chloride 1,4-dioxane solution (4:1), and the mixture was stirred at 50° C. for 30 min. The reaction mixture was evaporated under reduced pressure, to the obtained residue was added water and the mixture was extracted with ethyl acetate. The mixture was washed with water and saturated brine, and dried over anhydrous sodium sulfate. The solvent was evaporated under reduced pressure, to the obtained pale-yellow solid were added ethanol (5 mL) and concentrated hydrochloric acid (1 mL), and the mixture was stirred at 50° C. for 4 hr. To red precipitate collected by filtration were added water, ethyl acetate, saturated aqueous sodium hydrogen carbonate, and the mixture was extracted with ethyl acetate and further extracted with chloroform. The solvent was evaporated under reduced pressure. To the resulting brown precipitate were added methanol, chloroform and sodium sulfate, and the mixture was stirred and filtered. The solvent was evaporated under reduced pressure, and the resulting precipitate was washed with diisopropyl ether to give compound 208 (235 mg) as a yellow solid.

MS (ESI) m/z: 422 [M+H];

$^1$H-NMR (DMSO-d$_6$) δ (ppm): 1.46-1.51 (2H, m), 1.63 (2H, brs), 2.55-2.60 (2H, m), 3.20-3.27 (4H, m), 3.80 (2H, s), 4.48 (2H, brs), 5.11 (2H, s), 6.89 (1H, dd, J=2.6, 8.5 Hz), 7.04 (1H, d, J=7.8 Hz), 7.14 (1H, d, J=2.3 Hz), 7.23 (1H, s), 7.30-7.45 (7H, m).

Example 209

Synthesis of 2-[3-amino-4-hydroxy-3-(hydroxymethyl)butyl]-5,6-bis(4-methylphenoxy)-9H-xanthen-9-one hydrochloride (compound 209)

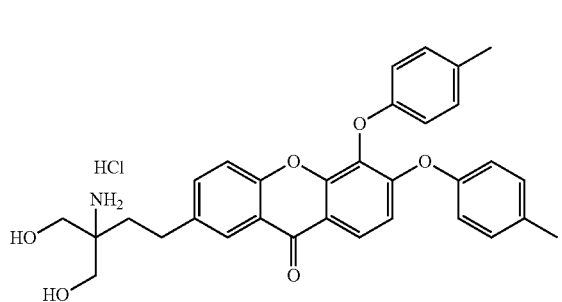 [SMILES: Cc1ccc(Oc2ccc3c(=O)c4cc(CCC(N)(CO)CO)ccc4oc3c2Oc2ccc(C)cc2)cc1 ; Cl]

The compound of Example 104 was synthesized by a method To similar to that in Example 83 and using the corresponding starting materials and reagents. As a byproduct of the synthesis, compound 209 (7 mg) was obtained as a pale-brown powder.

MS (ESI) m/z: 526 [M+H];

$^1$H-NMR (DMSO-d$_6$) δ (ppm): 1.81-1.86 (2H, m), 2.25 (3H, s), 2.30 (3H, s), 2.72-2.77 (2H, m), 3.55 (4H, d, J=4.9 Hz), 5.45 (2H, t, J=5.1 Hz), 6.91-6.98 (5H, m), 7.12 (2H, d, J=8.4 Hz), 7.23 (2H, d, J=8.4 Hz), 7.47 (1H, d, J=8.6 Hz), 7.68 (1H, dd, J=8.6, 1.8 Hz), 7.88 (3H, brs), 8.05-8.08 (2H, m).

Example 210

Synthesis of 6-[3-amino-4-hydroxy-3-(hydroxymethyl)butyl]-2-[4-(trifluoromethyl)benzoyl]-9H-thioxanthene hydrochloride 1) Synthesis of t-butyl {2,2-dimethyl-5-[2-(7-tributylstannyl-9H-thioxanthen-3-yl)ethyl]-1,3-dioxan-5-yl}carbamate (compound 210-1)

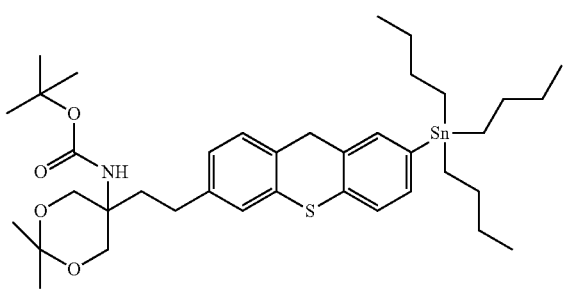 [SMILES: CCC[CH2][Sn]([CH2]CCC)([CH2]CCC)[c]1ccc2c(c1)Cc1ccc(CCC3(NC(=O)OC(C)(C)C)COC(C)(C)OC3)cc1S2]

To a solution of Reference Example compound 9 (500 mg) in tetrahydrofuran (2.8 mL) were added triphenylphosphine (43 mg), lithium chloride (175 mg), tris(dibenzylideneacetone)dipalladium(0)chloroform adduct (30 mg), and bistributyltin (1.05 ml), and the mixture was stirred at 100° C. for 4 hr. Further, tris(dibenzylideneacetone)dipalladium(0)chloroform adduct (30 mg) was added, and the mixture was heated under reflux for 1.5 hr, triphenylphosphine (43 mg) was added, and the mixture was further heated under reflux for 1.5 hr. Water was added to the reaction mixture, and the mixture was filtered through celite. The filtrate was extracted with ethyl acetate, washed with saturated brine, and dried over anhydrous sodium sulfate. The solvent was evaporated under reduced pressure, and the obtained residue was purified by silica gel column chromatography to give compound 210-1 (162 mg) as a yellow powder.

$^1$H-NMR (DMSO-d$_6$) δ (ppm): 0.84 (9H, t, J=7.2 Hz), 1.02-1.06 (6H, m) 1.24-1.32 (12H, m), 1.40 (9H, s), 1.46-1.54 (6H, m), 1.91-1.95 (2H, m), 2.42-2.46 (2H, m), 3.66 (2H, d, J=11.7H), 3.81 (2H, s), 3.86 (2H, d, J=11.4 Hz), 6.62 (1H, brs), 7.05 (1H, dd, J=1.1, 7.7H), 7.26-7.27 (2H, m), 7.33 (1H, d, J=7.6 Hz), 7.42 (1H, d, J=7.6 Hz), 7.44 (1H, s).

2) Synthesis of t-butyl [2,2-dimethyl-5-(2-{7-[4-(trifluoromethyl)benzoyl]-9H-thioxanthen-3-yl}ethyl)-1,3-dioxan-5-yl]carbamate (compound 210-2)

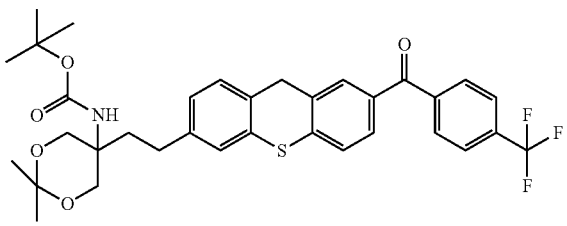 [SMILES: CC(C)(C)OC(=O)NC1(CCc2ccc3c(c2)Sc2ccc(C(=O)c4ccc(C(F)(F)F)cc4)cc2C3)COC(C)(C)OC1]

To compound 210-1 (162 mg) were added bis(triphenylphosphine)palladium(II)dichloride (3.8 mg), benzene (0.5 mL) and 4-(trifluoromethyl)benzoyl chloride (0.042 ml), and the mixture was stirred at 100° C. for 1.5 hr. The reaction mixture was concentrated, and the obtained residue was purified by silica gel column chromatography to give compound 210-2 (29 mg) as a white powder.

$^1$H-NMR (DMSO-d$_6$) δ (ppm): 1.31 (3H, s), 1.32 (3H, m), 1.40 (9H, s), 1.91-1.95 (2H, m), 2.42-2.46 (2H, m), 3.66 (2H, d, J=11.6H), 3.86 (2H, d, J=11.3H), 3.96 (2H, s), 6.65 (1H, brs), 7.10 (1H, d, J=7.3H), 7.30 (1H, s), 7.33 (1H, d, J=7.8H), 7.62-7.69 (2H, m), 7.82 (1H, s), 7.90-7.95 (4H, m).

3) Synthesis of 6-[3-amino-4-hydroxy-3-(hydroxymethyl)butyl]-2-[4-(trifluoromethyl)benzoyl]-9H-thioxanthene hydrochloride (compound 210)

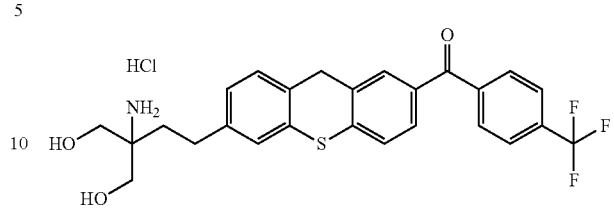

To compound 210-2 (29 mg) was added 2M hydrogen chloride ethanol solution (3 mL), and the mixture was stirred at 50° C. for 5 hr. The reaction mixture was concentrated, and the obtained residue was washed with diethyl ether to give compound 210 (14 mg) as a white powder.

MS (ESI) m/z: 488 [M+H];

$^1$H-NMR (DMSO-d$_6$) δ (ppm): 1.75-1.80 (2H, m), 2.57-2.61 (2H, m) 3.51 (4H, d, J=4.9H), 3.97 (2H, s), 5.39 (2H, d, J=5.0H), 7.15 (1H, dd, J=1.2, 7.1H), 7.35-7.37 (2H, m), 7.63-7.69 (2H, m), 7.80-7.83 (4H, m), 7.90-7.96 (4H, m).

Example 211

Synthesis of 2-(4-amino-5-hydroxy-4-methylpentyl)-3-chloro-6-(trifluoromethyl)-9H-thioxanthen-9-one hydrochloride 1) Synthesis of 4-bromo-2-chloro-1-methoxybenzene (compound 211-1)

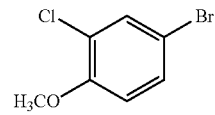

4-Bromo-2-chlorophenol (25.0 g) was dissolved in N,N-dimethylformamide (150 ml), potassium carbonate (33.2 g) and methyl iodide (25.6 g) were added, and the mixture was stirred at 60° C. for 2 hr. The reaction mixture was poured into water, extracted with ethyl acetate, washed with saturated brine, dried over anhydrous sodium sulfate. The solvent was evaporated under reduced pressure to give compound 211-1 (26.7 g) as a pale-yellow solid.

$^1$H-NMR (CDCl$_3$) δ (ppm): 3.88 (3H, s), 6.79 (1H, d, J=9.4 Hz), 7.32 (1H, dd, J=8.6, 2.4 Hz), 7.49 (1H, d, J=2.4 Hz).

2) Synthesis of 3-chloro-4-methoxybenzenethiol (compound 211-2)

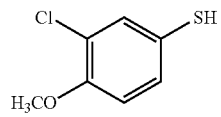

Triisopropylsilane thiol (6.20 g) was dissolved in tetrahydrofuran (60 ml), cesium carbonate (12.7 g) was added, and the mixture was stirred at room temperature for 15 min. A solution of compound 211-1 (7.21 g) in toluene (150 ml) and tetrakis(triphenylphosphine)palladium (1.13 g) were added, and the mixture was stirred at 100° C. for 8 hr. Water was added to the reaction mixture, and the mixture was extracted with ethyl acetate, washed with saturated brine, and dried over anhydrous sodium sulfate. The solvent was evaporated under reduced pressure, and to a solution of the obtained residue in tetrahydrofuran (65.0 ml) was added dropwise tetra n-butylammonium fluoride (1M tetrahydrofuran solution, 65 ml) at room temperature, and the mixture was stirred for 2 hr. To the reaction mixture was added 1M hydrochloric acid (100 ml), and the mixture was extracted with ethyl acetate, washed with saturated brine, and dried over anhydrous sodium sulfate. The solvent was evaporated under reduced pressure, and the obtained residue was purified by silica gel column chromatography to give compound 211-2 (5.90 g) as a white solid.

$^1$H-NMR (CDCl$_3$) δ (ppm): 3.40 (1H, s), 3.87 (3H, s), 6.81 (1H, d, J=8.6 Hz), 7.19 (1H, dd, J=8.6, 2.4 Hz), 7.35 (1H, d, J=2.4 Hz).

3) Synthesis of 2-iodo-4-(trifluoromethyl)benzoic acid (compound 211-3)

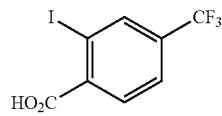

To a solution of 2-amino-4-(trifluoromethyl)benzoic acid (25.0 g) in diluted sulfuric acid (prepared from concentrated sulfuric acid (60 ml) and water (600 ml)) were added dropwise aqueous sodium nitrite solution (prepared from sodium nitrite (12.4 g) and water (60 ml)) at 0° C. An aqueous potassium iodide solution (prepared from potassium iodide (30.0 g) and water (60 ml)) was added dropwise, and the mixture was gradually heated to 80° C. and stirred at the same temperature for 1 hr. The reaction mixture was cooled, 2% aqueous sodium thiosulfate solution was added and the mixture was stirred for a while. The precipitated solid was collected by filtration to give a solid (30.5 g). A method similar to the above was performed to give a solid (22.0 g) from 2-amino-4-(trifluoromethyl)benzoic acid (25.0 g). The obtained solids were combined and purified by silica gel column chromatography to give compound 211-3 (39.5 g) as a pale-yellow solid.

$^1$H-NMR (DMSO-d$_6$) δ (ppm): 7.82-7.90 (2H, m), 8.27 (1H, s), 13.8 (1H, brs).

4) Synthesis of 2-[(3-chloro-4-methoxyphenyl)thio]-4-(trifluoromethyl)benzoic acid (compound 211-4)

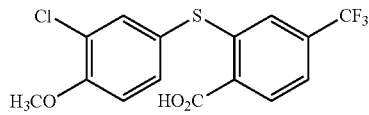 [SMILES: COc1ccc(Sc2cc(C(F)(F)F)ccc2C(=O)O)cc1Cl]

To a solution of compound 211-2 (5.80 g) and compound 211-3 (10.1 g) in N,N-dimethylformamide (90 ml) was added copper powder (360 mg), and the mixture was stirred at 120° C. for 3 hr. The reaction mixture was cooled, 1M hydrochloric acid and ethyl acetate were added, an insoluble material was filtered off, and the mixture was extracted with ethyl acetate. The organic layer was washed with water and saturated brine, dried over anhydrous sodium sulfate. The solvent was evaporated under reduced pressure and the residue was purified by silica gel column chromatography and the obtained solid was washed with hexane to give compound 211-4 (12.6 g) as a white solid.

$^1$H-NMR (DMSO-d$_6$) δ (ppm): 3.95 (3H, s), 6.90 (1H, s), 7.33 (1H, d, J=8.6 Hz), 7.55-7.61 (2H, m), 7.71 (1H, d, J=2.4 Hz), 8.12 (1H, d, J=8.6 Hz), 13.8 (1H, brs).

5) Synthesis of 3-chloro-2-hydroxy-6-(trifluoromethyl)-9H-thioxanthen-9-one (compound 211-5)

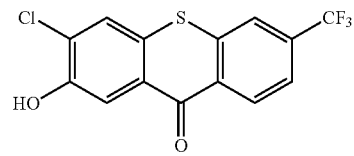 [SMILES: O=c1c2ccc(C(F)(F)F)cc2sc2cc(Cl)c(O)cc12]

To compound 211-4 (9.64 g) was added cooled concentrated hydrochloric acid (50.0 ml) at 0° C., and the mixture was stirred at room temperature for 50 min. The reaction mixture was poured into cold water, extracted with ethyl acetate, washed with water and saturated brine, and dried over anhydrous sodium sulfate. The solvent was evaporated under reduced pressure. To the residual solid was added diisopropyl ether, and the mixture was stirred at room temperature and then at 0° C., and the precipitated solid was collected by filtration to give a yellow solid. To a solution of the yellow solid in methylene chloride (200 ml) was added dropwise boron tribromide (1M methylene chloride solution, 41 ml) at 0° C. over 20 min, and the mixture was stirred at the same temperature for 2 hr. Further, boron tribromide (1M methylene chloride solution, 41 ml) was added dropwise at 0° C., and the mixture was stirred at room temperature overnight. The reaction mixture was poured into cold water, and the mixture was extracted with ethyl acetate, washed with water, and dried over anhydrous sodium sulfate.

The solvent was evaporated under reduced pressure, and the residual solid was suspended in cooled diisopropyl ether and collected by filtration to give compound 211-5 (4.00 g) as a yellow solid. The residue of the filtrate was purified by silica gel column chromatography and the obtained solid was suspended in methylene chloride and collected by filtration to give compound 211-5 (1.35 g) as a yellow solid.

$^1$H-NMR (DMSO-d$_6$) δ (ppm): 7.85 (1H, d, J=8.6 Hz), 8.02 (1H, s). 8.09 (1H, s), 8.37 (1H, s), 8.59 (1H, d, J=8.6 Hz), 11.1 (1H, s).

6) Synthesis of 3-chloro-2-(trifluoromethanesulfonyloxy)-6-(trifluoromethyl)-9H-thioxanthen-9-one (compound 211-6)

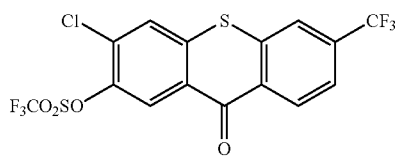

To a solution of compound 211-5 (5.35 g) in methylene chloride (50 ml) was added pyridine (6.40 g), and a solution of trifluoromethanesulfonic anhydride (5.48 g) in methylene chloride (10 ml) was added dropwise at 0° C., and the mixture was stirred at room temperature for 2 hr. The reaction mixture was ice-cooled, saturated aqueous sodium hydrogen carbonate solution was added, and the mixture was extracted with ethyl acetate, washed with water, and dried over anhydrous sodium sulfate. The solvent was evaporated under reduced pressure. The residual solid was suspended in cooled hexane and collected by filtration to give compound 211-6 (5.89 g) as a brown powder.

$^1$H-NMR (DMSO-$d_6$) δ (ppm): 7.94 (1H, dd, J=10.2, 8.6 Hz), 8.46 (1H, s), 8.50 (1H, s), 8.56-8.63 (2H, m).

7) Synthesis of 4-(iodomethyl)-4-methyl-1,3-oxazolidin-2-one (compound 211-7)

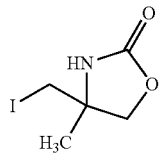

To a solution of t-butyl (2-hydroxy-1-hydroxymethyl-1-methyl)ethylcarbamate (19.5 g) in tetrahydrofuran (300 ml) that can be synthesized by a known method (e.g., WO 2007/069712, p. 81) was added potassium t-butoxide (10.7 g) at 0° C., and the mixture was stirred at room temperature overnight. The precipitated solid was collected by filtration, and added to 1M hydrochloric acid (100 ml). An aqueous solution thereof was concentrated under reduced pressure, and ethanol was added to the residue, and the precipitate was filtered off. The filtrate was concentrated under reduced pressure, and acetone was added to the residue. The precipitated solid was collected by filtration to give a white solid (9.45 g). 500 mg from the white solid was dissolved in pyridine (2 mL), p-toluenesulfonylchloride (763 mg) was added, and the mixture was stirred at room temperature overnight. To the reaction mixture was added saturated aqueous sodium hydrogen carbonate solution, and the mixture was extracted with methylene chloride, dried over anhydrous sodium sulfate and the solvent was evaporated m under reduced pressure. To the residue were added sodium iodide (857 mg) and methyl ethyl ketone (50.0 ml), and the mixture was stirred at 80° C. for 14 hr. The reaction mixture was concentrated under reduced pressure, and methylene chloride (100 ml) was added to the residue. The mixture was filtered and the filtrate was concentrated under reduced pressure to give compound 211-7 (0.92 g) as a brown oil.

$^1$H-NMR (CDCl$_3$) δ (ppm): 1.56 (3H, s), 3.34 (2H, s), 4.16 (1H, d, J=8.7 Hz), 4.31 (1H, d, J=9.2 Hz), 6.03 (1H, brs).

8) Synthesis of 4-methyl-4-(2-propynyl)-1,3-oxazolidin-2-one (compound 211-8)

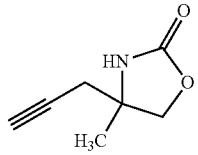

To a solution of lithium acetylide ethylenediamine complex (2.10 g) in dimethylsulfoxide (20 ml) was added compound 211-7 (1.83 g) by small portions at 10° C., and the mixture was stirred at the same temperature for 1 hr. The reaction mixture was slowly poured into cold water, and the mixture was extracted with methylene chloride and ethyl acetate, and dried over anhydrous sodium sulfate. The solvent was evaporated under reduced pressure and the residue was purified by silica gel column chromatography to give compound 211-8 (0.16 g) as a brown oil.

$^1$H-NMR (CDCl$_3$) δ (ppm): 1.47 (3H, s), 2.11 (1H, t, J=2.6 Hz), 2.46 (1H, dd, J=16.4, 2.6 Hz), 2.52 (1H, dd, J=16.4, 2.6 Hz), 4.11 (1H, d, J=8.7 Hz), 4.27 (1H, d, J=8.7 Hz), 5.59 (1H, brs).

9) Synthesis of 4-{3-[3-chloro-9-oxo-6-(trifluoromethyl)-9H-thioxanthen-2-yl]-2-propynyl}-4-methyl-1,3-oxazolidin-2-one (compound 211-9)

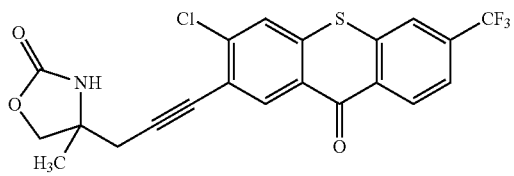 [SMILES: CC1(CC#Cc2cc3c(=O)c4ccc(C(F)(F)F)cc4sc3cc2Cl)COC(=O)N1]

To a solution of compound 211-6 (449 mg), compound 211-8 (160 mg), triethylamine (190 mg) and tetrakis(triphenylphosphine)palladium (110 mg) in N,N-dimethylformamide (8 mL) were added copper iodide (26.0 mg) and tetra n-butylammoniumiodide (530 mg), and the mixture was stirred at 70° C. for 3 hr. The reaction mixture was cooled, water was added, and the mixture was extracted with ethyl acetate, washed with water and saturated brine, dried over anhydrous sodium sulfate. The solvent was evaporated under reduced pressure and the residue was purified by silica gel column chromatography to give compound 211-9 (443 mg) as a pale-yellow solid.

$^1$H-NMR (CDCl$_3$) δ (ppm): 1.59 (3H, s), 2.80 (1H, d, J=16.9 Hz), 2.87 (1H, d, J=16.9 Hz), 4.20 (1H, d, J=8.7 Hz), 4.38 (1H, d, J=8.7 Hz), 5.30 (1H, s), 7.67 (1H, s), 7.72 (1H, dd, J=8.5, 1.3 Hz), 7.85 (1H, s), 8.66 (1H, s), 8.70 (1H, d, J=8.2 Hz).

10) Synthesis of 4-{3-[3-chloro-9-oxo-6-(trifluoromethyl)-9H-thioxanthen-2-yl]propyl}-4-methyl-1,3-oxazolidin-2-one (compound 211-10)

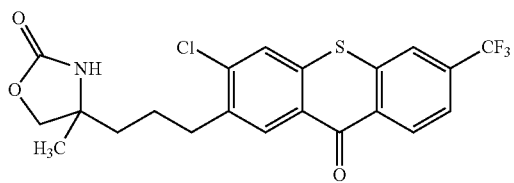 [SMILES: CC1(CCCc2cc3c(=O)c4ccc(C(F)(F)F)cc4sc3cc2Cl)COC(=O)N1]

To a mixed solution of compound 211-9 (440 mg) in monochlorobenzene (20 ml) and 1,4-dioxane (30 ml) was added 10% palladium carbon (containing about 50% water, 500 mg), and the mixture was stirred under a hydrogen atmosphere at room temperature for 2 hr. The reaction mixture was filtered, and the filtrate was evaporated under reduced pressure. The residue was purified by silica gel column chromatography to give compound 211-10 (150 mg) as a white solid.

$^1$H-NMR (CDCl$_3$) δ (ppm): 1.36 (3H, s), 1.65-1.83 (4H, m), 2.84-2.95 (2H, m), 4.06 (1H, d, J=8.7 Hz), 4.16 (1H, d, J=8.7 Hz), 5.23 (1H, brs), 7.64 (1H, s), 7.70 (1H, dd, J=8.5, 1.3 Hz), 7.85 (1H, s), 8.44 (1H, s), 8.70 (1H, d, J=8.2 Hz).

11) Synthesis of t-butyl {4-[3-chloro-9-oxo-6-(trifluoromethyl)-9H-thioxanthen-2-yl]-1-(hydroxymethyl)-1-methylbutyl}carbamate (compound 211-11)

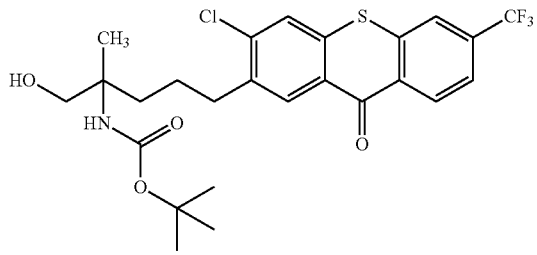 [SMILES: CC(CO)(CCCc1cc2c(=O)c3ccc(C(F)(F)F)cc3sc2cc1Cl)NC(=O)OC(C)(C)C]

A mixed solution of compound 211-10 (150 mg), di-t-butylcarbonate (110 mg), triethylamine (67.0 mg) and N,N-dimethylaminopyridine (catalytic amount) in tetrahydrofuran and N,N-dimethylformamide (2:1, 8 mL) was stirred at room temperature for 2 hr. Water was added to the reaction mixture, and the mixture was extracted with ethyl acetate, washed with water and saturated brine, and dried over anhydrous sodium sulfate. The solvent was evaporated under reduced pressure and to a solution of the residue in methanol (10 ml) were added water (0.3 mL) and potassium carbonate (300 mg), and the mixture was stirred at room temperature overnight. Water was added to the reaction mixture, and the mixture was extracted with ethyl acetate, washed with water and saturated brine, dried over anhydrous sodium sulfate. The solvent was evaporated under reduced pressure and the residue was purified by silica gel column chromatography to give compound 211-11 (130 mg) as a pale-yellow solid.

$^1$H-NMR (CDCl$_3$) δ (ppm): 1.17 (3H, s), 1.43 (9H, s), 1.64-1.97 (4H, m), 2.83-2.93 (2H, m), 3.59-3.70 (2H, m), 4.03 (1H, brs), 4.59 (1H, brs), 7.63 (1H, s), 7.70 (1H, dd, J=8.7, 1.5 Hz), 7.85 (1H, s), 8.47 (1H, s), 8.71 (1H, d, J=8.7 Hz).

12) Synthesis of 2-(4-amino-5-hydroxy-4-methylpentyl)-3-chloro-6-(trifluoromethyl)-9H-thioxanthen-9-one hydrochloride (compound 211)

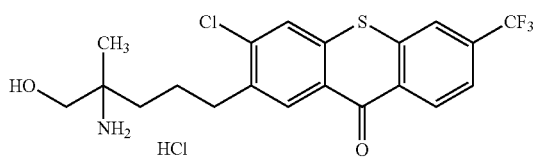 [SMILES: CC(N)(CO)CCCc1cc2c(=O)c3ccc(C(F)(F)F)cc3sc2cc1Cl ; Cl]

To compound 211-11 (130 mg) was added hydrogen chloride-containing 1,4-dioxane (4M, 5 mL), and the mixture was stirred at room temperature for 2 hr. The reaction mixture was concentrated, and the obtained residue was washed with 1,4-dioxane to give compound 211 (91.0 mg) as a pale-yellow solid.

MS (ESI) m/z: 430 [M+H];

$^1$H-NMR (C$_5$D$_5$N) δ (ppm): 1.72 (3H, s), 1.98-2.17 (2H, m), 2.24-2.43 (2H, m), 2.83 (2H, t, J=7.7 Hz), 4.12 (1H, d, J=11.3 Hz), 4.22 (1H, d, J=11.8 Hz), 7.76 (1H, dd, J=8.7, 1.5 Hz), 7.84 (1H, s), 8.22 (1H, s), 8.61 (1H, s), 8.81 (1H, d, J=8.2 Hz).

Example 212

Synthesis of 2-[3-amino-4-hydroxy-3-(hydroxymethyl)butyl]-6-(4-cyanophenoxy)-9H-xanthen-9-one hydrochloride (compound 212)

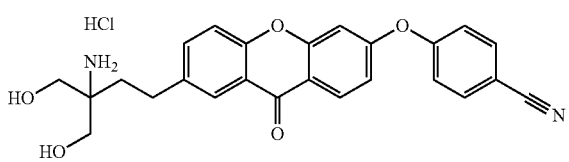 [SMILES: Cl ; N#Cc1ccc(Oc2ccc3c(=O)c4cc(CCC(N)(CO)CO)ccc4oc3c2)cc1]

Reference Example compound 14 (470 mg), 4 Å molecular sieves (470 mg), and 4-cyanophenylboronic acid (294 mg) were dissolved in methylene chloride (10 ml), triethylamine (0.558 ml) and copper acetate (363 mg) were added, and the mixture was stirred at room temperature for 3 hr. The solvent in the reaction mixture was evaporated under reduced pressure, and the obtained residue was purified by silica gel column chromatography to give t-butyl [5-(2-{7-[6-(4-cyanophenoxy)-9-oxo-9H-xanthen-2-yl}ethyl)-2,2-dimethyl-1,3-dioxan-5-yl]carbamate (198 mg) as a white powder. To the obtained white powder were added tetrahydrofuran-methanol (1:1) mixed solution (40 ml) and p-toluenesulfonic acid monohydrate (30 mg), and the mixture was stirred at room temperature for 4 hr. The solvent in the reaction mixture was evaporated under reduced pressure, to the obtained residue was added saturated aqueous sodium hydrogen carbonate solution, and the mixture was extracted with ethyl acetate. The organic layer was dried over anhydrous magnesium sulfate, and the solvent was evaporated under reduced pressure. The residue was purified by silica gel chromatography to give t-butyl {3-[6-(4-cyanophenoxy)-9-oxo-9H-xanthen-2-yl]-1,1-bis(hydroxymethyl) propyl}carbamate (108 mg) as a colorless transparent oil. To this oil was added 4M hydrogen chloride 1,4-dioxane solution (2 mL) and the mixture was stirred at room temperature for 3 hr. To the reaction mixture was added diethyl ether, and the precipitate was collected by filtration to give compound 212 (84 mg) as a white powder.

MS (ESI) m/z: 431 [M+H];

$^1$H-NMR (DMSO-d$_6$) δ (ppm): 1.81-1.90 (2H, m), 2.72-2.81 (2H, m) 3.55 (4H, d, J=5.1H), 5.44 (2H, t, J=5.1 Hz), 7.20 (1H, dd, J=8.7, 2.2 Hz), 7.32 (1H, d, J=2.4 Hz), 7.35-7.39 (2H, m), 7.61 (1H, d, J=8.6 Hz), 7.73 (1H, dd, J=8.6, 2.3 Hz), 7.84 (3H, brs), 7.48-7.93 (2H, m), 8.08 (1H, d, J=2.1 Hz), 8.26 (1H, d, J=8.8 Hz).

The compounds of the following Examples 213, 214 were synthesized from the corresponding Example compounds by a method similar to that in Example 212.

TABLE 32

| Ex. No. | | salt | MS(ESI) m/z [M + 1] |
|---|---|---|---|
| 213 | 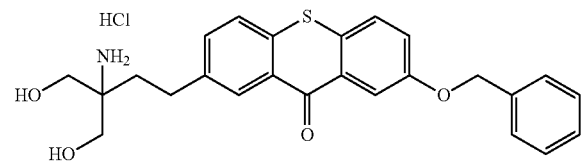 [SMILES: NC(CO)(CO)CCc1ccc2sc3ccc(OCc4ccccc4)cc3c(=O)c2c1 ; Cl] | HCl | 431 |
| 214 | 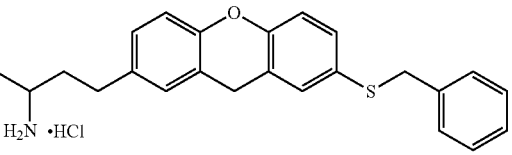 | HCl | 449 |

Example 215

Synthesis of 2-[3-amino-4-hydroxy-3-(hydroxymethyl)butyl]-7-benzyloxy-9H-thioxanthen-9-one hydrochloride (compound 215)

To a solution of Reference Example compound 1-5 (13.1 g) in methanol (50 ml) and N,N-dimethylformamide (100 ml) was added 10% palladium carbon (containing about 50% water, 3.0 g), and the mixture was stirred under a hydrogen atmosphere at room temperature for 4.5 hr. The reaction mixture was filtered through celite and concentrated. To the residue was added water, and the mixture was extracted with ethyl acetate, washed with water and saturated brine, and dried over anhydrous sodium sulfate. The solvent was evaporated under reduced pressure, and ethanol (50 ml) was added to the obtained residue, concentrated hydrochloric acid (10 ml) was added, and the mixture was stirred at 80° C. for 5 hr. Further, ethanol (50 ml) was added, and the mixture was stirred at room temperature for one day. The precipitate was washed with diethyl ether to give compound 215 (7.0 g) as a yellow solid.

MS (ESI) m/z: 436 [M+H];

$^1$H-NMR (DMSO-$d_6$) δ (ppm): 1.85-1.90 (2H, m), 2.77-2.81 (2H, m), 3.56 (4H, d, J=4.9H), 5.27 (2H, s), 5.45 (2H, t, J=5.0H), 7.34-7.44 (3H, m), 7.51-7.54 (3H, m), 7.66 (1H, dd, J=1.2, 8.5 Hz), 7.82 (2H, dd, J=4.0, 8.7 Hz), 7.90 (3H, brs), 8.03 (1H, d, J=2.8 Hz), 8.37 (1H, s).

Example 216

Synthesis of 2-amino-4-(7-benzylthio-9H-xanthen-2-yl)-1-butanol hydrochloride (compound 216)

[2-(7-Bromo-9H-xanthen-2-yl)ethyl][(t-butyloxycarbonyl)amino]diethyl malonate (15.2 g), which is a synthetic intermediate for Reference Example compound 21, was dissolved in tetrahydrofuran (300 ml), lithium borohydride (1 g) was added, and the mixture was stirred for 2 days. To the reaction mixture was added 1M hydrochloric acid, and the solvent was evaporated under reduced pressure. The reaction mixture was added to 1M hydrochloric acid, and the mixture was extracted with ethyl acetate, washed with water and saturated brine, and dried over anhydrous sodium sulfate. The solvent was evaporated under reduced pressure and the obtained residue was purified by silica gel column chromatography to give t-butyl [3-(7-bromo-9H-xanthen-2-yl)-1-(hydroxymethyl)propyl]carbamate (6.8 g). A solution of the obtained t-butyl [3-(7-bromo-9H-xanthen-2-yl)-1-(hydroxymethyl)propyl]carbamate (6 g), acetonedimethylacetal (4.5 mL) and catalytic amount of p-toluenesulfonic acid in acetone (100 ml) was stirred for 6 hr. The reaction mixture was concentrated under reduced pressure, and the residue was extracted with ethyl acetate, washed with water and saturated brine, and dried over anhydrous sodium sulfate. The solvent was evaporated under reduced pressure to give t-butyl 4-[2-(7-bromo-9H-xanthen-2-yl)ethyl]-2,2-dimethyl-1,3-oxazolidine-3-carboxylate (5 g) as a yellow powder. The obtained t-butyl 4-[2-(7-bromo-9H-xanthen-2-yl)ethyl]-2,2-dimethyl-1,3-oxazolidine-3-carboxylate (1 g) was dissolved in 1,4-dioxane (10 ml), α-toluenethiol (0.3 mL), tris(dibenzylideneacetone)dipalladium(0) chloroform adduct (100 mg), 4,5-bis(diphenylphosphino)-9,9-dimethylxanthene (Xantphos) (150 mg), and N,N-diisopropylethylamine (0.900 ml) were added, and the mixture was heated under reflux for 9 hr. Water was added to the reaction mixture, and the mixture was extracted with ethyl acetate, washed with water and saturated brine, and dried over anhydrous sodium sulfate. The solvent was evaporated under reduced pressure, and the obtained residue was purified by silica gel column chromatography. The solvent was evaporated from the eluate to give t-butyl 4-[2-(7-benzylthio-9H-xanthen-2-yl)ethyl]-2,2-dimethyl-1,3-oxazolidine-3-carboxylate (0.5 g). To the obtained t-butyl 4-[2-(7-benzylthio-9H-xanthen-2-yl)ethyl]-2,2-dimethyl-1,3-oxazolidine-3-carboxylate (0.45 g) was added 1M hydrogen chloride ethanol solution (5 ml) and the mixture was stirred at 60° C. for 2.5 hr. The reaction mixture was concentrated to give compound 216 (280 mg) as a white powder.

MS (ESI) m/z: 392 [M+H];

$^1$H-NMR (DMSO-$d_6$) δ (ppm): 1.72-1.87 (2H, m), 2.58-2.66 (2H, m), 3.01-3.08 (2H, m), 3.44-3.52 (1H, m), 3.58-3.66 (1H, m), 3.97 (2H, s), 4.17 (2H, s), 5.28 (1H, t, J=5.1 Hz), 6.95-7.02 (2H, m), 7.03-7.11 (2H, m), 7.14-7.33 (6H, m), 7.86 (3H, brs).

The compound of the following Example 217 was synthesized from the corresponding Example compound by a method similar to that in Example 216.

TABLE 33

| Ex. No. | | salt | MS(ESI) m/z [M + 1] |
|---|---|---|---|
| 217 | 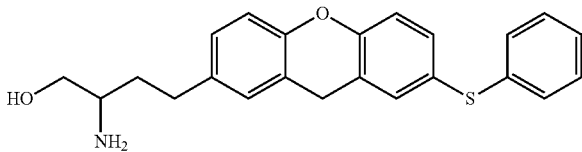 | | 392 |

Example 218

Synthesis of mono(2-amino-2-hydroxymethyl-4-{9-oxo-7-[3-(trifluoromethyl)phenoxy]-9H-xanthen-3-yl}butyl)phosphate 1) Synthesis of di-t-butyl{[4-(2-{9-oxo-7-[3-(trifluoromethyl)phenoxy]-9H-xanthen-3-yl}ethyl)-4,5-dihydro-1,3-oxazol-4-yl]methyl}phosphate (compound 218-1)

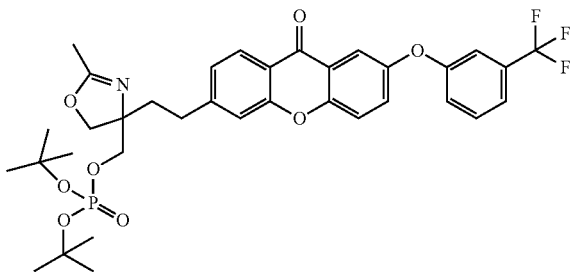 [SMILES: CC1=NC(CCc2ccc3c(=O)c4cc(Oc5cccc(C(F)(F)F)c5)ccc4oc3c2)(COP(=O)(OC(C)(C)C)OC(C)(C)C)CO1]

To a solution of compound 83 (190 mg) in N,N-dimethylformamide (3.7 mL) were added N,N-diisopropylethylamine (0.190 ml) and trimethyl orthoacetate (0.102 ml), and the mixture was stirred at 120° C. for 3 hr. To the reaction mixture were further added N,N-diisopropylethylamine (0.085 ml) and trimethyl orthoacetate (0.051 ml), and the mixture was stirred at 120° C. for 2.5 hr. Water was added to the reaction mixture, and the mixture was extracted with ethyl acetate, washed with water and saturated brine, and dried over anhydrous sodium sulfate. The solvent was evaporated under reduced pressure to give a brown oil. To a solution of the brown oil in methylene chloride (3.7 mL) and acetonitrile (3.25 ml) were added 1H-tetrazole (52 mg) and di-t-butyldiethyl phosphoramidite (0.209 ml), and the mixture was stirred at room temperature for 2 hr. The reaction solution was ice-cooled, t-butyl hydroperoxide-containing decane solution (5-6 M, 0.450 ml) was added, and the mixture was stirred at room temperature for 1.5 hr. To the reaction mixture was added saturated aqueous sodium hydrogen carbonate solution, and the mixture was extracted with methylene chloride. The organic layer was dried over anhydrous sodium sulfate, and the solvent was evaporated under reduced pressure. The obtained residue was purified by silica gel column chromatography to give compound 218-1 (214 mg) as a yellow oil.

$^1$H-NMR (DMSO-$d_6$) δ (ppm): 1.40 (9H, s), 1.40 (9H, s), 1.80-1.92 (2H, m), 1.92 (3H, s), 2.67-2.73 (1H, m), 2.78-2.86 (1H, m), 3.78-3.85 (2H, m), 4.10-4.17 (2H, m), 7.37 (1H, d, J=8.9 Hz), 7.41 (1H, d, J=8.1 Hz), 7.45 (1H, s), 7.56-7.58 (2H, m), 7.66-7.71 (3H, m), 7.76-7.79 (1H, m), 8.09 (1H, d, J=8.1 Hz).

2) Synthesis of mono(2-amino-2-hydroxymethyl-4-{9-oxo-7-[3-(trifluoromethyl)phenoxy]-9H-xanthen-3-yl}butyl)phosphate (compound 218)

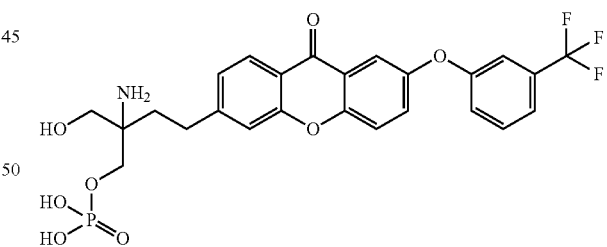

Compound 218-1 (214 mg) was dissolved in ethanol (5 mL), concentrated hydrochloric acid (1 mL) was added, and the mixture was stirred at 50° C. for 5 hr. The solvent was concentrated under reduced pressure, to the residue were added methanol and propylene oxide, and the resulting solid was washed with methanol to give compound 218 (92 mg) as a pale-yellow solid.

MS (ESI) m/z: 554 [M+H];

$^1$H-NMR (MeOD) δ (ppm): 2.02-2.15 (2H, m), 2.87-2.94 (2H, m), 3.74 (2H, s), 4.03 (2H, d, J=5.6 Hz), 7.31 (1H, d, J=8.2 Hz), 7.34 (1H, s), 7.39 (1H, dd, J=1.1, 8.5 Hz), 7.48 (1H, d, J=7.7 Hz), 7.55 (1H, s), 7.58-7.62 (2H, m), 7.70 (1H, d, J=9.0 Hz), 7.78 (1H, d, J=3.0 Hz), 8.18 (1H, d, J=8.3 Hz).

The compounds of the following Examples 219-288 were synthesized from the corresponding Example compounds by a method similar to that in Example 218.

TABLE 34

| Ex. No. | Structure | salt | MS(ESI) m/z [M + 1] |
|---|---|---|---|
| 219 | | | 502 |
| 220 | | | 504 |
| 221 | | | 520 |
| 222 | | | 504 |
| 223 | | | 500 |
| 224 | | | 554 |

TABLE 34-continued
| Ex. No. | salt | MS(ESI) m/z [M + 1] |
|---|---|---|
| 225 | | 554 |
| 226 | | 480 |
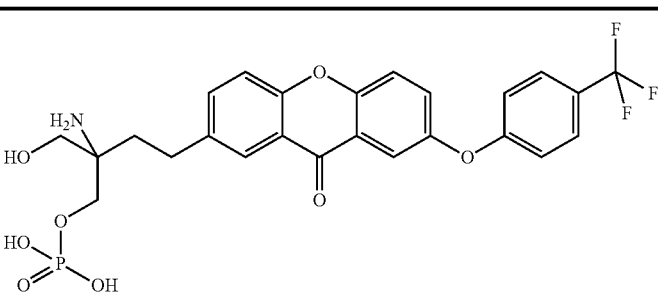
TABLE 35
| Ex. No. | salt | MS(ESI) m/z [M + 1] |
|---|---|---|
| 227 | | 494 |
| 228 | | 570 |
| 229 | | 500 |

TABLE 35-continued

| Ex. No. | | salt | MS(ESI) m/z [M + 1] |
|---|---|---|---|
| 230 | | | 504 |
| 231 | | | 500 |
| 232 | | | 554 |
| 233 | | | 452 |
| 234 | | | 466 |

TABLE 36

| Ex. No. | | salt | MS(ESI) m/z [M + 1] |
|---|---|---|---|
| 235 | | | 500 |
| 236 | | | 520 |

TABLE 36-continued
| Ex. No. | | salt | MS(ESI) m/z [M + 1] |
|---|---|---|---|
| 237 | ![structure] | | 504 |
| 238 | ![structure] | | 516 |
| 239 | ![structure] | | 570 |
| 240 | ![structure] | | 554 |
| 241 | ![structure] | | 516 |
| 242 | ![structure] | | 520 |
TABLE 37
| Ex. No. | | salt | MS(ESI) m/z [M + 1] |
|---|---|---|---|
| 243 |  | | 570 |

TABLE 37-continued
| Ex. No. | | salt | MS(ESI) m/z [M + 1] |
|---|---|---|---|
| 244 | 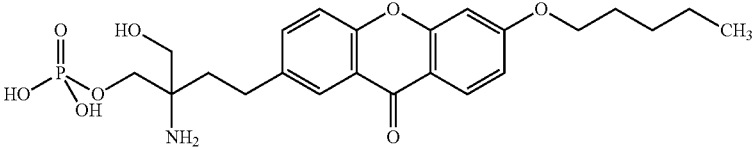 [SMILES: CCCCCOc1ccc2c(=O)c3cc(CCC(N)(CO)COP(=O)(O)O)ccc3oc2c1] | | 480 |
| 245 | 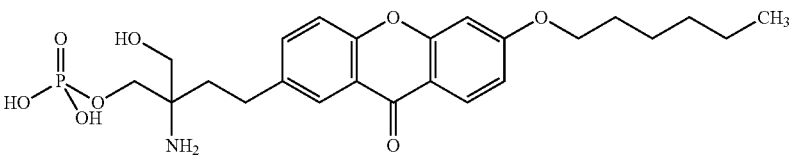 [SMILES: CCCCCCOc1ccc2c(=O)c3cc(CCC(N)(CO)COP(=O)(O)O)ccc3oc2c1] | | 494 |
| 246 | 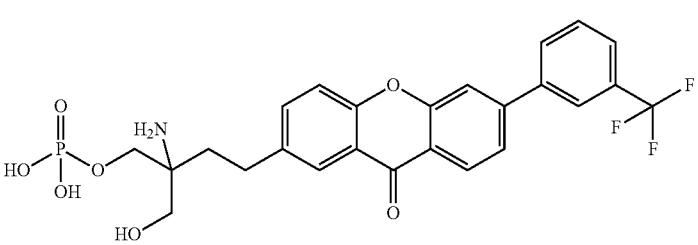 [SMILES: NC(CO)(CCc1ccc2oc3cc(-c4cccc(C(F)(F)F)c4)ccc3c(=O)c2c1)COP(=O)(O)O] | | 538 |
| 247 | 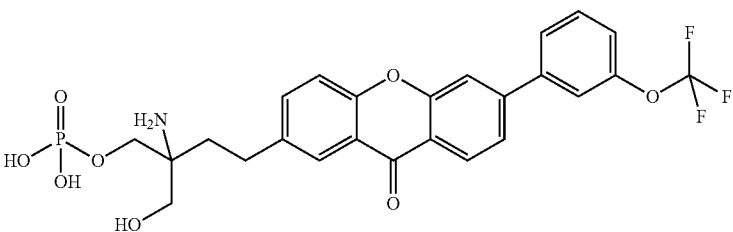 [SMILES: NC(CO)(CCc1ccc2oc3cc(-c4cccc(OC(F)(F)F)c4)ccc3c(=O)c2c1)COP(=O)(O)O] | | 554 |
| 248 | 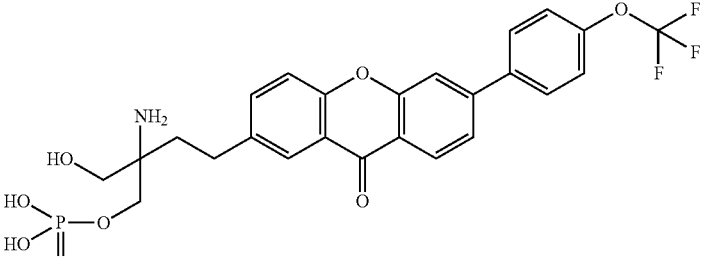 | | 554 |
| 249 | 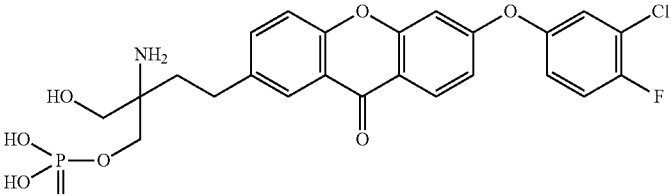 | | 538 |

TABLE 37-continued

| Ex. No. | | salt | MS(ESI) m/z [M + 1] |
|---|---|---|---|
| 250 | (structure) | | 500 |

TABLE 38

| Ex. No. | | salt | MS(ESI) m/z [M + 1] |
|---|---|---|---|
| 251 | (structure) | | 516 |
| 252 | (structure) | | 520 |
| 253 | (structure) | | 520 |

TABLE 38-continued

| Ex. No. | | salt | MS(ESI) m/z [M + 1] |
|---|---|---|---|
| 254 | | | 500 |
| 255 | | | 570 |
| 256 | | | 486 |
| 257 | | | 504 |
| 258 | | | 504 |

TABLE 39
| Ex. No. | | salt | MS(ESI) m/z [M + 1] |
|---|---|---|---|
| 267 | 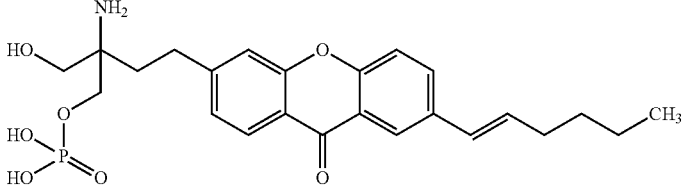 [SMILES: CCCC/C=C/c1ccc2oc3cc(CCC(N)(CO)COP(=O)(O)O)ccc3c(=O)c2c1] | | 476 |
| 260 | 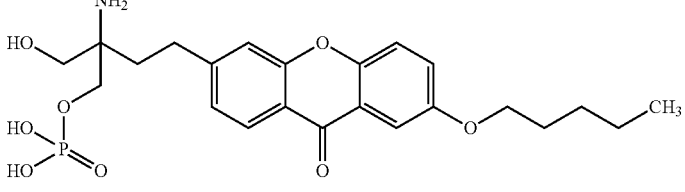 | | 480 |
| 261 | 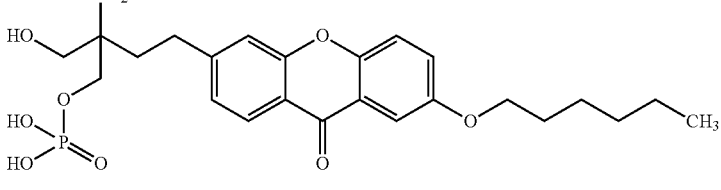 | | 494 |
| 262 | 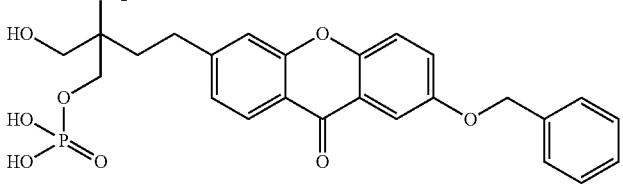 | | 500 |
| 263 | 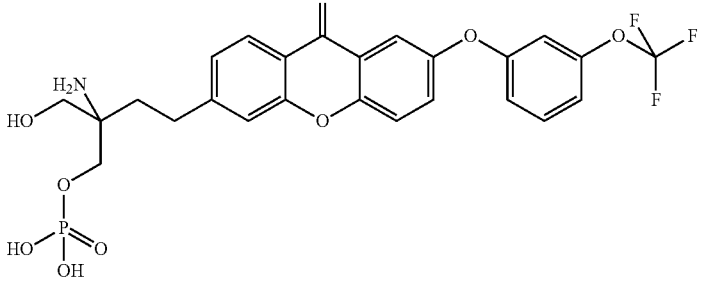 | | 570 |
| 264 | 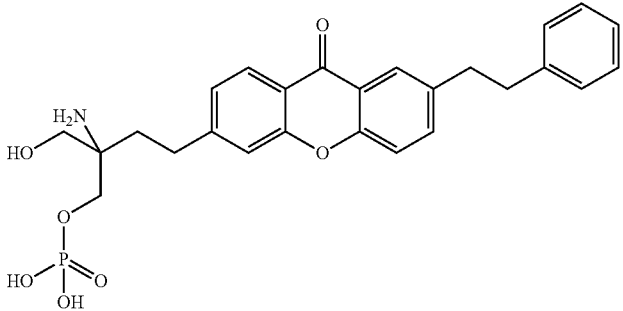 [SMILES: NC(CO)(CCc1ccc2c(=O)c3cc(CCc4ccccc4)ccc3oc2c1)COP(=O)(O)O] | | 498 |

TABLE 39-continued

| Ex. No. | salt | MS(ESI) m/z [M + 1] |
|---|---|---|
| 265 | | 478 |
| 266 | | 554 |

TABLE 40

| Ex. No. | salt | MS(ESI) m/z [M + 1] |
|---|---|---|
| 267 | | 510 |
| 268 | | 512 |
| 269 | | 534 |

TABLE 40-continued

| Ex. No. | | salt | MS(ESI) m/z [M + 1] |
|---|---|---|---|
| 270 | | | 554 |
| 271 | | | 538 |
| 272 | | | 550 |
| 273 | | | 500 |
| 274 | | | 520 |

TABLE 41

| Ex. No. | | salt | MS(ESI) m/z [M + 1] |
|---|---|---|---|
| 275 | | | 504 |

TABLE 41-continued

| Ex. No. | | salt | MS(ESI) m/z [M + 1] |
|---|---|---|---|
| 276 | | | 516 |
| 277 | | | 500 |
| 278 | | | 570 |
| 279 | | | 554 |
| 280 | | | 500 |
| 281 | | | 504 |

TABLE 41-continued
| Ex. No. | | salt | MS(ESI) m/z [M + 1] |
|---|---|---|---|
| 282 | 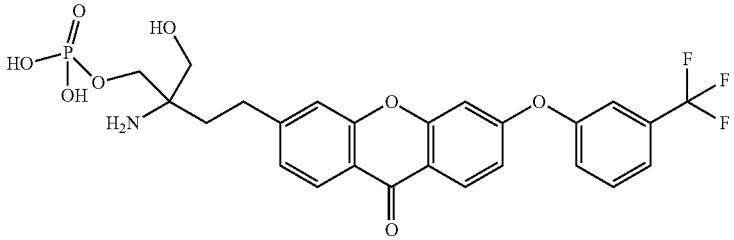 [SMILES: NC(CO)(CCc1ccc2c(=O)c3ccc(Oc4cccc(C(F)(F)F)c4)cc3oc2c1)COP(=O)(O)O] | | 554 |
TABLE 42
| Ex. No. | | salt | MS(ESI) m/z [M + 1] |
|---|---|---|---|
| 283 | 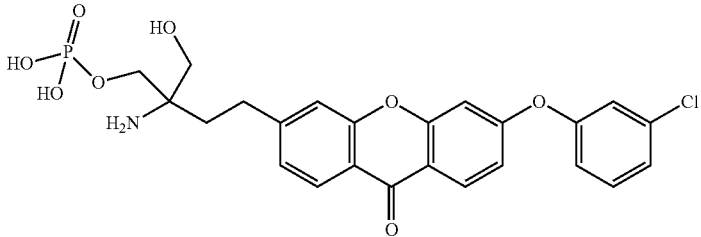 [SMILES: NC(CO)(CCc1ccc2c(=O)c3ccc(Oc4cccc(Cl)c4)cc3oc2c1)COP(=O)(O)O] | | 520 |
| 284 | 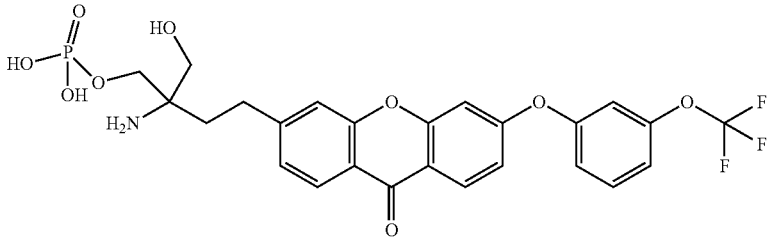 [SMILES: NC(CO)(CCc1ccc2c(=O)c3ccc(Oc4cccc(OC(F)(F)F)c4)cc3oc2c1)COP(=O)(O)O] | | 570 |
| 285 | 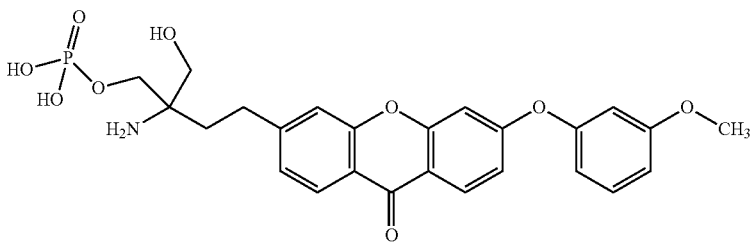 [SMILES: COc1cccc(Oc2ccc3c(=O)c4ccc(CCC(N)(CO)COP(=O)(O)O)cc4oc3c2)c1] | | 516 |
| 286 | 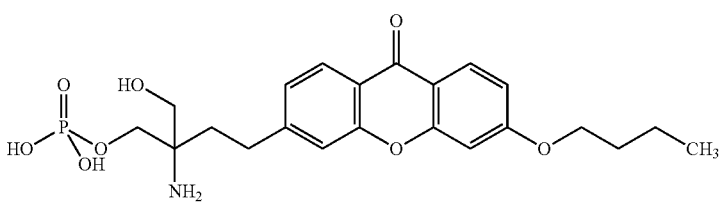 [SMILES: CCCCOc1ccc2c(=O)c3ccc(CCC(N)(CO)COP(=O)(O)O)cc3oc2c1] | | 466 |

TABLE 42-continued

| Ex. No. | | salt | MS(ESI) m/z [M + 1] |
|---|---|---|---|
| 287 | | | 480 |
| 288 | | | 494 |

Example 289

Synthesis of mono{2-amino-2-hydroxymethyl-4-[7-(4-chlorophenoxy)-9-oxo-9H-thioxanthen-2-yl]butyl}phosphate 1) Synthesis of t-butyl {3-[7-(4-chlorophenoxy)-9-oxo-9H-thioxanthen-2-yl]-1,1-bis(hydroxymethyl)propyl}carbamate (compound 289-1)

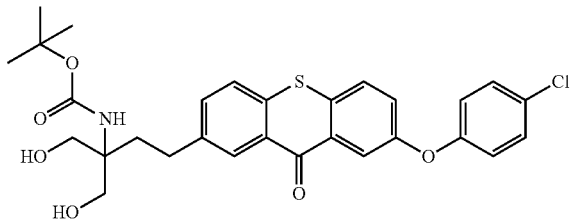 [SMILES: CC(C)(C)OC(=O)NC(CO)(CO)CCc1ccc2sc3ccc(Oc4ccc(Cl)cc4)cc3c(=O)c2c1]

To the compound (323 mg) of Example 50 were added methanol (5 mL), N,N-dimethylformamide (15 ml), N,N-diisopropylethylamine (0.190 ml), and di-tert-butyl dicarbonate (247 mg), and the mixture was stirred at 70° C. for 2.5 hr. Water was added to the reaction mixture, and the mixture was m extracted with ethyl acetate, washed with water and saturated brine, and dried over anhydrous sodium sulfate. The solvent was evaporated under reduced pressure, and the obtained residue was purified by silica gel column chromatography to give compound 289-1 (220 mg) as a yellow powder.

$^1$H-NMR (DMSO-d$_6$) δ (ppm): 1.41 (9H, s), 1.87-1.92 (2H, m), 2.64-2.69 (2H, m), 3.45 (2H, dd, J=5.7, 10.6 Hz), 3.55 (2H, dd, J=5.8, 10.8 Hz), 4.65 (2H, t, J=5.6 Hz), 6.10 (1H, brs), 7.17-7.20 (2H, m), 7.49-7.53 (2H, m), 7.58 (1H, dd, J=2.7, 8.6 Hz), 7.62 (1H, dd, J=1.6, 8.5 Hz), 7.80 (1H, d, J=8.4 Hz), 7.91 (1H, d, J=2.9 Hz), 7.93 (1H, d, J=9.6 Hz), 8.27 (1H, d, J=1.6 Hz).

2) Synthesis of t-butyl {3-[7-(4-chlorophenoxy)-9-oxo-9H-thioxanthen-2-yl]-1-[(dimethoxyphosphonooxy)methyl]-1-(methoxymethoxymethyl)propyl}carbamate (compound 289-2)

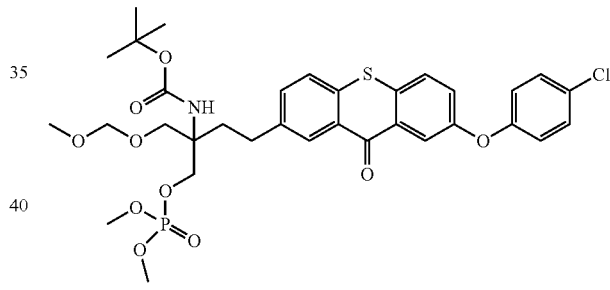

To compound 289-1 (220 mg) were added methylene chloride (40 ml) and N,N-diisopropylethylamine (0.105 ml), and the mixture was stirred at 50° C. After confirmation of dissolution, and the mixture was allowed to cool to room temperature, methoxymethyl chloride (0.040 ml) was added, and the mixture was stirred for one day. Water was added to the reaction mixture, and the mixture was extracted with methylene chloride, washed with saturated brine, and dried over anhydrous sodium sulfate. The solvent was evaporated under reduced pressure, and the obtained residue was purified by silica gel column chromatography. The obtained t-butyl {3-[7-(4-chlorophenoxy)-9-oxo-9H-thioxanthen-2-yl]-1-(hydroxymethyl)-1-(methoxymethoxymethyl)propyl}carbamate (150 mg) was dissolved in pyridine (3.7 mL) and methylene chloride (3.7 mL), carbon tetrabromide (1.0 g) and trimethyl phosphite (0.35 ml) were added, and the mixture was stirred at room temperature for 5 hr. To the reaction mixture was added saturated aqueous sodium hydrogen carbonate solution at 0° C., and the mixture was extracted with methylene chloride, and dried over anhydrous sodium sulfate. The solvent was evaporated and the obtained residue was purified by silica gel column chromatography to give compound 289-2 (190 mg) as a yellow oil.

$^1$H-NMR (DMSO-d$_6$) δ (ppm): 1.41 (9H, s), 1.84-2.01 (2H, m) 2.67-2.73 (2H, m), 3.39 (3H, s), 3.55 (1H, d, J=9.7 Hz), 3.64-3.69 (7H, m), 4.06-4.09 (1H, m), 4.16-4.20 (1H, m), 4.60 (2H, s), 6.83 (1H, brs), 7.19 (2H, d, J=8.7 Hz), 7.51 (2H, d, J=8.7 Hz), 7.58 (1H, dd, J=2.5, 8.8 Hz), 7.62 (1H, d, J=8.5 Hz), 7.82 (1H, d, J=8.2 Hz), 7.90 (1H, d, J=2.4 Hz), 7.94 (1H, d, J=8.8 Hz), 8.28 (1H, s).

3) Synthesis of mono{2-amino-2-hydroxymethyl-4-[7-(4-chlorophenoxy)-9-oxo-9H-thioxanthen-2-yl]butyl}phosphate (compound 289)

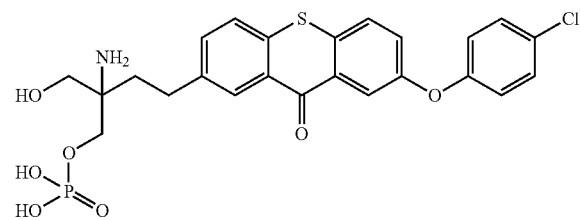 [SMILES: NC(CO)(CCc1ccc2sc3ccc(Oc4ccc(Cl)cc4)cc3c(=O)c2c1)COP(=O)(O)O]

To compound 289-2 (190 mg) was added 2M hydrogen chloride ethanol solution (4 mL), and the mixture was stirred at room temperature for one day and concentrated. To the obtained residue were added methylene chloride (5 mL) and acetonitrile (3 mL), and the mixture was cooled to −5° C. Iodotrimethylsilane (0.190 ml) was added, and the mixture was stirred at −5° C. for 5 hr. To the reaction mixture was added methanol, and water and diethyl ether were added. The resulting solid was washed with methanol to give compound 289 (92 mg) as a yellow powder.

MS (ESI) m/z: 536 [M+H];
$^1$H-NMR (MeOD) δ (ppm): 2.05-2.09 (2H, m), 2.84-2.89 (2H, m), 3.75 (2H, s), 4.10 (2H, d, J=5.3 Hz), 7.07-7.12 (2H, m), 7.40-7.44 (2H, m), 7.48 (1H, dd, J=2.9, 8.7 Hz), 7.65-7.71 (2H, m), 7.77 (1H, d, J=8.7 Hz), 8.04 (1H, d, J=2.7 Hz), 8.42 (1H, d, J=1.2 Hz).

The compounds of the following Examples 290-299 were synthesized from the corresponding Example compounds by a method similar to that in Example 289.

TABLE 43

| Ex. No. | | salt | MS(ESI) m/z [M + 1] |
|---|---|---|---|
| 290 | | | 516 |
| 291 | | | 570 |
| 292 | | | 520 |
| 293 | | | 537 |

TABLE 43-continued

| Ex. No. | salt | MS(ESI) m/z [M + 1] |
|---|---|---|
| 294 | | 516 |
| 295 | | 520 |
| 296 | | 536 |
| 297 | | 570 |

TABLE 44

| Ex. No. | salt | MS(ESI) m/z [M + 1] |
|---|---|---|
| 298 | | 516 |

TABLE 44-continued

| Ex. No. | | salt | MS(ESI) m/z [M + 1] |
|---|---|---|---|
| 299 | 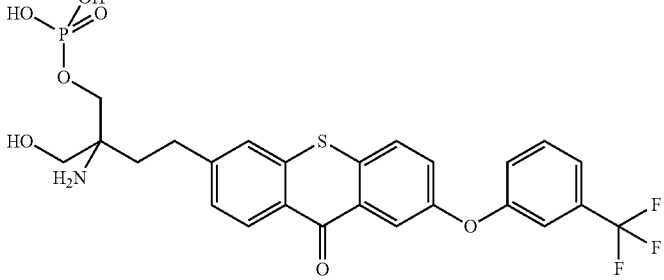 | | 570 |

Example 300

Synthesis of mono(2-amino-2-hydroxymethyl-4-{9-oxo-6-[3-(trifluoromethyl)phenoxy]-9H-thioxanthen-2-yl}butyl)phosphate 1) Synthesis of t-butyl [5-(2-{9-oxo-6-[3-(trifluoromethyl)phenoxy]-9H-thioxanthen-2-yl}ethyl)-2,2-dimethyl-1,3-dioxan-5-yl]carbamate (compound 300-1)

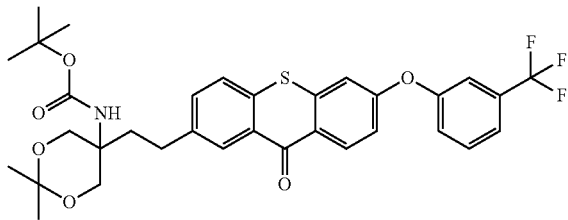 [SMILES: CC(C)(C)OC(=O)NC1(CCc2ccc3sc4cc(Oc5cccc(C(F)(F)F)c5)ccc4c(=O)c3c2)COC(C)(C)OC1]

Reference Example compound 7 (1.62 g), 4 Å molecular sieves (1.62 g), and 3-(trifluoromethyl)phenylboronic acid (1.27 g) were dissolved in methylene chloride (33 ml), triethylamine (1.86 ml) and copper acetate (1.21 g) were added, and the mixture was stirred at room temperature for one day. The solvent in the reaction mixture was evaporated under reduced pressure, and the obtained residue was purified by silica gel column chromatography to give compound 300-1 (555 mg) as a yellow powder.

$^1$H-NMR (DMSO-$d_6$) δ (ppm): 1.33 (3H, S) 1.34 (3H, s), 1, 42 (9H, s), 2.01-2.05 (2H, m), 2.62-2.66 (2H, m), 3.71 (2H, d, J=11.7H), 3.91 (2H, d, J=11.5 Hz), 6.70 (1H, brs), 7.21 (1H, dd, J=2.4, 8.8 Hz), 7.49 (1H, d, J=2.4 Hz), 7.52 (1H, d, J=8.2 Hz), 7.58-7.60 (2H, m). 7.65 (1H, d, J=7.9 Hz), 7.71 (1H, d, J=8.0 Hz), 7.73 (1H, d, J=8.3 Hz), 8.28 (1H, d, J=1.4 Hz), 8.50 (1H, d, J=8.5 Hz).

2) Synthesis of t-butyl (1,1-bis(hydroxymethyl)-3-{9-oxo-6-[3-(trifluoromethyl)phenoxy]-9H-thioxanthen-2-yl}propyl)carbamate (compound 300-2)

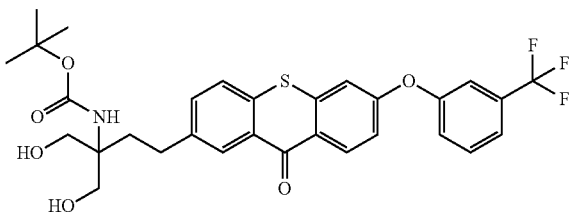 [SMILES: CC(C)(C)OC(=O)NC(CO)(CO)CCc1ccc2sc3cc(Oc4cccc(C(F)(F)F)c4)ccc3c(=O)c2c1]

Compound 300-1 (370 mg) was dissolved in methanol (6 mL), p-toluenesulfonic acid.monohydrate (34 mg) was added, and the mixture was stirred at room temperature for one day. To the reaction mixture was added saturated aqueous sodium hydrogen carbonate solution, and the mixture was extracted with ethyl acetate, washed with saturated brine, and dried over anhydrous sodium sulfate. The solvent was evaporated under reduced pressure, and the obtained residue was purified by silica gel column chromatography to give compound 300-2 (330 mg) as a yellow oil.

$^1$H-NMR (DMSO-$d_6$) δ (ppm): 1.41 (9H, S) 1.88-1.92 (2H, m), 2.65-2.69 (2H, m), 3.46 (2H, dd, J=5.7, 10.7 Hz), 3.55 (2H, dd, J=5.8, 10.8 Hz), 4.66 (2H, t, J=5.7 Hz), 6.11 (1H, brs), 7.21 (1H, dd, J=2.5, 9.2 Hz), 7.49 (1H, d, J=2.3 Hz), 7.52 (1H, d, J=8.1 Hz), 7.59-7.61 (2H, m), 7.65 (1H, d, J=7.9 Hz), 7.70-7.75 (2H, m), 8.30 (1H, d, J=1.1 Hz), 8.50 (1H, d, J=8.8 Hz).

3) Synthesis of t-butyl (1-(hydroxymethyl)-1-(methoxymethoxymethyl)-3-{9-oxo-6-[3-(trifluoromethyl)phenoxy]-9H-thioxanthen-2-yl}propyl) carbamate (compound 300-3)

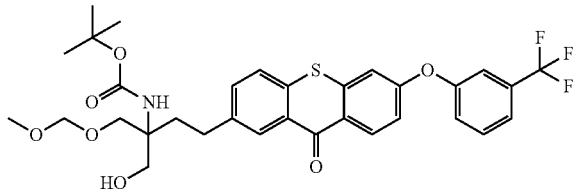 [SMILES: COCOCC(CO)(CCc1ccc2sc3cc(Oc4cccc(C(F)(F)F)c4)ccc3c(=O)c2c1)NC(=O)OC(C)(C)C]

To compound 300-2 (330 mg) were added methylene chloride (5.6 mL), N,N-diisopropylethylamine (0.130 ml), and methoxymethylchloride (0.055 ml), and the mixture was stirred for 4 hr. The reaction mixture was concentrated under reduced pressure, and the obtained residue was purified by silica gel to column chromatography. The recovered starting material (compound 300-2) (150 mg) was subjected to the reaction and purification again by similar methods, and combined with the reaction product of the first time. The solvent was evaporated under reduced pressure to give compound 300-3 (254 mg) as a yellow powder.

$^1$H-NMR (DMSO-$d_6$) δ (ppm): 1.41 (9H, s), 1.83-2.01 (2H, m), 2.62-2.76 (2H, m), 3.26 (3H, s), 3.45-3.49 (1H, m), 3.54-3.60 (2H, m), 3.66 (1H, d, J=9.3 Hz), 4.56 (2H, s), 4.79 (1H, t, J=5.6 Hz), 6.30 (1H, brs), 7.21 (1H, dd, J=2.4, 8.8 Hz), 7.48 (1H, d, J=2.4 Hz), 7.52 (1H, d, J=8.0 Hz), 7.59-7.61 (2H, m), 7.65 (1H, d, J=7.8 Hz), 7.70-7.75 (2H, m), 8.30 (1H, d, J=1.1 Hz), 8.50 (1H, d, J=8.8 Hz).

4) Synthesis of t-butyl (1-[(dimethoxyphosphonooxy)methyl]-1-(methoxymethoxymethyl)-3-{9-oxo-6-[3-(trifluoromethyl)phenoxy]-9H-thioxanthen-2-yl}propyl)carbamate (compound 300-4)

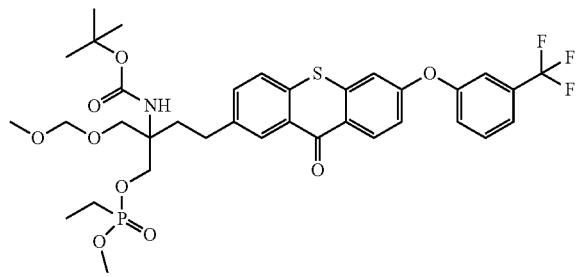 [SMILES: CCP(=O)(OC)OCC(CCc1ccc2sc3cc(Oc4cccc(C(F)(F)F)c4)ccc3c(=O)c2c1)(COCOC)NC(=O)OC(C)(C)C]

Compound 300-3 (254 mg) was dissolved in pyridine (5.0 ml) and methylene chloride (5.0 ml), carbon tetrabromide (1.33 g) and trimethyl phosphate (0.473 ml) were added, and the mixture was stirred at room temperature for 5 hr. To the reaction mixture was added saturated aqueous sodium hydrogen carbonate solution at 0° C., and the mixture was extracted with methylene chloride, and dried over anhydrous sodium sulfate. The solvent m was evaporated and the obtained residue was purified by silica gel column chromatography to give compound 300-4 (271 mg) as a yellow powder.

$^{1}$H-NMR (DMSO-d$_{6}$) δ (ppm): 1.42 (9H, s), 1.82-2.03 (2H, m), 2.70-2.74 (2H, m), 3.29 (3H, s), 3.56 (1H, d, J=9.6 Hz), 3.65-3.70 (7H, m), 4.07-4.11 (1H, m), 4.17-4.21 (1H, dd, J=4.6, 9.8 Hz), 4.61 (2H, s), 6.83 (1H, brs), 7.21 (1H, dd, J=2.3, 8.7 Hz), 7.49 (1H, d, J=2.3 Hz), 7.52 (1H, d, J=8.0z), 7.59-7.61 (2H, m), 7.65 (1H, d, J=8.0 Hz), 7.70-7.77 (2H, m), 8.30 (1H, d, J=1.7 Hz), 8.50 (1H, d, J=8.8 Hz).

5) Synthesis of mono(2-amino-2-hydroxymethyl-4-{9-oxo-6-[3-(trifluoromethyl)phenoxy]-9H-thioxanthen-2-yl}butyl) phosphate (compound 300)

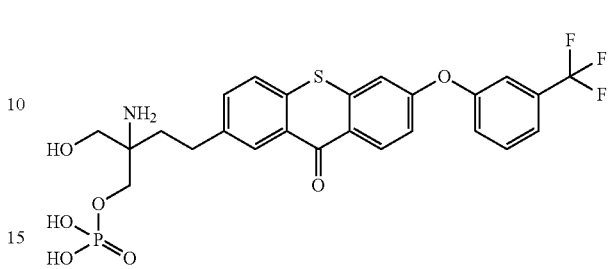

To compound 300-4 (190 mg) was added 4M hydrogen chloride 1,4-dioxane solution (4 mL), and the mixture was stirred at room temperature for one day and concentrated under reduced pressure. To the obtained residue was added methylene chloride (4 mL), iodotrimethylsilane (0.260 ml) was added, and the mixture was stirred at room temperature for 5.5 hr. To the reaction mixture was added methanol, and the solvent was evaporated under reduced pressure. To the residue were added water and methanol, and the resulting solid was washed with methanol to give compound 300 (155 mg) as a yellow powder.

MS (ESI) m/z: 570 [M+H];

$^{1}$H-NMR (DMSO-d$_{6}$) δ (ppm): 1.87-1.92 (2H, m), 2.75-2.79 (2H, m), 3.55-3.62 (2H, m), 3.91 (2H, d, J=7.8 Hz), 7.16 (1H, dd, J=2.2, 9.1 Hz), 7.42 (1H, dd, J=1.8 Hz), 7.50 (1H, d, J=8.0 Hz), 7.56-7.73 (5H, m), 8.27 (1H, s), 8.45 (1H, d, J=8.9 Hz).

The compounds of the following Examples 301-314 were synthesized from the corresponding starting materials by a method similar to that in Example 300.

TABLE 45

| Ex. No. | | MS(ESI) m/z salt [M + 1] |
|---|---|---|
| 301 | (structure) | 570 |
| 302 | (structure) | 536 |

TABLE 45-continued
| Ex. No. | | salt | MS(ESI) m/z [M + 1] |
|---|---|---|---|
| 303 | 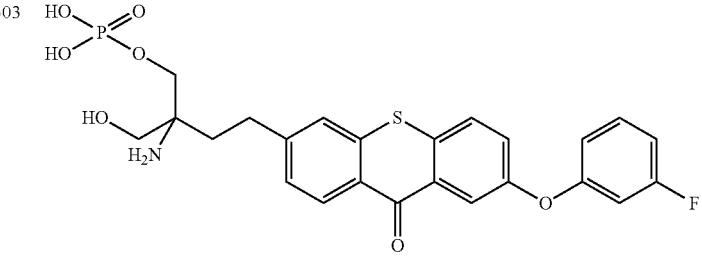 | | 520 |
| 304 | 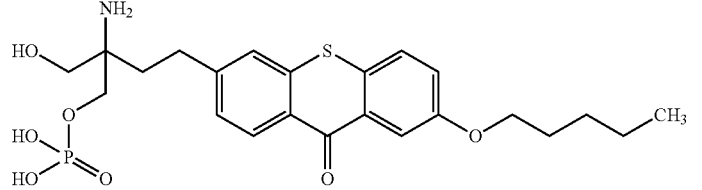 [SMILES: CCCCCOc1ccc2sc3cc(CCC(N)(CO)COP(=O)(O)O)ccc3c(=O)c2c1] | | 496 |
| 305 | 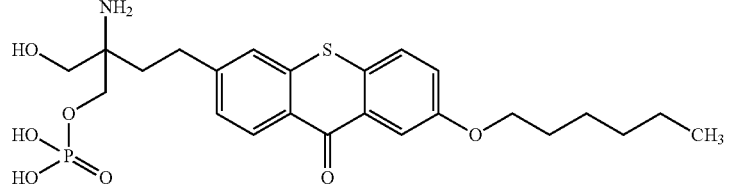 | | 510 |
| 306 | 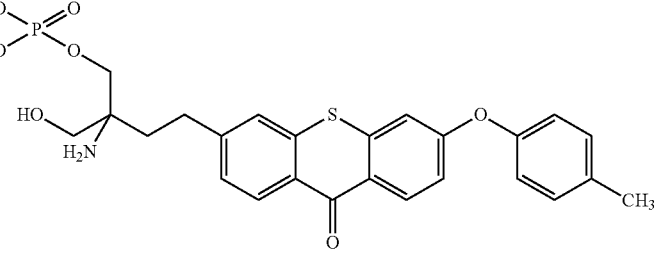 | | 516 |
| 307 | 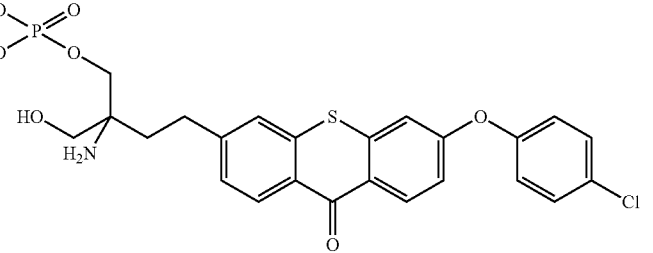 | | 536 |
| 308 | 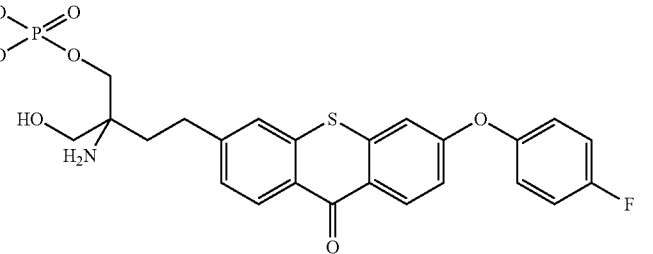 | | 520 |

TABLE 46

| Ex. No. | salt | MS(ESI) m/z [M + 1] |
|---|---|---|
| 309 | | 520 |
| 310 | | 536 |
| 311 | | 496 |
| 312 | | 510 |
| 313 | | 526 |
| 314 | | 554 |

Example 315

Synthesis of 3-[3-amino-4-hydroxy-3-(hydroxymethyl)butyl]-7-hexyloxy-9H-fluoren-9-one hydrochloride (compound 315)

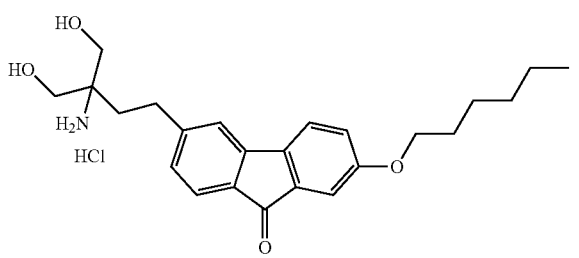 [SMILES: CCCCCCOc1ccc2c(c1)C(=O)c1ccc(CCC(N)(CO)CO)cc1-2 ; Cl]

To Reference Example compound 24 (150 mg) were added potassium carbonate (137 mg), N,N-dimethylformamide (3.3 mL), and 1-bromohexane (69 μl), and the mixture was stirred at room temperature for one day. 1-Bromohexane (34 μl) was further added and the mixture was stirred at room temperature for one day. Water was added to the reaction mixture, and the mixture was extracted with ethyl acetate, washed with water and saturated brine, and dried over anhydrous sodium sulfate. The solvent was evaporated under reduced pressure to give t-butyl {5-[2-(7-hexyloxy-9-oxo-9H-fluoren-3-yl)ethyl]-2,2-dimethyl-1,3-dioxan-5-yl}carbamate (174 mg) as a yellow solid. To the obtained yellow solid was added 2N hydrochloric acid ethanol solution (10 ml) and the mixture was stirred at 50° C. for 3 hr.

The reaction mixture was concentrated, and the obtained residue was washed with diethyl ether to give compound 315 (98 mg) as an orange solid.

MS (ESI) m/z: 398 [M+H].

Example 316

Synthesis of 3-[3-amino-4-hydroxy-3-(hydroxymethyl)butyl]-7-(3-chlorophenoxy)-9H-fluoren-9-one hydrochloride (compound 316)

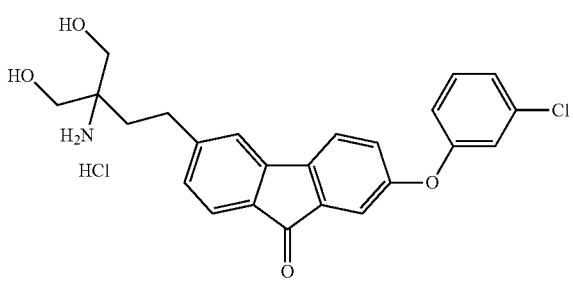 [SMILES: NC(CO)(CO)CCc1ccc2c(c1)-c1ccc(Oc3cccc(Cl)c3)cc1C2=O ; Cl]

To a suspension of Reference Example compound 24 (150 mg), 4 Å molecular sieves (250 mg), and 3-chlorophenylboronic acid (172 mg) in methylene chloride (5.5 mL) were added triethylamine (0.307 ml) and copper acetate (200 mg), and the mixture was stirred at room temperature for 19 hr. The reaction mixture was filtered through celite and concentrated. The obtained residue was purified by silica gel column chromatography to give t-butyl (5-{2-[7-(3-chlorophenoxy)-9-oxo-9H-fluoren-3-yl]ethyl}-2,2-dimethyl-1,3-dioxan-5-yl)carbamate as a yellow oil. To the obtained a yellow oil was added 2N hydrochloric acid ethanol solution (10 ml), and the mixture was stirred at 50° C. for 2.5 hr. The reaction mixture was concentrated, and the obtained residue was washed with diethyl ether to give compound 316 (178 mg) as a yellow solid.

MS (ESI) m/z: 424 [M+H].

Example 317

Synthesis of 3-[3-amino-4-hydroxy-3-(hydroxymethyl)butyl]-7-heptyloxy-9H-fluoren-9-one hydrochloride (compound 317)

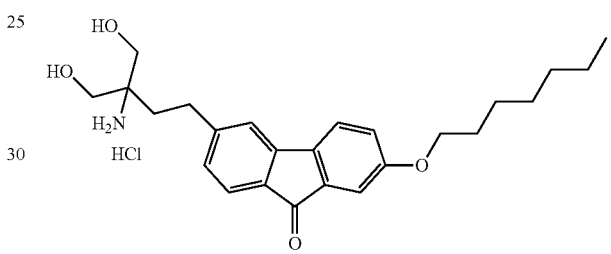

By similar reactions and treatments as in Example 315 except that 1-bromoheptane was used instead of 1-bromohexane, compound 317 (131 mg) was obtained as a yellow solid.

MS (ESI) m/z: 412 [M+H].

Example 318

Synthesis of 3-[3-amino-4-hydroxy-3-(hydroxymethyl)butyl]-7-octyloxy-9H-fluoren-9-one hydrochloride (compound 318)

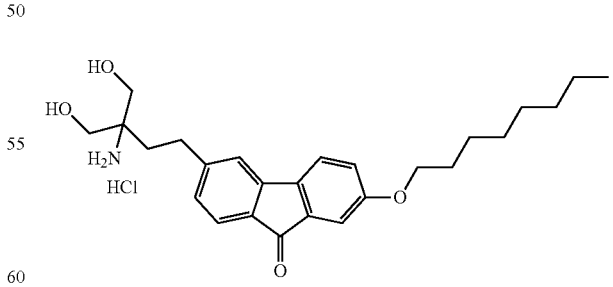

By similar reactions and treatments as in Example 315 except that 1-bromooctane was used instead of 1-bromohexane, compound 318 (116 mg) was obtained as a yellow solid.

MS (ESI) m/z: 426 [M+H].

Example 319

Synthesis of 3-[3-amino-4-hydroxy-3-(hydroxymethyl)butyl]-7-nonyloxy-9H-fluoren-9-one hydrochloride (compound 319)

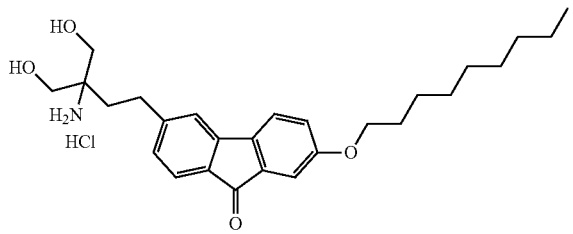 [SMILES: CCCCCCCCCOc1ccc2c(c1)C(=O)c1ccc(CCC(N)(CO)CO)cc1-2 ; Cl]

By similar reactions and treatments as in Example 315 except that 1-bromononane was used instead of 1-bromohexane, compound 319 (152 mg) was obtained as a yellow solid.

MS (ESI) m/z: 440 [M+H].

Experimental Example 1

Evaluation of Peripheral Blood Lymphocyte Count-Decreasing Effect in Mice

The compound of the present invention was dissolved or suspended in 20% cyclodextrin (manufactured by NIHON SHOKUHIN KAKO CO., LTD), and intraperitoneally administered to a 7- to 10-week-old male BALB/c mice (CHARLES RIVER LABORATORIES, JAPAN INC.) at a dose of 0.001-10 mg/kg body weight. After 24 hr from the administration of the compound of the present invention, peripheral blood (about 0.3 ml) was drawn from the postcava of the mouse with a heparin sodium (manufactured by NovoNordisk)-treated tuberculin syringe (manufactured by TERUMO CORPORATION) under ether anesthesia. The blood (0.1 ml) was hemolysed with an automatic hemolysis processing apparatus (TQ-Prep, manufactured by BECKMAN COULTER, Inc.), and the number of lymphocytes was counted with a Flow Cytometer (CYTOMICS FC 500, manufactured by BECKMAN COULTER, Inc.) by a gating method using scattering at the front and the side of the laser beam as indices and using Flow-Count™ Fluorospheres (manufactured by BECKMAN COULTER, Inc.), whose standard particle count is known, as internal standard. A dose necessary for 50% reduction of the lymphocyte count of vehicle group as 100% was calculated and used as $ED_{50}$ value (mg/kg body weight). The results are shown below.

TABLE 47

| test compound | $ED_{50}$ (mg/kg body weight) |
| --- | --- |
| Example 20 | 0.05 |
| Example 22 | 0.07 |
| Example 23 | 0.03 |
| Example 41 | 0.37 |
| Example 44 | 0.01 |
| Example 54 | 0.02 |
| Example 55 | 0.03 |
| Example 76 | 0.04 |
| Example 83 | 0.05 |
| Example 105 | 0.22 |
| Example 108 | 0.05 |
| Example 116 | 0.09 |

TABLE 47-continued

| test compound | $ED_{50}$ (mg/kg body weight) |
| --- | --- |
| Example 138 | 0.06 |
| Example 143 | 0.14 |
| Example 164 | 0.04 |
| Example 172 | 0.09 |
| Example 180 | 0.03 |

From the above-mentioned results, it was clarified that the compound of the present invention has a superior peripheral blood lymphocyte decreasing action.

Experimental Example 2

Effect on Heart Rate of Rat Under Anesthesia

Male Sprague-Dawley (IGS) rats were anesthetized by intraperitoneal administration of Nembutal (manufactured by DAINIPPON PHARMACEUTICAL CO., LTD.), and fixed at the dorsal position. Electrodes were mounted on four limbs, electrocardiogram was recorded by a standard limb lead II using an electrocardiogram amplifier (AC-601 g, manufactured by NIHON KOHDEN CORPORATION). The heart rate was counted using an instant heart rate meter unit (AT-601 g, manufactured by NIHON KOHDEN CORPORATION) and an electrocardiographic wave as a trigger. The compound of the present invention was dissolved in 20% cyclodextrin (manufactured by NIHON SHOKUHIN KAKO CO., LTD) and intravenously administered over 30 seconds at a dose of 0.001-10 mg/kg body weight. The heart rate was measured before the administration, and 1, 2, 3, 4, 5, 10 and 15 min after the administration. In Example 218, Example 246, Example 276, Example 296, Example 300 and Example 312, the heart rate of the rat did not decrease by 20% or more as compared to the value before administration until the dose became 0.03 mg/kg body weight.

INDUSTRIAL APPLICABILITY

Since the compound of the present invention has a superior peripheral blood lymphocyte decreasing action, it can be expected to show a superior immunosuppressive action, rejection suppressive action and allergy suppressive action, and is considered to be effective for the treatment or prophylaxis of autoimmune diseases; prophylaxis or suppression of resistance or acute rejection or chronic rejection of transplantation of organ or tissue; treatment or prophylaxis of graft-versus-host (GvH) disease due to bone marrow transplantation; or treatment or prophylaxis of allergic diseases. Moreover, the compound of the present invention is considered to be a compound showing reduced side effects such as a decrease in the heart rate and the like.

This application is based on a patent application No. 2012-097741 filed in Japan (filing date: Apr. 23, 2012), the contents of which are incorporated in full herein by this reference.

The invention claimed is:

1. An amine compound represented by the following formula (I)

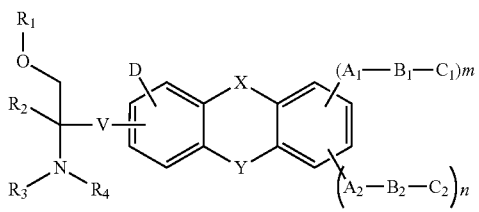

(I)

wherein $R_1$ is a hydrogen atom or $P(=O)(OH)_2$,

V is a $C_{1-4}$ alkylene or a $C_{2-4}$ alkenylene, $R_2$ is a hydrogen atom, or a $C_{1-4}$ alkyl optionally substituted by a hydroxy group or a halogen atom, $R_3$ and $R_4$ are the same or different and each is a hydrogen atom or a $C_{1-4}$ alkyl, X is a single bond, an oxygen atom, a sulfur atom, methylene, —CO—, —SO—, —SO$_2$— or —NR$_5$— wherein $R_5$ is a hydrogen atom or a $C_{1-4}$ alkyl optionally having substituent(s), $A_1$ and $A_2$ are the same or different and each is a single bond, an oxygen atom, a sulfur atom, —CO—, —SO—, —SO$_2$— or —NR$_6$— wherein $R_6$ is a hydrogen atom, a $C_{1-6}$ alkyl optionally having substituent(s), a $C_{1-7}$ acyl optionally having substituent(s) or a $C_{2-7}$ alkoxycarbonyl, Y is C=O, $B_1$ and $B_2$ are the same or different and each is a single bond, a $C_{1-10}$ alkylene optionally having substituent(s), a $C_{2-10}$ alkenylene optionally having substituent(s) or a $C_{2-10}$ alkynylene optionally having substituent(s), $C_1$ and $C_2$ are the same or different and each is a hydrogen atom, a halogen atom, a $C_{6-10}$ aryl optionally having substituent(s), a heteroaryl with 5 to 10 ring-constituting atoms optionally having substituent(s), which contains 1 or 2 nitrogen atoms, 1 or 2 oxygen atoms or 1 or 2 sulfur atoms as the ring-constituting atom(s), a $C_{3-7}$ cycloalkyl optionally having substituent(s), which is optionally fused with benzene optionally having substituent(s), or a heterocycloalkyl with 5 to 7 ring-constituting atoms optionally having substituent(s), which contains 1 or 2 nitrogen atoms or 1 or 2 oxygen atoms as the ring-constituting atoms, and is optionally fused with benzene optionally having substituent(s), D is a hydrogen atom, a halogen atom or a $C_{1-4}$ alkyl optionally having substituent(s), m is 0 or 1, and n is 0 or 1, or a pharmaceutically acceptable acid addition salt thereof.

2. The compound according to claim 1, wherein both $R_3$ and $R_4$ are hydrogen atoms, or a pharmaceutically acceptable acid addition salt thereof.

3. The compound according to claim 1, wherein n is 0, or a pharmaceutically acceptable acid addition salt thereof.

4. The compound according to claim 1, wherein V is $CH_2CH_2$, or a pharmaceutically acceptable acid addition salt thereof.

5. The compound according to claim 1, wherein $C_1$ is a hydrogen atom, a $C_{6-10}$ aryl optionally having substituent(s) or a heteroaryl with 5 to 10 ring-constituting atoms optionally having substituent(s), which contains 1 or 2 nitrogen atoms, 1 or 2 oxygen atoms or 1 or 2 sulfur atoms as the ring-constituting atom(s), or a pharmaceutically acceptable acid addition salt thereof.

6. The compound according to claim 1, wherein $A_1$ is a single bond, an oxygen atom, a sulfur atom or —CO—, or a pharmaceutically acceptable acid addition salt thereof.

7. The compound according to claim 1, wherein $R_2$ is hydroxymethyl, or a pharmaceutically acceptable acid addition salt thereof.

8. The compound according to claim 1, wherein $R_1$ is a hydrogen atom, or a pharmaceutically acceptable acid addition salt thereof.

9. The compound according to claim 1, wherein the compound of the formula (I) is any of the following a to hh, or a pharmaceutically acceptable acid addition salt thereof:

a. 2-[3-amino-4-hydroxy-3-(hydroxymethyl)butyl]-6-[3-(trifluoromethyl)phenoxy]-9H-thioxanthen-9-one,
b. 2-[3-amino-4-hydroxy-3-(hydroxymethyl)butyl]-6-(4-chlorophenoxy)-9H-thioxanthen-9-one,
c. 2-[3-amino-4-hydroxy-3-(hydroxymethyl)butyl]-7-[3-(trifluoromethyl)phenoxy]-9H-thioxanthen-9-one,
d. 2-[3-amino-4-hydroxy-3-(hydroxymethyl)butyl]-7-(3-chlorophenoxy)-9H-thioxanthen-9-one,
e. 2-[3-amino-4-hydroxy-3-(hydroxymethyl)butyl]-6-(4-fluorophenoxy)-9H-xanthen-9-one,
f. 2-[3-amino-4-hydroxy-3-(hydroxymethyl)butyl]-6-(4-methoxyphenoxy)-9H-xanthen-9-one,
g. 6-[3-amino-4-hydroxy-3-(hydroxymethyl)butyl]-2-[3-(trifluoromethyl)phenoxy]-9H-xanthen-9-one,
h. 3-[3-amino-4-hydroxy-3-(hydroxymethyl)butyl]-6-hexyloxy-9H-thioxanthen-9-one,
i. 6-[3-amino-4-hydroxy-3-(hydroxymethyl)butyl]-2-[(1E)-hex-1-en-1-yl]-9H-xanthen-9-one,
j. 3-[3-amino-4-hydroxy-3-(hydroxymethyl)butyl]-6-(4-methoxyphenoxy)-9H-xanthen-9-one,
k. 2-[3-amino-4-hydroxy-3-(hydroxymethyl)butyl]-7-pentyloxy-9H-xanthen-9-one,
l. 2-[3-amino-4-hydroxy-3-(hydroxymethyl)butyl]-7-hexyloxy-9H-xanthen-9-one,
m. 2-[3-amino-4-hydroxy-3-(hydroxymethyl)butyl]-6-(3-chloro-4-fluorophenoxy)-9H-xanthen-9-one,
n. 2-[3-amino-4-hydroxy-3-(hydroxymethyl)butyl]-6-(trifluoromethyl)phenyl1-9H-xanthen-9-one,
o. 3-[3-amino-4-hydroxy-3-(hydroxymethyl)butyl]-6-pentyloxy-9H-xanthen-9-one,
p. 2-[3-amino-4-hydroxy-3-(hydroxymethyl)butyl]-6-[3-(trifluoromethoxy)phenyl]-9H-xanthen-9-one,
q. 6-[3-amino-4-hydroxy-3-(hydroxymethyl)butyl]-2-(3-chloro-4-fluorophenoxy)-9H-xanthen-9-one,
r. mono(2-amino-2-hydroxymethyl-4-{9-oxo-6-[3-(trifluoromethyl)phenoxy]-9H-thioxanthen-2-yl}butyl)phosphate,
s. mono{2-amino-4-[6-(4-chlorophenoxy)-9-oxo-9H-thioxanthen-2-yl]-2-hydroxymethylbutyl}phosphate,
t. mono(2-amino-2-hydroxymethyl-4-{9-oxo-7-[3-(trifluoromethyl)phenoxy]-9H-thioxanthen-2-yl}butyl)phosphate,
u. mono{2-amino-4-[7-(3-chlorophenoxy)-9-oxo-9H-thioxanthen-2-yl]-2-hydroxymethylbutyl}phosphate,
v. mono{2-amino-4-[6-(4-fluorophenoxy)-9-oxo-9H-xanthen-2-yl]-2-hydroxymethylbutyl}phosphate,
w. mono{2-amino-2-hydroxymethyl-4-[6-(4-methoxyphenoxy)-9-oxo-9H-xanthen-2-yl]butyl }phosphate,
x. mono(2-amino-2-hydroxymethyl-4-{9-oxo-7-[3-(trifluoromethyl)phenoxy]-9H-xanthen-3-yl}butyl)phosphate,
y. mono[2-amino-4-(6-hexyloxy-9-oxo-9H-thioxanthen-3-yl)-2-(hydroxymethyl)butyl]phosphate,
z. mono(2-amino-4-{7-[(1E)-hex-1-en-1-yl]-9-oxo-9H-xanthen-3-yl }-2-(hydroxymethyl)butyl)phosphate, aa. mono{2-amino-2-hydroxymethyl-4-[6-(4-methoxyphenoxy)-9-oxo-9H-xanthen-3-yl]butyl}phosphate,
bb. mono[2-amino-2-hydroxymethyl-4-(9-oxo-7-pentyloxy-9H-xanthen-2-yl)butyl]phosphate,
cc. mono[2-amino-4-(7-hexyloxy-9-oxo-9H-xanthen-2-yl)-2-hydroxymethylbutyl]phosphate,
dd. mono{2-amino-4-[6(3-chloro-4-fluorophenoxy)-9-oxo-9H-xanthen-2-yl]-2-hydroxymethylbutyl}phosphate,
ee. mono{2-amino-2-hydroxymethyl-4-[9-oxo-6-[3-(trifluoromethyl)phenyl]-9H-xanthen-2-yl]butyl}phosphate,
ff. mono[2-amino-2-hydroxymethyl-4-(9-oxo-6-pentyloxy-9H-xanthen-3-yl)butyl]phosphate,
gg. mono(2-amino-2-hydroxymethyl-4-{9-oxo-6-[3-(trifluoromethoxy)phenyl]-9H-xanthen-2-yl}butyl)phosphate and
hh. mono{2-amino-4-[7-(3-chloro-4-fluorophenoxy)-9-oxo-9H-xanthen-3-yl]-2-(hydroxymethyl)butyl}phosphate.

10. A pharmaceutical composition comprising the compound of claim 1 or a pharmaceutically acceptable acid addition salt thereof, and a pharmaceutically acceptable carrier.

11. A method for treating an autoimmune disease selected from the group consisting of rheumatoid arthritis, multiple sclerosis, encephalomyelitis, systemic lupus erythematosus, lupus nephritis, nephrotic syndrome, psoriasis and Type I diabetes mellitus; suppressing resistance or acute rejection or chronic rejection of transplantation of organ or tissue; treating a graft-versus-host (GvH) disease due to bone marrow transplantation; or treating an allergic disease, comprising:
administering an effective amount of the compound according to claim 1 or a pharmaceutically acceptable acid addition salt thereof to a patient in need thereof.

12. The method according to claim 11, wherein the allergic disease is atopic dermatitis, allergic rhinitis or asthma.

13. A method for treating an autoimmune disease selected from the group consisting of rheumatoid arthritis, multiple sclerosis, encephalomyelitis, systemic lupus erythematosus, lupus nephritis, nephrotic syndrome, psoriasis and Type I diabetes mellitus; suppressing resistance or acute rejection or chronic rejection of transplantation of organ or tissue; treating a graft-versus-host (GvH) disease due to bone marrow transplantation; or treating an allergic disease, comprising:
administering an effective amount of the compound according to claim 9 or a pharmaceutically acceptable acid addition salt thereof to a patient in need thereof.

* * * * *